United States Patent
Mellstedt et al.

(10) Patent No.: US 10,550,113 B2
(45) Date of Patent: Feb. 4, 2020

(54) 2-PHENYL-3H-IMIDAZO[4,5-B]PYRIDINE DERIVATES USEFUL AS INHIBITORS OF MAMMALIAN TYROSINE KINASE ROR1 ACTIVITY

(71) Applicant: Kancera AB, Solna (SE)

(72) Inventors: Hakan Mellstedt, Stockholm (SE); Styrbjorn Bystrom, Taby (SE); Jan Vagberg, Sollentuna (SE); Elisabeth Olsson, Sollentuna (SE)

(73) Assignee: KANCERA AB, Solna (SE)

( * ) Notice: Subject to any disclaimer, the term of this patent is extended or adjusted under 35 U.S.C. 154(b) by 203 days.

(21) Appl. No.: 15/545,523

(22) PCT Filed: Feb. 1, 2016

(86) PCT No.: PCT/EP2016/052091
§ 371 (c)(1),
(2) Date: Jul. 21, 2017

(87) PCT Pub. No.: WO2016/124553
PCT Pub. Date: Aug. 11, 2016

(65) Prior Publication Data
US 2018/0002329 A1    Jan. 4, 2018

(30) Foreign Application Priority Data
Feb. 2, 2015 (EP) .................................... 15153394

(51) Int. Cl.
*C07D 471/04* (2006.01)
(52) U.S. Cl.
CPC ................. *C07D 471/04* (2013.01)
(58) Field of Classification Search
CPC .................................................. C07D 471/04
See application file for complete search history.

(56) References Cited

U.S. PATENT DOCUMENTS 7,622,479 B2    11/2009  Oda et al.

FOREIGN PATENT DOCUMENTS

| WO | 2003/045929 A1 | 5/2003 |
|---|---|---|
| WO | 2004/016270 A1 | 2/2004 |
| WO | 2004/016611 A1 | 2/2004 |
| WO | 2006/066913 A2 | 6/2006 |
| WO | 2006/066914 A2 | 6/2006 |
| WO | 2006/080821 A1 | 8/2006 |
| WO | 2006/125958 A1 | 11/2006 |
| WO | 2007/028135 A2 | 3/2007 |
| WO | 2007/072017 A2 | 6/2007 |
| WO | 2007/083978 A1 | 7/2007 |
| WO | 2008/121063 A1 | 10/2008 |
| WO | 2008/121064 A1 | 10/2008 |
| WO | 2009/001021 A1 | 12/2008 |
| WO | 2009/111277 A1 | 9/2009 |
| WO | 2011/066211 A1 | 6/2011 |

(Continued)

OTHER PUBLICATIONS

Wang, T., et al. "Discovery of azabenzimidazole derivatives as potent, selective inhibitors of TBK1/IKKε kinases." Bioorganic & Medicinal Chemistry Letters. (2012), vol. 22, pp. 2063-2069. (Year: 2012).*

Balaian et al., "A Highly Selective Anti-ROR1 Monoclonal Antibody Inhibits Human Acute Myeloid Leukemia CD34+ Cell Survival and Self-Renewal", Blood Journal, 2012, Abstract 2560, 2 pages.

Bicocca et al, "Crosstalk between ROR1 and the Pre-B Receptor Promotes Survival of t(1;19) Acute Lymphoblastic Leukemia", Cancer Cell, vol. 22, Nov. 13, 2012, pp. 656-667.

Chiorazzi et al., "Chronic Lymphocytic Leukemia", The New England Journal of Medicine, vol. 352 , No. 8, Feb. 24, 2005, pp. 804-815.

(Continued)

*Primary Examiner* — Andrew D Kosar
*Assistant Examiner* — John S Kenyon
(74) *Attorney, Agent, or Firm* — Renner, Otto, Boisselle & Sklar, LLP

(57) ABSTRACT

A compound of formula (I') or (I") or a pharmaceutically acceptable salt thereof. The compound is an inhibitor of mammalian kinase enzyme activity, including ROR1 tyrosine kinase activity and may be used in the treatment of disorders associated with such activity.

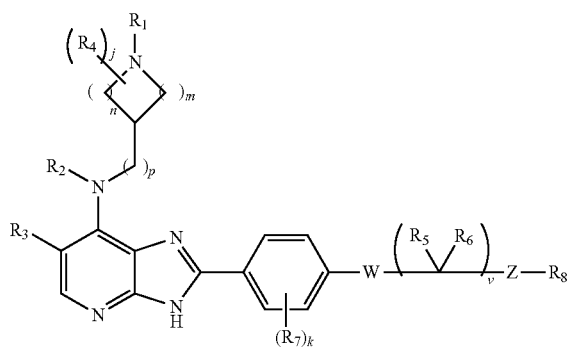

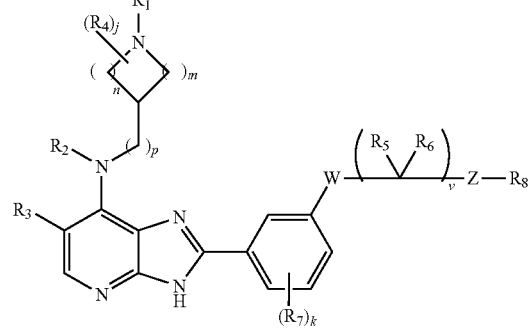

17 Claims, No Drawings

(56) References Cited

FOREIGN PATENT DOCUMENTS

WO  2011/079902 A2  7/2011
WO  2013/116291 A1  8/2013

OTHER PUBLICATIONS

Choudhury et al., "Silencing of ROR1 and FMOD with siRNA results in apoptosis of CLL cells", British Journal of Haematology, vol. 151, Aug. 31, 2010, pp. 327-335.
Christodoulides et al., Adipogenesis and WNT signalling, Trends Endocrinol Metab., vol. 2, No. 1, Jan. 23, 2009, pp. 1-18.
Damle et al., "Ig V Gene Mutation Status and CD38 Expression as Novel Prognostic Indicators in Chronic Lymphocytic Leukemia", Blood, vol. 94, No. 6, Sep. 15, 1999, pp. 1840-1847.
Daneshmanesh et al., "Ror1, a cell surface receptor tyrosine kinase is expressed in chronic lymphocytic leukemia and may serve as a putative target for therapy", International Union Against Cancer, 2008, vol. 123, 2008, pp. 1190-1195.
Glass et al., "Agrin Acts via a MuSK Receptor Complex", Cell, vol. 85, May 17, 1996, pp. 513-523.
Hamblin et al., Blood, vol. 94, No. 6, Sep. 15, 1999, pp. 1848-1854.
Hojjat-Farsangi et al, "Inhibition of the Receptor Tyrosine Kinase ROR1 by Anti-ROR1 Monoclonal Antibodies and siRNA Induced Apoptosis of Melanoma Cells", PLoS One, vol. 8, Issue 4, e61167, Apr. 2013, pp. 1-10.
Klein et al., "Gene Expression Profiling of B Cell Chronic Lymphocytic Leukemia Reveals a Homogeneous Phenotype Related to Memory B Cells", The Journal of Experimental Medicine, vol. 194, No. 11, Dec. 3, 2001, pp. 1625-1638.
Masiakowski et al., "A Novel Family of Cell Surface Receptors with Tyrosine Kinase-like Domain", The Journal of Biological Chemistry, vol. 67, No. 36, Dec. 25, 1992, pp. 6181-16190.
Reddy et al., "Human neural tissues express a truncated Ror1 receptor tyrosine kinase, lacking both extracellular and transmembrane domains", Oncogene, vol. 13, No. 7, Oct. 3, 1996, Abstract. 1 page.
Rosenwald et al., "Relation of Gene Expression Phenotype to Immunoglobulin Mutation Genotype in B Cell Chronic Lymphocytic Leukemia", The Journal of Experimental Medicine, vol. 194, No. 11, Dec. 3, 2001, pp. 1639-1647.
Sanchez-Solana et al., "Mouse Resistin Modulates Adipogenesis and Glucose Uptake in 3T3-L1 Preadipocytes Through the ROR1 Receptor", Molecular Endocrinology, vol. 26, No. 1, Jan. 2012, pp. 110-127.
Valenzuela et al., "Receptor Tyrosine Kinase Specific for the Skeletal Muscle Lineage: Expression in Embryonic Muscle, at the Neuromuscular Junction, and after Injury", Neuron, vol. 15, Sep. 1995, pp. 573-584.
Wang et al., "Discovery of azabenzimidazole derivatives as potent, selectrive inhibitors of TBK1/IKK kinases". Bioorganic & Medicinal Chemistry Letters, vol. 22, No. 5, 2012, pp. 2063-2069.
Xiangming et al., "p-TsOH Catalyzed synthesis of 2-arylsubstituted benzimidazoles", ARKIVOC, vol. xiii, 2007, pp. 150-154.
Yadagiri et al., "Convenient Routes to Substituted Benzimidazoles and Imadazolo[4,5-b]Pyridines Using Nitrobenzene as Oxidant", Synthetic Communications, vol. 20, No. 7, 1990, pp. 955-963.
Yamaguchi et al., "NKX2-1/TITF1/TTF-1-Induced ROR1 s Required to Sustain EGFR Survival Signaling in Lung Adenocarcinoma", Cancer Cell, vol. 21, Mar. 20, 2012, pp. 348-361.
Yang et al., "A Versatile Method for the Synthesis of Benzimidazoles from o-Nitroanilines and Aldehydes in One Step via a Reductive Cyclization", Synthesis, No. 1, 2005, pp. 47-56.
Yoda et al., "Expression and Function of the Ror-Family Receptor Tyrosine Kinases During Development: Lessons from Genetic Analyses of Nematodes, Mice, and Humans", Journal of Receptors and Signal Transduction, vol. 23, No. 1, 2003, pp. 1-15.
Zhang et al., "ROR1 is Expressed in Human Breast Cancer and Associated with Enhanced Tumor-Cell Growth", PLoS ONE, vol. 7, Issue 3, e33127, Mar. 2012, pp. 1-12.
Zhang et al., "The Onco-Embryonic Antigen ROR1 s Expressed by a Variety of Human Cancers", The American Journal of Pathology, vol. 181, No. 6, Dec. 2012, pp. 1903-1910.
International Search Report for corresponding International Application No. PCT/EP2016/052091 dated Apr. 1, 2016.
Written Opinion of the International Searching Authority for corresponding International Application No. PCT/EP2016/052091 dated Apr. 1, 2016.
International Preliminary on Patentability for corresponding International Application No. PCT/EP2016/052091 dated Oct. 26, 2016.
Wang et al., "Discovery of azabenzimidazole derivatives as potent, selective inhibitors of TBK1/IKK kinases", Bioorganic & Medicinal Chemistry Letters, vol. 22, No. 5, Jan. 9, 2012, pp. 2063-2069.

* cited by examiner

2-PHENYL-3H-IMIDAZO[4,5-B]PYRIDINE DERIVATES USEFUL AS INHIBITORS OF MAMMALIAN TYROSINE KINASE ROR1 ACTIVITY

This application is a national phase of International Application No. PCT/EP2016/052091 filed Feb. 1, 2016 and published in the English language, which claims priority to EP Application No. 15153394.0 filed Feb. 2, 2015.

FIELD OF THE INVENTION

The present invention relates to certain 2-phenyl-3h-imidazo[4,5-b]pyridine derivates that are useful as inhibitors of mammalian kinase enzyme activity, including ROR1 tyrosine kinase activity. The invention further relates to certain 2-phenyl-3h-imidazo[4,5-b]pyridine derivates for use in therapy, e.g. for the treatment of medical conditions in which the modulation of human kinase enzyme activity is beneficial. Examples of such a condition include various hyperproliferative diseases, e.g. hematological tumors such as chronic lymphocytic leukemia (CLL), acute myeloid leukemia (AML), acute lymphoblastic leukemia (ALL) or mantle cell lymphoma, and also solid tumors such as lung, ovarian, breast or pancreatic tumors. Other examples of such a condition include obesity-associated metabolic complications, autoimmune diseases and inflammatory conditions.

BACKGROUND OF THE INVENTION

Chronic lymphocytic leukemia (CLL) originates from B lymphocytes which differ in activation and maturation stage and are derived from antigen experienced B cells with different immunoglobulin heavy chain variable (IgVH) gene mutations (Chiorazzi N et al., *N. Engl. J. Med.*, 2005, 352, 804-15). Patients with mutated IgVH genes have a better prognosis compared to patients with unmutated genes (Damle R N et al., *Blood* 1999, 94, 1840-7; Hamblin T J et al., *Blood*, 1999, 94, 1848-54). Global gene expression profiling studies have revealed partly distinguishing but in general overlapping expression profiles in mutated and unmutated leukemic B cells, suggesting a common phenotype (Klein U et al., *J. Exp. Med.*, 2001, 194, 1625-38; Rosenwald A et al., *J. Exp. Med.*, 2001, 194, 1639-47).

Gene expression profiling studies showed a 43.8 fold increase of the orphan receptor tyrosine kinase (RTK) ROR1 in CLL cells (Klein U et al., *J. Exp. Med.*, 2001, 194, 1625-38). ROR1 is a member of the RTK family of orphan receptors related to muscle specific kinase (MUSK) and Trk neurotrophin receptors (Glass D J, et al., *Cell*, 1996, 85, 513-23; Masiakowski P et al., *J. Biol. Chem.*, 1992, 267, 26181-90; Valenzuela D M et al., *Neuron*, 1995, 15, 573-84). ROR receptors are cell surface receptors participating in signal transduction, cell-cell interaction, regulation of cell proliferation, differentiation, cell metabolism and survival (Masiakowski P et al., *Biol. Chem.*, 1992, 267, 26181-90; Yoda A et al., *J. Recept. Signal Transduct. Res.*, 2003, 23, 1-15). They are evolutionarily highly conserved between different species e. g. human, mouse, *Drosophila*, and *C. elegans*, suggesting important biological functions.

The human ROR1 gene has a coding region of 2814 bp with a predicted 937 amino acids sequence and 105 kDa protein size including an Ig-like domain, cysteine-rich domain, kringle domain, tyrosine kinase domain, and proline-rich domain (Yoda A et al., *J. Recept. Signal Transduct. Res.*, 2003, 23, 1-15). ROR1 is located on chromosomal region 1p31.3 (http://www.ensembl.org), a region where chromosomal aberrations are not frequently seen in hematological malignancies. The human ROR1 is expressed at the gene level in heart, lung, and kidney but less in placenta, pancreas and skeletal muscles (Reddy U R et al., *Oncogene*, 1996, 13, 1555-9). Importantly, there is an almost complete absence of ROR1 protein expression in normal human adult tissues and organs. ROR1 was originally cloned from a neuroblastoma cell line (Masiakowski P et al., *J. Biol. Chem.*, 1992, 267, 26181-90) and subsequently a shorter form lacking the entire extracellular domain but containing the transmembrane domain was isolated from a fetal brain library. Truncated ROR1 (t-Ror1) gene has been reported in fetal and adult human central nervous system, in human leukemias, lymphoma cell lines, and in a variety of human cancers derived from neuroectoderm (Reddy U R et al., *Oncogene*, 1996, 13, 1555-9). A shorter transcript from exons 1-7 including a short part of intron 7 has also been described with a predicted length of 393 amino acids and a molecular weight of 44 kDa (Ensembl ID; ENSG00000185483).

Gene profiling and protein expression studies of patients with chronic lymphocytic leukemia (CLL) has revealed increased expression of ROR1, while mature leucocytes from healthy donors do not express this protein (Danesh-Manesh, A H et al., *Int. J. Cancer*, 2008, 123, 1190-5). Silencing of ROR1 with siRNA in CLL cells resulted in apoptosis, while siRNA treatment of B cells from normal donors did not (Choudhury, A et al., *Brit. J. Haematol.*, 2010, 151, 327-35).

Acute myeloid leukemic (AML) stem cells (CD34$^+$) may potentially account for the resistance for many cytotoxic drugs. In an in vitro assay, a chimeric antibody against ROR1 (UC99961) inhibited in a dose-dependent manner colony formation of ROR1$^+$ AML stem cells but not ROR$^-$ AML cells and not normal CD34$^+$ stem cells. The results suggest that targeting ROR may represent an important component to eradicate malignant stem cells in AML and potentially also other refractory cancer-stem-cell-driven malignancies (Balaian L et al, *Blood*, ASH Annual Meeting) 2012, Abstract 2560). In acute lymphoblastic leukemia (ALL) ROR1 is up-regulated modulating in a counterbalancing manner with pre-BCR signaling pathways leading to activation of AKT, ERK and MEK. siRNA transfection induced impaired growth of ALL cells and apoptosis (Bicocca V et al, *Cancer Cell*, 22, 656-667, 2012).

Human breast cancer cells, but not normal breast epithelia cells also express ROR1. The intensity of ROR1 expression was higher in patients with hormone receptor negative tumors as well as in those with a low degree of cell differentiation, i.e. in patients with a poor prognosis. Silencing of ROR1 impaired the growth in vitro of human breast cancer cells and in immune-deficient mice. The results support the notion that ROR1 is of biological and clinical significance in breast cancer and may be a potential target for therapy (Zang S et al, *PLoS One*, 7(3): e31127, 2012).

In human lung adenocarcinoma cells ROR1 was overexpressed. The ROR1 kinase activity sustained a favorable prosurvival balance between the proliferative PI3K/AKT and apoptotic p38 signaling, partly through ROR1 kinase-dependent src activation as well as kinase-independent sustainment of EGFR/ERBB3 phosphorylation and PI3K activation. ROR1 knock-down effectively inhibited the growth of lung cancer cells in vitro and in vivo irrespective of EGFR status including those cells resistant to the EGFR tyrosine kinase inhibitor gefitinib. These data also indicate an important biological role of ROR1 in lung cancer and a structure for targeted therapy (Yamaguchi et al, *Cancer Cell*, 21, 348-361, 2012). Unexpectedly CLL cells showed an overexpression of ERBB2 and phosphorylation of src/PI3K, AKT/mTOR/CREB. The ROR1 tyrosine kinase inhibitors described in this work (see below) dephosphorylated ROR1/src/PI3K/AKT/mTOR/CREB which preceded apoptosis of CLL cells (own unpublished observations).

In another study, a number of solid tumor tissues (lung, ovarian, pancreatic) expressed ROR1 but not the normal cell counterpart. ROR1 expression was associated with high-grade histology and activation of AKT and CREB. Silencing of ROR1 using shRNA induced apoptosis of pancreatic and ovarian cancer cell lines and down regulation of the ROR1 protein as well as of activated AKT and CREB (Zhan S et al, *American Journal of Pathology*, 181:1903-1910, 2012).

Melanoma cells have been shown to express ROR1. ROR1 siRNA induced down regulation of ROR1 both at the mRNA and protein level, which preceded apoptosis. Targeting ROR1 of the melanoma cells by ROR1 directed monoclonal antibodies induced a significant apoptosis not requiring immune cells or complement. The degree of apoptosis induced by the antibodies varied between the cell lines (Hodjat-Farsangi M et al, *PLoS One*, 8, e61167, 2013).

Furthermore, it has recently been shown that ROR1 plays an important role in adipogenesis and glucose homeostasis in 3T3-L1 cells (Sanchez-Solana, B, Laborda, J and Baladron, V, *Molecular Endocrinology* 26: 110-127, 2012). Hence, manipulating the WNT pathway, e.g. by modulation of ROR1, to alter adipose cellular makeup may constitute an attractive drug-development target to combat obesity-associated metabolic complications (Christodoulides, C, Lagathu, C, Sethi, J K and Vidal-Puig, A, *Trends Endocrinol. Metab.*, 2009 January; 20(1):16-24).

The above described data serve to illustrate the validity of modulating ROR1 activity for treatment of disorders and diseases that include not only chronic lymphocytic leukemia (CLL) but also other hematological malignancies as well as solid tumors and obesity-associated metabolic complications.

Antibody inhibitors of ROR1 have been described in the literature; see e.g. PCT Int. Appl. WO2011079902. There are, however, no small molecule inhibitors of ROR1 known in the art.

Substituted imidazo[4,5-b]pyridine compounds are well known in the art, see e.g. PCT Int. Appl. WO2003045929, WO2004016270, WO2004016611, WO2006066913, WO2006066914, WO2006080821, WO2006125958, WO2007028135, WO2007072017, WO2007083978, WO2008121063, WO2008121064, WO2009001021, WO2009111277, WO2011066211, WO2013116291, and Wang, T. et al. *Bioorg. Med. Chem. Lett.*, 22(5), 2063-2069, 2012. However, it has not previously been shown that such compounds are capable of modulating ROR1 activity.

SUMMARY OF THE INVENTION

A first aspect is a compound of formula (I') or (I")

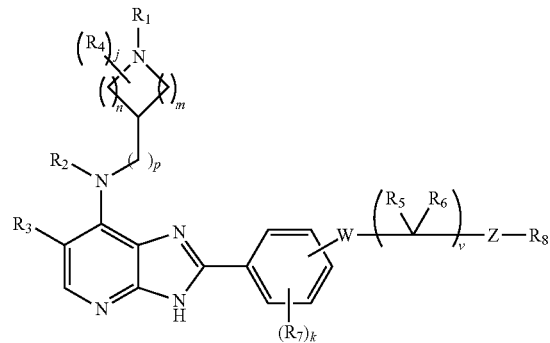

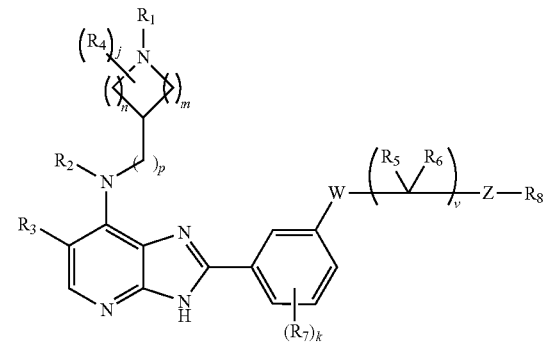

or a pharmaceutically acceptable salt thereof, wherein
m is 1 or 2;
n is 2 or 3;
p is 0 or 1;
$R_1$ is H, C1-C6 alkyl, C1-C6 alkyl-Q-$(CH_2)_x$, or $R_{1a}$—X—;
Q is O or S;
x is an integer of from 1 to 3;
X is a direct bond or $(CH_2)_s$—Y—$(CH_2)_t$;
Y is a direct bond, O or S;
s is 1 or 2;
t is 0 or 1;
$R_{1a}$ is a cyclic moiety selected from 3- to 6-membered carbocyclyl and 5- to 6-membered heterocyclyl, said cyclic moiety optionally being substituted by one or more $R_{1b}$;
each $R_{1b}$ is independently selected from halogen, C1-C6 alkyl, $R_{1c}$O—, $R_{1d}$C(O)N($R_{1e}$)—, cyano, $R_{1f}R_{1g}$N—, $R_{1h}$S$(O)_2$—, $R_{1i}$S—, C3-C6 carbocyclyl, and 5- to 6-membered heterocyclyl; and two $R_{1b}$ attached to adjacent atoms of the cyclic moiety may form, together with the atoms to which they are attached, a 5- or 6-membered ring;
each $R_{1c}$, $R_{1d}$, $R_{1e}$, $R_{1f}$, $R_{1g}$, $R_{1h}$ and $R_{1i}$ is independently selected from H and C1-C6 alkyl;
$R_2$ is H or C1-C6 alkyl;
$R_3$ is halogen;
j is an integer of from 0 to 4;
$R_4$ is C1-C3 alkyl;
W is a direct bond, O, S, $CR_{w1}R_{w2}$, or $NR_{w3}$;
$R_{w1}$ and $R_{w2}$ are independently selected from H and C1-C3 alkyl;
$R_{w3}$ is H or C1-C3 alkyl;
v is 1 or 2;

each $R_5$ and $R_6$ is independently selected from H and C1-C3 alkyl;

k is an integer of from 0 to 2;

each $R_7$ is independently selected from halogen, C1-C3 alkyl, and $R_{7a}O$;

each $R_{7a}$ is independently from C1-C3 alkyl;

Z—$R_8$ is $C(O)NR_8R_9$ or $NR_{10}C(O)R_8$;

$R_8$ is selected from $R_{8a}(CR_{8b}R_{8c})_q$—, $R_{8d}O$—, and C1-C6 alkyl, said alkyl optionally being substituted by a moiety selected from $R_{8e}R_{8f}N$— and $R_{8g}O$—;

q is an integer of from 0 to 2;

$R_{8a}$ is a cyclic moiety selected from C3-C7 carbocyclyl and 5- to 7-membered heterocyclyl, said cyclic moiety optionally being substituted by one or more moieties selected from halogen, C1-C6 alkyl, C3-C5 cycloalkyl, and $R_{8h}O$;

$R_{8b}$ and $R_{8c}$ are independently selected from H and C1-C3 alkyl; or $R_{8d}$ is H, C1-C6 alkyl, or C3-C6 cycloalkyl;

$R_{8e}$ and $R_{8f}$ are independently selected from H and C1-C6 alkyl; or $R_{8e}$ and $R_{8f}$, together with the nitrogen atom to which they are both attached, form a 5- or 6 membered heterocyclyl optionally containing a further heteroatom in the ring;

$R_{8g}$ is H or C1-C6 alkyl;

$R_{8h}$ is H or C1-C6 alkyl;

$R_9$ is H or C1-C6 alkyl; or $R_8$ and $R_9$, together with the nitrogen atom to which they are both attached, form a 5- or 6 membered heterocyclyl optionally containing a further heteroatom in the ring;

$R_{10}$ is H or C1-C3 alkyl;

and any alkyl is saturated or unsaturated and is optionally substituted by one or more F.

A further aspect is a compound of formula (I') or (I") for use in therapy.

A still further aspect is a compound of formula (I') or (I"), or a pharmaceutically acceptable salt thereof, for use as an inhibitor of tyrosine kinase ROR1 activity in a mammal; preferably a human.

A still further aspect is a pharmaceutical composition comprising a compound of formula ((I') or (I"), or a pharmaceutically acceptable salt thereof, and optionally a pharmaceutically acceptable excipient.

A still further aspect is a compound of formula (I') or (I"), or a pharmaceutically acceptable salt thereof, for use in the treatment of a condition or disorder in which the modulation of the activity of mammalian, e.g. human, tyrosine kinase ROR1 is beneficial, e.g. a malignant hyperproliferative disorder, an obesity-associated metabolic complication, an autoimmune disease or an inflammatory condition.

One aspect is a compound of formula (I') or (I"), or a pharmaceutically acceptable salt thereof, for use in the treatment of a malignant hyperproliferative disorder, an obesity-associated metabolic complication, an autoimmune disease or an inflammatory condition.

A further aspect is the use of a compound of formula (I') or (I") in the manufacturing of a medicament for use in the treatment of a condition or disorder in which the modulation of the activity of mammalian, e.g. human, tyrosine kinase ROR1 is beneficial, e.g. a malignant hyperproliferative disorder, an obesity-associated metabolic complication, an autoimmune disease or an inflammatory condition.

Examples of malignant hyperproliferative disorders include, but are not limited to, hematological tumors such as chronic lymphocytic leukemia (CLL), acute myeloid leukemia (AML), acute lymphoblastic leukemia (ALL) or mantle cell lymphoma, and also solid tumors such as lung, ovarian, breast or pancreatic tumors.

A further aspect is a method of treatment of a condition or disorder in which the modulation of the activity of mammalian, e.g. human, tyrosine kinase ROR1 is beneficial, e.g. a malignant hyperproliferative disorder, an obesity-associated metabolic complication, an autoimmune disease or an inflammatory condition, by administering a therapeutically effective amount of a compound of formula (I') or (I") to a mammal, preferably a human, in need of such treatment.

DETAILED DESCRIPTION OF THE INVENTION

Unless otherwise specified, any term used herein is to be given its conventional meaning. For example, the term alkyl either alone or as part of a radical, includes straight or branched chain alkyl of the general formula $C_nH_{2n+1}$.

The term "C1-C6 alkyl" refers to an alkyl moiety having 1, 2, 3, 4, 5 or 6 carbon atoms.

Said alkyl may be saturated or, when having at least two carbon atoms, unsaturated (i.e. alkenyl or alkynyl).

The term "carbocyclyl" refers to a cyclic moiety containing only carbon atoms in the ring.

The carbocyclcyl may be saturated, such as cyclohexyl, unsaturated and non-aromatic, such as cyclohexenyl, or aromatic, such as phenyl.

The term "C3-C6 cycloalkyl" refers to a cycloalkyl moiety having 3, 4, 5 or 6 carbon atoms in the ring, i.e. cyclopropyl, cyclobutyl, cyclopentyl or cyclohexyl.

The term "heterocyclyl" refers to a cyclic moiety containing carbon atoms and at least one heteroatom in the ring. The heterocyclyl may be saturated, or unsaturated and non-aromatic or aromatic. When aromatic, the heterocyclyl is referred as a "heteroaryl".

The term "heteroatom" preferably refers to N, O or S.

The term "5- or 6-membered heteroaryl" refers to a heteroaryl containing either 5 or 6 atoms in the ring.

The term "phenyl" refers to a moiety of formula

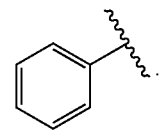 [SMILES: *c1ccccc1]

The term "benzyl" refers to a moiety of formula

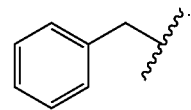 [SMILES: *Cc1ccccc1]

The term "halogen" refers to F, Cl, Br or I, in particular to F, Cl or Br.

The term "hydroxy" refers to a radical of the formula —OH.

The term "cyano" refers to a radical of the formula —C≡N, i.e. CN.

A moiety of the type RO is a moiety of formula

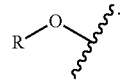

A moiety of the type RS is a moiety of formula

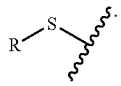

A moiety of the type C(O)NRR' is a moiety of formula

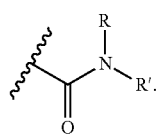

A moiety of the type NRC(O)R' is a moiety of formula

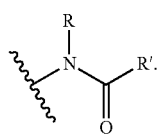

A moiety of the type RS(O)$_2$ is a moiety of formula

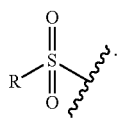

A moiety of the type N(R)(R') (which also may be written RR'N or NRR') is a moiety of formula

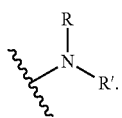

"Optional" or "optionally" means that the subsequently described event or circumstance may but need not occur, and that the description includes instances where the event or circumstance occurs and instances in which it does not.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "excipient" refers to pharmaceutically acceptable chemicals, such as known to those of ordinary skill in the art of pharmacy to aid the administration of the medicinal agent. It is a compound that is useful in preparing a pharmaceutical composition, generally safe, non-toxic and neither biologically nor otherwise undesirable, and includes excipients that are acceptable for veterinary use as well as human pharmaceutical use. Exemplary excipients include binders, surfactants, diluents, disintegrants, antiadherents, and lubricants.

"Therapeutically effective amount" means an amount of a compound that, when administered to a subject for treating a disease state, is sufficient to effect such treatment for the disease state. The "therapeutically effective amount" will vary depending on the compound, the disease state being treated, the severity of the disease treated, the age and relative health of the subject, the route and form of administration, the judgment of the attending medical or veterinary practitioner, etc.

As used herein the terms "treatment" or "treating" is an approach for obtaining beneficial or desired results including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total) whether detectable or undetectable. The term can also mean prolonging survival as compared to expected survival without the treatment.

The term mammal refers to a human or any mammalian animal, e.g. a primate, a farm animal, a pet animal, or a laboratory animal. Examples of such animals are monkeys, cows, sheep, horses, pigs, dogs, cats, rabbits, mice, rats etc. Preferably, the mammal is a human.

The term "malignant hyperproliferative disorder" refers to any malignant growth or tumor caused by abnormal and uncontrolled cell division; it may spread to other parts of the body through the lymphatic system or the blood stream and includes both solid tumors and blood-borne tumors. Exemplary cancers include adrenocortical carcinoma, AIDS-related cancers, AIDS-related lymphoma, anal cancer, anorectal cancer, appendix cancer, childhood cerebellar astrocytoma, childhood cerebral astrocytoma, basal cell carcinoma, biliary cancer, extrahepatic bile duct cancer, intrahepatic bile duct cancer, urinary bladder cancer, bone and joint cancer, osteosarcoma and malignant fibrous histiocytoma, brain tumor, brain stem glioma, cerebellar astrocytoma, cerebral astrocytoma/malignant glioma, ependymoma, medulloblastoma, visual pathway and hypothalamic glioma, breast cancer, bronchial adenomas/carcinoids, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary syndrome, endometrial cancer, esophageal cancer, extracranial germ cell tumor, extragonadal germ cell tumor, eye cancer, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin's lymphoma, hypo pharyngeal cancer, ocular cancer, Kaposi's sarcoma, renal cancer, laryngeal cancer, acute lymphoblastic leukemia, acute myeloid leukemia, hairy cell leukemia, lip and oral cavity cancer, lung cancer, non-small cell lung cancer, small cell lung cancer, non-Hodgkin's lymphoma, primary central nervous system lymphoma, Waldenstrom's macroglobulinemia, intraocular (eye) melanoma, Merkel cell carcinoma, malignant mesothelioma, metastatic squamous neck cancer, cancer of the tongue, multiple endocrine neoplasia syndrome, myelodysplastic syndromes, myelodysplastic/myeloproliferative diseases, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, para-nasal sinus and nasal cavity cancer, parathyroid cancer, penile cancer, pheochromocytoma, pineoblastoma and supratentorial primitive neuroectodermal tumors, pituitary tumor, plasma cell neoplasm/multiple myeloma, pleuropulmonary blastoma, prostate cancer, rhabdomyosarcoma, salivary gland cancer, Ewing's sarcoma family of tumors, soft tissue sarcoma, uterine cancer, uterine sarcoma, skin cancer (non-melanoma), skin cancer (melanoma), small intestine cancer, squamous cell carcinoma, testicular cancer, throat cancer, thymoma, thymoma and thymic carcinoma, thyroid cancer, transitional cell cancer of the renal pelvis and ureter and other urinary organs, gestational trophoblastic tumor, urethral cancer, vaginal cancer, vulvar cancer, and Wilm's tumor.

The term "autoimmune disorder" refers to any disorder arising from an inappropriate immune response of the body against substances and tissues normally present in the body (autoimmunity). Such response may be restricted to certain organs or involve a particular tissue in different places. Exemplary autoimmune disorders are acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease (one of two types of idiopathic inflammatory bowel disease "IBD"), Cushing's Syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis (or Idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Hashimoto's thyroiditis, Henoch-Schonlein purpura, herpes gestationis (aka gestational pemphigoid), Hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, Majeed syndrome, Ménière's disease, microscopic polyangiitis, mixed connective tissue disease, morphea, Mucha-Habermann disease (aka pityriasis lichenoides et varioliformis acuta), multiple sclerosis, myasthenia gravis, myositis, narcolepsy, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with streptococcus), paraneoplastic cerebellar degeneration, paroxysmal nocturnal hemoglobinuria (PNH), Parry Romberg syndrome, Parsonage-Turner syndrome, pars planitis, pemphigus vulgaris, pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome another form of APS, Schnitzler syndrome, Scleritis, Scleroderma, Serum Sickness, Sjögren's syndrome, spondyloarthropathy, stiff person syndrome, subacute bacterial endocarditis (SBE), Susac's syndrome, Sweet's syndrome, sympathetic ophthalmia, systemic lupus erythematosis, Takayasu's arteritis, temporal arteritis (also known as "giant cell arteritis"), thrombocytopenia, Tolosa-Hunt syndrome, transverse myelitis, ulcerative colitis (one of two types of idiopathic inflammatory bowel disease "IBD"), undifferentiated connective tissue disease different from mixed connective tissue disease, undifferentiated spondyloarthropathy, urticarial vasculitis, vasculitis, vitiligo, and Wegener's granulomatosis.

The term "inflammatory disorder" refers to a pathological state associated with inflammation, typically caused by leukocyte infiltration. The inflammatory disorder may be acute or chronic. Exemplary inflammatory disorders include inflammatory skin diseases, including, without limitation, psoriasis and atopic dermatitis, systemic scleroderma and sclerosis, responses associated with inflammatory bowel disease (IBD) (such as Crohn's disease and ulcerative colitis), ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms, cerebral edema secondary to stroke, cranial trauma, hypovolemic shock, asphyxia, adult respiratory distress syndrome, acute-lung injury, Behcet's Disease, dermatomyositis, polymyositis, multiple sclerosis (MS), dermatitis, meningitis, encephalitis, uveitis, osteoarthritis, lupus nephritis, autoimmune diseases such as rheumatoid arthritis (RA), Sjögren's syndrome, vasculitis, diseases involving leukocyte diapedesis, central nervous system (CNS) inflammatory disorder, multiple organ injury syndrome secondary to septicemia or trauma, alcoholic hepatitis, bacterial pneumonia, antigen-antibody complex mediated diseases including glomerulonephritis, sepsis, sarcoidosis, immunopathologic responses to tissue or organ transplantation, inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis, etc.

The term "obesity-associated metabolic complication" refers generally to the metabolic complications due to obesity, often referred to as the metabolic syndrome, which syndrome is characterized by plasma lipid disorders (atherogenic dyslipidemia), raised blood pressure, elevated plasma glucose, and a prothrombotic state. Clinical consequences of the metabolic syndrome are e.g. coronary heart disease and stroke, type 2 diabetes and its complications, fatty liver, and cholesterol gallstones.

The compounds of formula (I') and (I'') are positional isomers (regioisomers), which herein below will be represented by a common formula (I)

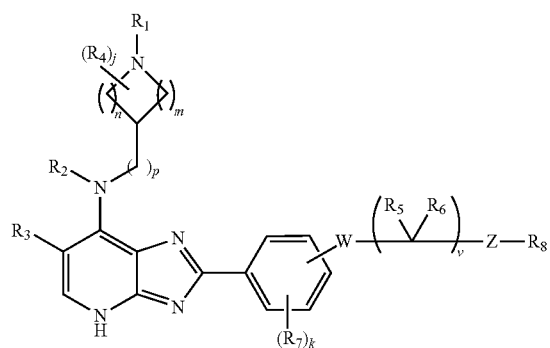

(I)

wherein the moiety —W—(CR$_5$R$_6$)$_v$—Z—R$_8$ is in either para position (formula (I')), or in meta position (formula (I'')). Consequently, unless otherwise specified or apparent from the context, any reference to a compound of formula (I) is to be construed as referring equally to both regioisomers (I') and (I''). In some embodiments, however, the compound is as represented by formula (I'). In some other embodiments, the compound is as represented by formula (I'').

It should be realized that three tautomers exist of the compound of formula (I). The compound of formula (I) should be construed as encompassing not only the 3H-imidazo[4,5-b]pyridine form, but also the tautomeric 1H-imidazo[4,5-b]pyridine form

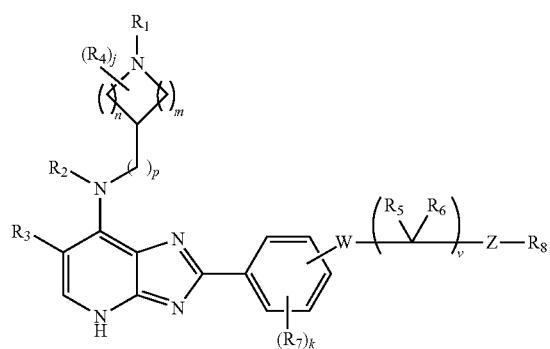

(I)

and the tautomeric 4H-imidazo[4,5-b]pyridine form

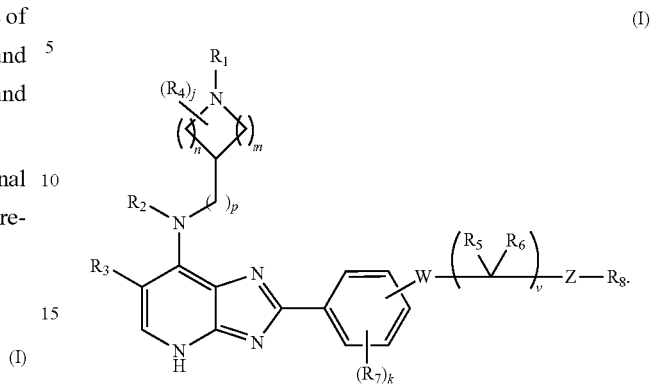

(I)

Therefore, any explicit reference to a 3H-imidazo[4,5-b]pyridine also encompasses the corresponding 1H-imidazo[4,5-b]pyridine and 4H-imidazo[4,5-b]pyridine tautomers.

Furthermore, any reference to a compound of formula (I) is to be construed as referring equally to any of the below described embodiments thereof, unless otherwise specified or apparent from the context.

In a compound of formula (I) as defined herein, m is an integer selected from 1 and 2, and n is an integer selected from 2 and 3. In some embodiments, m is 1 and n is 2 or 3, or m is 2 and n is 2. In some embodiments, m is 2 and n is 2, or m is 1 and n is 3. In some embodiments, m is 1. In some embodiments, m is 1 and n is 2. In some other embodiments, m is 1 and n is 3. In some embodiments, m is 2. In some embodiments, m is 2 and n is 2. In some other embodiments, m is 2 and n is 3. In some embodiments, n is 3. In some other embodiments, n is 2. In those embodiments where n is 2, the compound may be represented by formula (Ia)

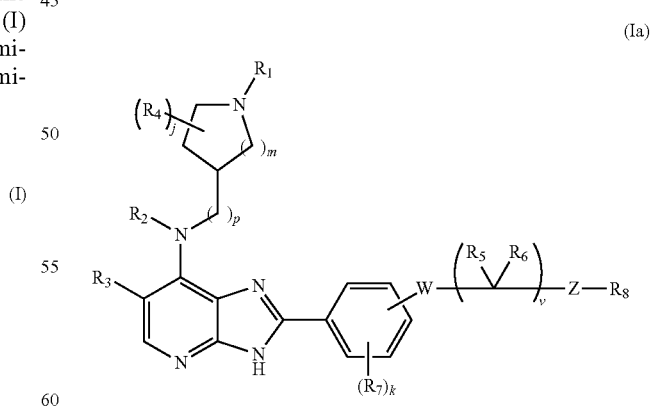

(Ia)

wherein R$_1$, R$_2$, R$_3$, R$_4$, R$_5$, R$_6$, R$_7$, R$_8$, W, Z, j, k, m, p and v are as defined herein.

In a compound of formula (I), e.g. of formula (Ia), m is 1 or 2. In some particular embodiments of a compound of formula (Ia), m is 2. In such embodiments, the compound may be represented by formula (Ia1)

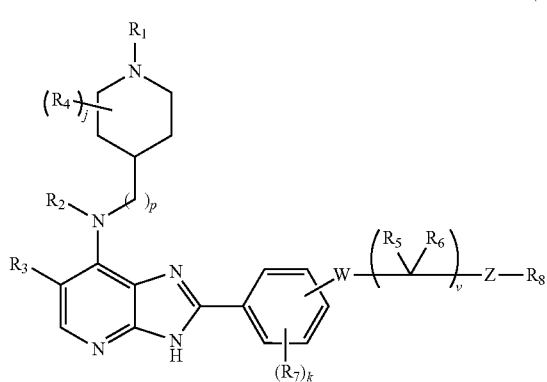

(Ia1)

wherein $R_1$, $R_2$, $R_3$, $R_4$, $R_5$, $R_6$, $R_7$, $R_8$, W, Z, j, k, p and v are as defined herein.

In some other particular embodiments of a compound of formula (Ia), m is 1. In such embodiments, the compound may be represented by formula (Ia2)

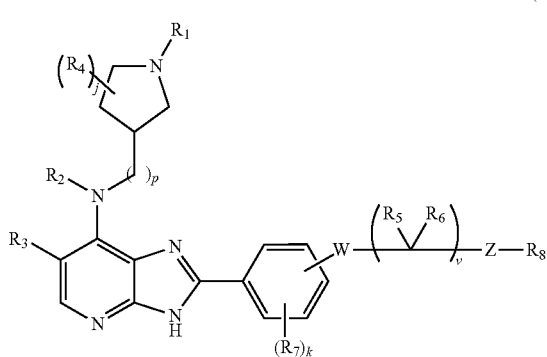

(Ia2)

wherein $R_1$, $R_2$, $R_3$, $R_4$, $R_5$, $R_6$, $R_7$, $R_8$, W, Z, j, k, p and v are as defined herein.

In a compound of formula (I), p is 0 or 1. In some embodiments, p is 1. In some other embodiments, p is 0. When p is 0, the compound may be represented by formula (Ib1)

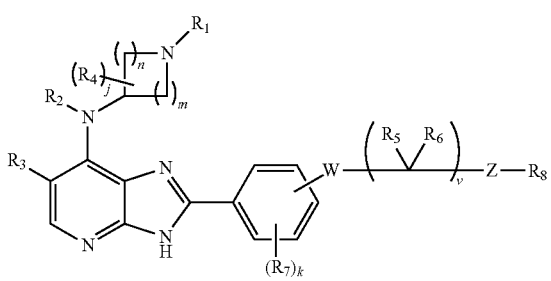

(Ib1)

wherein $R_1$, $R_2$, $R_3$, $R_4$, $R_5$, $R_6$, $R_7$, $R_8$, W, Z, j, k, m, n and v are as defined herein.

When p is 1, the compound may be represented by formula (Ib2)

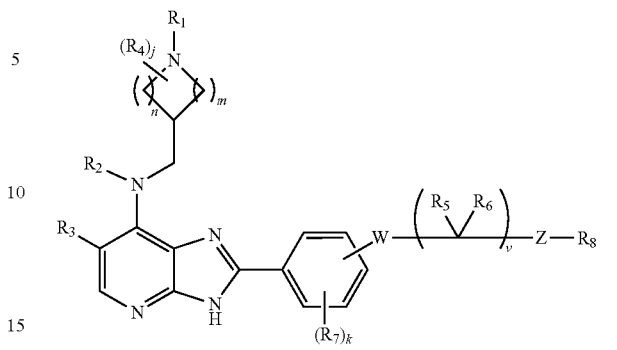

(Ib2)

wherein $R_1$, $R_2$, $R_3$, $R_4$, $R_5$, $R_6$, $R_7$, $R_8$, W, Z, j, k, m, n and v are as defined herein.

In a compound of formula (I), $R_1$ is H, C1-C6 alkyl, C1-C6 alkyl-Q-$(CH_2)_x$, or $R_{1a}$—X—. In some embodiments, $R_1$ is H, C1-C6 alkyl or $R_{1a}$—X—. In some embodiments, $R_1$ is H or C1-C6 alkyl. In some embodiments, $R_1$ is C1-C6 alkyl. In some embodiments, $R_1$ is C1-C6 alkyl, C1-C6 alkyl-Q-$(CH_2)_x$, or $R_{1a}$—X—. In some embodiments, $R_1$ is C1-C6 alkyl or $R_{1a}$—X—. In some embodiments, $R_1$ is $R_{1a}$—X—. In some other embodiments, $R_1$ is C1-C6 alkyl or C1-C6 alkyl-Q-$(CH_2)_x$. In some embodiments, $R_1$ is C1-C6 alkyl-Q-$(CH_2)_x$.

When $R_1$ is C1-C6 alkyl, it e.g. may be C1-C5 alkyl, C1-C4 alkyl, or C1-C3 alkyl, such as methyl or ethyl, in particular methyl. In some embodiments, when $R_1$ is C1-C6 alkyl, said alkyl is selected from methyl, ethyl, n-propyl, isopropyl, tert-butyl, neopentyl and n-hexyl; e.g. from methyl, ethyl, isopropyl and tert-butyl.

In the moiety C1-C6 alkyl-Q-$(CH_2)_x$, x is an integer of from 1 to 3, and Q is O or S. In some embodiments, x is 1 or 2. In some other embodiments, x is 2 or 3. In some embodiments x is 2. In some embodiments, Q is O. In some embodiments, the moiety C1-C6 alkyl-Q-$(CH_2)_x$ more particularly is C1-C3 alkyl-Q-$(CH_2)_x$, or C1-C2 alkyl-Q-$(CH_2)_x$, e.g. $CH_3$-Q-$(CH_2)_x$. In some particular embodiments, the moiety C1-C6 alkyl-Q-$(CH_2)_x$ is C1-C3 alkyl-O—$(CH_2)_x$, e.g. C1-C3 alkyl-O—$(CH_2)_2$, or $CH_3O(CH_2)_x$, such as $CH_3O(CH_2)_2$.

In the moiety $R_{1a}$—X—, X is a direct bond or $(CH_2)_s$—Y—$(CH_2)_t$. In some embodiments, X is a direct bond. In some other embodiments, X is $(CH_2)_s$—Y—$(CH_2)_t$.

In some embodiments, X is a direct bond only when $R_{1a}$ is an optionally substituted cyclic moiety selected from 3- to 6-membered carbocyclyl, e.g. X is a direct bond only when $R_{1a}$ is an optionally substituted cyclic moiety selected from saturated or unsaturated non-aromatic 3- to 6-membered carbocyclyl. In some particular embodiments, X is a direct bond only when $R_{1a}$ is optionally substituted C3-C6 cycloalkyl.

In the moiety $(CH_2)_s$—Y—$(CH_2)_t$, s is 1 or 2; t is 0 or 1; and Y is a direct bond, O or S. In some embodiments, s is 1 and t is 0 or 1. In some embodiments, s is 2 and t is 0 or 1. In some embodiments, s is 1 or 2 and t is 0. In some embodiments, s is 1 or 2 and t is 1. In some embodiments, s is 1 and t is 1, or s is 2 and t is 0. In some embodiments, s is 1 and t is 1. In some embodiments, s is 2 and t is 0.

The moiety Y is O, S or a direct bond. In some embodiments, Y is O or S, e.g. Y is O. In some embodiments, when Y is O or S, e.g. Y is O, s is 2. In some embodiments, when Y is O or S, e.g. Y is O, s is 2 and t is 0. In some embodiments, Y is a direct bond, i.e. the moiety X is $(CH_2)_s$—$(CH_2)_t$, or X is $(CH_2)_u$, where u is the sum of s and t, i.e. u is 1, 2 or 3. In some embodiments, when Y is a direct bond, u is 1 or 2. In some embodiments, when Y is a direct bond, u is 1. In some embodiments, when Y is a direct bond, u is 2.

In some embodiments, where $R_1$ is $R_{1a}$—X—, the compound of formula (I) may be represented by formula (Ic)

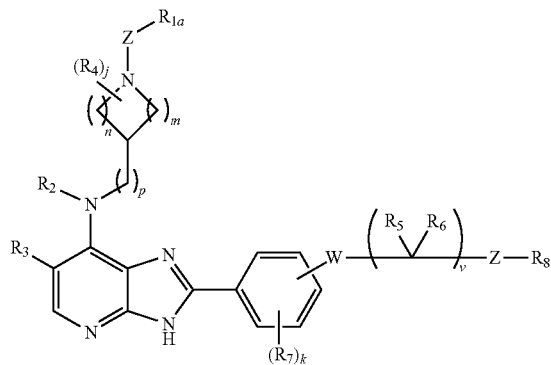
(Ic)

wherein $R_{1a}$, $R_2$, $R_3$, $R_4$, $R_5$, $R_6$, $R_7$, $R_8$, W, X, Z, j, k, m, n, p and v are as defined herein.

In some embodiments, when X is $(CH_2)_s$—Y—$(CH_2)_t$, a compound of formula (Ic) may be represented by formula (Id)

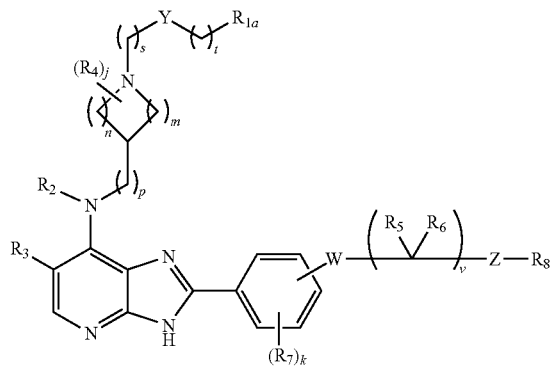
(Id)

wherein $R_{1a}$, $R_2$, $R_3$, $R_4$, $R_5$, $R_6$, $R_7$, $R_8$, W, Y, Z, j, k, m, n, p, s, t and v are as defined herein.

In some embodiments of a compound of formula (Id), t is 0, and the compound may then be represented by formula (Id1)

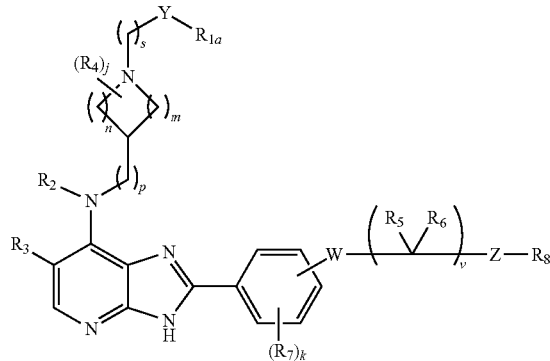
(Id1)

wherein $R_{1a}$, $R_2$, $R_3$, $R_4$, $R_5$, $R_6$, $R_7$, $R_8$, W, Y, Z, j, k, m, n, p, s, and v are as defined herein.

In some embodiments of a compound of formula (Id), Y is a direct bond, and the compound may then be represented by formula (Id2)

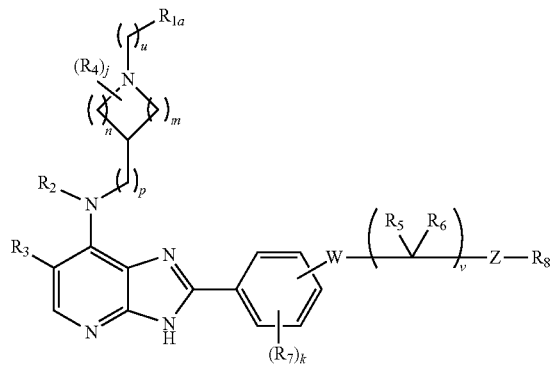
(Id2)

wherein $R_{1a}$, $R_2$, $R_3$, $R_4$, $R_5$, $R_6$, $R_7$, $R_8$, W, Z, j, k, m, n, p, and v are as defined herein, and u=s+t, i.e. u is 1, 2 or 3.

In those embodiments of a compound of formula (Id2) where u is 1, the compound may be represented by formula (Id3)

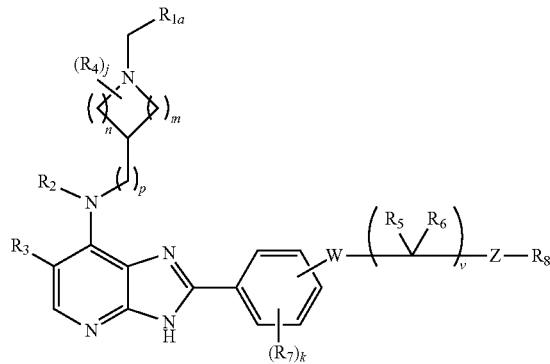
(Id3)

wherein $R_{1a}$, $R_2$, $R_3$, $R_4$, $R_5$, $R_6$, $R_7$, $R_8$, W, Z, j, k, m, n, p, and v are as defined herein.

In some other particular embodiments of a compound of formula (Id2), u is 2 and the compound may then be represented by formula (Id4)

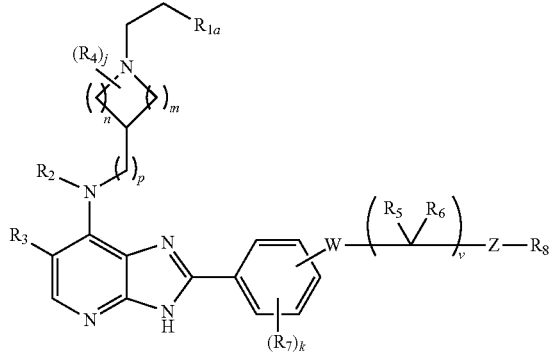

(Id4)

wherein $R_{1a}$, $R_2$, $R_3$, $R_4$, $R_5$, $R_6$, $R_7$, $R_8$, W, Z, j, k, m, n, p, and v are as defined herein.

In a compound of any one of the formulas (Ic), (Id), (Id1), (Id2), (Id3) and (Id4), $R_{1a}$ is a cyclic moiety selected from 3- to 6-membered carbocyclyl and 5- or 6-membered heterocyclyl, said cyclic moiety optionally being substituted by one or more moieties $R_{1b}$, e.g. 0, 1, 2 or 3 $R_{1b}$.

In some embodiments, the cyclic moiety of $R_{1a}$ is 3- to 6-membered carbocyclyl.

When the cyclic moiety of $R_{1a}$ is 3- to 6-membered carbocyclyl, said carbocyclyl may be saturated or unsaturated and non-aromatic or (when 6-membered) aromatic. In some embodiments, when the cyclic moiety is 3- to 6-membered carbocyclyl, it more specifically is 4- to 6-membered carbocyclyl, or 5- or 6-membered carbocyclyl, such as 6-membered carbocyclyl, e.g. hexyl or phenyl, in particular phenyl.

In some embodiments, the cyclic moiety of $R_{1a}$ is 5- or 6-membered heterocyclyl.

When the cyclic moiety of $R_{1a}$ is 5- or 6-membered heterocyclyl, said heterocyclyl may be saturated or unsaturated, and non-aromatic or aromatic, and having one or more heteroatoms in the ring, independently selected from N, O and S. In some embodiments, the heterocyclyl is 5-membered. In some embodiments, the heterocyclyl is 6-membered.

In some embodiments, the heterocyclyl contains 1, 2, 3 or 4 heteroatoms, independently selected from N, O and S; or 1, 2 or 3 heteroatoms independently selected from N, O and S; or 1 or 2 heteroatoms independently selected from N, O and S; or 1 heteroatom selected from N, O and S.

In some embodiments, when the cyclic moiety of $R_{1a}$ is heterocyclyl, it more particularly is heteroaryl.

In some embodiments, the cyclic moiety of $R_{1a}$ is selected from C3-C6 cycloalkyl, phenyl and 5- or 6-membered heteroaryl. In some embodiments, the cyclic moiety is selected from C5-C6 cycloalkyl, phenyl, and 5- or 6-membered heteroaryl. In some embodiments, the cyclic moiety is selected from hexyl, phenyl and 5- or 6-membered heteroaryl. In some embodiments, the cyclic moiety is selected from phenyl and 5- or 6-membered heteroaryl. In some embodiments, the cyclic moiety is phenyl. In some other embodiments, the cyclic moiety is 5- or 6-membered heteroaryl. In some other embodiments, the cyclic moiety is C3-C6 cycloalkyl, e.g. C4-C6 cycloalkyl, or C5-C6 cycloalkyl, especially hexyl.

In some embodiments, when the cyclic moiety of $R_{1a}$ is 5- or 6-membered heteroaryl, it more particularly is 5-membered heteroaryl, e.g. 5-membered heteroaryl containing 1 or 2 heteroatoms independently selected from N, O and S.

In some other embodiments, when the cyclic moiety of $R_{1a}$ is 5- or 6-membered heteroaryl, it more particularly is 6-membered heteroaryl, e.g. pyridyl.

The cyclic moiety of $R_{1a}$ optionally is substituted by one or more $R_{1b}$. In some embodiments, the cyclic moiety optionally is substituted by 1, 2 or 3 $R_{1b}$, e.g. 1 or 2 $R_{1b}$, or 1 moiety $R_{1b}$. In some embodiments, the cyclic moiety is unsubstituted.

In some embodiments, the compound of formula (Ic) may be represented by formula (Ie)

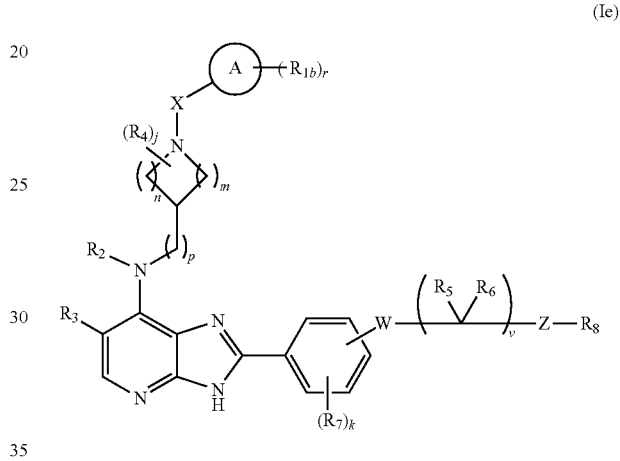

(Ie)

wherein $R_{1b}$, $R_2$, $R_3$, $R_4$, $R_5$, $R_6$, $R_7$, $R_8$, W, X, Z, j, k, m, n, p and v are as defined herein, ring A represents the cyclic moiety of $R_{1a}$, as defined herein above, and r is an integer of from 0 to 3.

In formula (Ie), r represents the number of substituents $R_{1b}$ on ring A, and r is 0, 1, 2 or 3. In some embodiments, r is an integer of from 1 to 3. In some other embodiments, r is 1 or 2. In some embodiments, r is 2. In some embodiments, r is 3. In some embodiments, r is an integer of from 0 to 2. In some embodiments, r is 0 or 1. In some embodiments, r is 1. In some embodiments, r is 0.

In some embodiments, ring A is a cyclic moiety selected from C3-C6 cycloalkyl, phenyl and 5- or 6-membered heteroaryl. In some embodiments, said heteroaryl is selected from thienyl, furanyl, 1H-pyrrolyl, thiazolyl and piperidyl.

In some of these embodiments, when ring A is 5- or 6-membered heteroaryl, r is 0 or 1, e.g. r is 0. In some embodiments, when ring A is 5- or 6-membered heteroaryl, r is 1.

In some embodiments, when ring A is 5-membered heteroaryl, $R_{1a}$ may be represented by formula (IIa) or (IIb)

(IIa)

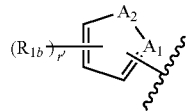
(IIb)

wherein each $R_{1b}$ is as defined herein; $A_1$ is CH or N; $A_2$ is O, S, NH or $NR_{1b}$; r' is r when $A_2$ is O, S or NH, and r' is r-1 when $A_2$ is $NR_{1b}$.

In some embodiments, when $R_{1a}$ is a moiety of formula (IIa) or (IIb), $A_1$ is N. In some embodiments, $A_1$ is N and $A_2$ is O or S, e.g. S. In some other embodiments, when $R_{1a}$ is a moiety of formula (IIa) or (IIb), $A_1$ is N and $A_2$ is $NR_{1b}$.

In some other embodiments, when $R_{1a}$ is a moiety of formula (IIa) or (IIb), $A_1$ is CH. In some embodiments, when $A_1$ is CH, $A_2$ is O, S, or $NR_{1b}$, e.g. $A_1$ is O or S.

In some particular embodiments, when $A_1$ is CH, $A_2$ is O. In some other particular embodiments, when $A_1$ is CH, $A_2$ is S.

In some embodiments, when $R_{1a}$ is a moiety of formula (IIa) or (IIb), $A_1$ is CH or N; and $A_2$ is O, S, or $NR_{1b}$.

In some embodiments, when $R_{1a}$ is a moiety of formula (IIa) or (IIb), r' is 0, 1 or 2, in particular r' is 0 or 1. In some embodiments, r' is 0. In some other embodiments, r' is 1.

In some embodiments, when $R_{1a}$ is a moiety of formula (IIa) or (IIb), $R_{1b}$ is C1-C6 alkyl, e.g. C1-C3 alkyl, in particular $CH_3$.

In some embodiments, when $R_{1a}$ is a moiety of formula (IIa) or (IIb), it more particularly is a moiety of formula (IIa). In some other embodiments, when $R_{1a}$ is a moiety of formula (IIa) or (IIb), it more particularly is a moiety of formula (IIb).

In some particular embodiments of a compound of formula (Ie), ring A is phenyl, i.e. the compound may be represented by formula (If)

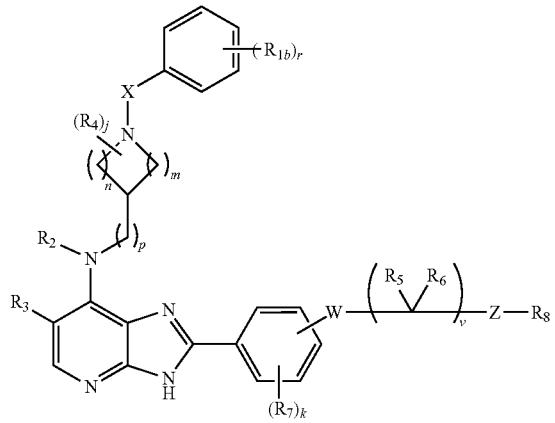
(If)

wherein each $R_{1b}$, $R_2$, $R_3$, $R_4$, $R_5$, $R_6$, $R_7$, $R_8$, W, X, Z, j, k, m, n, p, r and v are as defined herein.

In some embodiments of a compound of formula (If), r is 0, 1 or 2, or r is 0 or 1, or r is 0. In some other embodiments, r is 1, 2, or 3, e.g. r is 1 or 2, or r is 1.

In some embodiments of a compound of formula (If), one $R_{1b}$ is attached in para position, i.e. the compound may be represented by formula (Ig)

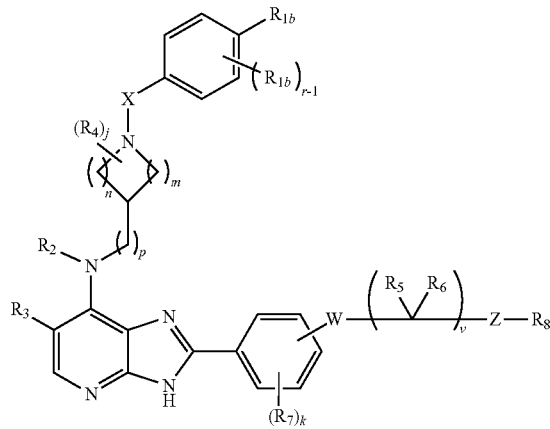
(Ig)

wherein $R_{1b}$, $R_2$, $R_3$, $R_4$, $R_5$, $R_6$, $R_7$, $R_8$, W, X, Z, j, k, m, n, p, and v are as defined herein, and
r is 1, 2 or 3, e.g. r is 1 or 2, or r is 1.

In some particular embodiments of a compound of formula (Ig), r is 1, i.e. the compound may be represented by formula (Ih)

(Ih)

wherein $R_{1b}$, $R_2$, $R_3$, $R_4$, $R_5$, $R_6$, $R_7$, $R_8$, W, X, Z, j, k, m, n, p, and v are as defined herein.

In some further embodiments of a compound of formula (If), when r is 1, 2 or 3, e.g. r is 1 or 2, at least one moiety $R_{1b}$ is attached in meta position on the phenyl ring. In some embodiments, r is 1 and $R_{1b}$ is attached in meta position on the phenyl ring. In some embodiments of a compound of formula (If), r is 2 or 3 and at least one $R_{1b}$ is attached in meta position. For example, in some embodiments of compound of formula (Ig), r is 2 and one $R_{1b}$ is attached in meta position on the phenyl ring, i.e. the compound may be represented by formula (Ii)

(Ii)

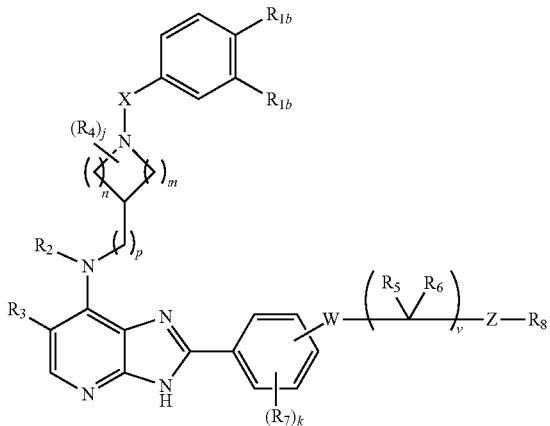

wherein each $R_{1b}$, $R_2$, $R_3$, $R_4$, $R_5$, $R_6$, $R_7$, $R_8$, W, X, Z, j, k, m, n, p, and v are as defined herein.

In some further embodiments of a compound of formula (If), one $R_{1b}$ is attached in ortho position, i.e. the compound may be represented by formula (Ij)

(Ij)

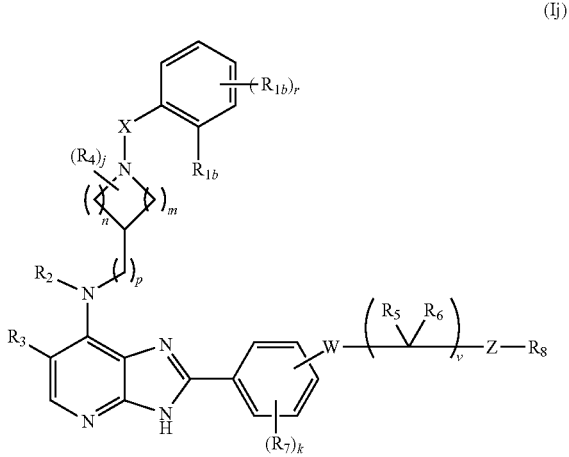

wherein each $R_{1b}$, $R_2$, $R_3$, $R_8$, $R_9$, $R_5$, $R_6$, each $R_7$, X, W, k, m, n and p are as defined herein, and r is 1, 2 or 3; e.g. r is 1 or 2; or r is 1.

In a compound of formula (I), e.g. of formula (Ie), (If), (Ig), (Ih), (Ii) or (Ij), each $R_{1b}$ is independently selected from halogen, C1-C6 alkyl, $R_{1c}O$, $R_{1d}C(O)N(R_{1e})$, cyano, $R_{1f}R_{1g}N$, $R_{1h}S(O)_2$, $R_{1i}S$, 3- to 6-membered carbocyclyl and 5- or 6-membered heterocyclyl; or two $R_{1b}$ are attached to adjacent atoms of the cyclic moiety and form, together with the atoms to which they are attached, a 5- or 6-membered ring.

In some embodiments, each $R_{1b}$ is independently selected from halogen, C1-C6 alkyl, $R_{1c}O$, $R_{1d}C(O)N(R_{1e})$, cyano, $R_{1f}R_{1g}N$, $R_{1h}S(O)_2$, $R_{1i}S$, and 5- or 6-membered heterocyclyl; or two $R_{1b}$ are attached to adjacent atoms of the cyclic moiety and form, together with the atoms to which they are attached, a 5- or 6-membered ring.

In some embodiments, each $R_{1b}$ is independently selected from halogen, C1-C6 alkyl, $R_{1c}O$, $R_{1d}C(O)N(R_{1e})$, cyano, $R_{1f}R_{1g}N$, $R_{1h}S(O)_2$, $R_{1i}S$, 3- to 6-membered carbocyclyl and 5- or 6-membered heterocyclyl.

In some embodiments, each $R_{1b}$ is independently selected from halogen, C1-C6 alkyl, $R_{1c}O$, $R_{1d}C(O)N(R_{1e})$, cyano, $R_{1f}R_{1g}N$, $R_{1h}S(O)_2$, $R_{1i}S$, and 5- or 6-membered heterocyclyl.

In some embodiments, each $R_{1b}$ is independently selected from halogen, C1-C6 alkyl, $R_{1c}O$, and 5- or 6-membered heterocyclyl.

In some embodiments, each $R_{1b}$ is independently selected from halogen, C1-C6 alkyl, and $R_{1c}O$; e.g. each $R_{1b}$ is independently selected from C1-C6 alkyl and $R_{1c}O$, or each $R_{1b}$ is $R_{1c}O$.

In some embodiments, each $R_{1b}$ is independently selected from halogen and C1-C6 alkyl, e.g. each $R_{1b}$ is C1-C6 alkyl.

For example, in some embodiments, when the cyclic moiety, to which each $R_{1b}$ is attached, is heterocyclyl, e.g. 5- or 6-membered heteroaryl, each $R_{1b}$ is selected from C1-C6 alkyl.

In some embodiments, each $R_{1b}$ is independently selected from halogen and $R_{1c}O$, e.g. each $R_{1b}$ is halogen.

In some embodiments, each $R_{1b}$ is independently selected from halogen, C1-C6 alkyl, and $R_{1c}O$, or two $R_{1b}$ are attached to adjacent atoms of the cyclic moiety and form, together with the atoms to which they are attached, a 5- or 6-membered ring.

In some embodiments, each $R_{1b}$ is independently selected from C1-C6 alkyl, and $R_{1c}O$, or two $R_{1b}$ are attached to adjacent atoms of the cyclic moiety and form, together with the atoms to which they are attached, a 5- or 6-membered ring.

In some embodiments, each $R_{1b}$ is independently selected from halogen and $R_{1c}O$, or two $R_{1b}$ are attached to adjacent atoms of the cyclic moiety and form, together with the atoms to which they are attached, a 5- or 6-membered ring.

In some embodiments, each $R_{1b}$ is independently selected from $R_{1c}O$, or two $R_{1b}$ are attached to adjacent atoms of the cyclic moiety and form, together with the atoms to which they are attached, a 5- or 6-membered ring.

In some embodiments, two $R_{1b}$ are attached to adjacent atoms of the cyclic moiety and form, together with the atoms to which they are attached, a 5- or 6-membered ring.

In some embodiments of a compound of formula (Ie), e.g. in some embodiments of a compound of formula (If), or formula (Ig), r is 2 or 3, in particular 2, and two $R_{1b}$ are attached to adjacent atoms of ring A and form, together with the atoms to which they are attached, a 5- or 6-membered ring. In some of these embodiments, the compound is a compound of formula (Ii).

As noted herein above, any alkyl moiety in a compound of formula (I) may optionally be substituted by one or more F. Thus, when any $R_{1b}$ is or contains an alkyl moiety, said alkyl moiety may optionally be substituted by one or more F.

When $R_{1b}$ is halogen, said halogen e.g. may be selected from F and Cl.

When $R_{1b}$ is C1-C6 alkyl, said C1-C6 alkyl e.g. may be selected from C1-C4 alkyl, or from C1-C3 alkyl, e.g. $CH_3$. In some embodiments, when $R_{1b}$ is C1-C6 alkyl, said alkyl is $CH_3$ or $CF_3$.

In a moiety $R_{1c}O$, $R_{1c}$ is selected from H and C1-C6 alkyl, e.g. from H and C1-C4 alkyl, or from H and C1-C3 alkyl. In some embodiments, $R_1$ is selected from H, $CH_3$, $CF_2H$, $CH_3CH_2$, and $(CH_3)_2CH_2$. In some embodiments, $R_1$ is selected from C1-C6 alkyl, e.g. from C1-C4 alkyl, e.g. from C1-C3 alkyl, e.g. from $CH_3$, $CF_2H$, $CH_3CH_2$, and $(CH_3)_2CH_2$. In some embodiments, $R_1$ is $CH_3$, optionally substituted by one or more F.

In a moiety $R_{1d}C(O)N(R_{1e})$, $R_{1d}$ and $R_{1e}$ are independently selected from H and C1-C6 alkyl.

In some embodiments, $R_{1d}$ and $R_{1e}$ are independently selected from H and C1-C4 alkyl, e.g. from H and C1-C3 alkyl, or from H and $CH_3$. In some embodiments, $R_{1d}$ is C1-C6 alkyl, or C1-C4 alkyl, or C1-C3 alkyl, e.g. $CH_3$, and $R_{1e}$ is as herein defined. In some embodiments, $R_{1d}$ is C1-C6 alkyl, or C1-C4 alkyl, or C1-C3 alkyl, e.g. $CH_3$, and $R_{1e}$ is H.

In a moiety $R_{1f}R_{1g}N$, $R_{1f}$ and $R_{1g}$ are independently selected from H and C1-C6 alkyl. In some embodiments, $R_{1f}$ and $R_{1g}$ are independently selected from H and C1-C4 alkyl, e.g. from H and C1-C3 alkyl, or from H and $CH_3$. In some embodiments, $R_{1f}$ and $R_{1g}$ are both C1-C6 alkyl, or both are C1-C4 alkyl, or both are C1-C3 alkyl, e.g. both are $CH_3$.

In a moiety $R_{1h}S(O)_2$, $R_{1h}$ is selected from H and C1-C6 alkyl. In some embodiments, $R_{1h}$ is selected from H and C1-C4 alkyl, e.g. from H and C1-C3 alkyl, or from H and $CH_3$. In some embodiments, $R_{1h}$ is C1-C6 alkyl, or C1-C4 alkyl, or C1-C3 alkyl, e.g. $CH_3$.

In a moiety $R_{1i}S$, $R_{1i}$ is selected from H and C1-C6 alkyl. In some embodiments, $R_{1i}$ is selected from H and C1-C4 alkyl, e.g. from H and C1-C3 alkyl, or from H and $CH_3$. In some embodiments, $R_1$ is C1-C6 alkyl, or C1-C4 alkyl, or C1-C3 alkyl, e.g. $CH_3$.

When $R_{1b}$ is 3- to 6-membered carbocyclyl or 5- or 6-membered heterocyclyl, $R_{1b}$ more particularly is 5- or 6-membered heteroaryl, or 5-membered heteroaryl, said heterocyclyl containing 1 or more heteroatoms independently selected from N, O and S, e.g. 1, 2, 3 or 4 heteroatoms independently selected from N, O and S. For example, when $R_{1b}$ is 5-membered heteroaryl, said heteroaryl may be a nitrogen-containing heteroaryl, such as a triazolyl, e.g. 1H-1,2,4-triazol-1-yl. In some embodiments, when $R_{1b}$ is 3- to 6-membered carbocyclyl or 5- or 6-membered heterocyclyl, the compound is as represented by formula (Ih).

When two $R_{1b}$ are attached to adjacent atoms of the cyclic moiety and form, together with the atoms to which they are attached, a 5- or 6-membered ring, said ring may be saturated or unsaturated and aromatic or non-aromatic and may optionally contain one or more heteroatoms. In some embodiments, said ring is contains 1 or 2 heteroatoms, e.g. 1 or 2 O. In some embodiments, said ring is non-aromatic, e.g. saturated or mono-unsaturated, e.g. sharing a double bond with the cycle to which it is fused, and optionally contains 1 or 2 heteroatoms, e.g. 1 or 2 O. In some embodiments, said ring is 5-membered. In some other embodiments, said ring is 6-membered. In some embodiments, said ring is selected from

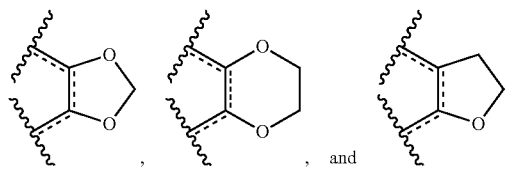
, , and wherein a bond represented by "===" may be a double or single bond (provided that the atom valence is respected). For, in some embodiments of a compound of formula (If), e.g. in some embodiments of a compound of formula (Ig), R1a is a moiety of formula (IIc)

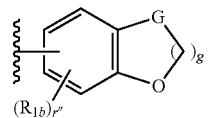

(IIc)

wherein R1b is as defined herein, G is O or $CH_2$, g is 1 or 2; and r" is 0 or 1, e.g. r" is 0.

In some embodiments, when $R_{1a}$ is a moiety of formula (IIc), G is O. In some other embodiments, when $R_{1a}$ is a moiety of formula (IIc), G is $CH_2$.

In some embodiments, when $R_{1a}$ is a moiety of formula (IIc), g is 1. In some other embodiments, when $R_{1a}$ is a moiety of formula (IIc), g is 2.

In a compound of formula (I), the moiety $R_2$ is H or C1-C6 alkyl, e.g. H or C1-C4 alkyl, or H or C1-C3 alkyl, in particular H or $CH_3$. In some embodiments, $R_2$ is C1-C6 alkyl, or C1-C4 alkyl, or C1-C3 alkyl, in particular $CH_3$. In some embodiments, $R_2$ is H.

In a compound of formula (I), the moiety $R_3$ is halogen. In some embodiments, $R_3$ is Cl or Br.

In some embodiments, $R_3$ is Cl. In some other embodiments, $R_3$ is Br.

In a compound of formula (I), j is an integer of from 0 to 4, e.g. from 0 to 3, or from 0 to 2. In some embodiments, j is 0 or 1. In still other embodiments, j is 0.

The moiety $R_4$ is C1-C3 alkyl, e.g. C1-C2 alkyl, such as $CH_3$.

In a compound of formula (I), the moiety W is a direct bond, O, S, $CR_{w1}R_{w2}$, or $NR_{w3}$. In some embodiments, W is O, S, $CR_{w1}R_{w2}$, or $NR_{w3}$. In some embodiments, W is O, S, or $CR_{w1}R_{w2}$. In some embodiments, W is O or $CR_{w1}R_{w2}$. In some embodiments, W is O. In some other embodiments, W is $CR_{w1}R_{w2}$. In still other embodiments, W is O or S. In some embodiments, W is O, S, or $NR_{w3}$, e.g. W is O or $NR_{w3}$. In still other embodiments, W is O, $CR_{w1}R_{w2}$, or $NR_{w3}$.

In some embodiments, W is a direct bond, O, $CR_{w1}R_{w2}$, or $NR_{w3}$, e.g. W is a direct bond, O, or $CR_{w1}R_{w2}$; or W is a direct bond or $CR_{w1}R_{w2}$, e.g. W is a direct bond. In still other embodiments, W is a direct bond, O, or $NR_{w3}$, e.g. W is a direct bond, or $NR_{w3}$, or W is $NR_{w3}$.

In the moiety $CR_{w1}R_{w2}$, $R_{w1}$ and $R_{w2}$ are independently selected from H and C1-C3 alkyl. In some embodiments, $R_{w1}$ and $R_{w2}$ are independently selected from H and $CH_3$. In some embodiments, both $R_{w1}$ and $R_{w2}$ are H. In some embodiments, at least one of $R_{w1}$ and $R_{w2}$ is H, e.g. $R_{w2}$ is H and $R_{w1}$ is as defined herein above.

In the moiety $NR_{w3}$, $R_{w3}$ is H or C1-C3 alkyl, e.g. $R_{w3}$ is H or $CH_3$. In some embodiments, $R_{w3}$ is C1-C3 alkyl, e.g. $R_{w3}$ is $CH_3$. In some other embodiments, $R_{w3}$ is H.

In some embodiments W is a direct bond, O, S, $CH_2$, $CH(CH_3)$, $C(CH_3)_2$, NH, or $N(CH_3)$; or W is a direct bond, O, $CH_2$, $CH(CH_3)$, $C(CH_3)_2$, NH, or $N(CH_3)$; or W is a direct bond, O, $CH_2$, or NH; or W is a direct bond, O or NH; or W is a direct bond or O; in particular W is O.

In some embodiments W is a O, S, $CH_2$, $CH(CH_3)$, $C(CH_3)_2$, NH, or $N(CH_3)$; or W is O, $CH_2$, $CH(CH_3)$, $C(CH_3)_2$, NH, or $N(CH_3)$; or W is O, $CH_2$, or NH; or W is O or NH.

In some embodiments W is a direct bond, O, S, $CH_2$, $CH(CH_3)$, or $C(CH_3)_2$; or W is a direct bond, O, $CH_2$, $CH(CH_3)$, or $C(CH_3)_2$; or W is a direct bond, O, or $CH_2$; or W is a direct bond, or $CH_2$.

In some embodiments W is a O, S, $CH_2$, $CH(CH_3)$, or $C(CH_3)_2$; or W is O, $CH_2$, $CH(CH_3)$, or $C(CH_3)_2$; or W is O or $CH_2$; or W is $CH_2$.

In some embodiments W is a direct bond, O, S, NH, or $N(CH_3)$; or W is a direct bond, O, NH, or $N(CH_3)$; or W is a direct bond, NH or $N(CH_3)$; or W is a direct bond or NH; or W is NH.

In some embodiments W is O, S, NH, or $N(CH_3)$; or W is O, NH, or $N(CH_3)$; or W is NH or $N(CH_3)$.

In some embodiments, W is a direct bond, O or S, or W is O or S.

In embodiments where W is O, the compound may be represented by formula (Ik)

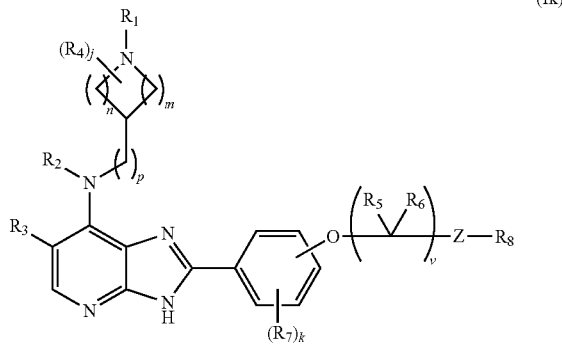

(Ik)

wherein $R_1$, $R_2$, $R_3$, $R_4$, $R_5$, $R_6$, $R_7$, $R_8$, Z, j, k, m, n, p and v are as defined herein.

In a compound of formula (I), v is 1 or 2. In some embodiments, v is 1. In some other embodiments, v is 2. The moieties $R_5$ and R % are each independently selected from H and C1-C3 alkyl. In some embodiments, each $R_5$ and each R % is independently selected from H and $CH_3$. In some embodiments, each $R_5$ is selected from H and C1-C3 alkyl, e.g. from H and $CH_3$, and each R % is H. In some embodiments, each $R_5$ and R % is H. For example, in some particular embodiments, v is 1 and $R_5$ and R % are independently selected from H and $CH_3$, in particular both are H. In some other particular embodiments, v is 2 and each $R_5$ as well as each R % is independently selected from H and $CH_3$, in particular all are H.

In some particular embodiments, the moiety $W—(CR_5R_6)_v$ is $CH_2$, $CH_2CH_2$, $OCH_2$, $OC(CH_3)_2$, $OCH_2CH_2$, $NHCH_2$, $N(CH_3)CH_2$ or $NHCH_2CH_2$.

In a compound of formula (I), k is an integer of from 0 to 2. In some embodiments, k is 0 or 1, e.g. k is 0. In some other embodiments, k is 1 or 2, e.g. k is 1. In some embodiments, k is 2.

When k is 1 or 2, each moiety $R_7$ is independently selected from halogen, C1-C3 alkyl, and $R_{7a}O$. In some embodiments, each $R_7$ is independently selected from halogen and C1-C3 alkyl. In some other embodiments, each $R_7$ is independently selected from halogen and $R_{7a}O$. In some other embodiments, each $R_7$ is independently selected from C1-C3 alkyl and $R_{7a}O$. In some other embodiments, each $R_7$ is independently selected from C1-C3 alkyl. In still other embodiments, each $R_7$ is independently selected from halogen.

When any $R_7$ is C1-C3 alkyl, said alkyl more particularly may be $CH_3$. When any $R_7$ is halogen, said halogen more particularly may be F or Cl, e.g. F. In $R_{7a}O$, the moiety $R_{7a}$ is selected from C1-C3 alkyl. In some embodiments, any $R_{7a}$ is $CH_3$. In some embodiments, $R_7$ is selected from F, $CH_3$ and $CH_3O$.

In a compound of formula (I) as defined herein, $R_8$ is selected from $R_{8a}(CR_{8b}R_{8c})_q$, $R_{8d}O$ and C1-C6 alkyl, said C1-C6 alkyl optionally being substituted by a moiety selected from $NR_{8e}R_{8f}$ and $OR_{8g}$.

In some embodiments $R_8$ is selected from $R_{8a}(CR_{8b}R_{8c})_q$ and C1-C6 alkyl, said C1-C6 alkyl optionally being substituted by a moiety selected from $NR_{8e}R_{8f}$ and $OR_{8g}$.

In some embodiments $R_8$ is $R_{8a}(CR_{8b}R_{8c})_q$. In such embodiments, the compound may be represented by formula (Im)

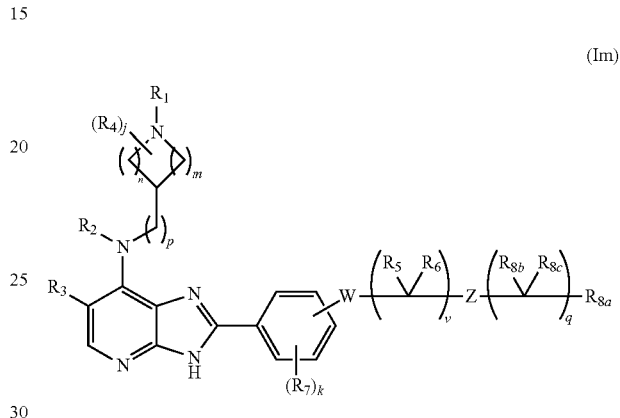

(Im)

wherein $R_1$, $R_2$, $R_3$, $R_4$, $R_5$, $R_6$, $R_7$, $R_{8a}$, $R_{8b}$, $R_{8c}$, W, Y, Z, j, k, m, n, p, q and v are as defined herein.

In some other embodiments $R_8$ is selected from $R_{8d}O$ and C1-C6 alkyl, said C1-C6 alkyl optionally being substituted by a moiety selected from $NR_{8e}R_{8f}$ and $OR_{8g}$.

In some other embodiments $R_8$ is C1-C6 alkyl, said C1-C6 alkyl optionally being substituted by a moiety selected from $NR_{8e}R_{8f}$ and $OR_{8g}$.

In some embodiments, $R_8$ is C1-C6 alkyl.

Furthermore, when Z is $C(O)NR_8R_9$, $R_8$ together with $R_9$ and the nitrogen atom to which they are both attached, may form a 5- or 6 membered heterocyclyl optionally containing a further heteroatom in the ring.

In a moiety $R_{8d}O$, $R_{8d}$ is C1-C6 alkyl, e.g. $R_{8d}$ is C1-C4 alkyl, or $R_{8d}$ is C1-C3 alkyl, in particular $R_{8d}$ is $CH_3$.

When $R_8$ is C1-C6 alkyl, said alkyl e.g. is C1-C4 alkyl, or C1-C3 alkyl, in particular $CH_3$.

When $R_8$ is C1-C6 alkyl substituted by a moiety selected from $NR_{8e}R_{8f}$ and $OR_{8g}$, said alkyl e.g. is C1-C4 alkyl or C2-C4 alkyl, in particular C2-C3 alkyl.

In some embodiments, $R_8$ is C1-C6 alkyl substituted by $NR_{8e}R_{8f}$, or $R_8$ is C1-C4 alkyl substituted by $NR_{8e}R_{8f}$, or $R_8$ is C2-C4 alkyl substituted by $NR_{8e}R_{8f}$, or $R_8$ is C2-C3 alkyl substituted by $NR_{8e}R_{8f}$.

In some other embodiments, $R_8$ is C1-C6 alkyl substituted by $OR_{8g}$, or $R_8$ is C1-C4 alkyl substituted by $OR_{8g}$, or $R_8$ is C2-C4 alkyl substituted by $OR_{8g}$, or $R_8$ is C2-C3 alkyl substituted by $OR_{8g}$.

In some embodiments, when $R_8$ is C1-C6 alkyl substituted by a moiety $NR_{8e}R_{8f}$ or $OR_{8g}$, said alkyl more particularly is C2-C6 alkyl comprised of a C1-C3 alkylene normal chain, e.g. a C2-C3 alkylene normal chain, or a C2 alkylene chain, which chain is optionally substituted by one or more C1-C3 alkyl groups, e.g. one or more methyl and/or ethyl groups, or one or more methyl groups.

In some embodiments, when $R_8$ is C1-C6 alkyl substituted by a moiety $NR_{8e}R_{8f}$ or $OR_{8g}$, $R_8$ may be represented by formula (III)

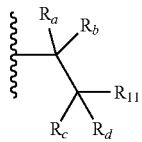
(III)

wherein each one of $R_a$, $R_b$, $R_c$ and $R_d$ is selected from H and $CH_3$, and $R_{11}$ is $NR_{8e}R_{8f}$ or $OR_{8g}$.

In some embodiments, when $R_8$ is a moiety of formula (III), at least two of $R_a$, $R_b$, $R_c$ and $R_d$ are H. In some embodiments, when $R_8$ is a moiety of formula (III), at least three of $R_a$, $R_b$, $R_c$ and $R_d$ are H. In some embodiments, when $R_8$ is a moiety of formula (III), $R_a$, $R_b$, $R_c$ and $R_d$ are all H, i.e. $R_8$ is a moiety of formula (IIIa)

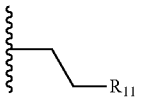
(IIIa)

wherein $R_{11}$ is as defined herein.

In some other embodiments, when $R_8$ is a moiety of formula (III), two of $R_a$, $R_b$, $R_c$ and $R_d$ are $CH_3$, and the two others are H. In some other embodiments, when $R_8$ is a moiety of formula (III), $R_a$ and $R_b$ are both $CH_3$, and $R_c$ and $R_d$ are both H, i.e. $R_8$ is a moiety of formula (IIIb)

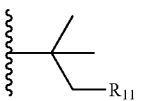
(IIIb)

wherein $R_{11}$ is as defined herein.

In still other embodiments, when $R_8$ is a moiety of formula (III), $R_a$ and $R_b$ are both H, and $R_c$ and $R_d$ are both $CH_3$, i.e. $R_8$ is a moiety of formula (IIIc)

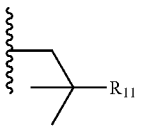
(IIIc)

wherein $R_{11}$ is as defined herein.

In some other embodiments, when $R_8$ is a moiety of formula (III), any one of $R_a$, $R_b$, $R_c$ and $R_d$ is $CH_3$, and the three others are H. For example, in some embodiments, $R_8$ is a moiety of formula (IIId)

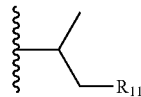
(IIId)

wherein $R_{11}$ is as defined herein.

In some embodiments, $R_{11}$ is $NR_{8e}R_{8f}$. In some other embodiments, $R_{11}$ is $OR_{8g}$. In some embodiments, when $R_{11}$ is $OR_{8g}$, $R_8$ is a moiety of formula (IIIe)

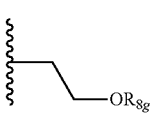
(IIIe)

wherein $R_{8g}$ is as defined herein.

In some other embodiments, when $R_8$ is C1-C6 alkyl substituted by a moiety $R_{11}$, as defined herein, $R_8$ more particularly is

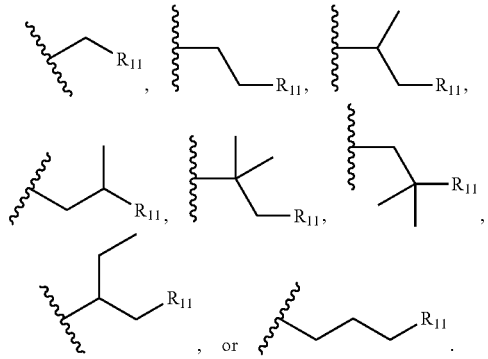

In some of these embodiments, $R_{11}$ is $NR_{8e}R_{8f}$. In some other of these embodiments, $R_{11}$ is $R_{8g}O$.

In some other embodiments, when $R_8$ is C1-C6 alkyl substituted by a moiety $R_{11}$, which moiety is selected from $NR_{8e}R_{8f}$ or $R_{8g}O$, $R_8$ more particularly is

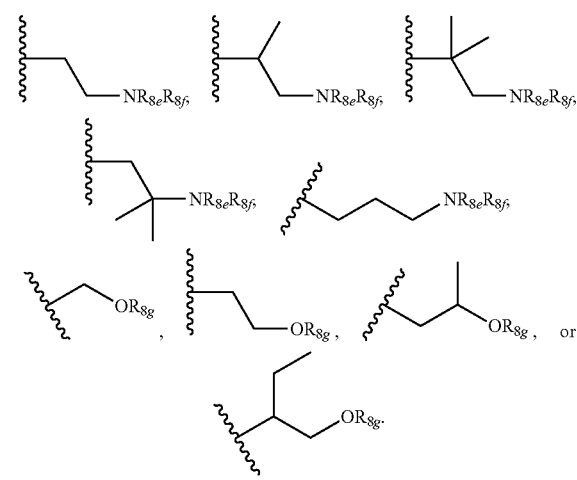

In the moiety $NR_{8e}R_{8f}$, $R_{8e}$ and $R_{8f}$ are independently selected from H and C1-C6 alkyl, e.g. from H and C1-C4 alkyl, or from H and C1-C3 alkyl, or from H and C1-C2 alkyl, or from H and $CH_3$; or $R_{8e}$ and $R_{8f}$ together with the nitrogen atom to which they are both attached, form a 5- or 6 membered heterocyclyl optionally containing a further heteroatom in the ring.

In some embodiments, $R_{8e}$ and $R_{8f}$ are both independently selected from H and C1-C6 alkyl, e.g. from H and C1-C4 alkyl, or from H and C1-C3 alkyl, or from H and C1-C2 alkyl, or from H and $CH_3$. In some embodiments, $R_{8e}$ and $R_{8f}$ are both independently selected from C1-C6 alkyl, or from C1-C4 alkyl, or from C1-C3 alkyl, or from C1-C2 alkyl, both are $CH_3$.

In some embodiments, $R_{8e}$ and $R_{8f}$, together with the nitrogen atom to which they are both attached, form a 5- or 6 membered heterocyclyl optionally containing a further heteroatom in the ring. In some embodiments, the heterocyclyl is 5-membered. In some other embodiments, the heterocyclyl is 6-membered. When the heterocyclyl contains a further heteroatom, such heteroatom e.g. may be selected from N, O and S. If the heterocyclyl contains a further nitrogen atom in the ring, such nitrogen atom may be substituted by C1-C3 alkyl, e.g. $CH_3$, or unsubstituted (i.e. —NH— or —N=). In some embodiments, when $R_{8e}$ and $R_{8f}$, together with the nitrogen atom to which they are both attached, form a 5- or 6 membered heterocyclyl, the heterocyclyl is morpholino.

The moiety $R_{8g}$ is H or C1-C6 alkyl, or H or C1-C4 alkyl, or H or C1-C3 alkyl, e.g. $R_{8g}$ is selected from H, $CH_3$ and $(CH_3)_2CH$, or from H and $(CH_3)_2CH$. In some embodiments, $R_{8g}$ is H. In some other embodiments, $R_{8g}$ is C1-C6 alkyl, or C1-C4 alkyl, e.g. C1-C3 alkyl, e.g. $R_{8g}$ is selected from $CH_3$ and $(CH_3)_2CH$, or $R_{8g}$ is $(CH_3)_2CH$.

In some embodiments, when $R_8$ is C1-C6 alkyl substituted by a moiety selected from $R_{8e}R_{8f}N$ and $R_{8g}O$, $R_8$ is selected from

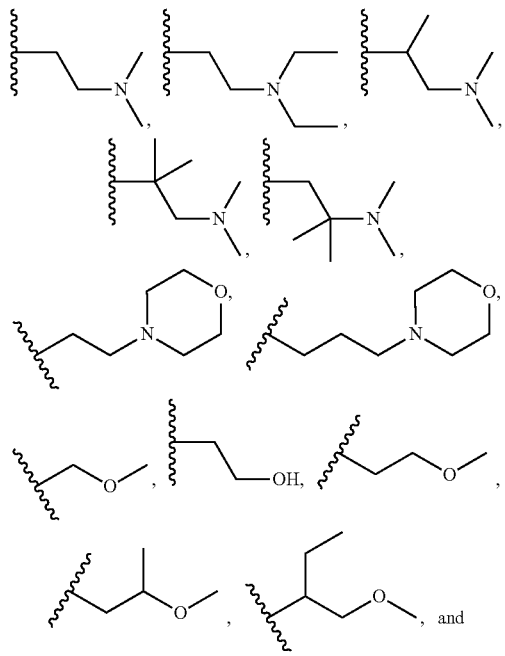

In some embodiments, $R_8$ is selected from C1-C6 alkyl, or C1-C4 alkyl, or C1-C3 alkyl, e.g. methyl or isopropyl; $R_{8d}O$, e.g. methoxy; and C1-C6 alkyl substituted by $NR_{8e}R_{8f}$ or $OR_{8g}$, such as a moiety of formula (III), e.g. a moiety of formula (IIIa), (IIIb), (IIIc), (IIId) or (IIIe), in particular a moiety selected from

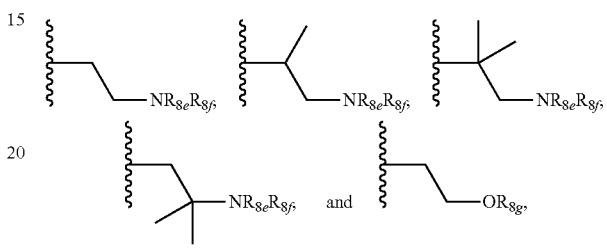

wherein $R_{8e}$, $R_{8f}$ and $R_{8g}$ are as defined herein.

In some embodiments, when $R_8$ is a moiety of formula (III), said moiety is selected from

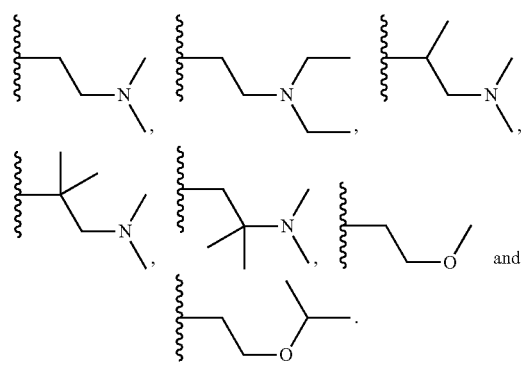

In the moiety $R_{8a}(CR_{8b}R_{8c})_q$, q is an integer of from 0 to 2, and $R_{8a}$ is a cyclic moiety selected from C3-C7 carbocyclyl and 5- to 7-membered heterocyclyl, said cyclic moiety optionally being substituted by one or more moieties selected from halogen, C1-C6 alkyl, C3-C5 cycloalkyl, and $R_{8h}O$. In some embodiments, said cyclic moiety is 5 or 6-membered.

In some embodiments, the cyclic moiety of $R_{8a}$ is C3-C7 carbocyclyl.

When the cyclic moiety of $R_{8a}$ is C3-C7 carbocyclyl, said carbocyclyl e.g. may be C3-C6 carbocyclyl, or C5-C6 carbocyclyl, or C6 carbocyclyl. In some embodiments, said carbocyclyl is C4-C7 carbocyclyl, e.g. C5-C7 carbocyclyl.

In some embodiments, said carbocyclyl is C3-C7 cycloalkyl or phenyl, such as C3-C6 cycloalkyl or phenyl, in particular C5-C6 cycloalkyl or phenyl. In some embodiments, said carbocyclyl is C4-C7 cycloalkyl or phenyl, such as C5-C7 cycloalkyl or phenyl, in particular cyclohexyl or phenyl. In some other embodiments, said carbocyclyl is C3-C7 cycloalkyl, in particular C3-C6 cycloalkyl, such as C5-C6 cycloalkyl. In still other embodiments, said carbocyclyl is phenyl.

In some embodiments, the cyclic moiety of $R_{8a}$ is 5- to 7-membered heterocyclyl, in particular 5- or 6-membered heterocyclyl. Said heterocyclyl may be non-aromatic and saturated or unsaturated, e.g. saturated; or aromatic, i.e. a heteroaryl. In some embodiments, the heterocyclyl is non-aromatic, e.g. saturated. In some other embodiments, the heterocyclyl is aromatic, i.e. heteroaryl. Said heterocyclyl contains one or more heteroatoms, e.g. 1, 2, 3 or 4 heteroatoms, or 1, 2 or 3 heteroatoms, or 1 or 2 heteroatoms, e.g. 1 heteroatom, selected from N, O and S. When the cyclic moiety contains a nitrogen atom, said nitrogen may be substituted, e.g. by C1-C3 alkyl, e.g. $CH_3$, or may be unsubstituted (i.e. —NH— or —N=).

In some particular embodiments, said heterocyclyl is 5-membered. In some other particular embodiments, said heterocyclyl is 6-membered. In some embodiments, the heterocyclyl is 5- or 6-membered saturated heterocyclyl. In some other embodiments, the heterocyclyl is 5- or 6-membered heteroaryl.

In some embodiments, when said heterocyclyl is saturated heterocyclyl, it contains one heteroatom in the ring, which heteroatom is selected from N, O and S, in particular from N and O.

In some embodiments, when said heterocyclyl is 5- or 6-membered heteroaryl, said heteroaryl contains one N in the ring, and optionally one or more further ring heteroatoms selected from N, O and S, or from N and O.

In some embodiments, when said heterocyclyl is 5- or 6-membered heteroaryl, said heteroaryl more particularly is 6-membered, e.g. 6-membered heteroaryl containing one or two N in the ring.

In some embodiments, said heterocyclyl is selected from:

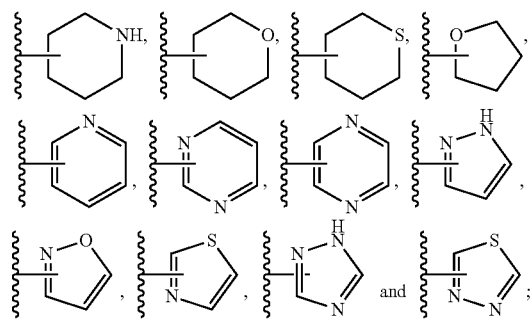

e.g. from:

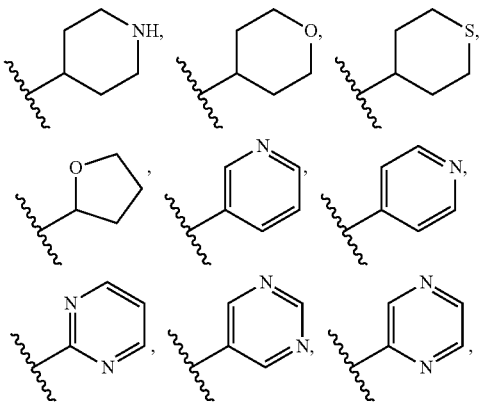

-continued

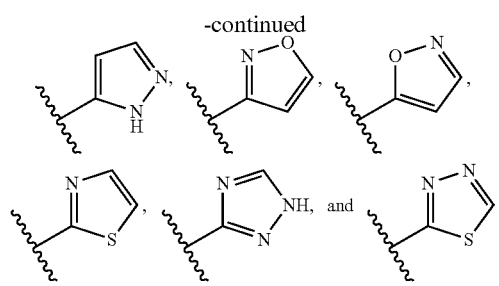

In formula $R_{8a}(CR_{8b}R_{8c})_q$, q is an integer of from 0 to 2. In some embodiments, q is 0 or 1, e.g. q is 0. In some embodiments, q is 1 or 2, e.g. q is 1. In still other embodiments, q is 2. The moieties $R_{8b}$ and $R_{8c}$ are each independently selected from H and C1-C3 alkyl, e.g. from H and C1-C2 alkyl, or from H and $CH_3$. In some embodiments, each $R_{8b}$ and each $R_{8c}$ is H. In some embodiments, each $R_{8b}$ is H and each $R_{8c}$ is as defined herein above, e.g. $R_{8c}$ is H or $CH_3$. In some particular embodiments, q is 0 or 1 and when q is 1, $R_{8b}$ and $R_{8c}$ are both H. In some other particular embodiments, q is 1 or 2 and each $R_{8b}$ and $R_{8c}$ is H. In still some other particular embodiments, q is 1 and $R_{8b}$ and $R_{8c}$ are both H.

In some embodiments, $R_{8a}(CR_{8b}R_{8c})_q$ is a moiety of formula

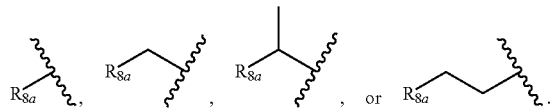

The cyclic moiety of $R_{8a}$ optionally is substituted by one or more moieties selected from halogen, C1-C6 alkyl, C3-C5 cycloalkyl, and $R_{8h}O$, e.g. one or more moieties selected from halogen, C1-C6 alkyl, and $R_{8h}O$, or one or more, e.g. 1-3, moieties selected from C1-C6 alkyl, or from C1-C4 alkyl, or C1-C3 alkyl, e.g. one or more $CH_3$. In some other embodiments, the cyclic moiety of $R_{8a}$ optionally is substituted by one or more moieties selected from $R_{8h}O$. In some other embodiments, the cyclic moiety of $R_{8a}$ optionally is substituted by one or more moieties selected from halogen, C1-C6 alkyl, and C3-C5 cycloalkyl, or from halogen and C1-C6 alkyl.

In a moiety $R_{8h}O$, $R_{8h}$ is H or C1-C6 alkyl, e.g. C1-C3 alkyl, such as $CH_3$. When the cyclic moiety of $R_{8a}$ is substituted by a halogen, such halogen e.g. may be F or Cl, e.g. Cl. When the cyclic moiety is substituted by C1-C6 alkyl, such alkyl e.g. may be C1-C5 alkyl, or C1-C4 alkyl, or C1-C3 alkyl, such as $CH_3$.

In some embodiments, the cyclic moiety of $R_{8a}$ is optionally substituted by one or more, e.g. 1 or 2 moieties as mentioned herein above, e.g. selected from $CH_3$, $CH_3O$ and Cl. In some embodiments, the cyclic moiety of $R_{8a}$ is unsubstituted or substituted by one moiety, e.g. one moiety selected from $CH_3$, $(CH_3)_3CH$, $CH_3O$ and Cl. In some embodiments, the cyclic moiety of $R_{8a}$ is unsubstituted.

The moiety $R_9$ is H or C1-C6 alkyl, or H or C1-C4 alkyl; e.g. H or C1-C3 alkyl, such as H or $CH_3$, or $R_8$ and $R_9$, together with the nitrogen atom to which they are both attached, form a 5- or 6 membered heterocyclyl optionally containing a further heteroatom in the ring. In some embodiments, $R_9$ is H or C1-C6 alkyl, or H or C1-C4 alkyl; e.g. H or C1-C3 alkyl, in particular H or $CH_3$. In some embodiments, $R_9$ is H. In some other embodiments, $R_9$ is C1-C6 alkyl, or C1-C4 alkyl, e.g. C1-C3 alkyl, such as $CH_3$.

In some embodiments, $R_8$ and $R_9$, together with the nitrogen atom to which they are both attached, form a 5- or 6 membered heterocyclyl optionally containing a further heteroatom in the ring. In some embodiments, the heterocyclyl is 5-membered. In some other embodiments, the heterocyclyl is 6-membered. When the heterocyclyl contains a further heteroatom, such heteroatom e.g. may be selected from N, O and S. If the heterocyclyl contains a further N in the ring, such N may be substituted by C1-C3 alkyl, e.g. by a $CH_3$, or may be unsubstituted (i.e. —NH— or —N=).

In some embodiments, $R_8$ and $R_9$ are both selected from H and C1-C6 alkyl. In some embodiments $R_8$ and $R_9$ are both selected from H and C1-C4 alkyl, e.g. both are selected from H and C1-C3 alkyl; or from H and $CH_3$. In some embodiments, $R_9$ is selected from H and C1-C6 alkyl, or H and C1-C4 alkyl, or H and C1-C3 alkyl, or H and $CH_3$, e.g. $R_9$ is H; and $R_8$ is C1-C6 alkyl, or C1-C4 alkyl, or C1-C3 alkyl, e.g. $R_8$ is $CH_3$. In some particular embodiments, $R_8$ is $CH_3$ and $R_9$ is H.

The moiety $R_{10}$ is H or C1-C6 alkyl, or H or C1-C4 alkyl; e.g. H or C1-C3 alkyl, such as H or $CH_3$. In some embodiments, $R_{10}$ is H.

In a compound of formula (I), Z is $C(O)NR_9$ or $NR_{10}C(O)$. When Z is $C(O)NR_9$, $R_8$ is attached to the amide nitrogen, i.e. Z—$R_8$ is $C(O)NR_8R_9$. When Z is $NR_{10}C(O)$, $R_8$ is attached to the carbonyl carbon, Z—$R_8$ is $NR_{10}C(O)R_8$.

In some embodiments, Z is $C(O)NR_9$. In these embodiments, the compound may be represented by formula (In)

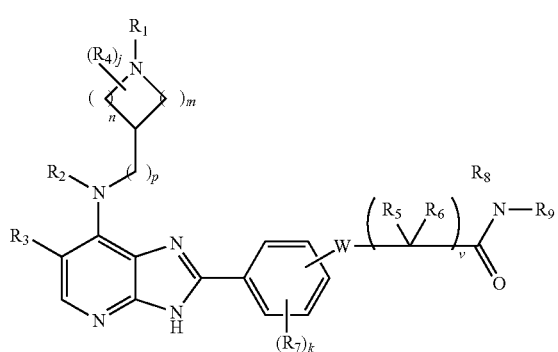

(In)

wherein $R_1$, $R_2$, $R_3$, $R_4$, $R_5$, $R_6$, $R_7$, $R_8$, $R_9$, W, j, k, m, n, p, and v are as defined herein.

In some other embodiments, Z is $NR_{10}C(O)$. In these embodiments, the compound may be represented by formula (Io)

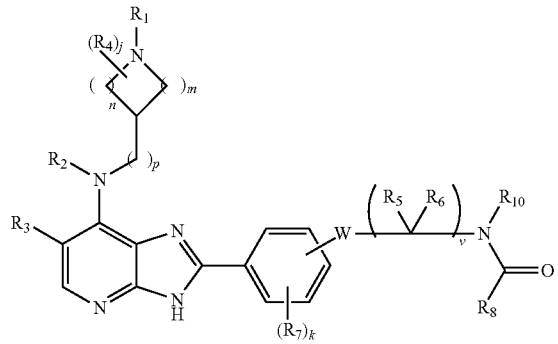

(Io)

wherein $R_1$, $R_2$, $R_3$, $R_4$, $R_5$, $R_6$, $R_7$, $R_8$, $R_{10}$, W, j, k, m, n, p, and v are as defined herein.

It should be realized that unless mutually exclusive or incompatible, the various features of the embodiments may be freely combined to give rise to further embodiments within the scope of formula (I). For example, in some embodiments, a compound of formula (Ia1) also is a compound of formula (Ib1), which may be represented by formula (Ip)

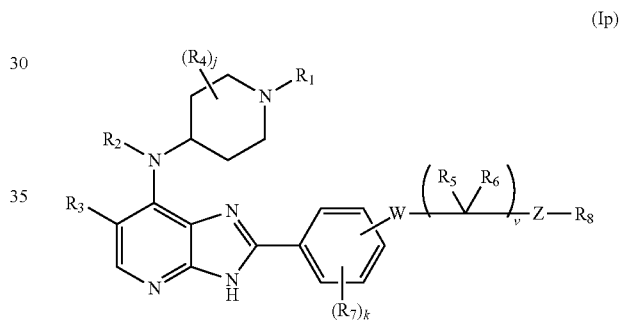

(Ip)

wherein $R_1$, $R_2$, $R_3$, $R_4$, $R_5$, $R_6$, $R_7$, $R_8$, W, Z, j, k, and v are as defined herein.

Likewise, in some embodiments, a compound of formula (Ip) also is a compound of formula (Id2). In some of these embodiments, the compound also is a compound of formula (Ie), and may be represented by formula (Iq)

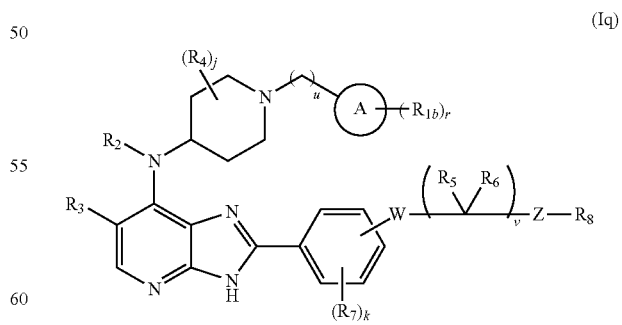

(Iq)

wherein each $R_{1b}$, $R_2$, $R_3$, $R_4$, $R_5$, $R_6$, $R_7$, $R_8$, ring A, W, Z, j, k, r, u, and v are as defined herein.

Furthermore, in some embodiments, a compound of formula (Iq) also is is a compound of formula (If), and may be represented by formula (Ir)

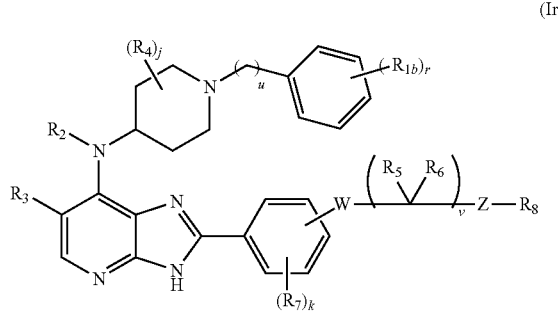

(Ir)

wherein each $R_{1b}$, $R_2$, $R_3$, $R_4$, $R_5$, $R_6$, $R_7$, $R_8$, W, Z, j, k, r, u, and v are as defined herein.

In some other embodiments, a compound of formula (Ia2) also is a compound of formula (Ib1), which may be represented by formula (Is)

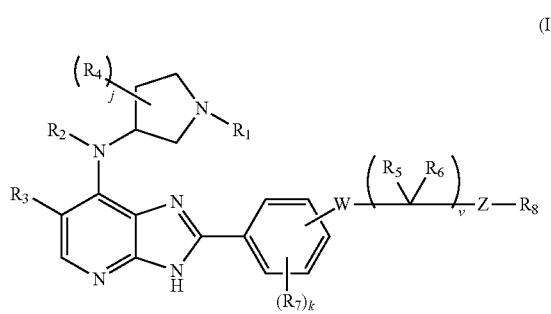

(Is)

wherein $R_1$, $R_2$, $R_3$, $R_4$, $R_5$, $R_6$, $R_7$, $R_8$, W, Z, j, k, and v are as defined herein.

A compound of formula (Ia2), e.g. of formula (Is), also may be a compound of formula (Id2), which may be represented by formula (It)

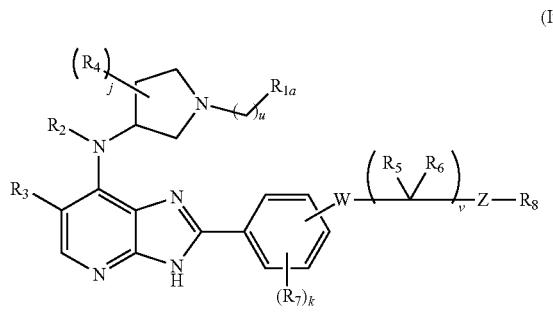

(It)

wherein each $R_{1a}$, $R_2$, $R_3$, $R_4$, $R_5$, R %, $R_7$, $R_8$, W, Z, j, k, u, and v are as defined herein.

Furthermore, in some embodiments a compound of formula (It) also is a compound of formula (Ie), and may be represented by formula (Iu)

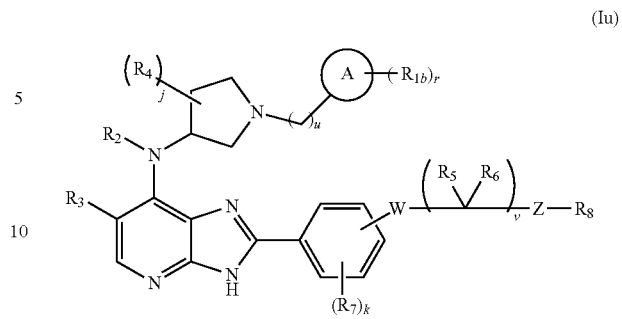

(Iu)

wherein each $R_{1b}$, $R_2$, $R_3$, $R_4$, $R_5$, $R_6$, $R_7$, $R_8$, ring A, W, Z, j, k, r, u, and v are as defined herein.

In some embodiments, a compound of formula (Iu) also is a compound of formula (If), which may be represented by formula (Iv)

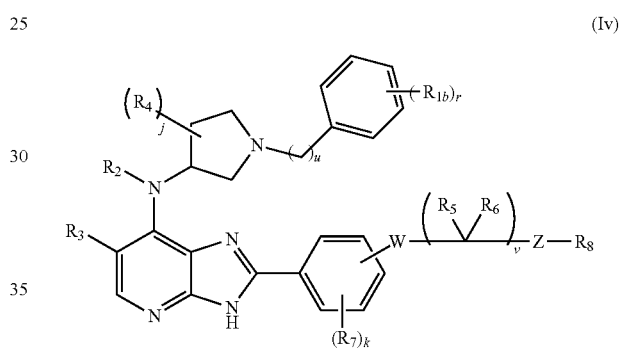

(Iv)

wherein each $R_{1b}$, $R_2$, $R_3$, $R_4$, $R_5$, $R_6$, $R_7$, $R_8$, W, Z, j, k, r, u, and v are as defined herein.

In some embodiments, a compound of formula (Ia2), or (Is), or (It), or (Iu), or (Iv) also is a compound of formula (Io). For example, in some embodiments, the compound is one as represented by formula (Iw)

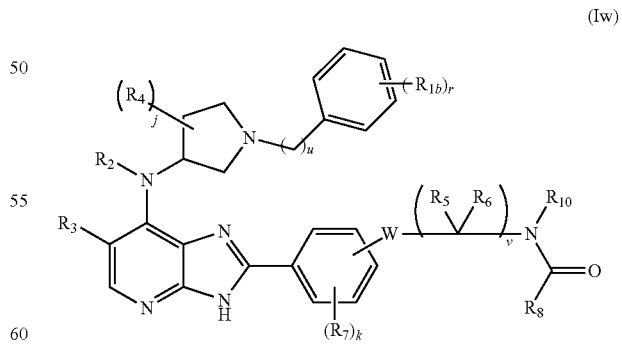

(Iw)

wherein each $R_{1b}$, $R_2$, $R_3$, $R_4$, $R_5$, $R_6$, $R_7$, $R_8$, $R_{10}$, W, j, k, r, u, and v are as defined herein.

In some embodiments, a compound of formula (Iw) also is a compound of formula (Id3), which may be represented by formula (Ix)

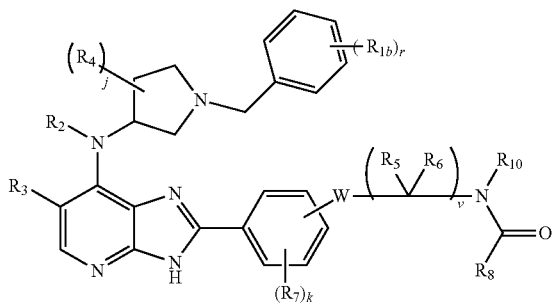

(Ix)

wherein each $R_{1b}$, $R_2$, $R_3$, $R_4$, $R_5$, $R_6$, $R_7$, $R_8$, $R_{10}$, W, j, k, r, and v are as defined herein.

In some further embodiments of a compound of formula (I), e.g. in a compound of any of the above formulas (Ia) to (Ix), j is 0, i.e. the compound is as represented by formula (Iy)

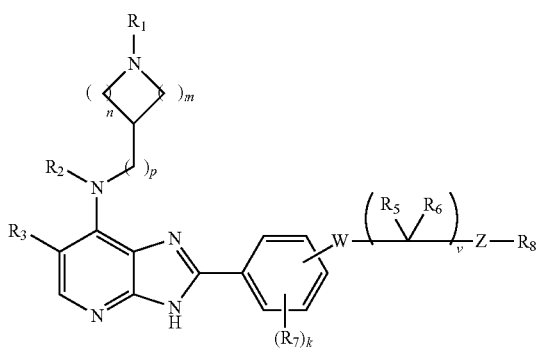

(Iy)

wherein $R_1$, $R_2$, $R_3$, $R_5$, R %, $R_7$, $R_8$, W, Z, k, m, n, p and v are as defined herein.

Any other combination of features within the scope of formula (I) is contemplated according to the present invention. For example, in some embodiments, a compound of formula (Iv), or formula (Iw) or formula (Ix) also is a compound of formula (Ij). In some other embodiments, a compound of formula (Ir) also is a compound of formula (Ig), or of formula (Ih) or of formula (Ii), or of formula (Ij).

In some embodiments of a compound of formula (I), e.g. in some embodiments of a compound according to any one of the above formulas (Ia) to (Iy), $R_2$ is H and $R_3$ is Cl or Br, in particular Cl. In some embodiments of a compound of formula (I), e.g. in some embodiments of a compound according to any one of the above formulas (Ia) to (Iy), $R_2$ is H, $R_3$ is Cl or Br. In some of these embodiments, $R_8$ is C1-C6 alkyl and $R_9$ or $R_{10}$ is H or C1-C3 alkyl, in particular H.

Many other combinations of the above described features of a compound within the scope of formula (I) are conceivable, whether or not the features have been specifically illustrated in any of the above formulas (Ia) to (Iy); all such possible combinations are considered to fall within the scope of the invention.

For example, in some embodiments of a compound of formula (I), e.g. in some embodiments of a compound of any one of the formulas (Ic), (Id), (Id1), (Id2), (Id3) or (Id4), $R_{1a}$ is a cyclic moiety selected from 5- or 6-membered carbocyclyl and 5- or 6-membered heterocyclyl, in particular a (hetero)aromatic cyclic moiety, said cyclic moiety optionally being substituted by one or more $R_{1b}$, e.g. 0, 1, 2 or 3 $R_{1b}$. In some of these embodiments, each $R_{1b}$ is independently selected from halogen, C1-C6 alkyl, $R_{1c}O$, $R_{1d}C(O)N(R_{1e})$, cyano, $R_{1f}R_{1g}N$, $R_{1h}S(O)_2$, $R_{1i}S$, 5- or 6-membered carbocyclyl and 5- or 6-membered heterocyclyl; or two $R_{1b}$ are attached to adjacent atoms of the cyclic moiety and form, together with the atoms to which they are attached, a 5- or 6-membered ring.

In some embodiments, when $R_1$ is $R_{1a}$—X—, optionally substituted by one or more $R_{1b}$, i.e. the compound is of formula (Ic), e.g. a compound of formula (Id), (Id1), (Id2), (Id3), (Id4), (Ie), (If), (Ig), (Ih), (Ii), (Ij), (Iq), (Ir), (It), (Iu), (Iv), or (Ix), each $R_{1b}$ is independently selected from halogen, C1-C3 alkyl, $R_{1c}O$—, $R_{1d}C(O)N(R_{1e})$—, cyano, $R_{1f}R_{1g}N$—, $R_{1h}S(O)_2$—, $R_{1i}S$—, C3-C6 carbocyclyl, and 5- to 6-membered heterocyclyl; and, when at least two $R_{1b}$ are present, two $R_{1b}$ may be attached to adjacent atoms of the cyclic moiety and form, together with the atoms to which they are attached, a 5- or 6-membered ring containing one or more heteroatoms in the ring, e.g. one or more oxygen atoms; and each $R_{1c}$, $R_{1d}$, $R_{1e}$, $R_{1f}$, $R_{1g}$, $R_{1h}$ and $R_{1i}$ is independently selected from H and C1-C3 alkyl.

In some embodiments, when $R_1$ is $R_{1a}$—X—, optionally substituted by one or more $R_{1b}$, i.e. the compound is of formula (Ic), e.g. of formula (Id), (Id1), (Id2), (Id3), (Id4), (If), (Ig), (Ih), (Ii), (Ij), (Iq), (It), (Iu), (Iv), (Iw), or (Ix), each $R_{1b}$ is independently selected from halogen, C1-C3 alkyl, $R_{1c}O$—, $R_{1d}C(O)N(R_{1e})$—, cyano, $R_{1f}R_{1g}N$—, $R_{1h}S(O)_2$—, $R_{1i}S$—, C3-C6 cycloalkyl, and 5- to 6-membered heteroaryl; and, when at least two $R_{1b}$ are present, two $R_{1b}$ may be attached to adjacent atoms of the cyclic moiety and form, together with the atoms to which they are attached, a 5- or 6-membered ring containing one or two oxygen atoms in the ring; and each $R_{1c}$, $R_{1d}$, $R_{1e}$, $R_{1f}$, $R_{1g}$, $R_{1h}$ and $R_{1i}$ is independently selected from H and C1-C3 alkyl.

In some embodiments, when $R_1$ is $R_{1a}$—X—, optionally substituted by one or more $R_{1b}$, i.e. $R_1$ is a compound of formula (Ic), e.g. a compound of formula (Id), (Id1), (Id2), (Id3), (Id4), (If), (Ig), (Ih), (Ii), (Ij), (Iq), (It), (Iu), (Iv), (Iw), or (Ix), each $R_{1b}$ is independently selected from F, Cl, $CH_3$, $CF_3$, OH, $CH_3O$, $CHF_2O$, $CH_3CH_2O$, $(CH_3)_2CHO$, $CH_3C(O)NH$, CN, $(CH_3)_2N$, $CH_3S(O)_2$, $CH_3S$, and

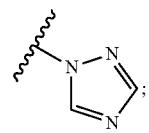 [SMILES: *n1cncn1]

and, when at least two $R_{1b}$ are present, two $R_{1b}$ may be attached to adjacent atoms of the cyclic moiety and form, together with the atoms to which they are attached, a 5- or 6-membered ring; selected from

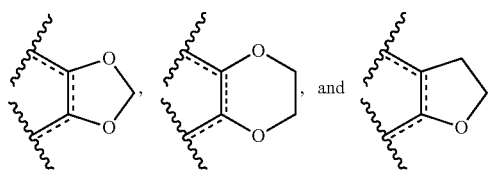

wherein a bond represented by "═══" may be a double or single bond (provided that atomic valence is respected).

In some further embodiments of a compound of formula (I), e.g. in some embodiments of a compound of any one of the formulas (Ic), (Id), (Id1), (Id2), (Id3) or (Id4), $R_{1a}$ is a cyclic moiety selected from C3-C6 cycloalkyl, phenyl and 5- or 6-membered heteroaryl, said cyclic moiety optionally being substituted by one or more $R_{1b}$, e.g. 0, 1, 2 or 3 $R_{1b}$. In some of these embodiments, each $R_{1b}$ is independently selected from halogen, C1-C6 alkyl, $R_{1c}O$, $R_{1d}C(O)N(R_{1e})$, cyano, $R_{1f}R_{1g}N$, $R_{1h}S(O)_2$, $R_{1i}S$, and 5-membered heteroaryl; or two $R_{1b}$ are attached to adjacent atoms of the cyclic moiety and form, together with the atoms to which they are attached, a 5- or 6-membered ring.

In some further embodiments of a compound of formula (I), e.g. in some embodiments of a compound of any one of the formulas (Ia) to (Iy), $R_2$ is H or $CH_3$, in particular H; $R_3$ is Cl or Br, in particular Cl; and $R_9$ is H or $CH_3$, in particular H, or $R_{10}$ is H or $CH_3$, in particular H. In some of these embodiments, $R_8$ is C1-C6 alkyl, in particular $CH_3$. In some other of these embodiments, $R_8$ is C1-C6 alkyl substituted by a moiety selected from $R_{8e}R_{8f}N$— and $R_{8g}O$—, in particular $R_{8e}R_{8f}N$—. In some of these embodiments, $R_8$ is a moiety of formula (III).

Furthermore, in some embodiments, each $R_5$ and $R_6$ is H, and $R_7$ is absent (i.e. k is 0). For example, in some embodiments of a compound of formula (I), e.g. in some embodiments of a compound of any one of the formulas (Ia) to (Iy), $R_2$ is H or $CH_3$, in particular H; $R_3$ is Cl or Br, in particular Cl; each $R_5$ and $R_6$ is H, $R_7$ is absent; $R_8$ is C1-C6 alkyl, in particular $CH_3$; Z is $C(O)NR_9$, and $R_9$ is H or $CH_3$, in particular H; or Z is $N(R_{10})C(O)$ and $R_{10}$ is H or $CH_3$, in particular H.

Furthermore, in some embodiments of a compound of formula (I), e.g. in some embodiments of a compound of any one of the formulas (Ia), (Ia1), (Ia2), (Ib1), (Ib2), (Ik), (Io), or (Is), $R_1$ is H, C1-C6 alkyl, or $R_{1a}$—X—, wherein X is a direct bond and $R_{1a}$ is C3-C6 cycloalkyl. In some of these embodiments, $R_2$ is H or $CH_3$, in particular H; $R_3$ is Cl or Br, in particular Cl; and $R_9$ is H or $CH_3$, in particular H. Furthermore, in some of these embodiments, $R_8$ is C1-C6 alkyl, in particular $CH_3$.

In some further embodiments of a compound of formula (I), e.g. in some embodiments of a compound of any one of the formulas (Ia), (Ia), (Ia1), (Ia2), (Ib1), (Ib2), (Ik), (Io), or (Is), $R_1$ is H or C1-C6 alkyl, in particular C1-C6 alkyl. In some of these embodiments, Z is $C(O)NR_9$, and $R_9$ is H or $CH_3$, in particular H. Furthermore, in some of these embodiments, $R_8$ is C1-C6 alkyl, in particular $CH_3$. In some of these embodiments, $R_2$ is H or $CH_3$, in particular H; $R_3$ is Cl or Br, in particular Cl.

In some embodiments of a compound of formula (I), m is 1 or 2; n is 2 or 3, in particular 2; p is 0 or 1; $R_1$ is H, C1-C6 alkyl or $R_{1a}$—X—, in particular C1-C6 alkyl or $R_{1a}$—X—; X is a direct bond or $(CH_2)_s$—Y—$(CH_2)_t$; Y is a direct bond or O; s is 1 or 2; t is 0; $R_{1a}$ is a cyclic moiety selected from 3- to 6-membered carbocyclyl and 5- or 6-membered heterocyclyl, said cyclic moiety optionally being substituted by one or more $R_{1b}$; each $R_{1b}$ is independently selected from halogen, C1-C6 alkyl, $R_{1c}O$—, $R_{1d}C(O)N(R_{1e})$—, cyano, $R_{1f}R_{1g}N$—, $R_{1h}S(O)_2$—, $R_{1i}S$—, 3- to 6-membered carbocyclyl, and 5- or 6-membered heterocyclyl; or two $R_{1b}$ are attached to adjacent atoms of the cyclic moiety and form, together with the atoms to which they are attached, a 5- or 6-membered ring; each $R_{1c}$, $R_{1d}$, $R_{1e}$, $R_{1f}$, $R_{1g}$, $R_{1h}$ and $R_{1i}$ is independently selected from H and C1-C6 alkyl; $R_2$ is H or C1-C6 alkyl; W is O or $CH_2$; $R_8$ is selected from $R_{8d}O$—, and C1-C6 alkyl, said alkyl optionally being substituted by a moiety selected from $R_{8e}R_{8f}N$— and $R_{8g}O$—; $R_{8d}$ is H or C1-C6 alkyl; $R_{8e}$ and $R_{8f}$ are independently selected from H and C1-C6 alkyl; $R_{8g}$ is H or C1-C6 alkyl; $R_9$ is H or C1-C6 alkyl; each $R_5$ and each $R_6$ is H; $R_7$ is absent; and any alkyl is saturated and is optionally substituted by one or more F.

In some embodiments, the compound of formula (I) more particularly is a compound of formula (In), wherein
m is 1 or 2; n is 2 or 3; p is 0 or 1;
$R_1$ is H, C1-C6 alkyl, or $R_{1a}$—X—;
X is a direct bond or $(CH_2)_s$—Y—$(CH_2)_t$;
Y is a direct bond, O or S;
s is 1 or 2; t is 0 or 1;
$R_{1a}$ is a cyclic moiety selected from 3- to 6-membered carbocyclyl and 5- or 6-membered heterocyclyl, said cyclic moiety optionally being substituted by one or more $R_{1b}$;
each $R_{1b}$ is independently selected from halogen, C1-C6 alkyl, $R_{1c}O$—, $R_{1d}C(O)N(R_{1e})$—, cyano, $R_{1f}R_{1g}N$—, $R_{1h}S(O)_2$—, $R_{1i}S$—, and C3-C6 carbocyclyl or 5- or 6-membered heterocyclyl; or two $R_{1b}$ are attached to adjacent atoms of the cyclic moiety and form, together with the atoms to which they are attached, a 5- or 6-membered ring;
each $R_{1c}$, $R_{1d}$, $R_{1e}$, $R_{1f}$, $R_{1g}$, $R_{1h}$ and $R_{1i}$ is independently selected from H and C1-C6 alkyl;
$R_2$ is H or C1-C6 alkyl;
$R_3$ is halogen;
j is 0;
W is O, S, $CR_{w1}R_{w2}$, or $NR_{w3}$;
$R_{w1}$ and $R_{w2}$ are independently selected from H and C1-C3 alkyl;
$R_{w3}$ is H or C1-C3 alkyl;
v is 1;
$R_5$ and $R_6$ are independently selected from H and C1-C3 alkyl;
k is an integer of from 0 to 2;
each $R_7$ is independently selected from C1-C3 alkyl;
$R_8$ is selected from $R_{8a}(CR_{8b}R_{8c})_q$—, $R_{8d}O$—, and C1-C6 alkyl, said alkyl optionally being substituted by a moiety selected from $R_{8e}R_{8f}N$— and $R_{8g}O$—;
q is 1 or 2;
$R_{8a}$ is a cyclic moiety selected from C3-C6 cycloalkyl and 5- or 6-membered saturated heterocyclyl, said cyclic moiety optionally being substituted by C1-C3 alkyl;
$R_{8b}$ and $R_{8c}$ are H;
$R_{8d}$ is H, C1-C6 alkyl, or C3-C6 cycloalkyl;
$R_{8e}$ and $R_{8f}$ are independently selected from H and C1-C6 alkyl; or
$R_{8e}$ and $R_{8f}$, together with the nitrogen atom to which they are both attached, form a 5- or 6 membered heterocyclyl optionally containing a further heteroatom in the ring;
$R_{8g}$ is H or C1-C6 alkyl;
$R_{8h}$ is H or C1-C6 alkyl;
$R_9$ is H or C1-C6 alkyl; or
$R_8$ and $R_9$, together with the nitrogen atom to which they are both attached, form a 5- or 6 membered heterocyclyl optionally containing a further heteroatom in the ring; and any alkyl is saturated or unsaturated and is optionally substituted by one or more F.

In some other embodiments, the compound of formula (I) more particularly is a compound of formula (Ia), e.g. of formula (Ia1), or of formula (Ia2), wherein
p is 0 or 1;
$R_1$ is H, C1-C6 alkyl, C1-C6 alkyl-Q-$(CH_2)_x$, or $R_{1a}$—X—,
Q is O;
x is 2;
X is a direct bond or $(CH_2)_s$—Y—$(CH_2)_t$;

Y is a direct bond or O;
s is 1 or 2; t is 0;
$R_{1a}$ is a cyclic moiety selected from 3- to 6-membered carbocyclyl and 5- or 6-membered heterocyclyl, said cyclic moiety optionally being substituted by one or more $R_{1b}$;
each $R_{1b}$ is independently selected from halogen, C1-C6 alkyl, $R_{1c}$O—, $R_{1d}$C(O)N($R_{1e}$)—, cyano, $R_{1f}R_{1g}$N—, $R_{1h}$S(O)$_2$—, $R_{1i}$S—, C3-C6 carbocyclyl, and 5- or 6-membered heterocyclyl; or two $R_{1b}$ are attached to adjacent atoms of the cyclic moiety and form, together with the atoms to which they are attached, a 5- or 6-membered ring;
each $R_{1c}$, $R_{1d}$, $R_{1e}$, $R_{1f}$, $R_{1g}$, $R_{1h}$, and $R_{1i}$ is independently selected from H and C1-C6 alkyl;
e.g. from H and C1-C3 alkyl; or from H and $CH_3$;
$R_2$ is H or C1-C6 alkyl;
$R_3$ is halogen;
j is an integer of from 0 to 4;
$R_4$ is C1-C3 alkyl;
W is a direct bond, O, $CR_{w1}R_{w2}$, or $NR_{w3}$;
$R_{w1}$, $R_{w2}$ and $R_{w3}$ are independently selected from H and $CH_3$; e.g. $R_{w1}$ and $R_{w2}$ are H, and $R_{w3}$ is H or $CH_3R_{w3}$; or $R_{w1}$, $R_{w2}$ and $R_{w3}$ are H;
v is 1 or 2;
each $R_5$ and $R_6$ is independently selected from H and C1-C3 alkyl;
k is an integer of from 0 to 2;
each $R_7$ is independently selected from halogen, C1-C3 alkyl, and $R_{7a}$O;
each $R_{7a}$ is independently from C1-C3 alkyl;
Z—$R_8$ is C(O)$NR_8R_9$ or $NR_{10}$C(O)$R_8$;
$R_8$ is selected from $R_{8a}(CR_{8b}R_{8c})_q$—, $R_{8d}$O—, and C1-C6 alkyl, said alkyl optionally being substituted by a moiety selected from $R_{8e}R_{8f}$N— and $R_{8g}$O—;
q is an integer of from 0 to 2;
$R_{8a}$ is a cyclic moiety selected from C3-C7 carbocyclyl and 5- to 7-membered heterocyclyl, said cyclic moiety optionally being substituted by one or more moieties selected from halogen, C1-C3 alkyl and $R_{8h}$O;
$R_{8b}$ and $R_{8c}$ are independently selected from H and C1-C3 alkyl, e.g. from H and $CH_3$;
$R_{8d}$ is C1-C6 alkyl; e.g. C1-C3 alkyl;
$R_{8e}$ and $R_{8f}$ are independently selected from C1-C6 alkyl; e.g. from C1-C3 alkyl; or
$R_{8e}$ and $R_{8f}$ together with the nitrogen atom to which they are both attached, form a 5- or 6 membered heterocyclyl optionally containing a further heteroatom in the ring;
$R_{8g}$ is H or C1-C6 alkyl; e.g. H or C1-C3 alkyl;
$R_{8h}$ is H or C1-C6 alkyl; e.g. H or C1-C3 alkyl;
$R_9$ is H or C1-C6 alkyl; e.g. H or C1-C3 alkyl;
$R_{10}$ is H or C1-C3 alkyl; e.g. H or $CH_3$;
and any alkyl is saturated and is optionally substituted by one or more F.

In some other embodiments, the compound of formula (I) is a compound of formula (Ia), or of formula (Ia1), in particular of formula (Ip), wherein
$R_1$ is C1-C6 alkyl, $R_{1a}$—$CH_2$—, or $R_{1a}$—$CH_2CH_2$—; e.g. C1-C6 alkyl or $R_{1a}$—$CH_2$—;
$R_{1a}$ is a cyclic moiety selected from phenyl and 5- or 6-membered heteroaryl, said cyclic moiety optionally being substituted by one or more $R_{1b}$, e.g. optionally substituted by 1-3 $R_{1b}$;
each $R_{1b}$ is independently selected from halogen, C1-C6 alkyl, $R_{1c}$O—, and 5- or 6-membered heterocyclyl; or two $R_{1b}$ are attached to adjacent atoms of the cyclic moiety and form, together with the atoms to which they are attached, a 5- or 6-membered ring;
each $R_{1c}$, is independently selected from H and C1-C6 alkyl;
$R_2$ is H;
$R_3$ is Cl or Br;
j is 0;
W is a direct bond, O, $CH_2$, NH, or N($CH_3$);
v is 1 or 2;
each $R_5$ and $R_6$ is independently selected from H and C1-C3 alkyl;
k is an integer of from 0 to 2;
each $R_7$ is independently selected from halogen, C1-C3 alkyl, and $R_{7a}$O;
each $R_{7a}$ is independently from C1-C3 alkyl;
Z—$R_8$ is C(O)$NR_8R_9$ or $NR_{10}$C(O)$R_8$;
$R_8$ is selected from $R_{8a}(CR_{8b}R_{8c})_q$, $R_{8d}$O, and C1-C6 alkyl, e.g. $R_{8a}(CR_{8b}R_{8c})_q$ and C1-C6 alkyl, said alkyl optionally being substituted by a moiety selected from $R_{8e}R_{8f}$N— and $R_{8g}$O—;
q is an integer of from 0 to 2;
$R_{8a}$ is a cyclic moiety selected from C3-C7 carbocyclyl and 5- or 6-membered heterocyclyl, said cyclic moiety optionally being substituted by one or more moieties selected from halogen, C1-C3 alkyl and $R_{8h}$O;
$R_{8b}$ and $R_{8c}$ are independently selected from H and C1-C3 alkyl, e.g. from H and $CH_3$;
$R_{8d}$ is C1-C6 alkyl, e.g. C1-C3 alkyl;
$R_{8e}$ and $R_{8f}$ are independently selected from C1-C6 alkyl; e.g. from C1-C3 alkyl; or
$R_{8e}$ and $R_{8f}$ together with the nitrogen atom to which they are both attached, form a 5- or 6 membered heterocyclyl optionally containing a further heteroatom in the ring;
$R_{8g}$ is H or C1-C6 alkyl, e.g. H or C1-C3 alkyl;
$R_{8h}$ is H or C1-C6 alkyl, e.g. H or C1-C3 alkyl;
$R_9$ is H or C1-C6 alkyl; e.g. H or C1-C3 alkyl;
$R_{10}$ is H or C1-C3 alkyl, e.g. H or $CH_3$;
and any alkyl is saturated and is optionally substituted by one or more F.

In some embodiments of a compound of formula (Ia), or of formula (Ia1), in particular of formula (Ip),
$R_1$ is C1-C6 alkyl, or $R_{1a}$—$CH_2$—,
$R_{1a}$ is a cyclic moiety selected from phenyl and 5- or 6-membered aryl, said cyclic moiety optionally being substituted by one or more $R_{1b}$, e.g. 1-3 $R_{1b}$, or 1-2 $R_{1b}$, each $R_{1b}$ independently selected from halogen, C1-C6 alkyl, $R_{1c}$O—, and 5- or 6-membered heterocyclyl; or two $R_{1b}$ are attached to adjacent atoms of the cyclic moiety and form, together with the atoms to which they are attached, a 5- or 6-membered ring;
each $R_{1c}$, is independently selected from H and C1-C6 alkyl;
$R_2$ is H;
$R_3$ is Cl or Br;
j is 0;
W is a direct bond, O, $CH_2$, or NH;
v is 1 or 2;
each $R_5$ and $R_6$ is independently selected from H and C1-C3 alkyl;
k is an integer of from 0 to 2;
each $R_7$ is independently selected from halogen, C1-C3 alkyl, and $R_{7a}$O;
each $R_{7a}$ is independently from C1-C3 alkyl;
Z—$R_8$ is C(O)$NR_8R_9$ or $NR_{10}$C(O)$R_8$;
$R_8$ is selected from $R_{8a}(CR_{8b}R_{8c})_q$, $R_{8d}$O, and C1-C6 alkyl, said alkyl optionally being substituted by a moiety selected from $R_{8e}R_{8f}$N— and $R_{8g}$O—;
q is an integer of from 0 to 2;
$R_{8a}$ is a cyclic moiety selected from C3-C7 carbocyclyl and 5- to 7-membered heterocyclyl, said cyclic moiety optionally being substituted by one or more moieties selected from halogen, C1-C3 alkyl and $R_{8h}$O;

$R_{8b}$ and $R_{8c}$ are independently selected from H and C1-C3 alkyl, e.g. from H and CH$_3$;
$R_{8d}$ is C1-C6 alkyl, e.g. C1-C3 alkyl;
$R_{8e}$ and $R_{8f}$ are independently selected from C1-C6 alkyl; e.g. from C1-C3 alkyl; or
$R_{8e}$ and $R_{8f}$, together with the nitrogen atom to which they are both attached, form a 5- or 6 membered heterocyclyl optionally containing a further heteroatom in the ring;
$R_{8g}$ is H or C1-C6 alkyl, e.g. H or C1-C3 alkyl;
$R_{8h}$ is H or C1-C6 alkyl, e.g. H or C1-C3 alkyl;
$R_9$ is H or C1-C6 alkyl, e.g. H or C1-C3 alkyl;
$R_{10}$ is H or C1-C3 alkyl, e.g. H or CH$_3$;
and any alkyl is saturated and is optionally substituted by one or more F.

In some embodiments of a compound of formula (Ia), or of formula (Ia1), in particular of formula (Ip),
$R_1$ is C1-C6 alkyl, or $R_{1a}$—CH$_2$—,
$R_{1a}$ is a cyclic moiety selected from phenyl and 5- or 6-membered aryl, said cyclic moiety optionally being substituted by one or more $R_{1b}$, e.g. 1-3 $R_{1b}$;
each $R_{1b}$ is independently selected from halogen, C1-C6 alkyl, $R_{1c}$O—, and 5- or 6-membered heteroaryl, or two $R_{1b}$ are attached to adjacent atoms of the cyclic moiety and form, together with the atoms to which they are attached, a 5- or 6-membered ring;
each $R_{1c}$ is independently selected from H and C1-C6 alkyl;
$R_2$ is H;
$R_3$ is Cl or Br;
j is 0;
W is a direct bond, O, CH$_2$, NH or N(CH$_3$);
v is 1 or 2;
each $R_5$ and $R_6$ is independently selected from H and CH$_3$;
k is an integer of from 0 to 2;
each $R_7$ is independently selected from F, CH$_3$, and CH$_3$O;
Z—$R_8$ is C(O)NR$_8$R$_9$ or NR$_{10}$C(O)R$_8$;
$R_8$ is selected from $R_{8a}(CR_{8b}R_{8c})_q$—, and C1-C6 alkyl, said alkyl optionally being substituted by a moiety selected from $R_{8e}R_{8f}$N— and $R_{8g}$O—;
q is an integer of from 0 to 2;
$R_{8a}$ is a cyclic moiety selected from C3-C7 carbocyclyl and 5- to 7-membered heterocyclyl, said cyclic moiety optionally being substituted by one or more moieties selected from halogen, C1-C3 alkyl and $R_{8h}$O;
$R_{8b}$ and $R_{8c}$ are independently selected from H and C1-C3 alkyl, e.g. from H and CH$_3$;
$R_{8d}$ is C1-C6 alkyl, e.g. C1-C3 alkyl;
$R_{8e}$ and $R_{8f}$ are independently selected from C1-C6 alkyl; e.g. from C1-C3 alkyl; or
$R_{8e}$ and $R_{8f}$, together with the nitrogen atom to which they are both attached, form a 5- or 6 membered heterocyclyl optionally containing a further heteroatom in the ring;
$R_{8g}$ is H or C1-C6 alkyl, e.g. H or C1-C3 alkyl;
$R_{8h}$ is H or C1-C6 alkyl, e.g. H or C1-C3 alkyl;
$R_9$ is H or C1-C6 alkyl, e.g. H or C1-C3 alkyl;
$R_{10}$ is H or C1-C3 alkyl, e.g. H or CH$_3$;
and any alkyl is saturated and is optionally substituted by one or more F.

In some of the above embodiments, Z—$R_8$ is C(O)NR$_8$R$_9$, i.e. the compound is as represented by formula (In). In some other of the above embodiments, Z—$R_8$ is NR$_{10}$C(O)R$_8$, i.e. the compound is as represented by formula (Io).

In some of the above embodiments, $R_8$ is $R_{8a}(CR_{8b}R_{8c})_q$—, i.e. the compound is as represented by formula (Im). In some of these embodiments, the cyclic moiety of $R_{8a}$ is phenyl or 5- or 6-membered heteroaryl, in particular 5- or 6-membered heteroaryl.

For example, in some embodiments, the compound is as represented by formula (Im), or a pharmaceutically acceptable salt thereof, wherein
m is 1 or 2;
n is 2 or 3;
p is 0 or 1;
$R_1$ is H, C1-C6 alkyl or $R_{1a}$—X—; in particular C1-C6 alkyl or $R_{1a}$—X—;
X is a direct bond or CH$_2$ or (CH$_2$)$_2$; in particular CH$_2$;
$R_{1a}$ is a cyclic moiety selected from phenyl and 5- or 6-membered heteroaryl, said cyclic moiety optionally being substituted by one or more $R_{1b}$;
each $R_{1b}$ is independently selected from halogen, C1-C6 alkyl, $R_{1c}$O—, $R_{1d}$C(O)N(R$_{1e}$)—, cyano, $R_{1f}R_{1g}$N—, $R_{1h}$S(O)$_2$—, $R_{1i}$S—, C3-C6 carbocyclyl, and 5- to 6-membered heterocyclyl; and two $R_{1b}$ attached to adjacent atoms of the cyclic moiety may form, together with the atoms to which they are attached, a 5- or 6-membered ring;
each $R_{1c}$, $R_{1d}$, $R_{1e}$, $R_{1f}$, $R_{1g}$, $R_{1h}$ and $R_{1i}$ is independently selected from H and C1-C6 alkyl;
$R_2$ is H or C1-C6 alkyl; in particular $R_2$ is H;
$R_3$ is halogen; e.g. $R_3$ is Cl or Br;
W is a direct bond, O, S, CR$_{w1}$R$_{w2}$, or NR$_{w3}$; in particular W is a direct bond, O, R$_{w1}$R$_{w2}$, or NR$_{w3}$;
$R_{w1}$ and $R_{w2}$ are independently selected from H and C1-C3 alkyl;
$R_{w3}$ is H or C1-C3 alkyl;
v is 1 or 2; in particular v is 1;
each $R_5$ and $R_6$ is independently selected from H and C1-C3 alkyl;
k is an integer of from 0 to 2; in particular k is 0;
each $R_7$ is independently selected from halogen, C1-C3 alkyl, and $R_{7a}$O;
each $R_{7a}$ is independently from C1-C3 alkyl;
Z—$R_8$ is C(O)NR$_8$R$_9$ or NR$_{10}$C(O)R$_8$;
q is an integer of from 0 to 2; in particular q is 0 or 1;
$R_{8a}$ is a cyclic moiety selected from phenyl and 5- or 6-membered heteroaryl, said cyclic moiety optionally being substituted by one or more moieties selected from halogen, C1-C6 alkyl, C3-C5 cycloalkyl, and $R_{8h}$O; e.g. from halogen and C1-C6 alkyl;
$R_{8b}$ and $R_{8c}$ are independently selected from H and C1-C3 alkyl;
$R_{8h}$ is H or C1-C6 alkyl;
$R_9$ is H or C1-C6 alkyl; or
$R_{10}$ is H or C1-C3 alkyl;
and any alkyl is saturated or unsaturated, in particular saturated, and is optionally substituted by one or more F.

In some embodiments, the compound is as represented by formula (Im), or a pharmaceutically acceptable salt thereof, wherein
m is 1 or 2;
n is 2 or 3;
p is 0 or 1;
$R_1$ is C1-C6 alkyl or $R_{1a}$—CH$_2$—;
$R_{1a}$ is a cyclic moiety selected from phenyl and 5- or 6-membered heteroaryl, said cyclic moiety optionally being substituted by one or more $R_{1b}$;
each $R_{1b}$ is independently selected from halogen, C1-C6 alkyl, $R_{1c}$O—; and two $R_{1b}$ attached to adjacent atoms of the cyclic moiety may form, together with the atoms to which they are attached, a 5- or 6-membered ring;
each $R_{1c}$ is independently selected from H and C1-C6 alkyl;
$R_2$ is H;
$R_3$ is Cl or Br;
W is a direct bond, O, $R_{w1}R_{w2}$, or NR$_{w3}$; in particular W is O or NR$_{w3}$;

$R_{w1}$ and $R_{w2}$ are independently selected from H and C1-C3 alkyl;

$R_{w3}$ is H or C1-C3 alkyl;

v is 1;

$R_5$ and $R_6$ are independently selected from H and C1-C3 alkyl; in particular $R_5$ and $R_6$ are independently selected from H and $CH_3$; or both are H;

k is 0;

Z—$R_8$ is $C(O)NR_8R_9$ or $NR_{10}C(O)R_8$;

q is 0 or 1;

$R_{8a}$ is a cyclic moiety selected from phenyl and 5- or 6-membered heteroaryl, in particular 5- or 6-membered heteroaryl, said cyclic moiety optionally being substituted by one or more moieties selected from halogen and C1-C6 alkyl;

$R_{8b}$ and $R_{8c}$ are independently selected from H and C1-C3 alkyl;

$R_9$ is H or C1-C6 alkyl; or $R_{10}$ is H or C1-C3 alkyl;

and any alkyl is saturated, and is optionally substituted by one or more F.

In some embodiments of a compound of formula (Im), n is 2, i.e. the compound also is a compound of formula (Ia). In some embodiments, a compound of formula (Im) also is a compound of formula (Ia1). In some embodiments, a compound of formula (Im) also is a compound of formula (Ib1), e.g. of formula (Ip).

In some embodiments, a compound of formula (Im) also is a compound of formula (Ie).

In some embodiments, the compound of formula (Im) also is a compound of formula (In).

For example, in some particular embodiments of a compound of formula (Im), m is 2;

n is 2;

p is 0;

$R_1$ is C1-C6 alkyl or $R_{1a}$—$CH_2$—;

$R_{1a}$ is a cyclic moiety selected from phenyl and 5- or 6-membered heteroaryl, said cyclic moiety optionally being substituted by one or more $R_{1b}$;

each $R_{1b}$ is independently selected from halogen, C1-C6 alkyl, $R_{1c}O$—; and two $R_{1b}$ attached to adjacent atoms of the cyclic moiety may form, together with the atoms to which they are attached, a 5- or 6-membered ring;

each $R_{1c}$ is independently selected from H and C1-C6 alkyl;

$R_2$ is H;

$R_3$ is Cl or Br;

W is a direct bond, O, $R_{w1}R_{w2}$, or $NR_{w3}$; in particular W is O or $NR_{w3}$;

$R_{w1}$ and $R_{w2}$ are independently selected from H and C1-C3 alkyl; e.g. from H and $CH_3$;

$R_{w3}$ is H or C1-C3 alkyl; e.g. H and $CH_3$;

v is 1;

$R_5$ and $R_6$ are independently selected from H and C1-C3 alkyl; in particular $R_5$ and $R_6$ are independently selected from H and $CH_3$; or both are H;

k is 0;

Z—$R_8$ is $C(O)NR_8R_9$;

q is 0 or 1;

$R_{8a}$ is a cyclic moiety selected from phenyl and 5- or 6-membered heteroaryl, in particular 5- or 6-membered heteroaryl, said cyclic moiety optionally being substituted by one or more moieties selected from halogen and C1-C6 alkyl;

$R_{8b}$ and $R_{8c}$ are independently selected from H and C1-C3 alkyl;

$R_9$ is H or C1-C6 alkyl;

and any alkyl is saturated, and is optionally substituted by one or more F.

In some of the above embodiments, the compound is a compound of formula (If), e.g. of formula (Ig), e.g. of formula (Ih) or (Ii). In some other of the above embodiments of a compound of formula (Im), $R_1$ is C1-C6 alkyl, or C1-C4 alkyl, or C1-C3 alkyl, or $CH_3$.

In some embodiments of a compound of formula (I), each $R_{8b}$ is independently selected from H and $CH_3$;

each $R_{8c}$ is independently selected from H and $CH_3$;

$R_{8d}$ is C1-C3 alkyl;

$R_{8e}$ and $R_{8f}$ are independently selected from C1-C3 alkyl; or $R_{8e}$ and $R_{8f}$ together with the nitrogen atom to which they are both attached, form a 5- or 6 membered heterocyclyl optionally containing a further heteroatom in the ring;

$R_{8g}$ is H or C1-C6 alkyl;

$R_{8h}$ is C1-C3 alkyl;

$R_9$ is H or $CH_3$; or $R_{10}$ is H or $CH_3$.

In some embodiments of a compound of formula (I), each $R_{8b}$ is H;

each $R_{8c}$ is H;

$R_{8d}$ is C1-C3 alkyl;

$R_{8e}$ and $R_{8f}$ are independently selected from C1-C3 alkyl; or $R_{8e}$ and $R_{8f}$ together with the nitrogen atom to which they are both attached, form a 5- or 6 membered heterocyclyl optionally containing a further heteroatom in the ring;

$R_{8g}$ is H or C1-C3 alkyl;

$R_{8h}$ is $CH_3$; and $R_9$ is H or $CH_3$; or $R_{10}$ is H or $CH_3$.

Some compounds of formula (I) may exist as different optical isomers. In some embodiments, when the compound of formula (I) exists as an R and an S isomer, the compound is provided as an R isomer. In some other embodiments, when the compound of formula (I) exists as an R and an S isomer, the compound is provided as an S isomer.

As noted herein, in any embodiment, any alkyl is unsaturated or saturated, unless otherwise specified or apparent from the context. However, preferably, any alkyl is saturated alkyl, and in some embodiments, every alkyl is saturated unless otherwise specifically indicated.

As already pointed out herein above, and unless the contrary is apparent from the context or specified, any reference herein to a compound of formula (I) also should be construed as a reference to a compound of any of the embodiments thereof, e.g. the embodiments illustrated in any of the formulas (Ia) to (Iy). Furthermore, the compound of any one of the formulas (Ia), (Ia1), (Ia2) etc. may exist either as the para-regioisomer or the meta-regioisomer according to formulas (I') and (I'').

Therefore, in some embodiments, a compound according to any one of the above formulas (Ia) to (Iy) is a para-regioisomer according to formula (I'). In some other embodiments, said compound is a meta-regioisomer according to formula (I'').

The compounds of formula (I) may be prepared by the person of ordinary skill in the art, using conventional methods of chemical synthesis. The preparation of intermediates and compounds according to the present invention may in particular be illustrated by the following Schemes 1-5.

Scheme 1

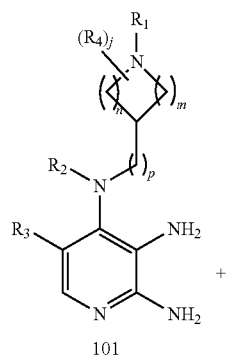
101

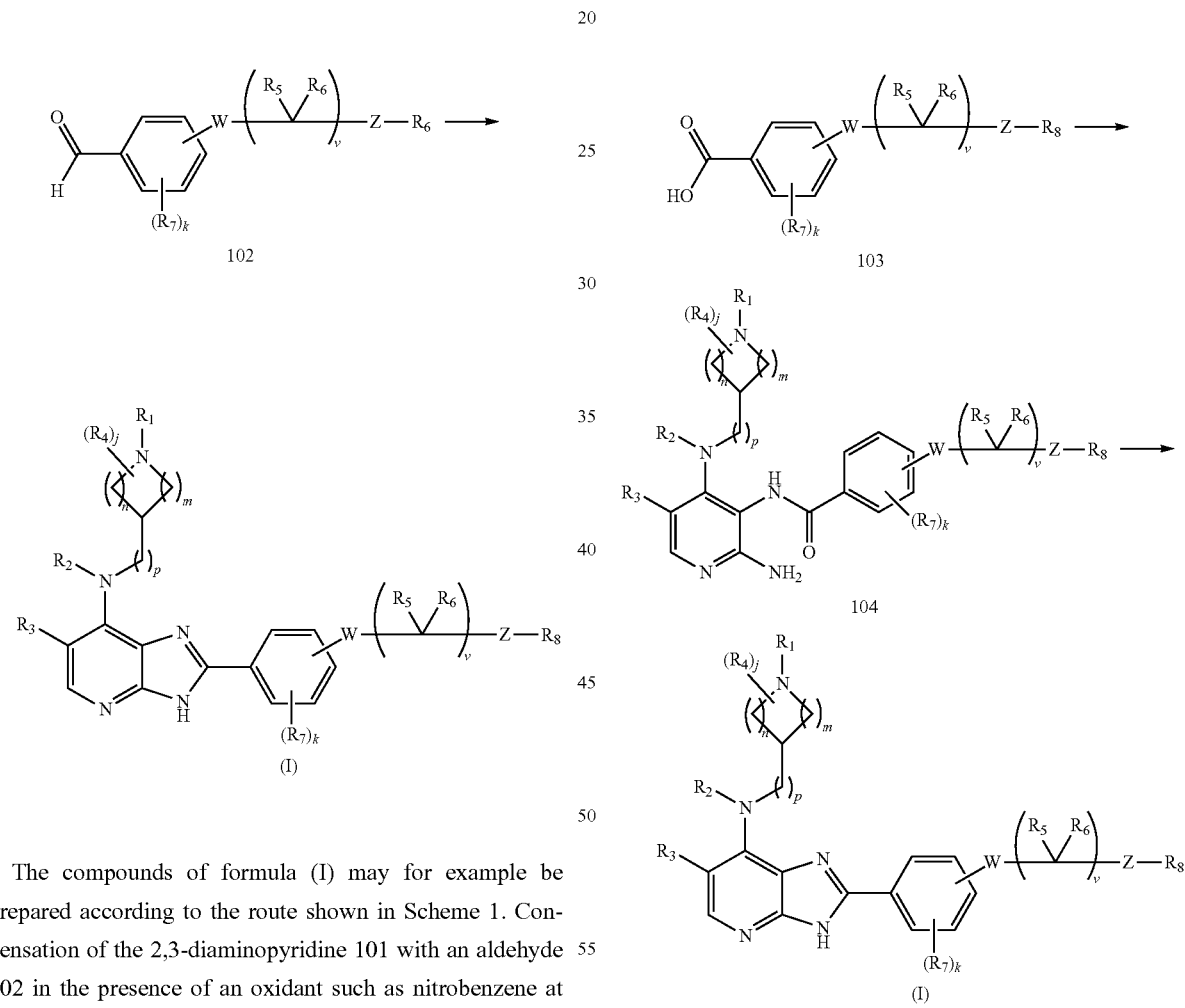

The compounds of formula (I) may for example be prepared according to the route shown in Scheme 1. Condensation of the 2,3-diaminopyridine 101 with an aldehyde 102 in the presence of an oxidant such as nitrobenzene at 150-160° C. results in the formation of imidazopyridine of formula (I) (Yadagiri, B and Lown, W J, *Synth. Communications*, 1990, 20(7), 955-963).

Alternatively, 101 and 102 can be transformed into the compound of formula (I) in the presence of air and p-toluenesulfonic acid in DMF at 80° C. (Xiangming, H, et al., *ARKIVOC*, 2007, xiii, 150-154).

Scheme 2

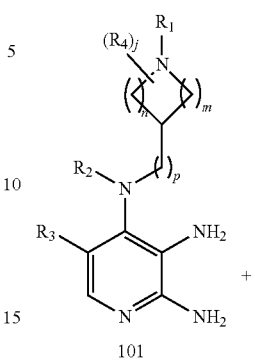
101

The synthesis of a compound of formula (I) can alternatively be achieved by the sequence shown in Scheme 2. Treatment of the 2,3-diaminopyridine 101 with an appropriate carboxylic acid 103 in the presence of a suitable coupling agent, such as 1-propanephosphonic acid cyclic anhydride or TBTU, gives the intermediate amide 104 which then is heated in acetic acid between 140-160° C. to yield the compound of formula (I).

Scheme 3

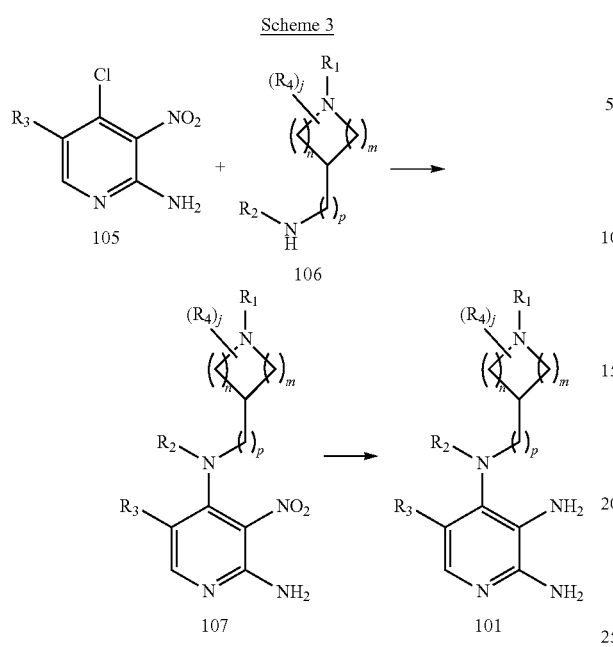

The requisite 2,3-diaminopyridines 101 can be prepared by the sequence outlined in Scheme 3. Treatment of the 4-chloro-3-nitro-2-aminopyridine 105 with an appropriate amine 106 in iso-propanol at elevated temperature generates the intermediate 107 via an aromatic nucleophilic substitution. Intermediate 107 is then easily reduced to the desired 2,3-diaminopyridine 101 by a suitable reducing agent, such as iron metal, zinc metal or $SnCl_2$ under acidic conditions.

Compounds of formula (I) may alternatively be prepared in one step starting from the intermediate 107, performing the reduction and cyclization steps in a one-pot reaction as shown in Scheme 4. Formation of compounds of formula (I) from 107 and aldehyde 102 is then accomplished with sodium dithionite in ethanol and water at 60-70° C. (Yang, D, et al., *Synthesis*, 2005, 47-56).

Scheme 4

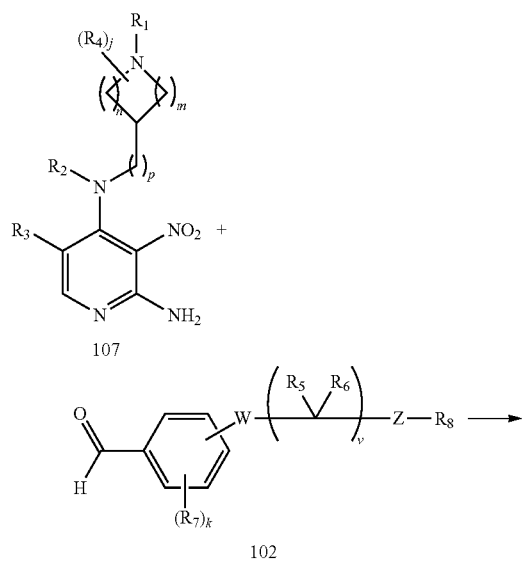

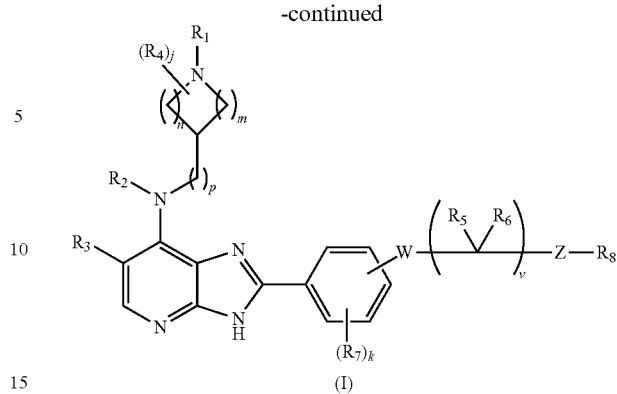

An alternative method of preparation of compounds of formula (I) is shown in Scheme 5. This method involves the introduction of the amine 106 in the last step via aromatic nucleophilic substitution of chloride in the imidazo[4,5-b]pyridine intermediate 108 at 120-160° C. in n-BuOH. (Wang, T, et al., *Bioorg. Med. Chem. Lett.*, 2012, 2063-2069).

Intermediate 108 may be prepared by the method shown in Scheme 1.

Scheme 5

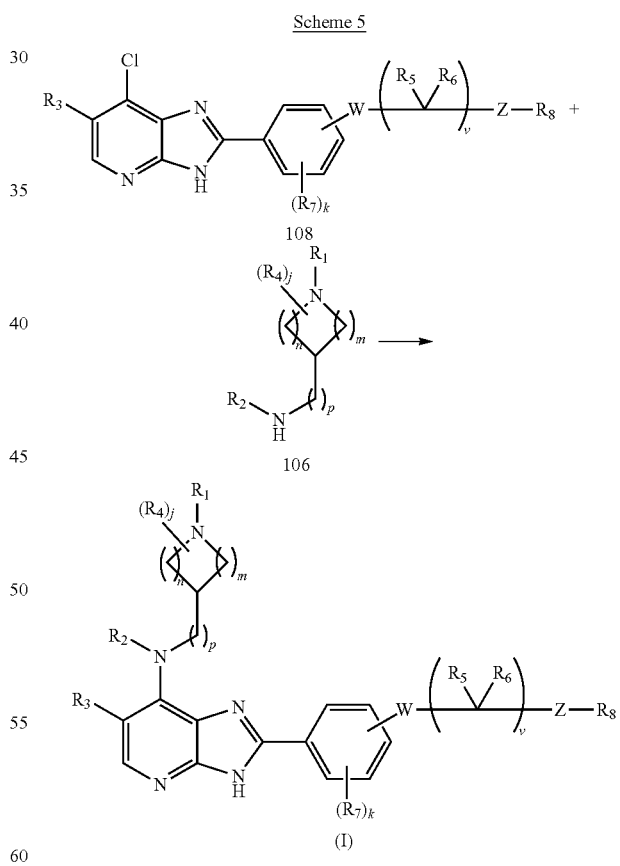

The necessary starting materials for preparation of the compounds of formula (I) are either commercially available, or may be prepared by methods known in the art.

The reactions described below in the experimental section may be carried out to give a compound of the invention in the form of a free base or as an acid addition salt. The term pharmaceutically acceptable salt of a compound refers to a salt that is pharmaceutically acceptable, as defined herein, and that possesses the desired pharmacological activity of the parent compound. A pharmaceutically acceptable acid addition salt may be obtained by dissolving the free base in a suitable organic solvent and treating the solution with an acid, in accordance with conventional procedures for preparation of acid addition salts from free bases.

Examples of addition salts include salts formed with inorganic acids, e.g. hydrochloric acid, hydrobromic acid, sulfuric acid, nitric acid, phosphoric acid; or formed with organic acids, e.g. acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, or trimethylacetic acid.

The compounds of formula (I) may possess one or more chiral carbon atoms, and may therefore be obtained in the form of optical isomers, e.g. as a pure enantiomer, or as a mixture of enantiomers (racemate) or as a mixture of diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes described herein may include, for example, solvents, reagents, catalysts, and protecting group and deprotecting group reagents. Examples of protecting groups are t-butoxycarbonyl (Boc), benzyl, trityl (triphenylmethyl) and trimethylsilyl. The methods described above may also additionally include steps, either before or after the steps described specifically herein, to add or to remove suitable protecting groups in order to ultimately allow synthesis of the compounds. In addition, various synthetic steps may be performed in an alternate sequence or order to give the desired compounds. Synthetic chemistry transformations and protecting group methodologies are known in the art and include, for example, those described in R. C. Larock, *Comprehensive Organic Transformations*, VCH Publishers (1989); L. Fieser and M. Fieser, *Fieser and Fieser's Reagents for Organic Synthesis*, John Wiley and Sons (1994); L. A. Paquette, ed., *Encyclopedia of Reagents for Organic Synthesis*, John Wiley and Sons (1995); T. H. Greene and P. G. M. Wuts, *Protective Groups in Organic Synthesis*, $3^{rd}$ Ed., John Wiley and Sons (1999); and P. J. Kocieński, *Protecting Groups*, Georg Thieme Verlag, (2000) and subsequent editions thereof.

The present invention includes pharmaceutical compositions comprising at least one compound according to formula (I), or an individual isomer, racemic or non-racemic mixture of isomers or a pharmaceutically acceptable salt thereof, together with at least one pharmaceutically acceptable excipient, e.g. a carrier, and optionally other therapeutic and/or prophylactic ingredients.

A pharmaceutical composition according to the invention may be for topical (local) or systemic administration, e.g. for enteral administration, such as rectal or oral administration, or for parenteral administration to a mammal (especially a human), and comprises a therapeutically effective amount of a compound according to the invention or a pharmaceutically acceptable salt thereof, as active ingredient, in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, the disease to be treated and the mode of administration.

For enteral, e.g. oral, administration, the compounds of the invention may be formulated in a wide variety of dosage forms. The pharmaceutical compositions and dosage forms may comprise a compound or compounds of the present invention or pharmaceutically acceptable salt(s) thereof as the active component. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The formulation of the active compound may comprise an encapsulating material as carrier, providing a capsule in which the active component, with or without carriers, is surrounded by a carrier, which is in association with it.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compounds of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intratumoral, intracutaneous and subcutaneous injection or infusion.

Thus, for parenteral administration, the pharmaceutical compositions of the invention may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant. Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and cholorobutanol.

For inhalation or nasal administration, suitable pharmaceutical formulations are as particles, aerosols, powders, mists or droplets, e.g. with an average size of about 10 µm in diameter or less. For example, compositions for inhalation may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of the invention also may be administered topically, to the skin or to a mucous membrane. For topical application, the pharmaceutical composition may be e.g. a lotion, a gel, a paste, a tincture, a transdermal patch, a gel for transmucosal delivery.

The composition may be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene compound, emulsifying wax and water. Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water. The pharmaceutical compositions of this invention may also be topically applied to the lower intestinal tract by rectal suppository formulation or in a suitable enema formulation. Suitable pharmaceutical excipients, e.g. carriers, and methods of preparing pharmaceutical dosage forms are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient. In general, the compounds of the invention will be administered in a therapeutically effective amount by any of the accepted modes of administration for agents that serve similar utilities. Suitable daily dosages typically ranges from 1 to 1000 mg, e.g. 1-500 mg daily, or 1-50 mg daily, depending upon numerous factors such as the severity of the disease to be treated, the age and relative health of the patient, the potency of the compound used, the route and form of administration, and the indication towards which the administration is directed, etc. One of ordinary skill in the art of treating such diseases will be able, without undue experimentation and in reliance upon personal knowledge and the disclosure of this application, to ascertain a therapeutically effective amount of the compounds of the present invention for a given disease. Compounds of the invention may be administered as pharmaceutical formulations including those suitable for enteral or parenteral administration. The preferred manner of administration is generally oral using a convenient daily dosage regimen which can be adjusted according to the degree of affliction.

The compound of formula (I), as defined herein, or a pharmaceutically acceptable salt thereof, may be used in the treatment of a condition or disorder in which the modulation of the activity of mammalian, e.g. human, tyrosine kinase ROR1 is beneficial, e.g. a malignant hyperproliferative disorder, an obesity-associated metabolic complication, an autoimmune disorder or an inflammatory condition, as well as in a method for manufacturing a medicament in the treatment of such a disorder or condition.

In some embodiments, the compound of formula (I), or the pharmaceutically acceptable salt thereof, may be used in the treatment of a malignant hyperproliferative disorder or in a method for manufacturing a medicament in the treatment of such a disorder or condition.

In some embodiments, the compound of formula (I), as defined herein, or the pharmaceutically acceptable salt thereof, may be used in the treatment of a obesity-associated metabolic complication as well as in a method for manufacturing a medicament in the treatment of such a disorder or condition.

In some embodiments, the compound of formula (I), as defined herein, or the pharmaceutically acceptable salt thereof, may be used in the treatment of an autoimmune disorder as well as in a method for manufacturing a medicament in the treatment of such a disorder or condition.

In some embodiments, the compound of formula (I), as defined herein, or the pharmaceutically acceptable salt thereof, may be used in the treatment of an inflammatory disorder as well as in a method for manufacturing a medicament in the treatment of such a disorder or condition.

The invention will now be further illustrated by the following non-limiting examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent. All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The following abbreviations are used herein:

| n-BuOH | n-Butanol |
|--------|-----------|
| DCE    | 1,2-Dichloroethane |
| DCM    | Dichloromethane |
| DIPEA  | N,N-diisopropylethylamine |

-continued

| | |
|---|---|
| n-BuOH | n-Butanol |
| DMF | N,N-dimethylformamide |
| DMSO | Dimethyl sulfoxide |
| ESI | Electrospray ionization |
| EtOAc | Ethyl acetate |
| EtOH | Ethanol |
| HPLC | High Performance Liquid Chromatography |
| IPA | iso-Propanol |
| MeOH | Methanol |
| MS | Mass Spectrometry |
| NBS | N-Bromosuccinimide |
| NCS | N-Chlorosuccinimide |
| NMR | Nuclear Magnetic Resonance |
| T3P | 1-Propanephosphonic acid cyclic anhydride |
| TFA | Trifluoroacetic acid |

Examples and Intermediate Compounds

Experimental Methods $^1$H NMR and $^{13}$C NMR spectra were recorded on a Varian Inova 600 equipped with a triple resonance cold probe. All spectra were recorded using the residual solvent proton resonance or tetramethylsilane (TMS) as internal standard. Analytical HPLC was carried out on an Agilent Series 1100 system using either an ACE C8 (3 μm, 3.0×50 mm) column with 0.1% TFA in MilliQ H$_2$O/CH$_3$CN as mobile phase (Acidic system) or an XTerra (3.5 μm 3.0×50 mm) column with 10 mM pH10 NH$_4$HCO$_3$/CH$_3$CN as mobile phase (Basic system). Electrospray mass spectrometry (ES-MS) was performed using an Agilent 1100 Series Liquid Chromatograph/Mass Selective Detector (MSD) to obtain the pseudo molecular [M+H]$^+$ ion of the target molecules. Preparative HPLC was performed on a Gilson 306 HPLC system using either an ACE C8 (5 μm, 21×50 mm) column with 0.1% TFA in MilliQ H$_2$O/CH$_3$CN as mobile phase (Acidic system) or an XTerra Prep MS C18 (5 μm, 19×50 mm) column with 50 mM pH10 NH$_4$HCO$_3$/CH$_3$CN as mobile phase (Basic system). Fractions were collected based on the UV-signal at 254 nm. Preparative flash chromatography was performed on Merck silica gel 60 (230-400 mesh) or YMC gel 120 Å S-150 μm. Microwave reactions were performed with a Biotage Initiator instrument using 0.5-2 mL or 2-5 mL Biotage Process Vials fitted with aluminum caps and septa. The compounds were named using the software ACD Labs 10.0.

Intermediate 1

4,5-Dichloropyridin-2-amine

To a solution of 4-chloropyridine-2-amine (50.00 g, 0.389 mol) in EtOAc (400 mL) was added N-chloro succinimide (53.50 g, 0.401 mol) in one portion. The mixture was stirred over night (28 h) at room temperature, and was then filtered to remove precipitated succinimide. The filtrate was washed with aqueous 0.5M NaOH (8×50 mL), water (2×50 mL) and brine (2×50 mL). The organic phase was dried (Na$_2$SO$_4$), filtered and evaporated to furnish 59.4 g of crude light brown powder after vacuum drying. The dry isolated crude (with a purity of ca. 75% of the title compound) was slurried in hexane (800 mL) and stirred at reflux temperature for 15 min. The mixture was allowed to cool to 35° C. and was then filtered using a G3 glass frit filter. The filter cake was washed with hexane (ca. 200 mL) and dried on the filter to furnish 42.1 g (66%) of brown solid. The product was pure enough (96%) to be taken to the next step. $^1$H NMR (600 MHz, DMSO-d$_6$) δ ppm 8.02 (s, 1H) 6.65 (s, 1H) 6.42 (s, 2H). MS: (ESI+) m/z 163, 165, 167 [M+H]$^+$, di-chlorine isotopic pattern.

Intermediate 2

4,5-Dichloro-N-nitropyridine-2-amine 4,5-Dichloropyridin-2-amine (INTERMEDIATE 1, 45.2 g, 283.0 mmol) was added to 270 mL of ice cold conc. H$_2$SO$_4$, in small portions over ca 20 min. When dissolved, conc. HNO$_3$ (22 g) was added dropwise and the mixture was stirred at ca 5° C. for 3.5 h. LCMS indicated total conversion to expected product. The cold mixture was poured on crushed ice/water mixture (3 L), stirred for ca 5 min and then filtered. The solid was collected and slurried in ice cold water (500 mL) and filtered. The procedure was repeated until neutral pH. When semi dry on the filter, the solid was dissolved in EtOAc (ca. 3 L), washed with brine (ca. 100 mL) and the organic layer was dried with Na$_2$SO$_4$, filtered, and evaporated to furnish 46.2 g (78%) of 97% pure title product as beige-orange solid. $^1$H NMR (600 MHz, CD$_3$OD) δ ppm 8.47 (s, 1H) 8.08 (s, 1H). MS: (ESI$^+$) m/z 208, 210, 212 [M+H]$^+$, di-chlorine isotopic pattern.

Intermediate 3

4,5-Dichloro-3-nitropyridine-2-amine 4,5-Dichloro-N-nitropyridin-2-amine (INTERMEDIATE 2, 20.0 g, 96.2 mmol) was added to 200 mL of conc. H$_2$SO$_4$ at room temperature. After stirring at 40° C. for 2.5 h the mixture was cooled to below room temperature and poured onto crushed ice (2 L) while stirring. After the ice had melted, the volume was adjusted to ca. 2 L with ice cold water and the yellow precipitate was collected by filtration and washed with ice cold water until neutral pH (3×250 mL). The solid was allowed to semi-dry on the filter and was then dissolved in EtOAc (ca. 800 mL). The organic phase was washed with 0.25 M NaOH (3×30 mL), water (3×15 mL) and brine (15 mL), dried (Na$_2$SO$_4$), filtered and the solvent evaporated to furnish 11.7 g (59%) of 99% pure title product as yellow solid. $^1$H NMR (600 MHz, CD$_3$OD) δ ppm 8.26 (s, 1H). MS: (ESI+) m/z 208, 210, 212 [M+H]$^+$ chlorine isotopic pattern.

Intermediate 4

4,5-Dichloropyridine-2,3-diamine

To a mixture of 4,5-dichloro-3-nitropyridine-2-amine (INTERMEDIATE 3, 1.00 g, 4.81 mmol) in EtOH (15 mL), water (1 mL) and MeOH (2 mL) was added Fe(s) (1.47 g, 26.3 mmol, 5.46 equiv.) and conc. HCl (3 drops). The mixture was stirred at 80° C. LCMS indicated total conversion to the title product after 90 min. The mixture was allowed to cool to room temperature and aqueous 15% NaOH (6 drops) was added and the mixture was stirred for 15 minutes and then centrifuged resulting in a clear solution. The supernatant was collected and the solid centrifugate was washed with MeOH (10 mL) and centrifuged. The combined supernatants were filtered through a 0.45μ filter and the filtrate was evaporated to furnish 790 mg (92%) of title product as beige solid. $^1$H NMR (600 MHz, CD$_3$OD) δ ppm 7.40 (s, 11H). MS (ESI+) m/z 178, 180 [M+H]$^+$ chlorine isotopic pattern.

Intermediate 5

5-Bromo-4-chloropyridin-2-amine

The title product was prepared by the same procedure as the one used for 4,5-dichloropyridin-2-amine (INTERMEDIATE 1), with the exception that NCS was exchanged for NBS. $^1$H NMR (600 MHz, CD$_3$OD) δ ppm 8.03 (s, 1H) 6.73 (s, 1H). MS (ESI+) m/z 207, 209, 211 [M+H]$^+$ bromine-chlorine isotopic pattern.

Intermediate 6

5-Bromo-4-chloro-N-nitropyridin-2-amine

The title product was prepared by the same procedure as the one used for 4,5-dichloro-N-nitropyridin-2-amine (INTERMEDIATE 2). $^1$H NMR (600 MHz, CDCl$_3$) δ ppm 8.49 (s, 1H) 8.06 (s, 1H). MS (ESI$^+$) m/z 252, 254, 256 [M+H]$^+$, bromine-chlorine isotopic pattern.

Intermediate 7

5-Bromo-4-chloro-3-nitropyridin-2-amine

The title product was prepared by the same procedure as the one used for 4,5-dichloro-3-nitropyridin-2-amine (INTERMEDIATE 3). $^1$H NMR (600 MHz, CDCl$_3$) δ ppm 8.36 (s, 1H) 5.82 (br. s., 2H). MS (ESI$^+$) m/z 252, 254, 256 [M+H]$^+$, bromine-chlorine isotopic pattern.

Intermediate 8

N-[2-(Dimethylamino)ethyl]-2-(4-formylphenoxy)acetamide

To a 100 mL round bottomed flask charged with SOCl$_2$ (3.08 g, 25.9 mmol) and DCM (50 mL) was added 4-formylphenoxyacetic acid (3.11 g, 17.3 mmol) slowly as a powder at room temperature followed by a catalytic amount of DMF (200 μL). The inhomogeneous mixture was heated at reflux. The mixture had turned homogeneous after 3 h and was allowed to cool to room temperature. The mixture was then chilled in an ice bath and 2-dimethylaminoethyl-amine (1.98 g, 22.4 mmol)) and DIPEA (2.9 g, 22.4 mmol) in DCM (20 mL) were added dropwise at 0-5° C. The reaction was allowed to stir for two days. The organic phase was washed with sat. NaHCO$_3$ (3×10 mL), water (10 mL) and brine (10 mL). The combined aqueous wash phases were treated with sat.Na$_2$CO$_3$ (20 mL) and re-extracted with DCM (2×100 mL). The combined organic layers were dried (MgSO$_4$), filtered and evaporated to furnish 3.11 g (72%) of brown oil. The crude product was further purified by flash chromatography (silica, 8% MeOH in CHCl$_3$ containing 0.5% aqueous NH$_3$). Pure fractions were combined furnishing 2.5 g (58%) of pure title product as amber oil. $^1$H NMR (600 MHz, CD$_3$OD) δ ppm 9.87 (s, 1H) 7.90 (d, J=8.85 Hz, 2H) 7.17 (d, J=8.85 Hz, 2H) 4.64 (s, 2H) 3.43 (t, J=6.71 Hz, 2H) 2.50 (t, J=6.56 Hz, 2H) 2.28 (s, 6H). MS (ESI$^+$) m/z 251 [M+H]$^+$.

Intermediate 9

2-[4-(6,7-Dichloro-3H-imidazo[4,5-b]pyridin-2-yl)phenoxy]-N-[2-(dimethylamino)-ethyl]acetamide 4,5-Dichloropyridine-2,3-diamine (INTERMEDIATE 4, 170 mg, 0.96 mmol), p-toluenesulfonic acid (18 mg, 0.10 mmol) and N-[2-(dimethylamino)ethyl]-2-(4-formylphenoxy)acetamide (INTERMEDIATE 8, 234 mg, 0.96 mmol) were dissolved in DMF (4 mL) and the light brown mixture was stirred vigorously in a large test tube without cap at 80° C. for five days. More toluenesulfonic acid (18 mg, 0.10 mmol) was added after three and four days respectively. After cooling to room temperature water (6 mL) was added, followed by sat. NaHCO$_3$ (2 mL). The mixture was extracted with EtOAc (3×30 mL) and the combined organic phases were washed with water (3 mL) and brine (3 mL). The solvent was evaporated to yield 263 mg of crude product. The crude material was triturated with small portions of EtOAc twice. After each trituration the sample was centrifuged and the supernatant discarded. Finally the material was dried in a vacuum desiccator to afford 198 mg (51%) of title product as light tan solid. $^1$H NMR (600 MHz, DMSO-d$_6$) δ ppm 8.42 (s, 1H) 8.21 (d, J=8.8 Hz, 2H) 8.05 (t, J=5.3 Hz, 1H) 7.15 (d, J=8.9 Hz, 2H) 4.59 (s, 2H) 3.24 (q, J=6.4 Hz, 2H) 2.34 (t, J=6.7 Hz, 2H) 2.16 (s, 6H). MS (ESI$^+$) m/z 408 [M+H]$^+$.

HPLC-MS and $^1$H NMR revealed that the product was contaminated with ca. 10% of the des-chloro isomer, 2-[4-(6-chloro-3H-imidazo[4,5-b]pyridin-2-yl)phenoxy]-N-[2-(dimethylamino)ethyl]acetamide. The material was, however, used in the next step without further purification.

Intermediate 10

N,N-2-Trimethyl-2-nitropropanamine

To a stirred ice cold solution of 2-nitropropane (10.0 g, 112 mmol) and 40% aqueous dimethylamine (12.6 mL, 1 equiv, 112 mmol) was added drop wise a 37% solution of formaldehyde (24.3 mL, 1 equiv, 112 mmol) over 20 min. Stirring was continued to a full hour. The flask was removed from the ice bath and stirred at room temperature for 1 h. The reaction was then heated at 50° C. for 1 h. The cooled reaction mixture was extracted with diethyl ether (3×100 mL), and the combined organic phases washed with water (2×100 mL) and brine (100 mL). The organic layer was dried over Na$_2$SO$_4$, filtered and concentrated under vacuum at 20° C. to furnish 14.1 g of pale yellow oil. The crude material was distilled in a kugelrohr apparatus at 85-90° C. mantle temperature and 1 mm Hg, yielding 14.1 g, (86%) of the title product. The material was used without further purification for in the next step. $^1$H NMR (600 MHz, CDCl$_3$) δ ppm 2.83 (s, 2H) 2.25 (s, 6H) 1.55 (s, 6H). MS (ESI$^+$) m/z 147 [M+H]$^+$.

Intermediate 11

N$^1$,N$^1$,2-Trimethylpropane-1,2-diamine

To ice cold conc. HCl (30 mL, 360 mmol) was added N,N,2-trimethyl-2-nitropropan-1-amine (INTERMEDIATE 10, 4.0 g, 27.6 mmol). The mixture was stirred for 2 min and then Zn (10 g, 152 mmol) was added in small portions over 45 minutes. Initially the mixture turned white-cloudy. When approximately 60% of the Zn was added, the mixture stayed metal-gray. After all of the Zn was added the mixture was stirred overnight at room temperature. The reaction mixture was cooled with an ice bath, and solid NaOH pellets were added in small portions until pH>12 was obtained. Water (10-20 mL) was added to the viscous mixture which was then extracted with diethyl ether (4×40 mL). The combined organic phases were dried over $Na_2SO_4$, and the organic phase was added via a dropping funnel to a Claisen distillation apparatus. The ether was removed at a bath temperature of ca 55-60° C. When all of the solvent was removed, the bath temperature was increased to 135-140° C., and after a short fore run, 2.4 g (76%) of pure title product was collected at 117-122° C. $^1$H NMR (600 MHz, $CDCl_3$) δ ppm 2.33 (s, 6H) 2.18 (s, 2H) 1.91 (br. s., 2H) 1.07 (s, 6H). MS ($ESI^+$) m/z 117 $[M+H]^+$.

Intermediate 12

N-[2-(Dimethylamino)-1,1-dimethylethyl]-2-(4-formylphenoxy)acetamide

The title product was prepared according to the procedure used for INTERMEDIATE 8, using $N^1,N^1$,2-trimethylpropane-1,2-diamine (INTERMEDIATE 11) and 4-formylphenoxyacetic acid. $^1$H NMR (600 MHz, $CD_3OD$) δ ppm 9.87 (s, 1H) 7.90 (d, J=8.9 Hz, 2H) 7.15 (d, J=8.9 Hz, 2H) 4.58 (s, 2H) 2.58 (s, 2H) 2.31 (s, 6H) 1.36 (s, 6H). MS ($ESI^+$) m/z 279 $[M+H]^+$.

Intermediate 13

2-[4-(6,7-Dichloro-3H-imidazo[4,5-b]pyridin-2-yl)phenoxy]-N-[2-(dimethylamino)-1,1-dimethylethyl]acetamide The title product was prepared according to the procedure used for INTERMEDIATE 9, using N-[2-(dimethylamino)-1,1-dimethylethyl]-2-(4-formylphenoxy)acetamide (INTERMEDIATE 12), 4,5-dichloropyridine-2,3-diamine (INTERMEDIATE 4) and p-toluenesulfonic acid (1 eq). $^1$H NMR (600 MHz, DMSO-$d_6$) δ ppm 8.36 (s, 1H) 8.20 (d, J=8.9 Hz, 2H) 7.46 (s, 1H) 7.11 (d, J=8.9 Hz, 2H) 4.53 (s, 2H) 2.44 (s, 2H) 2.22 (s, 6H) 1.27 (s, 6H). MS (ESI+) m/z 436 $[M+H]^+$.

Intermediate 14

2-(4-Formylphenoxy)-N-methylacetamide

The title product was prepared according to the procedure used for INTERMEDIATE 8, using $MeNH_2$ (2M in THF) and 4-formylphenoxyacetic acid. $^1$H NMR (600 MHz, DMSO-$d_6$) δ ppm 9.88 (s, 1H) 8.11 (br. s., 1H) 7.88 (d, J=8.55 Hz, 2H) 7.14 (d, J=8.54 Hz, 2H) 4.60 (s, 2H) 2.66 (d, J=4.88 Hz, 3H). MS (ESI+) m/z 194 $[M+H]^+$.

Intermediate 15

2-[4-(6,7-Dichloro-3H-imidazo[4,5-b]pyridin-2-yl)phenoxyl]-N-methylacetamide

The title product was prepared according to the procedure used for INTERMEDIATE 9, using 2-(4-formylphenoxy)-N-methylacetamide (INTERMEDIATE 14, 267 mg, 1.5 mmol)), 4,5-dichloropyridine-2,3-diamine (INTERMEDIATE 4, 290 mg, 1.5 mmol)) and p-toluenesulfonic acid (285 mg, 1.5 mmol) in DMF (5 mL). After cooling to room temperature the product precipitated in the DMF solvent and was isolated by centrifugation. The supernatant was removed and the remaining solid was washed with EtOAc (2×1 mL) and centrifuged again after each cycle. The solid was dried in vacuum to yield 223 mg (42%) of 94% pure title product as pale beige solid. The material was taken to the next step without further purification. $^1$H NMR (600 MHz, DMSO-$d_6$) δ ppm 13.91 (br. s., 1H) 8.43 (s, 1H) 8.20 (d, J=8.5 Hz, 2H) 8.10 (d, J=4.3 Hz, 1H) 7.16 (d, J=8.9 Hz, 2H) 4.59 (s, 2H) 2.67 (d, J=4.6 Hz, 3H). MS (ESI+) m/z 351 $[M+H]^+$.

Intermediate 16

2-Dimethylamino-2-methyl-propionitrile

The title product was prepared according to the procedure described in J. W. Stanley, J. G. Beasley and I. W. Mathison, J. Org. Chem., 37 (23), 3746-3748, 1972.

Acetone cyanohydrin (8.51 g, 100 mmol) was slowly added to an ice-cold stirred solution of $Me_2NH$ (4.51, 100 mmol) in acetone (20 mL). After 2 h the acetone was evaporated (19-20° C. bath temperature) and the residue was extracted with $Et_2O$ (2×85 mL). The combined organic phases were washed with brine (7 mL) and dried over $Na_2SO_4$. The solvent was distilled off at atmospheric pressure to yield 11.387 g of title product as colorless liquid. $^1$H NMR (600 MHz, $CDCl_3$) δ ppm 2.37 (s, 6H) 1.51 (s, 6H).

The NMR spectrum showed that a small amount of acetone was present in the product. The material was, however, used in the next step without further purification.

Intermediate 17

$N^2,N^2$,2-Trimethylpropane-1,2-diamine dihydrochloride

To a stirred ice-cold slurry of $LiAlH_4$ (2.28 g, 60 mmol) in dry $Et_2O$ (50 mL) was added dropwise 2-dimethyl-amino-2-methyl-propionitrile (INTERMEDIATE 16, 3.37 g, 30 mmol) in dry $Et_2O$ (40 mL). The mixture was allowed to reach room temperature after 3.5 h and after 4 h $Et_2O$ (50 mL) was added followed by dropwise addition of sat. $Na_2CO_3$ until no bubbling was observed. The mixture was stirred overnight to give a fine white precipitate in the ether phase. Solid anhydrous $Na_2SO_4$ was added and the mixture was stirred for 30 min and was then filtered through a pad of Celite, which was washed with $Et_2O$. To the clear and colorless filtrate 1M HCl in $Et_2O$ (65 mL) was added. Precipitation of white solid occurred. The free flowing solids and $Et_2O$ were transferred to 50 mL Falcon tubes which were centrifuged. The supernatant was removed by pipette and the residue was dried in vacuum to yield 2.43 g of title product as white solid.

There was a brownish oily residue in the bottom of the flask which was treated with $Et_2O$ and sonicated to produce another 1.82 g of off-white solid material. $^1$H NMR showed only the desired product in excellent purity for both batches. Total yield: 4.25 g (75%). $^1$H NMR (600 MHz, $CD_3OD$) δ ppm 3.42 (s, 2H) 2.90 (s, 6H) 1.53 (s, 6H).

Intermediate 18

N-[2-(Dimethylamino)-2-methylpropyl]-2-(4-formylphenoxy)acetamide

The title product was prepared according to the procedure used for INTERMEDIATE 8, using $N^2,N^2$,2-trimethylpropane-1,2-diamine dihydrochloride (INTERMEDIATE 17), DIPEA (2.6 equivalents) and 4-formylphenoxyacetic acid. $^1$H NMR (600 MHz, CD$_3$OD) δ ppm 9.87 (s, 1H) 8.54 (s, 1H) 7.90 (d, 2H) 7.17 (d, 2H) 4.71 (s, 2H) 3.37 (s, 2H) 2.37 (s, 6H) 1.09 (s, 6H). MS (ESI+) m/z 279 [M+H]$^+$.

Intermediate 19

2-[4-(6,7-Dichloro-3H-imidazo[4,5-b]pyridin-2-yl) phenoxy]-N-[2-(dimethylamino)-2-methylpropyl] acetamide The title product was prepared according to the procedure used for INTERMEDIATE 9, using N-[2-(dimethylamino)-2-methylpropyl]-2-(4-formylphenoxy)acetamide (INTERMEDIATE 18), 4,5-dichloropyridine-2,3-diamine (INTERMEDIATE 4) and p-toluenesulfonic acid (1 eq). $^1$H NMR (600 MHz, CD$_3$OD) δ ppm 8.36 (s, 1H) 8.19 (d, J=9.16 Hz, 2H) 7.19 (d, J=8.85 Hz, 2H) 4.69 (s, 2H) 3.35 (s, 2H) 2.31 (s, 6H) 1.06 (s, 6H). MS (ESI+) m/z 436 [M+H]$^+$.

Intermediate 20

2-(4-Formylphenoxy)-N,N-dimethylacetamide

The title product was prepared according to the procedure used for INTERMEDIATE 8, using dimethyl amine (40% in water) and 4-formylphenoxyacetic acid. $^1$H NMR (600 MHz, CD$_3$OD) δ ppm 7.35 (d, J=8.85 Hz, 2H) 6.96 (d, J=8.85 Hz, 2H) 4.80 (s, 2H) 3.10 (s, 3H) 2.98 (s, 3H). MS (ESI+) m/z 208 [M+H]$^+$.

Intermediate 21

2-[4-(6,7-Dichloro-3H-imidazo[4,5-b]pyridin-2-yl) phenoxy]-N,N-dimethylacetamide The title product was prepared according to the procedure used for INTERMEDIATE 9, using 2-(4-formylphenoxy)-N,N-dimethylacetamide (INTERMEDIATE 20), 4,5-dichloropyridine-2,3-diamine (INTERMEDIATE 4) and p-toluenesulfonic acid (1 eq). $^1$H NMR (600 MHz, DMSO-d$_6$) δ ppm 13.81-13.97 (m, 1H) 8.42 (s, 1H) 8.17 (d, J=8.54 Hz, 2H) 7.11 (d, J=8.55 Hz, 2H) 4.95 (s, 2H) 3.02 (s, 3H) 2.86 (s, 3H). MS (ESI$^+$) m/z 365 [M+H]$^+$.

Intermediate 22

N$^4$-(1-Benzylpiperidin-4-yl)-5-chloro-N$^4$-methyl-3-nitropyridine-2,4-diamine To a slurry of 4,5-dichloro-3-nitropyridine-2-amine (INTERMEDIATE 3, 300 mg, 1.44 mmol) in IPA (6 mL) was added 1-benzyl-N-methylpiperidin-4-amine (309 mg, 1.51 mmol) and DIPEA (280 mg, 2.16 mmol, 380 μL). The mixture was stirred at 80° C. for 20 h. After cooling the solvent was evaporated and the crude residue dissolved in EtOAc (40 mL). Water (2 mL) and K$_2$CO$_3$ (ca 200 mg) were added, and the mixture was stirred for 10 min. forming clear layers. The aqueous phase was separated and the organic layer was washed with water (5×2 mL), dried over Na$_2$SO$_4$, filtered and the filtrate evaporated to furnish 531 mg (98%) of brown-yellow solid. Trituration with diethyl ether (ca 4 mL) furnished 451 mg (83%) of yellow powder. A second crop of the triturated material furnished 23 mg of brown solid, 95% pure. $^1$H NMR (600 MHz, CD$_3$OD) δ ppm 7.97 (s, 1H) 7.32 (d, J=4.58 Hz, 4H) 7.22-7.29 (m, 1H) 3.52 (s, 2H) 3.47-3.55 (m, 1H) 2.90-3.00 (m, 2H) 2.71 (s, 3H) 2.03-2.12 (m, 2H) 1.83-1.91 (m, 4H). MS (ESI$^+$) m/z 376, 378 [M+H]$^+$, chlorine isotopic pattern.

Intermediate 23

Methyl (4-{7-[(1-benzylpiperidin-4-yl)(methyl) amino]-6-chloro-3H-imidazo[4,5-b]pyridin-2-yl}phenoxy)acetate A mixture of N$^4$-(1-benzylpiperidin-4-yl)-5-chloro-N$^4$-methyl-3-nitropyridine-2,4-diamine (INTERMEDIATE 22, 376 mg, 1.0 mmol) and 4-formylphenoxyacetic acid (180 mg, 1.0 mmol) in EtOH (7 mL) was treated with a freshly prepared aqueous solution of 1.0 M Na$_2$S$_2$O$_4$ (3 mL, 3.0 mmol). The mixture was heated at 70° C. for 40 h. Upon cooling to room temperature precipitation was observed. Water (12 mL) was added which caused more precipitation. The light yellow precipitate was isolated by centrifugation. The supernatant was removed and the remaining solid was washed with several portions of water and centrifuged again after each cycle. The wet solid was dried in vacuum to yield 420 mg (83%) of essentially pure (4-{7-[(1-benzylpiperidin-4-yl)(methyl)amino]-6-chloro-3H-imidazo[4,5-b]pyridin-2-yl}phenoxy)acetic acid as light yellow solid. $^1$H NMR (600 MHz, DMSO-d$_6$) δ ppm 13.34 (br. s., 1H) 8.09 (d, J=8.9 Hz, 2H) 8.08 (s, 1H) 7.30-7.48 (m, 5H) 7.09 (d, J=8.9 Hz, 2H) 4.78 (s, 2H) 4.00 (br. s., 1H) 3.12 (s, 2H) 1.86-2.07 (m, 6H). MS (ESI$^+$) m/z 506 [M+H]$^+$.

The product from the previous step was dissolved in MeOH. A few drops of conc. H$_2$SO$_4$ were added and the mixture was heated at reflux for 3 h. The solvent was evaporated and the residue was taken up in DCM (75 mL). The organic phase was washed with sat. NaHCO$_3$ (5 mL) and brine (5 mL), dried over MgSO$_4$, and concentrated in vacuo to yield 406 mg of crude product as brown oil. The material was triturated with Et$_2$O to produce 362 mg (84%) of 90% pure title product as fine light gray solid. This material was used in the next step without further purification. $^1$H NMR (600 MHz, DMSO-d$_6$) δ ppm 8.10 (d, J=8.9 Hz, 2H) 8.04 (s, 1H) 7.29-7.36 (m, 4H) 7.22-7.26 (m, 1H) 7.10 (d, J=8.9 Hz, 2H) 4.90 (s, 2H) 3.88 (br. s., 1H) 3.72 (s, 3H) 3.47 (s, 2H) 3.14 (s, 3H) 2.90 (d, J=11.6 Hz, 2H) 2.02 (t, J=11.6 Hz, 2H) 1.91 (qd, J=11.4, 2.6 Hz, 2H) 1.82 (d, J=10.7 Hz, 2H). MS (ESI$^+$) m/z 520 [M+H]$^+$.

Intermediate 24

1-(3-Methylbenzyl)piperidin-4-amine

To a stirred mixture of 4-Boc-aminopiperidine (1001 mg, 5.0 mmol) and m-tolualdehyde (601 mg, 5.0 mmol) in DCE (30 mL) was added NaBH(OAc)$_3$ (1696 mg, 8.0 mmol). The mixture was stirred at room temperature for 22 h. Sat. NaHCO$_3$ (7 mL) was added and the mixture was stirred for 10 min. The mixture was diluted with DCM (40 mL) and the phases were separated. The organic phase was washed with sat. NaHCO$_3$ (7 mL) and brine (7 mL), dried over Na$_2$SO$_4$ and concentrated in vacuo to yield 1.414 g (93%) of tert-butyl [1-(3-methyl-benzyl)piperidin-4-yl]carbamate as off-white solid. HPLC indicated a purity of 98%. $^1$H NMR (600 MHz, CD$_3$OD) δ ppm 7.19 (t, J=7.5 Hz, 1H) 7.14 (s, 1H) 7.09 (t, J=7.8 Hz, 2H) 3.47 (s, 2H) 3.32-3.36 (m, 1H) 2.84 (d, J=11.3 Hz, 2H) 2.33 (s, 3H) 2.09 (t, J=11.3 Hz, 2H) 1.82 (d, J=11.9 Hz, 2H) 1.47 (dq, J=11.9, 2.8 Hz, 2H) 1.43 (s, 9H). MS (ESI$^+$) m/z 305 [M+H]$^+$.

The product from the previous step was dissolved in dioxane (15 mL). Conc. HCl (2 mL, 25 mmol) was added and the reaction mixture was stirred at RT for 2 h. The mixture was evaporated to a small volume and water (8 mL) was added. The resulting aqueous phase was washed with EtOAc (15 mL). The pH of the aqueous phase was adjusted with 8M NaOH to approximately pH12, and then extracted with EtOAc (3×25 mL). The combined organic phases were washed with brine (5 mL), dried over $Na_2SO_4$ and finally evaporated to yield 940 mg (92% over two steps) of pure title product as clear almost colorless oil. $^1$H NMR (600 MHz, $CD_3OD$) δ ppm 7.19 (t, J=7.6 Hz, 1H) 7.14 (s, 1H) 7.09 (t, J=8.2 Hz, 2H) 3.46 (s, 2H) 2.85 (d, J=12.2 Hz, 2H) 2.56-2.65 (m, 1H) 2.33 (s, 3H) 2.05 (td, J=11.9, 2.1 Hz, 2H) 1.79 (d, J=13.4 Hz, 2H) 1.40 (qd, J=12.0, 3.8 Hz, 2H). MS (ESI$^+$) m/z 205 [M+H]$^+$.

Intermediate 25

1-(4-Fluorobenzyl)piperidin-4-amine

The title product was prepared according to the procedure used for INTERMEDIATE 24, using 4-fluorobenzaldehyde instead of m-tolualdehyde. $^1$H NMR (600 MHz, $CD_3OD$) δ ppm 7.31-7.36 (m, 2H) 7.01-7.07 (m, 2H) 3.49 (s, 2H) 2.82-2.88 (m, 2H) 2.63 (tt, J=10.80, 4.30 Hz, 1H) 2.06 (td, J=11.90, 2.45 Hz, 2H) 1.78-1.83 (m, 2H) 1.37-1.45 (m, 2H). MS (ESI$^+$) m/z 209 [M+H]$^+$.

Intermediate 26

1-[(3-Methyl-2-thienyl)methyl]piperidin-4-amine

The title product was prepared according to the procedure used for INTERMEDIATE 24, using 3-methylthiophen-2-aldehyde instead of m-tolualdehyde. $^1$H NMR (600 MHz, $CD_3OD$) δ ppm 7.20 (d, J=4.9 Hz, 1H) 6.80 (d, J=5.2 Hz, 1H) 3.63 (s, 2H) 2.91 (d, J=12.2 Hz, 2H) 2.60 (tt, J=10.8, 4.2 Hz, 1H) 2.19 (s, 3H) 2.10 (td, J=11.7, 2.4 Hz, 2H) 1.80 (d, J=13.1 Hz, 2H) 1.41 (qd, J=11.9, 4.0 Hz, 2H). MS (ESI$^+$) m/z 211 [M+H]$^+$.

Intermediate 27

1-(4-Methylbenzyl)piperidin-4-amine

The title product was prepared according to the procedure used for INTERMEDIATE 24, using p-tolualdehyde instead of m-tolualdehyde. $^1$H NMR (600 MHz, $CD_3OD$) δ ppm 7.17-7.21 (m, 2H) 7.11-7.15 (m, 2H) 3.46 (s, 2H) 2.82-2.89 (m, 2H) 2.61 (tt, J=10.78, 4.23 Hz, 1H) 2.31 (s, 3H) 2.04 (td, J=11.98, 2.47 Hz, 2H) 1.76-1.83 (m, 2H) 1.36-1.45 (m, 2H). MS (ESI$^+$) m/z 205 [M+H]$^+$.

Intermediate 28

1-(1,3-Benzodioxol-5-ylmethyl)piperidin-4-amine

The title product was prepared according to the procedure used for INTERMEDIATE 24, using piperonal instead of m-tolualdehyde. $^1$H NMR (600 MHz, $CD_3OD$) δ ppm 6.83-6.85 (m, 1H) 6.74-6.77 (m, 2H) 5.92 (s, 2H) 3.42 (s, 2H) 2.81-2.88 (m, 2H) 2.61 (tt, J=10.83, 4.10 Hz, 1H) 2.03 (td, J=11.98, 2.29 Hz, 2H) 1.77-1.83 (m, 2H) 1.36-1.45 (m, 2H). MS (ESI$^+$) m/z 235 [M+H]$^+$.

Intermediate 29

1-(1,3-Thiazol-2-ylmethyl)piperidin-4-amine

The title product was prepared according to the procedure used for INTERMEDIATE 24, using 2-thiazolecarboxaldehyde instead of m-tolualdehyde. $^1$H NMR (600 MHz, $CD_3OD$) δ ppm 7.70 (d, J=3.4 Hz, 1H) 7.54 (d, J=3.4 Hz, 1H) 3.86 (s, 2H) 2.93 (d, J=12.2 Hz, 2H) 2.65 (tt, J=10.8, 4.3 Hz, 1H) 2.22 (td, J=11.9, 2.4 Hz, 2H) 1.83 (d, J=13.1 Hz, 2H) 1.46 (qd, J=11.9, 4.0 Hz, 2H). MS (ESI$^+$) m/z 198 [M+H]$^+$.

Intermediate 30

1-(Thiophen-3-ylmethyl)piperidin-4-amine

The title product was prepared according to the procedure used for INTERMEDIATE 24, using 3-thiophenecarboaldehyde instead of m-tolualdehyde. $^1$H NMR (600 MHz, $CD_3OD$) δ ppm 7.36 (dd, J=4.93, 2.93 Hz, 1H) 7.24 (ddt, J=2.93, 1.28, 0.74 Hz, 1H) 7.09 (dd, J=4.93, 1.28 Hz, 1H) 3.56 (s, 2H) 2.85-2.92 (m, 2H) 2.65 (tt, J=10.83, 4.30 Hz, 1H) 2.07 (td, J=11.98, 2.14 Hz, 2H) 1.79-1.86 (m, 2H) 1.39-1.48 (m, 2H). MS (ESI$^+$) m/z 197 [M+H]$^+$.

Intermediate 31

1-(4-Chlorobenzyl)piperidin-4-amine

The title product was prepared according to the procedure used for INTERMEDIATE 24, using 4-chlorobenzaldehyde instead of m-tolualdehyde. $^1$H NMR (600 MHz, $CD_3OD$) δ ppm 7.28-7.34 (m, 4H) 3.49 (s, 2H) 2.84 (d, J=12.2 Hz, 2H) 2.61 (tt, J=10.7, 4.3 Hz, 1H) 2.06 (td, J=11.9, 2.1 Hz, 2H) 1.80 (d, J=13.1 Hz, 2H) 1.40 (qd, J=11.9, 4.0 Hz, 2H). MS (ESI$^+$) m/z 225 [M+H]$^+$.

Intermediate 32

1-[(5-Methylfuran-2-yl)methyl]piperidin-4-amine

The title product was prepared according to the procedure used for INTERMEDIATE 24, using 5-methyl furfural instead of m-tolualdehyde. $^1$H NMR (600 MHz, $CD_3OD$) δ ppm 6.13 (dq, J=3.06, 0.46 Hz, 1H) 5.93 (dq, J=3.06, 1.07 Hz, 1H) 3.48 (s, 2H) 2.85-2.91 (m, 2H) 2.60 (tt, J=10.85, 4.25 Hz, 1H) 2.25 (dd, J=1.07, 0.46 Hz, 3H) 2.10 (td, J=11.95, 2.37 Hz, 2H) 1.78-1.85 (m, 2H) 1.42 (dddd, J=13.17, 11.95, 10.85, 3.90 Hz, 2H). MS (ESI$^+$) m/z 195 [M+H]$^+$.

Intermediate 33

(3S)-1-(3,4-Difluorobenzyl)pyrrolidin-3-amine

The title product was prepared according to the procedure used for INTERMEDIATE 24, using (S)-3-(Boc-amino)pyrrolidine instead of 4-Boc-aminopiperidine and 3,4-difluorobenzaldehyde instead of m-tolualdehyde. $^1$H NMR (600 MHz, $CD_3OD$) δ ppm 7.27 (ddd, J=11.60, 7.86, 2.06 Hz, 1H) 7.20 (dt, J=10.57, 8.30 Hz, 1H) 7.11-7.15 (m, 1H) 3.61 (d, J=12.97 Hz, 1H) 3.58 (d, J=12.97 Hz, 1H) 3.45 (dddd, J=8.50, 6.73, 4.88, 4.68 Hz, 1H) 2.76 (dd, J=9.70, 6.73 Hz, 1H) 2.70 (ddd, J=9.37, 8.34, 5.89 Hz, 1H) 2.52 (ddd, J=9.37, 8.21, 6.12 Hz, 1H) 2.31 (dd, J=9.70, 4.88 Hz, 1H) 2.19 (dddd, J=13.20, 8.50, 8.21, 5.89 Hz, 1H) 1.53 (dddd, J=13.20, 8.34, 6.12, 4.68 Hz, 1H). MS (ESI⁺) m/z 213 [M+H]⁺.

Intermediate 34

(3S)-1-(4-fluorobenzyl)pyrrolidin-3-amine

The title product was prepared according to the procedure used for INTERMEDIATE 24, using (S)-3-(Boc-amino) pyrrolidine instead of 4-Boc-aminopiperidine and 4-fluorobenzaldehyde instead of m-tolualdehyde. ¹H NMR (600 MHz, CD₃OD) δ ppm 7.32-7.37 (m, 2H) 7.02-7.07 (m, 2H) 3.61 (d, J=12.66 Hz, 1H) 3.58 (d, J=12.66 Hz, 1H) 3.44 (dddd, J=8.54, 6.75, 5.15, 4.77 Hz, 1H) 2.78 (dd, J=9.77, 6.75 Hz, 1H) 2.69 (ddd, J=9.34, 8.51, 6.00 Hz, 1H) 2.53 (ddd, J=9.34, 8.24, 6.05 Hz, 1H) 2.30 (dd, J=9.77, 5.15 Hz, 1H) 2.19 (dddd, J=13.29, 8.54, 8.24, 6.05 Hz, 1H) 1.52 (dddd, J=13.29, 8.24, 6.00, 4.77 Hz, 1H). MS (ESI⁺) m/z 195 [M+H]⁺.

Intermediate 35

(3S)-1-(4-Methoxybenzyl)pyrrolidin-3-amine

The title product was prepared according to the procedure used for INTERMEDIATE 24, using (S)-3-(Boc-amino) pyrrolidine instead of 4-Boc-aminopiperidine and 4-methoxybenzaldehyde instead of m-tolualdehyde. ¹H NMR (600 MHz, CD₃OD) δ ppm 7.24 (d, J=8.9 Hz, 2H) 6.87 (d, J=8.9 Hz, 2H) 3.78 (s, 3H) 3.55 (s, 2H) 3.40-3.45 (m, 1H) 2.80 (dd, J=9.9, 6.9 Hz, 1H) 2.67 (td, J=8.9, 6.3 Hz, 1H) 2.54 (ddd, J=9.5, 8.2, 6.1 Hz, 1H) 2.27 (dd, J=9.8, 5.2 Hz, 1H) 2.15-2.22 (m, 1H) 1.47-1.54 (m, 1H). MS (ESI⁺) m/z 207 [M+H]⁺.

Intermediate 36

1-(4-Methoxybenzyl)piperidin-4-amine

The title product was prepared according to the procedure used for INTERMEDIATE 24, using 4-methoxybenzaldehyde instead of m-tolualdehyde. ¹H NMR (600 MHz, CD₃OD) δ ppm 7.22 (d, J=8.9 Hz, 2H) 6.87 (d, J=8.5 Hz, 2H) 3.78 (s, 3H) 3.44 (s, 2H) 2.85 (d, J=12.2 Hz, 2H) 2.60 (tt, J=10.7, 4.3 Hz, 1H) 2.04 (td, J=11.9, 2.1 Hz, 2H) 1.79 (d, J=13.1 Hz, 2H) 1.39 (dq, J=12.1, 4.0 Hz, 2H). MS (ESI⁺) m/z 221 [M+H]⁺.

Intermediate 37

(3S)-1-(Thiophen-3-ylmethyl)pyrrolidin-3-amine

The title product was prepared according to the procedure used for INTERMEDIATE 24, using (S)-3-(Boc-amino) pyrrolidine instead of 4-Boc-aminopiperidine and 3-thiophenecarboxaldehyde instead of m-tolualdehyde. ¹H NMR (600 MHz, CD₃OD) δ ppm 7.36 (dd, 1H) 7.25-7.27 (ddt, J=2.93, 1.25, 0.77 Hz, 1H) 7.10 (dd, J=4.92, 1.25 Hz, 1H) 3.67 (d, J=12.97 Hz, 1H) 3.64 (d, J=12.97 Hz, 1H) 3.42-3.48 (ddt, J=8.70, 6.85, 4.98 Hz, 1H) 2.82 (dd, J=9.92, 6.85 Hz, 1H) 2.71 (ddd, J=9.57, 8.47, 6.07 Hz, 1H) 2.57 (ddd, J=9.57, 8.15, 6.07 Hz, 1H) 2.32 (dd, J=9.92, 5.21 Hz, 1H) 2.20 (dddd, J=13.24, 8.70, 8.15, 6.07 Hz, 1H) 1.53 (dddd, J=13.24, 8.48, 6.07, 4.76 Hz, 1H). MS (ESI⁺) m/z 183 [M+H]⁺.

Intermediate 38

1-(Furan-3-ylmethyl)piperidin-4-amine

The title product was prepared according to the procedure used for INTERMEDIATE 24, using 3-furaldehyde instead of m-tolualdehyde. ¹H NMR (600 MHz, CD₃OD) δ ppm 7.45 (t, J=1.68 Hz, 1H) 7.43 (dq, J=1.68, 0.80 Hz, 1H) 6.45 (dd, J=1.68, 0.80 Hz, 1H) 3.40 (s, 2H) 2.85-2.93 (m, 2H) 2.61 (tt, J=10.84, 4.20 Hz, 1H) 2.06 (td, J=11.88, 2.14 Hz, 2H) 1.79-1.86 (m, 2H) 1.41 (dddd, J=13.20, 11.88, 11.06, 3.84 Hz, 2H). MS (ESI⁺) m/z 181 [M+H]⁺.

Intermediate 39

(3S)-1-(1,3-Benzodioxol-5-ylmethyl)pyrrolidin-3-amine

The title product was prepared according to the procedure used for INTERMEDIATE 24, using (S)-3-(Boc-amino) pyrrolidine instead of 4-Boc-aminopiperidine and piperonal instead of m-tolualdehyde. ¹H NMR (600 MHz, CD₃OD) δ ppm 6.85 (dd, J=1.65, 0.40 Hz, 1H) 6.77-6.79 (m, J=7.91, 1.65, 0.46, 0.46 Hz, 1H) 6.75 (dd, J=7.91, 0.40 Hz, 1H) 5.92 (s, 2H) 3.54 (d, J=12.55 Hz, 1H) 3.51 (d, J=12.55 Hz, 1H) 3.44 (dddd, J=8.73, 6.83, 5.18, 4.70 Hz, 1H) 2.78 (dd, J=9.84, 6.83 Hz, 1H) 2.68 (ddd, J=9.52, 8.39, 6.05 Hz, 1H) 2.53 (ddd, J=9.52, 8.39, 6.05 Hz, 1H) 2.29 (dd, J=9.84, 5.18 Hz, 1H) 2.19 (dddd, J=13.25, 8.73, 8.39, 6.05 Hz, 1H) 1.52 (dddd, J=13.25, 8.39, 6.05, 4.70 Hz, 1H). MS (ESI⁺) m/z 221 [M+H]⁺.

Intermediate 40

(3S)-1-(1,3-Thiazol-2-ylmethyl)pyrrolidin-3-amine

The title product was prepared according to the procedure used for INTERMEDIATE 24, using (S)-3-(Boc-amino) pyrrolidine instead of 4-Boc-aminopiperidine and 2-thiazolecarboxaldehyde instead of m-tolualdehyde. ¹H NMR (600 MHz, CD₃OD) δ ppm 7.71 (d, J=3.1 Hz, 1H) 7.55 (d, J=3.4 Hz, 1H) 4.00 (s, J=14.6 Hz, 1H) 3.99 (s, J=14.6 Hz, 1H) 3.43-3.49 (m, 1H) 2.82-2.89 (m, 2H) 2.63 (dt, J=8.8, 6.3 Hz, 1H) 2.47 (dd, J=9.5, 4.9 Hz, 1H) 2.16-2.25 (m, 1H) 1.53-1.60 (m, 1H). MS (ESI⁺) m/z 184 [M+H]⁺.

Intermediate 41

(3S)-1-(3-Methylbenzyl)pyrrolidin-3-amine

The title product was prepared according to the procedure used for INTERMEDIATE 24, using (S)-3-(Boc-amino) pyrrolidine instead of 4-Boc-aminopiperidine and m-tolualdehyde. ¹H NMR (600 MHz, CD₃OD) δ ppm 7.20 (t, J=7.5 Hz, 1H) 7.16 (s, 1H) 7.11 (d, J=7.3 Hz, 1 H) 7.08 (d, J=7.6 Hz, 1H) 3.58 (d, J=12.5 Hz, 1H) 3.58 (d, J=12.5 Hz, 1H) 3.43-3.48 (m, 1H) 2.79 (dd, J=9.8, 6.7 Hz, 1H) 2.70 (td, J=9.0, 6.1 Hz, 1H) 2.54 (td, J=8.9, 6.1 Hz, 1H) 2.33 (s, 3H) 2.32 (dd, J=9.8, 5.2 Hz, 1H) 2.16-2.24 (m, 1H) 1.49-1.57 (m, 1H). MS (ESI⁺) m/z 191 [M+H]⁺.

Intermediate 42

(3S)-1-[(3-Methylthiophen-2-yl)methyl]pyrrolidin-3-amine

The title product was prepared according to the procedure used for INTERMEDIATE 24, using (S)-3-(Boc-amino)

pyrrolidine instead of 4-Boc-aminopiperidine and 3-methyl-2-thiophenecarboxaldehyde instead of m-tolualdehyde. $^1$H NMR (600 MHz, CD$_3$OD) δ ppm 7.19 (d, J=5.2 Hz, 1H) 6.80 (d, J=4.9 Hz, 1H) 3.76 (d, J=14.0 Hz, 1H) 3.76 (d, J=13.7 Hz, 1H) 3.41-3.47 (m, 1H) 2.84 (dd, J=9.8, 6.7 Hz, 1H) 2.76 (td, J=8.9, 5.8 Hz, 1H) 2.59 (td, J=8.8, 6.3 Hz, 1H) 2.37 (dd, J=9.8, 4.9 Hz, 1H) 2.21 (s, 3H) 2.16-2.21 (m, 1H) 1.49-1.56 (m, 1H). MS (ESI$^+$) m/z 197 [M+H]$^+$.

Intermediate 43

(3S)-1-[4-(Trifluoromethyl)benzyl]pyrrolidin-3-amine

The title product was prepared according to the procedure used for INTERMEDIATE 24, using (S)-3-(Boc-amino)pyrrolidine instead of 4-Boc-aminopiperidine and 4-trifluoromethyl-benzaldehyde instead of m-tolualdehyde. $^1$H NMR (600 MHz, CD$_3$OD) δ ppm 7.62 (d, J=7.9 Hz, 2H) 7.54 (d, J=7.9 Hz, 2H) 3.72 (d, J=13.1 Hz, 1H) 3.68 (d, J=12.8 Hz, 1H) 3.43-3.48 (m, 1H) 2.78 (dd, J=9.5, 6.7 Hz, 1H) 2.73 (td, J=8.9, 5.8 Hz, 1H) 2.55 (td, J=8.9, 6.1 Hz, 1H) 2.33 (dd, J=9.5, 4.9 Hz, 1H) 2.16-2.24 (m, 1H) 1.50-1.59 (m, 1H). MS (ESI$^+$) m/z 245 [M+H]$^+$.

Intermediate 44

(3S)-1-(4-Methylbenzyl)pyrrolidin-3-amine

The title product was prepared according to the procedure used for INTERMEDIATE 24, using (S)-3-(Boc-amino)pyrrolidine instead of 4-Boc-aminopiperidine and p-tolualdehyde instead of m-tolualdehyde. $^1$H NMR (600 MHz, CD$_3$OD) δ ppm 7.19-7.22 (m, 2H) 7.11-7.15 (m, 2H) 3.58 (d, J=12.53 Hz, 1H) 3.56 (d, J=12.53 Hz, 1H) 3.43 (dddd, J=8.75, 6.85, 5.18, 4.72 Hz, 1H) 2.79 (dd, J=9.87, 6.85 Hz, 1H) 2.68 (ddd, J=9.56, 8.38, 6.11 Hz, 1H) 2.54 (ddd, J=9.56, 8.14, 6.06 Hz, 1H) 2.31 (s, 3H) 2.29 (dd, J=9.87, 5.18 Hz, 1H) 2.19 (dddd, J=13.30, 8.75, 8.14, 6.11 Hz, 1H) 1.51 (dddd, J=13.30, 8.38, 6.06, 4.72 Hz, 1H). MS (ESI$^+$) m/z 191 [M+H]$^+$.

Intermediate 45

(3S)-1-(Thiophen-2-ylmethyl)pyrrolidin-3-amine

The title product was prepared according to the procedure used for INTERMEDIATE 24, using (S)-3-(Boc-amino)pyrrolidine instead of 4-Boc-aminopiperidine and thiophene-2-carboxaldehyde instead of m-tolualdehyde. $^1$H NMR (600 MHz, CD$_3$OD) δ ppm 7.31 (dd, J=4.9, 1.2 Hz, 1H) 6.97-6.99 (m, 1H) 6.95 (dd, J=5.0, 3.5 Hz, 1H) 3.84 (d, J=13.7 Hz, 1H) 3.83 (d, J=13.7 Hz, 1H) 3.41-3.47 (m, 1H) 2.84 (dd, J=9.8, 6.7 Hz, 1H) 2.74 (td, J=8.9, 6.1 Hz, 1H) 2.59 (td, J=8.8, 6.3 Hz, 1H) 2.35 (dd, J=9.8, 5.2 Hz, 1H) 2.15-2.24 (m, 1H) 1.49-1.57 (m, 1H). MS (ESI$^+$) m/z 183 [M+H]$^+$.

Intermediate 46

1-Cyclohexylpiperidin-4-amine

The title product was prepared according to the procedure used for INTERMEDIATE 24, using cyclohexanone instead of m-tolualdehyde. $^1$H NMR (600 MHz, CD$_3$OD) δ ppm 2.90 (d, J=12.2 Hz, 2H) 2.55-2.61 (m, 1H) 2.25-2.34 (m, 3H) 1.91 (d, J=10.4 Hz, 2H) 1.79-1.86 (m, 4H) 1.65 (d, J=13.1 Hz, 1H) 1.38 (qd, J=11.9, 4.0 Hz, 2H) 1.19-1.33 (m, 4H) 1.09-1.18 (m, 1H). MS (ESI$^+$) m/z 183 [M+H]$^+$.

Intermediate 47

(3S)-1-(3-Methoxybenzyl)pyrrolidin-3-amine

The title product was prepared according to the procedure used for INTERMEDIATE 24, using (S)-3-(Boc-amino)pyrrolidine instead of 4-Boc-aminopiperidine and 3-methoxybenzaldehyde instead of m-tolualdehyde. $^1$H NMR (600 MHz, CD$_3$OD) δ ppm 7.22 (dd, J=8.20, 7.43 Hz, 1H) 6.92 (dd, J=2.61, 1.52 Hz, 1H) 6.90 (ddd, J=7.43, 1.52, 0.90 Hz, 1H) 6.82 (ddd, J=8.20, 2.61, 0.90 Hz, 1H) 3.79 (s, 3H) 3.61 (d, J=12.60 Hz, 1H) 3.58 (d, J=12.60 Hz, 1H) 3.45 (dddd, J=8.75, 6.84, 5.14, 4.63 Hz, 1H) 2.80 (dd, J=9.87, 6.84 Hz, 1H) 2.70 (ddd, J=9.52, 8.44, 5.98 Hz, 1H) 2.55 (ddd, J=9.52, 8.14, 6.08 Hz, 1H) 2.32 (dd, J=9.87, 5.14 Hz, 1H) 2.20 (dddd, J=13.28, 8.75, 8.14, 5.98 Hz, 1H) 1.53 (dddd, J=13.28, 8.44, 6.08, 4.63 Hz, 1H). MS (ESI$^+$) m/z 207 [M+H]$^+$.

Intermediate 48

(3S)-1-(2-Methoxybenzyl)pyrrolidin-3-amine

The title product was prepared according to the procedure used for INTERMEDIATE 24, using (S)-3-(Boc-amino)pyrrolidine instead of 4-Boc-aminopiperidine and 2-methoxybenzaldehyde instead of m-tolualdehyde. $^1$H NMR (600 MHz, CD$_3$OD) δ ppm 7.27 (dd, J=7.43, 1.75 Hz, 1H) 7.26 (td, J=8.15, 7.43, 1.75 Hz, 1H) 6.96 (dd, J=8.15, 1.07 Hz, 1H) 6.91 (td, J=7.43, 1.07 Hz, 1H) 3.83 (s, 3H) 3.69 (d, J=12.77 Hz, 1H) 3.66 (d, J=12.77 Hz, 1H) 3.44 (dddd, J=8.84, 6.88, 5.08, 4.69 Hz, 1H) 2.83 (dd, J=9.96, 6.88 Hz, 1H) 2.75 (ddd, J=9.63, 8.35, 5.95 Hz, 1H) 2.58 (ddd, J=9.63, 8.16, 6.20 Hz, 1H) 2.37 (dd, J=9.96, 5.08 Hz, 1H) 2.19 (dddd, J=13.30, 8.84, 8.16, 5.95 Hz, 1H) 1.51 (dddd, J=13.30, 8.35, 6.20, 4.69 Hz, 1H). MS (ESI$^+$) m/z 207 [M+H]$^+$.

Intermediate 49

(3S)-1-(2-Methylbenzyl)pyrrolidin-3-amine

The title product was prepared according to the procedure used for INTERMEDIATE 24, using (S)-3-(Boc-amino)pyrrolidine instead of 4-Boc-aminopiperidine and 2-methylbenzaldehyde instead of m-tolualdehyde. $^1$H NMR (600 MHz, CD$_3$OD) δ ppm 7.23-7.29 (m, 1H) 7.09-7.18 (m, 3H) 3.63 (d, J=13.1 Hz, 1H) 3.60 (d, J=13.1 Hz, 1H) 3.43 (dddd, J=8.8, 6.6, 4.7, 4.6 Hz, 1H) 2.77 (dd, J=9.5, 6.7 Hz, 1H) 2.73 (td, J=8.9, 5.8 Hz, 1H) 2.53 (td, J=8.9, 6.1 Hz, 1H) 2.37 (s, 3H) 2.36 (dd, J=10.1, 5.2 Hz, 1H) 2.19 (dddd, J=13.5, 8.4, 8.2, 5.6 Hz, 1H) 1.48-1.56 (m, 1H). MS (ESI$^+$) m/z 191 [M+H]$^+$.

Intermediate 50

1-(2,4-Dimethoxybenzyl)piperidin-4-amine

The title product was prepared according to the procedure used for INTERMEDIATE 24, using 2,4-dimethoxybenzaldehyde instead of m-tolualdehyde. $^1$H NMR (600 MHz, CD$_3$OD) δ ppm 7.15 (d, J=8.2 Hz, 1H) 6.52 (d, J=2.4 Hz, 1H) 6.48 (dd, J=8.2, 2.4 Hz, 1H) 3.80 (s, 3H) 3.79 (s, 3H) 3.50 (s, 2H) 2.89 (d, J=12.2 Hz, 2H) 2.55-2.64 (m, 1H) 2.10

(td, J=12.1, 2.1 Hz, 2H) 1.79 (d, J=13.1 Hz, 2H) 1.41 (qd, J=12.2, 3.2 Hz, 2H). MS (ESI⁺) m/z 251 [M+H]⁺.

Intermediate 51

1-(2-Methoxybenzyl)piperidin-4-amine

The title product was prepared according to the procedure used for INTERMEDIATE 24, using 2-methoxybenzaldehyde instead of m-tolualdehyde. ¹H NMR (600 MHz, CD₃OD) δ ppm 7.27 (dd, J=7.44, 1.76 Hz, 1H) 7.26 (ddd, J=8.15, 7.44, 1.76 Hz, 1H) 6.96 (dd, J=8.15, 0.95 Hz, 1H) 6.91 (td, J=7.44, 1.02 Hz, 1H) 3.82 (s, 3H) 3.57 (s, 2H) 2.87-2.94 (m, 2H) 2.61 (tt, J=10.85, 4.23 Hz, 1H) 2.12 (td, J=12.05, 2.44 Hz, 2H) 1.76-1.83 (m, 2H) 1.43 (dddd, J=13.16, 12.05, 10.85, 3.93 Hz, 2H). MS (ESI⁺) m/z 221 [M+H]⁺.

Intermediate 52

1-(3-Methoxybenzyl)piperidin-4-amine

The title product was prepared according to the procedure used for INTERMEDIATE 24, using 3-methoxybenzaldehyde instead of m-tolualdehyde. ¹H NMR (600 MHz, CD₃OD) δ ppm 7.22 (dd, J=8.24, 7.48 Hz, 1H) 6.91 (dd, J=2.61, 1.61 Hz, 1H) 6.86-6.90 (dddt, J=7.48, 1.61, 0.96, 0.47 Hz, 1H) 6.82 (ddd, J=8.24, 2.61, 0.96 Hz, 1H) 3.79 (s, 3H) 3.48 (s, 2H) 2.82-2.90 (m, 2H) 2.62 (tt, J=10.89, 4.23 Hz, 1H) 2.06 (td, J=11.94, 2.46 Hz, 2H) 1.77-1.84 (m, 2H) 1.42 (dddd, J=13.12, 11.94, 10.89, 3.91 Hz, 2H). MS (ESI⁺) m/z 221 [M+H]⁺.

Intermediate 53

1-(2,3-Dihydro-1,4-benzodioxin-6-ylmethyl)piperidin-4-amine

The title product was prepared according to the procedure used for INTERMEDIATE 24, using 2,3-dihydro-1,4-benzodioxine-6-carbaldehyde instead of m-tolualdehyde. ¹H NMR (600 MHz, CD₃OD) δ ppm 6.81 (dd, J=1.7, 0.6 Hz, 2H) 6.76 (dd, J=8.2, 0.6 Hz, 1H) 6.74 (dd, J=8.2, 1.7 Hz, 1H) 4.20-4.23 (m, 4H) 3.39 (s, 2H) 2.82-2.87 (m, 2H) 2.62 (tt, J=10.8, 4.2, 4.1 Hz, 1H) 2.03 (td, J=11.9, 2.5 Hz, 2H) 1.77-1.83 (m, 2H) 1.41 (dddd, J=13.1, 11.9, 10.9, 3.9 Hz, 1H). MS (ESI⁺) m/z 249 [M+H]⁺.

Intermediate 54

1-(2,2-Dimethylpropyl)piperidin-4-amine

The title product was prepared according to the procedure used for INTERMEDIATE 24, using pivalaldehyde instead of m-tolualdehyde. ¹H NMR (600 MHz, CD₃OD) δ ppm 2.79 (d, J=12.2 Hz, 2H) 2.50-2.60 (m, 1H) 2.24 (td, J=11.9, 2.4 Hz, 2H) 2.06 (s, 2H) 1.68-1.76 (m, 2H) 1.41 (qd, J=11.7, 3.7 Hz, 2H) 0.87 (s, 9H). MS (ESI⁺) m/z 171 [M+H]⁺.

Intermediate 55

3-[(4-Aminopiperidin-1-yl)methyl]phenol

The title product was prepared according to the procedure used for INTERMEDIATE 24, using 3-hydroxybenzaldehyde instead of m-tolualdehyde. ¹H NMR (600 MHz, CD₃OD) δ ppm 7.13 (t, J=8.1 Hz, 1H) 6.76-6.80 (m, 2H) 6.70 (dd, J=6.9, 1.4 Hz, 1H) 3.47 (s, 2H) 3.01 (tt, J=11.4, 4.3 Hz, 1H) 2.95 (d, J=12.5 Hz, 2H) 2.10 (td, J=12.1, 2.1 Hz, 2H) 1.91-1.97 (m, 2H) 1.62 (qd, J=12.1, 4.0 Hz, 2H). MS (ESI⁺) m/z 207 [M+H]⁺.

Intermediate 56

1-[4-(Difluoromethoxy)benzyl]piperidin-4-amine

The title product was prepared according to the procedure used for INTERMEDIATE 24, using 4-(difluoromethoxy)benzaldehyde instead of m-tolualdehyde. ¹H NMR (600 MHz, CD₃OD) δ ppm 7.35 (d, J=8.9 Hz, 2H) 7.09 (d, J=8.9 Hz, 2H) 6.79 (t, J=74.5 Hz, 1H) 3.50 (s, 2H) 2.85 (d, J=12.2 Hz, 2H) 2.61 (tt, J=10.7, 4.3 Hz, 1H) 2.06 (td, J=11.9, 2.1 Hz, 2H) 1.77-1.84 (m, 2H) 1.40 (qd, J=11.9, 3.7 Hz, 2H). MS (ESI⁺) m/z 257 [M+H]⁺.

Intermediate 57

1-(4-Methoxy-3-methylbenzyl)piperidin-4-amine

The title product was prepared according to the procedure used for INTERMEDIATE 24, using 4-methoxy-3-methylbenzaldehyde instead of m-tolualdehyde. ¹H NMR (600 MHz, CD₃OD) δ ppm 7.08 (d, J=8.6 Hz, 1H) 7.07 (s, 1H) 6.83 (d, J=8.5 Hz, 1H) 3.81 (s, 3H) 3.41 (s, 2H) 2.85 (d, J=12.2 Hz, 2H) 2.58-2.67 (m, 1H) 2.17 (s, 3H) 2.03 (td, J=12.0, 2.0 Hz, 2H) 1.77-1.83 (m, 2H) 1.40 (qd, J=11.8, 3.9 Hz, 2H). MS (ESI⁺) m/z 235 [M+H]⁺.

Intermediate 58

1-(Pyridin-4-ylmethyl)piperidin-4-amine

The title product was prepared according to the procedure used for INTERMEDIATE 24, using pyridine-4-carbaldehyde instead of m-tolualdehyde. ¹H NMR (600 MHz, CD₃OD) δ ppm 8.44-8.49 (m, 2H) 7.41-7.44 (m, 2H) 3.56 (s, 2H) 2.80-2.87 (m, 2H) 2.63 (tt, J=10.81, 4.20 Hz, 1H) 2.11 (td, J=11.83, 2.44 Hz, 2H) 1.78-1.85 (m, 2H) 1.44 (dddd, J=13.03, 11.83, 10.81, 3.88 Hz, 2H). MS (ESI⁺) m/z 192 [M+H]⁺.

Intermediate 59

1-(Pyridin-3-ylmethyl)piperidin-4-amine

The title product was prepared according to the procedure used for INTERMEDIATE 24, using pyridine-3-carbaldehyde instead of m-tolualdehyde. ¹H NMR (600 MHz, CD₃OD) δ ppm 8.49 (dd, J=2.22, 0.70 Hz, 1H) 8.44 (dd, J=4.90, 1.65 Hz, 1H) 7.83 (ddd, J=7.83, 2.22, 1.65 Hz, 1H) 7.41 (ddd, J=7.83, 4.90, 0.70 Hz, 1H) 3.56 (s, 2H) 2.81-2.89 (m, 2H) 2.63 (tt, J=10.84, 4.20 Hz, 1H) 2.10 (td, J=11.83, 2.48 Hz, 2H) 1.77-1.85 (m, 2H) 1.41 (dddd, J=13.02, 11.83, 10.84, 3.88 Hz, 2H). MS (ESI⁺) m/z 192 [M+H]⁺.

Intermediate 60

1-[(1-Methyl-1H-pyrrol-2-yl)methyl]piperidin-4-amine

The title product was prepared according to the procedure used for INTERMEDIATE 24, using 1-methyl-1H-pyrrole-2-carbaldehyde instead of m-tolualdehyde. ¹H NMR (600 MHz, CD₃OD) δ ppm 6.59 (t, J=2.29 Hz, 1H) 5.93 (d, J=2.29 Hz, 2H) 3.62 (s, 3H) 3.42 (s, 2H) 2.85-2.93 (m, 2H) 2.61 (tt, J=10.86, 4.20 Hz, 1H) 2.01 (td, J=11.91, 2.25 Hz, 2H) 1.76-1.83 (m, 2H) 1.37 (dddd, J=13.00, 11.91, 10.94, 3.86 Hz, 2H). MS (ESI⁺) m/z 194 [M+H]⁺.

Intermediate 61

1-[(6-Methylpyridin-2-yl)methyl]piperidin-4-amine

The title product was prepared according to the procedure used for INTERMEDIATE 24, using 6-methylpyridine-2-carbaldehyde instead of m-tolualdehyde. ¹H NMR (600 MHz, CD₃OD) δ ppm 7.68 (t, J=7.71 Hz, 1H) 7.32 (d, J=7.71 Hz, 1H) 7.17 (d, J=7.71 Hz, 1H) 3.60 (s, 2H) 2.84-2.90 (m, 2H) 2.64 (tt, J=10.80, 4.23 Hz, 1H) 2.51 (s, 3H) 2.14 (td, J=11.89, 2.44 Hz, 2H) 1.77-1.84 (m, 2H) 1.44 (dddd, J=13.04, 11.89, 11.01, 3.94 Hz, 2H). MS (ESI⁺) m/z 206 [M+H]⁺.

Intermediate 62

N-{4-[(4-Aminopiperidin-1-yl)methyl]phenyl}acetamide

The title product was prepared according to the procedure used for INTERMEDIATE 24, using N-(4-formylphenyl)acetamide instead of m-tolualdehyde. ¹H NMR (600 MHz, CD₃OD) δ ppm 7.50 (d, J=8.5 Hz, 2H) 7.26 (d, J=8.5 Hz, 2H) 3.47 (s, 2H) 2.85 (d, J=12.2 Hz, 2H) 2.57-2.65 (m, 1H) 2.11 (s, 3H) 2.05 (td, J=11.7, 1.8 Hz, 2H) 1.77-1.83 (m, 2H) 1.40 (qd, J=11.9, 3.7 Hz, 2H). MS (ESI⁺) m/z 248 [M+H]⁺.

Intermediate 63

1-(4-Ethoxybenzyl)piperidin-4-amine

The title product was prepared according to the procedure used for INTERMEDIATE 24, using 4-ethoxybenzaldehyde instead of m-tolualdehyde. ¹H NMR (600 MHz, CD₃OD) δ ppm 7.21 (d, J=8.5 Hz, 2H) 6.85 (d, J=8.9 Hz, 2H) 4.02 (q, J=7.0 Hz, 2H) 3.44 (s, 2H) 2.85 (d, J=12.2 Hz, 2H) 2.55-2.65 (m, 1H) 2.04 (td, J=11.8, 1.7 Hz, 2H) 1.74-1.85 (m, 2H) 1.39 (qd, J=11.9, 3.7 Hz, 2H) 1.37 (t, J=7.0 Hz, 3H). MS (ESI⁺) m/z 235 [M+H]⁺.

Intermediate 64

1-[4-(1-Methylethoxy)benzyl]piperidin-4-amine

The title product was prepared according to the procedure used for INTERMEDIATE 24, using 4-(1-methylethoxy)benzaldehyde instead of m-tolualdehyde. ¹H NMR (600 MHz, CD₃OD) δ ppm 7.20 (d, J=8.5 Hz, 2H) 6.85 (d, J=8.5 Hz, 2H) 4.57 (spt, J=6.1, 6.0 Hz, 1H) 3.44 (s, 2H) 2.86 (d, J=12.2 Hz, 2H) 2.56-2.64 (m, 1H) 2.04 (td, J=11.9, 1.8 Hz, 2H) 1.76-1.83 (m, 2H) 1.40 (qd, J=11.9, 3.7 Hz, 2H) 1.29 (d, J=5.8 Hz, 6H). MS (ESI⁺) m/z 249 [M+H]⁺.

Intermediate 65

1-(4-Methoxy-3,5-dimethylbenzyl)piperidin-4-amine

The title product was prepared according to the procedure used for INTERMEDIATE 24, using 4-methoxy-3,5-dimethylbenzaldehyde instead of m-tolualdehyde. ¹H NMR (600 MHz, CD₃OD) δ ppm 6.96 (s, 2H) 3.70 (s, 3H) 3.39 (s, 2H) 2.85 (d, J=12.2 Hz, 2H) 2.56-2.66 (m, 1H) 2.25 (s, 6H) 2.03 (td, J=11.8, 2.0 Hz, 2H) 1.76-1.83 (m, 2H) 1.40 (qd, J=11.8, 3.9 Hz, 2H). MS (ESI⁺) m/z 249 [M+H]⁺.

Intermediate 66

4-[(4-Aminopiperidin-1-yl)methyl]benzonitrile

The title product was prepared according to the procedure used for INTERMEDIATE 24, using 4-formylbenzonitrile instead of m-tolualdehyde. ¹H NMR (600 MHz, CD₃OD) δ ppm 7.66-7.70 (m, 2H) 7.51-7.54 (m, 2H) 3.58 (s, 2H) 2.79-2.86 (m, 2H) 2.63 (tt, J=10.83, 4.22 Hz, 1H) 2.09 (td, J=11.86, 2.50 Hz, 2H) 1.77-1.83 (m, 2H) 1.42 (dddd, J=13.10, 11.86, 10.83, 3.95 Hz, 2H). MS (ESI⁺) m/z 216 [M+H]⁺.

Intermediate 67

3-[(4-Aminopiperidin-1-yl)methyl]benzonitrile

The title product was prepared according to the procedure used for INTERMEDIATE 24, using 3-formylbenzonitrile instead of m-tolualdehyde. ¹H NMR (600 MHz, CD₃OD) δ ppm 7.70-7.72 (m, 1H) 7.64-7.66 (m, 1H) 7.63 (ddd, J=7.73, 1.63, 1.22 Hz, 1H) 7.51 (td, J=7.73, 0.56 Hz, 1H) 3.56 (s, 2H) 2.80-2.86 (m, 2H) 2.63 (tt, J=10.80, 4.22 Hz, 1H) 2.09 (td, J=11.86, 2.50 Hz, 2H) 1.78-1.84 (m, 2H) 1.42 (dddd, J=13.00, 11.86, 10.80, 3.88 Hz, 2H). MS (ESI⁺) m/z 216 [M+H]⁺.

Intermediate 68

4-[(4-Aminopiperidin-1-yl)methyl]phenol

The title product was prepared according to the procedure used for INTERMEDIATE 24, using 4-hydroxybenzaldehyde instead of m-tolualdehyde. Due to the high water solubility of the title product, the aqueous phase in the deprotection step was evaporated to dryness and the product was isolated by leaching with MeOH. This procedure resulted in 84% pure product which was used in later steps without further purification. ¹H NMR (600 MHz, CD₃OD) δ ppm 7.13-7.17 (m, 2H) 6.73-6.77 (m, 2H) 3.52 (s, 2H) 3.09 (tt, J=11.50, 4.20 Hz, 1H) 2.98-3.05 (m, 2H) 2.14-2.22 (m, 2H) 1.95-2.02 (m, 2H) 1.60-1.70 (m, 2H). MS (ESI⁺) m/z 207 [M+H]⁺.

Intermediate 69

1-(3,4-Difluorobenzyl)piperidin-4-amine

The title product was prepared according to the procedure used for INTERMEDIATE 24, using 3,4-difluorobenzaldehyde instead of m-tolualdehyde. ¹H NMR (600 MHz, CD₃OD) δ ppm 7.26 (ddd, J=11.60, 7.86, 2.06 Hz, 1H) 7.19 (dt, J=10.61, 8.28 Hz, 1H) 7.09-7.13 (m, 1H) 3.48 (s, 2H) 2.80-2.86 (m, 2H) 2.63 (tt, J=10.83, 4.21 Hz, 1H) 2.06 (td, J=11.89, 2.45 Hz, 2H) 1.78-1.84 (m, 2H) 1.42 (dddd, J=13.09, 11.89, 10.83, 3.93 Hz, 2H). MS (ESI⁺) m/z 227 [M+H]⁺.

Intermediate 70

1-[4-(Dimethylamino)benzyl]piperidin-4-amine

The title product was prepared according to the procedure used for INTERMEDIATE 24, using 4-(dimethylamino)

benzaldehyde instead of m-tolualdehyde. $^1$H NMR (600 MHz, CD$_3$OD) δ ppm 7.14 (d, J=8.5 Hz, 2H) 6.74 (d, J=8.9 Hz, 2H) 3.41 (s, 2H) 2.91 (s, 6H) 2.86 (d, J=12.2 Hz, 2H) 2.57-2.65 (m, 1H) 2.03 (td, J=11.8, 1.7 Hz, 2H) 1.77-1.83 (m, 2H) 1.40 (qd, J=12.0, 3.7 Hz, 2H). MS (ESI$^+$) m/z 234 [M+H]$^+$.

Intermediate 71

1-[4-(Methylsulfonyl)benzyl]piperidin-4-amine

The title product was prepared according to the procedure used for INTERMEDIATE 24, using 4-(methylsulfonyl) benzaldehyde instead of m-tolualdehyde. $^1$H NMR (600 MHz, CD$_3$OD) δ ppm 7.91 (d, J=8.5 Hz, 2H) 7.61 (d, J=8.5 Hz, 2H) 3.61 (s, 2H) 3.11 (s, 3H) 2.84 (d, J=12.2 Hz, 2H) 2.63 (tt, J=10.8, 4.3 Hz, 1H) 2.10 (td, J=11.9, 2.4 Hz, 2H) 1.76-1.87 (m, 2H) 1.43 (qd, J=11.9, 3.5 Hz, 2H). MS (ESI$^+$) m/z 269 [M+H]$^+$.

Intermediate 72

1-(2,3-Dihydro-1-benzofuran-5-ylmethyl)piperidin-4-amine

The title product was prepared according to the procedure used for INTERMEDIATE 24, using 2,3-dihydro-1-benzofuran-5-carbaldehyde instead of m-tolualdehyde. $^1$H NMR (600 MHz, CD$_3$OD) δ ppm 7.16 (s, 1H) 7.01 (dd, J=8.1, 1.7 Hz, 1H) 6.66 (d, J=7.9 Hz, 1H) 4.52 (t, J=8.7 Hz, 2H) 3.42 (s, 2H) 3.18 (t, J=8.7 Hz, 2H) 2.85 (d, J=12.2 Hz, 2H) 2.55-2.66 (m, 1H) 2.03 (t, J=11.9 Hz, 2H) 1.75-1.83 (m, 2H) 1.39 (qd, J=12.0, 3.8 Hz, 2H). MS (ESI$^+$) m/z 233 [M+H]$^+$.

Intermediate 73

1-(Thiophen-2-ylmethyl)piperidin-4-amine

The title product was prepared according to the procedure used for INTERMEDIATE 24, using thiophene-2-carbaldehyde instead of m-tolualdehyde. $^1$H NMR (600 MHz, CD$_3$OD) δ ppm 7.31 (dd, J=4.4, 2.0 Hz, 1H) 6.92-6.98 (m, 2H) 3.73 (s, 2H) 2.90 (d, J=12.2 Hz, 2H) 2.59 (tt, J=10.7, 4.3 Hz, 1H) 2.09 (td, J=11.9, 2.1 Hz, 2H) 1.77-1.85 (m, 2H) 1.41 (qd, J=12.0, 3.8 Hz, 2H). MS (ESI$^+$) m/z 197 [M+H]$^+$.

Intermediate 74

1-(3,4-Dimethoxybenzyl)piperidin-4-amine

The title product was prepared according to the procedure used for INTERMEDIATE 24, using 3,4-dimethoxybenzaldehyde instead of m-tolualdehyde. $^1$H NMR (600 MHz, CD$_3$OD) δ ppm 6.97 (d, J=1.94 Hz, 1H) 6.89 (d, J=8.13 Hz, 1H) 6.84 (dd, J=8.13, 1.94 Hz, 1H) 3.83 (s, 3H) 3.82 (s, 3H) 3.45 (s, 2H) 2.83-2.90 (m, 2H) 2.63 (tt, J=10.89, 4.20 Hz, 1H) 2.05 (td, J=11.95, 2.26 Hz, 2H) 1.78-1.84 (m, 2H) 1.42 (dddd, J=13.11, 11.95, 10.89, 3.84 Hz, 2H). MS (ESI$^+$) m/z 251 [M+H]$^+$.

Intermediate 75

4-[(4-Aminopiperidin-1-yl)methyl]-2-methoxyphenol

The title product was prepared according to the procedure used for INTERMEDIATE 24, using 4-hydroxy-3-methoxybenzaldehyde instead of m-tolualdehyde. $^1$H NMR (600 MHz, CD$_3$OD) δ ppm 6.93-6.95 (m, 1H) 6.74-6.76 (m, 2H) 3.85 (s, 3H) 3.53 (s, 2H) 3.10 (tt, J=11.52, 4.27 Hz, 1H) 2.98-3.05 (m, 2H) 2.19 (td, J=12.24, 2.36 Hz, 2H) 1.96-2.02 (m, 2H) 1.62-1.71 (m, 2H). MS (ESI$^+$) m/z 237 [M+H]$^+$.

Intermediate 76

1-[4-(1H-1,2,4-Triazol-1-yl)benzyl]piperidin-4-amine

The title product was prepared according to the procedure used for INTERMEDIATE 24, using 4-(1H-1,2,4-triazol-1-yl)benzaldehyde instead of m-tolualdehyde. $^1$H NMR (600 MHz, CD$_3$OD) δ ppm 9.07 (s, 1H) 8.16 (s, 1H) 7.78 (d, J=8.9 Hz, 2H) 7.52 (d, J=8.5 Hz, 2H) 3.58 (s, 2H) 2.89 (d, J=12.2 Hz, 2H) 2.60-2.68 (m, 1H) 2.10 (td, J=11.9, 2.1 Hz, 2H) 1.79-1.86 (m, 2H) 1.43 (qd, J=11.9, 3.7 Hz, 2H). MS (ESI$^+$) m/z 258 [M+H]$^+$.

Intermediate 77

1-[4-Methylsulfanyl)benzyl]piperidin-4-amine

The title product was prepared according to the procedure used for INTERMEDIATE 24, using 4-(methylsulfanyl) benzaldehyde instead of m-tolualdehyde. $^1$H NMR (600 MHz, CD$_3$OD) δ ppm 7.20-7.29 (m, 4H) 3.48 (s, 2H) 2.88 (d, J=12.2 Hz, 2H) 2.75 (tt, J=11.0, 4.1 Hz, 1H) 2.46 (s, 3H) 2.07 (td, J=12.0, 2.3 Hz, 2H) 1.82-1.88 (m, 2H) 1.47 (qd, J=12.1, 3.5 Hz, 2H). MS (ESI$^+$) m/z 237 [M+H]$^+$.

Intermediate 78 tert-Butyl [(3S)-1-(2-phenylethyl)pyrrolidin-3-yl]carbamate (S)-(−)-3-(Boc-amino)pyrrolidine (931 mg, 5 mmol) and Cs$_2$CO$_3$ (2.44 g, 7.5 mmol) were suspended in CH$_3$CN (15 mL). The mixture was heated to reflux and (2-bromoethyl) benzene (1018 mg, 5.5 mmol) dissolved in CH$_3$CN (5 mL) was slowly added, and the mixture was stirred at reflux for 3 h. The mixture was allowed to cool down to room temperature and was diluted with water (8 mL) and the phases were separated. The organic phase was diluted with EtOAc (30 mL) and washed with water (2×5 mL) and brine (5 mL), dried over Na$_2$SO$_4$ and evaporated to dryness to yield 1.432 g of crude material. Purification by flash chromatography (5% MeOH in DCM) yielded 1.158 g (80%) of pure title product as white solid. $^1$H NMR (600 MHz, CD$_3$OD) δ ppm 7.27 (t, J=7.6 Hz, 2H) 7.21 (d, J=7.3 Hz, 2H) 7.17 (t, J=7.3 Hz, 1H) 4.09 (br. s., 1H) 2.91 (dd, J=9.9, 7.2 Hz, 1H) 2.80 (t, J=8.1 Hz, 2H) 2.65-2.76 (m, 3H) 2.62 (dt, J=8.5, 7.6 Hz, 1H) 2.46 (dd, J=9.5, 5.2 Hz, 1H) 2.22 (dddd, J=13.8, 8.3, 7.9, 6.3 Hz, 1H) 1.64 (td, J=13.5, 6.0 Hz, 1H) 1.44 (s, 9H). MS (ESI$^+$) m/z 291 [M+H]$^+$.

Intermediate 79

(3S)-1-(2-Phenylethyl)pyrrolidin-3-amine

The product from the previous step (INTERMEDIATE 78) was dissolved in dioxane (15 mL) and conc. HCl (2 mL, 25 mmol) was added and the reaction mixture was stirred at room temperature for 3 h. The mixture was evaporated to a small volume and water (10 mL) was added and the resulting aqueous phase was washed with EtOAc (15 mL). The pH of the aqueous phase was adjusted with 8M NaOH to ca. pH12, and was then extracted with DCM (3×20 mL). The combined organic phases were washed with brine (5 mL) and dried over $Na_2SO_4$ and finally evaporated to yield 698 mg (92%) of pure title product as clear almost colorless liquid. $^1$H NMR (600 MHz, $CD_3OD$) δ ppm 7.27 (t, J=7.5 Hz, 2H) 7.20-7.24 (m, J=7.0 Hz, 2H) 7.18 (t, J=7.3 Hz, 1H) 3.43-3.49 (m, 1H) 2.91 (dd, J=9.9, 6.9 Hz, 1H) 2.79-2.83 (m, 2H) 2.62-2.77 (m, 4H) 2.34 (dd, J=9.8, 5.5 Hz, 1H) 2.16-2.23 (m, 1H) 1.50-1.59 (m, 1H). MS (ESI$^+$) m/z 191 [M+H]$^+$.

Intermediate 80

1-(Cyclohexylmethyl)piperidin-4-amine

The title product was prepared according to the procedure used for INTERMEDIATE 79, using 4-boc-aminopiperidine instead of (S)-(−)-3-(boc-amino)pyrrolidine, and (bromomethyl)-cyclohexane instead of (2-bromoethyl)benzene. $^1$H NMR (600 MHz, $CD_3OD$) δ ppm 2.85 (d, J=12.2 Hz, 2H) 2.53-2.65 (m, 1H) 2.13 (d, J=6.7 Hz, 2H) 1.95 (td, J=11.9, 2.1 Hz, 2H) 1.75-1.84 (m, 4H) 1.72 (ddd, J=12.9, 3.3, 3.1 Hz, 2H) 1.65-1.70 (m, 1H) 1.47-1.56 (m, 1H) 1.41 (qd, J=11.9, 4.0 Hz, 2H) 1.14-1.32 (m, 3H) 0.90 (qd, J=12.1, 3.1 Hz, 2H). MS (ESI$^+$) m/z 197 [M+H]$^+$.

Intermediate 81

1-(2-Phenylethyl)piperidin-4-amine

The title product was prepared according to the procedure used for INTERMEDIATE 79, using 4-boc-aminopiperidine instead of (S)-(−)-3-(boc-amino)pyrrolidine. $^1$H NMR (600 MHz, $CD_3OD$) δ ppm 7.26 (t, J=7.5 Hz, 2H) 7.20 (d, J=7.0 Hz, 2H) 7.17 (t, J=7.3 Hz, 1H) 3.00 (d, J=12.2 Hz, 2H) 2.78-2.83 (m, 2H) 2.64 (tt, J=10.7, 4.3 Hz, 1H) 2.56-2.60 (m, 2H) 2.13 (td, J=12.0, 2.0 Hz, 2H) 1.83-1.89 (m, 2H) 1.44 (qd, J=12.0, 3.8 Hz, 2H). MS (ESI$^+$) m/z 205 [M+H]$^+$.

Intermediate 82

1-[2-(4-Methoxyphenyl)ethyl]piperidin-4-amine

The title product was prepared according to the procedure used for INTERMEDIATE 79, using 4-boc-aminopiperidine instead of (S)-(−)-3-(boc-amino)pyrrolidine, and 1-(2-bromoethyl)-4-methoxybenzene instead of (2-bromoethyl)benzene. $^1$H NMR (600 MHz, $CD_3OD$) δ ppm 7.11 (d, J=8.5 Hz, 2H) 6.83 (d, J=8.5 Hz, 2H) 3.75 (s, 3H) 2.99 (d, J=12.2 Hz, 2H) 2.71-2.78 (m, 2H) 2.60-2.68 (m, 1H) 2.52-2.58 (m, 2H) 2.12 (td, J=11.9, 1.5 Hz, 2H) 1.81-1.89 (m, 2H) 1.44 (qd, J=12.0, 2.6 Hz, 2H). MS (ESI$^+$) m/z 235 [M+H]$^+$.

Intermediate 83

1-(2-Phenoxyethyl)piperidin-4-amine

The title product was prepared according to the procedure used for INTERMEDIATE 79, using 4-boc-aminopiperidine instead of (S)-(−)-3-(boc-amino)pyrrolidine, and (2-bromoethoxy)benzene instead of (2-bromoethyl)benzene. $^1$H NMR (600 MHz, $CD_3OD$) δ ppm 7.23-7.29 (m, 2H) 6.89-6.95 (m, 3H) 4.12 (t, J=5.6 Hz, 2H) 3.01 (d, J=12.5 Hz, 2H) 2.80 (t, J=5.5 Hz, 2H) 2.64 (tt, J=10.8, 4.3 Hz, 1H) 2.21 (td, J=12.0, 2.3 Hz, 2H) 1.80-1.88 (m, 2H) 1.45 (qd, J=12.1, 4.0 Hz, 2H). MS (ESI$^+$) m/z 221 [M+H]$^+$.

Intermediate 84

1-Ethylpiperidin-4-amine

The title product was prepared according to the procedure used for INTERMEDIATE 79, using 4-boc-aminopiperidine instead of (S)-(−)-3-(boc-amino)pyrrolidine, and ethyl iodide instead of (2-bromoethyl)benzene. $^1$H NMR (600 MHz, $CD_3OD$) δ ppm 2.95-3.02 (m, 2H) 2.79 (tt, J=11.00, 3.80 Hz, 1H) 2.46 (q, J=7.25 Hz, 2H) 2.07 (td, J=11.99, 1.86 Hz, 2H) 1.86-1.93 (m, 2H) 1.49 (qd, J=11.99, 3.72 Hz, 2H) 1.11 (t, J=7.25 Hz, 3H). MS (ESI$^+$) m/z 129 [M+H]$^+$.

Intermediate 85

1-(1-Methylethyl)piperidin-4-amine

The title product was prepared according to the procedure used for INTERMEDIATE 79, using 4-boc-aminopiperidine instead of (S)-(−)-3-(boc-amino)pyrrolidine, and 2-bromopropane instead of (2-bromoethyl)benzene. The product was isolated as the dihydrochloride salt. $^1$H NMR (600 MHz, $CD_3OD$) δ ppm 3.56-3.61 (m, 2H) 3.56 (spt, J=6.71 Hz, 1H) 3.49 (tt, J=12.10, 4.31 Hz, 1H) 3.19 (td, J=13.08, 2.20 Hz, 2H) 2.27-2.34 (m, 2H) 2.07 (dddd, J=14.08, 13.08, 12.10, 4.20 Hz, 2H) 1.39 (d, J=6.71 Hz, 6H). MS (ESI$^+$) m/z 143 [M+H]$^+$.

Intermediate 86

1-Hexylpiperidin-4-amine

The title product was prepared according to the procedure used for INTERMEDIATE 79, using 4-boc-aminopiperidine instead of (S)-(−)-3-(boc-amino)pyrrolidine, and 1-bromohexane instead of (2-bromoethyl)benzene. $^1$H NMR (600 MHz, $CD_3OD$) δ ppm 2.89-2.97 (m, 2H) 2.67 (tt, J=10.93, 4.15 Hz, 1H) 2.31-2.37 (m, 2H) 2.00-2.09 (m, 2H) 1.81-1.88 (m, 2H) 1.47-1.55 (m, 2H) 1.39-1.48 (m, 2H) 1.26-1.38 (m, 6H) 0.91 (t, J=7.02 Hz, 3H). MS (ESI$^+$) m/z 185 [M+H]$^+$.

Intermediate 87

1-(2-Methylpropyl)piperidin-4-amine

The title product was prepared according to the procedure used for INTERMEDIATE 79, using 4-boc-aminopiperidine instead of (S)-(−)-3-(boc-amino)pyrrolidine, and 1-iodo-2-methylpropane instead of (2-bromoethyl)benzene. $^1$H NMR (600 MHz, $CD_3OD$) δ ppm 2.89-2.95 (m, 2H) 2.85 (tt, J=11.27, 4.25 Hz, 1H) 2.13 (d, J=7.32 Hz, 2H) 2.02 (td, J=12.05, 1.83 Hz, 2H) 1.86-1.91 (m, 2H) 1.76-1.85 (m, 1H) 1.55 (qd, J=12.00, 3.66 Hz, 2H) 0.91 (d, J=6.56 Hz, 6H). MS (ESI$^+$) m/z 157 [M+H]$^+$.

Intermediate 88

1-Propylpiperidin-4-amine

The title product was prepared according to the procedure used for INTERMEDIATE 79, using 4-boc-aminopiperidine instead of (S)-(−)-3-(boc-amino)pyrrolidine, and 1-iodopropane instead of (2-bromoethyl)benzene. The product was isolated as the dihydrochloride salt. $^1$H NMR (600 MHz, $CD_3OD$) δ ppm 3.67-3.73 (m, 2H) 3.49 (tt, J=12.00, 3.90 Hz, 1H) 3.12 (td, J=13.20, 2.50 Hz, 2H) 3.06-3.11 (m, 2H)

2.25-2.31 (m, 2H) 2.03 (dddd, J=13.70, 13.20, 12.00, 4.20 Hz, 2H) 1.77-1.85 (m, 2H) 1.02 (t, J=7.40 Hz, 3H). MS (ESI$^+$) m/z 143 [M+H]$^+$.

Intermediate 89

(3S)-1-Methylpyrrolidin-3-amine

The title product was prepared according to the procedure used for INTERMEDIATE 79, using iodomethane instead of (2-bromoethyl)benzene. The product was isolated as the dihydrochloride salt. $^1$H NMR (600 MHz, CD$_3$OD) δ ppm (two conformers) 4.17-4.29 (m, 1H) 4.05-4.18 (m, 2H) 3.85-3.95 (m, 1H) 3.74-3.86 (m, 2H) 3.53-3.63 (m, 1H) 3.40-3.51 (m, 1H) 3.18-3.30 (m, 2H) 3.06 (br. s., 3H) 3.00 (br. s., 3H) 2.65-2.78 (m, 1H) 2.48-2.62 (m, 1H) 2.25-2.37 (m, 1H) 2.16-2.28 (m, 1H). MS (ESI$^+$) m/z 101 [M+H]$^+$.

Intermediate 90

(3S)-1-Ethylpyrrolidin-3-amine

The title product was prepared according to the procedure used for INTERMEDIATE 79, using iodoethane instead of (2-bromoethyl)benzene. The product was isolated as the dihydrochloride salt. $^1$H NMR (600 MHz, CD$_3$OD) δ ppm (two conformers) 4.16-4.25 (m, 1H) 4.05-4.16 (m, 2H) 3.86-3.96 (m, 1H) 3.75-3.85 (m, 2H) 3.58 (dd, J=13.05, 8.77 Hz, 1H) 3.29-3.49 (m, 5H) 3.17-3.28 (m, 2H) 2.65-2.75 (m, 1H) 2.48-2.60 (m, 1H) 2.25-2.34 (m, 1H) 2.16-2.26 (m, 1H) 1.40 (t, J=7.32 Hz, 6H). MS (ESI$^+$) m/z 115 [M+H]$^+$.

Intermediate 91

(3S)-1-Propylpyrrolidin-3-amine

The title product was prepared according to the procedure used for INTERMEDIATE 79, using iodopropane instead of (2-bromoethyl)benzene. The product was isolated as the dihydrochloride salt. $^1$H NMR (600 MHz, CD$_3$OD) δ ppm 3.39-4.32 (m, 4H) 3.16-3.31 (m, 3H) 2.45-2.79 (m, 1H) 2.15-2.35 (m, 1H) 1.76-1.85 (m, 2H) 1.05 (t, J=7.40 Hz, 3H). MS (ESI$^+$) m/z 129 [M+H]$^+$.

Intermediate 92

(3S)-1-(1-Methylethyl)pyrrolidin-3-amine

The title product was prepared according to the procedure used for INTERMEDIATE 79, using 2-iodopropane instead of (2-bromoethyl)benzene. The product was isolated as the dihydrochloride salt. $^1$H NMR (600 MHz, CD$_3$OD) δ ppm (two conformers) 4.13-4.22 (m, 1H) 4.00-4.13 (m, 2H) 3.87 (t, J=9.46 Hz, 1H) 3.69-3.81 (m, 2H) 3.58-3.67 (m, 2H) 3.43-3.57 (m, 2H) 3.22-3.31 (m, 2H) 2.64-2.73 (m, 1H) 2.48-2.59 (m, 1H) 2.16-2.31 (m, 2H) 1.44 (d, J=6.26 Hz, 6H) 1.43 (d, J=6.56 Hz, 6H). MS (ESI$^+$) m/z 129 [M+H]$^+$.

Intermediate 93

1-(2-Methoxyethyl)piperidin-4-amine

The title product was prepared according to the procedure used for INTERMEDIATE 79, using 4-boc-aminopiperidine instead of (S)-(−)-3-(boc-amino)pyrrolidine, and bromoethyl methyl ether instead of (2-bromoethyl)benzene. The product was isolated as the dihydrochloride salt. $^1$H NMR (600 MHz, CD$_3$OD) δ ppm 3.74-3.78 (m, 2H) 3.72-3.77 (m, 2H) 3.46-3.53 (m, 1H) 3.41 (s, 3H) 3.35-3.38 (m, 2H) 3.20 (td, J=13.20, 2.29 Hz, 2H) 2.25-2.31 (m, 2H) 2.01-2.10 (m, 2H). MS (ESI$^+$) m/z 159 [M+H]$^+$.

Intermediate 94

5-Chloro-N$^4$-[1-(4-methoxybenzyl)piperidin-4-yl]-3-nitropyridine-2,4-diamine

To a slurry of 4,5-dichloro-3-nitropyridine-2-amine (INTERMEDIATE 3, 3.71 g, 17.8 mmol) in i-PrOH (50 mL) was added 1-(4-methoxybenzyl)piperidin-4-amine (INTERMEDIATE 36, 4.00 g, 18.17 mmol) and DIPEA (5.7 mL). The mixture was stirred at 50° C. over night. Monitoring by LCMS indicated full conversion to the title product. The reaction was allowed to cool to room temperature and was centrifuged. The supernatant was separated and the yellow solid was sequentially washed with EtOAc (1×25 mL), MeOH (2×25 mL), EtOAc (30 mL) and then dried in vacuum to furnish 6.70 g (85%) of 99% pure title product as yellow powder. $^1$H NMR (600 MHz, DMSO-d$_6$) δ ppm 7.87 (s, 1H) 7.76 (d, J=6.41 Hz, 1H) 7.57 (br. s., 2H) 7.19 (d, J=8.55 Hz, 2H) 6.87 (d, J=8.85 Hz, 2H) 3.83 (br. s., 1H) 3.73 (s, 3H) 3.38 (s, 2H) 2.67 (d, J=9.46 Hz, 2H) 2.03 (t, J=10.38 Hz, 2H) 1.87 (dd, J=13.12, 3.36 Hz, 2H) 1.49-1.57 (m, 2H). MS (ESI$^+$) m/z 392 [M+H]$^+$.

Intermediate 95

5-Chloro-3-nitro-N$^4$-piperidin-4-ylpyridine-2,4-diamine

The title product was prepared according to the procedure used for INTERMEDIATE 94, using 1-boc-4-aminopiperidine instead of 1-(4-methoxybenzyl)piperidin-4-amine, followed by N-boc deprotection using conc. HCl in dioxane at room temperature. $^1$H NMR (600 MHz, DMSO-d$_6$) δ ppm 7.88 (s, 1H) 7.81 (d, J=8.1 Hz, 1H) 7.59 (s, 2H) 3.86-3.95 (m, 1H) 2.89 (dt, J=12.7, 3.7 Hz, 2H) 2.47 (ddd, J=12.7, 10.6, 2.5 Hz, 2H) 1.81-1.87 (m, 2H) 1.35 (dddd, J=12.4, 10.6, 3.7 Hz, 2H). MS (ESI$^+$) m/z 272 [M+H]$^+$.

Intermediate 96

5-Bromo-N$^4$-[1-(4-methoxybenzyl)piperidin-4-yl]-3-nitropyridine-2,4-diamine

The title product was prepared according to the procedure used for INTERMEDIATE 94, using 5-bromo-4-chloro-3-nitropyridin-2-amine (INTERMEDIATE 7) instead of 4,5-dichloro-3-nitropyridine-2-amine. $^1$H NMR (600 MHz, DMSO-d$_6$) δ ppm 7.97 (s, 1H) 7.42 (s, 2H) 7.18 (d, J=8.55 Hz, 2H) 7.09 (d, 1H) 6.86 (d, 2H) 3.73 (s, 3H) 3.67 (br. s., 1H) 3.37 (s, 2H) 2.57-2.74 (m, 2H) 1.95-2.08 (m, 2H) 1.77-1.91 (m, 2H) 1.36-1.59 (m, 2H). MS (ESI$^+$) m/z 436 [M+H]$^+$.

Intermediate 97

5-Bromo-N$^4$-(1-methylpiperidin-4-yl)-3-nitropyridine-2,4-diamine

The title product was prepared according to the procedure used for INTERMEDIATE 94, using 5-bromo-4-chloro-3-nitropyridin-2-amine (INTERMEDIATE 7) instead of 4,5-dichloro-3-nitropyridine-2-amine and 1-methylpiperidin-4- amine hydrochloride instead of 1-(4-methoxybenzyl) piperidin-4-amine. $^1$H NMR (600 MHz, DMSO-d$_6$) δ ppm 8.02 (s, 1H) 7.45 (br. s., 2H) 6.93-7.14 (m, 1H) 3.68-3.93 (m, 1H) 3.33-3.46 (m, 2H) 2.88-3.11 (m, 2H) 2.70 (br. s., 3H) 2.06 (d, J=13.73 Hz, 2H) 1.70-1.93 (m, 2H). MS (ESI$^+$) m/z 330 [M+H]$^+$.

Intermediate 98

5-Bromo-N$^4$-[1-(2,3-dihydro-1-benzofuran-5-ylmethyl)piperidin-4-yl]-3-nitropyridine-2,4-diamine The title product was prepared according to the procedure used for INTERMEDIATE 94, using 5-bromo-4-chloro-3-nitropyridin-2-amine (INTERMEDIATE 7) instead of 4,5-dichloro-3-nitropyridine-2-amine and 1-(2,3-dihydro-1-benzofuran-5-ylmethyl)piperidin-4-amine (INTERMEDIATE 72) instead of 1-(4-methoxybenzyl)piperidin-4-amine. $^1$H NMR (600 MHz, DMSO-d$_6$) δ ppm 7.97 (s, 1H) 7.42 (s, 2H) 7.12 (s, 1H) 7.06-7.11 (m, 1H) 6.96 (d, J=8.24 Hz, 1H) 6.67 (d, J=8.24 Hz, 1H) 4.49 (t, J=8.70 Hz, 2H) 3.58-3.76 (m, 1H) 3.35 (s, 2H) 3.14 (t, J=8.70 Hz, 2H) 2.60-2.73 (m, 2H) 1.95-2.08 (m, 2H) 1.84 (d, J=10.07 Hz, 2H) 1.44-1.58 (m, 2H). MS (ESI$^+$) m/z 448 [M+H]$^+$.

Intermediate 99

5-Bromo-3-nitro-N$^4$-[1-(thiophen-2-ylmethyl)piperidin-4-yl]pyridine-2,4-diamine The title product was prepared according to the procedure used for INTERMEDIATE 94, using 5-bromo-4-chloro-3-nitropyridin-2-amine (INTERMEDIATE 7) instead of 4,5-dichloro-3-nitropyridine-2-amine and 1-(thiophen-2-ylmethyl)piperidin-4-amine (INTERMEDIATE 73) instead of 1-(4-methoxybenzyl)piperidin-4-amine. $^1$H NMR (600 MHz, DMSO-d$_6$) δ ppm 7.97 (s, 1H) 7.42 (br. s., 2H) 7.41 (dd, 1H) 7.11 (d, J=8.39 Hz, 1H) 6.95 (dd, 1H) 6.93-6.95 (m, 1H) 3.66 (br. s., 3H) 2.68-2.77 (m, 2H) 2.08 (t, J=10.38 Hz, 2H) 1.82-1.88 (m, 2H) 1.49-1.58 (m, 2H). MS (ESI$^+$) m/z 412 [M+H]$^+$.

Intermediate 100

5-Bromo-N$^4$-[(3S)-1-(2-methoxybenzyl)pyrrolidin-3-yl]-3-nitropyridine-2,4-diamine The title product was prepared according to the procedure used for INTERMEDIATE 94, using 5-bromo-4-chloro-3-nitropyridin-2-amine (INTERMEDIATE 7) instead of 4,5-dichloro-3-nitropyridine-2-amine and (3S)-1-(2-methoxybenzyl)pyrrolidin-3-amine (INTERMEDIATE 48) instead of 1-(4-methoxybenzyl)piperidin-4-amine. $^1$H NMR (600 MHz, DMSO-d$_6$) δ ppm 7.96 (s, 1H) 7.47 (d, 1H) 7.42 (br. s., 2H) 7.32 (dd, J=7.48, 1.68 Hz, 1H) 7.21 (dd, J=15.56, 1.83 Hz, 1H) 6.96 (d, J=8.24 Hz, 1H) 6.90 (t, J=6.87 Hz, 1H) 4.19-4.34 (m, 1H) 3.76 (s, 3H) 3.60 (d, J=3.05 Hz, 2H) 2.81 (td, J=8.70, 4.88 Hz, 1H) 2.63 (dd, J=9.92, 2.59 Hz, 1H) 2.54 (dd, J=9.77, 5.80 Hz, 1H) 2.31 (td, J=8.85, 6.71 Hz, 1H) 2.19 (dddd, J=12.97, 8.55, 4.43, 4.27 Hz, 1H) 1.63-1.78 (m, 1H). MS (ESI$^+$) m/z 422 [M+H]$^+$.

Intermediate 101

3-[4-(6-Chloro-7-{[1-(4-methoxybenzyl)piperidin-4-yl]amino}-3H-imidazo[4,5-b]pyridin-2-yl)phenyl]propanoic acid The title product was prepared according to the procedure used for the first part of INTERMEDIATE 23, using 5-chloro-N$^4$-[1-(4-methoxybenzyl)piperidin-4-yl]-3-nitropyridine-2,4-diamine (INTERMEDIATE 94) and 3-(4-formylphenyl)propionic acid. $^1$H NMR (600 MHz, DMSO-d$_6$) δ ppm 13.19 (br. s., 1H) 8.03 (d, J=8.2 Hz, 2H) 7.93 (s, 1H) 7.40 (d, J=8.2 Hz, 2H) 7.25 (d, J=8.2 Hz, 2H) 6.90 (d, J=8.2 Hz, 2H) 5.83 (d, J=9.2 Hz, 1H) 4.91-5.02 (m, 1H) 3.74 (s, 3H) 3.47 (br. s., 2H) 2.89 (t, J=7.6 Hz, 2H) 2.86 (br. s., 2H) 2.60 (t, J=7.6 Hz, 2H) 2.14 (br. s., 2H) 1.99 (d, J=11.0 Hz, 2H) 1.67 (q, J=11.3 Hz, 2H). MS (ESI$^+$) m/z 520 [M+H]$^+$.

Intermediate 102

2-(3-Formylphenoxy)-N-methylacetamide

Methyl bromoacetate (4.21 g, 38.5 mmol) in CH$_3$CN (15 mL) was added dropwise at room temperature to a slurry consisting of 3-hydroxybenzaldehyde (3.05 g, 35 mmol) and powdered potassium carbonate (5.18 g, 52.5 mmol) in CH$_3$CN (60 mL). After complete addition the mixture was heated to 80° C. for 1 h. The solids were removed by filtration and the filtrate was diluted with EtOAc (125 mL). The resulting organic phase was washed with water (15 mL) and brine (2×15 mL), dried over MgSO$_4$ and concentrated in vacuo to yield 6.796 g (99.6%) of essentially pure methyl (3-formylphenoxy)acetate as slightly yellow oil. $^1$H NMR (600 MHz, CDCl$_3$) δ ppm 9.98 (s, 1H) 7.53 (dt, J=7.6, 1.2 Hz, 1H) 7.49 (t, J=7.8 Hz, 1H) 7.37 (dd, J=2.7, 1.2 Hz, 1H) 7.24 (ddd, J=8.2, 2.7, 1.1 Hz, 1H) 4.72 (s, 2H) 3.83 (s, 3H). MS (ESI$^+$) m/z 195 [M+H]$^+$.

The crude methyl (3-formylphenoxy)acetate was dissolved in MeOH (5 mL) and MeNH$_2$ in MeOH (ca. 9.8 mol/L, 10.7 mL, 105 mmol) was added. The mixture became warm upon addition of MeNH$_2$. The reaction mixture was stirred for 30 min and the solvent was evaporated to yield the intermediate N-methyl-2-{3-[(methylimino)methyl]phenoxy}acetamide as amber oil. The oil was dissolved in DCM (20 mL) and 2M HCl (35 mL) was added. The mixture was stirred at room temperature for 2 h. DCM (100 mL) was added and the phases were separated. The organic phase was washed with 2M HCl (15 mL) and the combined aqueous phases were extracted with DCM (2×50 mL). The combined organic phases were washed with water (15 mL) and brine (15 mL), dried over MgSO$_4$ and the solvent evaporated to yield 6.116 g (90%) of 97% pure title product as off-white solid. $^1$H NMR (600 MHz, CD$_3$OD) δ ppm 9.96 (s, 1H) 7.57 (dt, J=7.3, 1.3 Hz, 1H) 7.53 (t, J=7.8 Hz, 1H) 7.49 (dd, J=2.6, 1.4 Hz, 1H) 7.33 (ddd, J=8.0, 2.7, 1.2 Hz, 1H) 4.59 (s, 2H) 2.82 (s, 3H). MS (ESI$^+$) m/z 194 [M+H]$^+$.

Intermediate 103

2-[3-(6,7-Dichloro-3H-imidazo[4,5-b]pyridin-2-yl)phenoxy]-N-methylacetamide 4,5-Dichloropyridine-2,3-diamine (INTERMEDIATE 4, 445 mg, 2.5 mmol), 2-(3-formylphenoxy)-N-methylacetamide (INTERMEDIATE 102, 483 mg, 2.5 mmol) and p-toluenesulfonic acid (476 mg, 2.5 mmol) were dissolved in DMF (8 mL). The mixture was stirred vigorously in a Pyrex tube without cap at 80° C. The mixture was allowed to cool to room temperature after 5 h 45 min. Precipitation occurred upon cooling. The precipitate was isolated by centrifugation. The supernatant was removed and the remaining solid was washed with EtOAc (3×2 mL) and centrifuged again after each cycle. The solid was dried in vacuum to yield 294 mg (33%) of 97% pure title product as beige solid. $^1$H NMR (600 MHz, DMSO-d$_6$) δ ppm 14.08

(br. s., 1H) 8.49 (s, 1H) 8.10-8.17 (m, 1H) 7.87 (br. s., 1H) 7.89 (br. s., 1H) 7.52 (t, J=8.1 Hz, 1H) 7.18 (ddd, J=8.3, 2.5, 0.8 Hz, 1H) 4.59 (s, 2H) 2.68 (d, J=4.6 Hz, 3H). MS (ESI$^+$) m/z 351 [M+H]$^+$. The material was taken to the next step without further purification.

Intermediate 104

5-Chloro-N$^4$-[1-(2-methylpropyl)piperidin-4-yl]-3-nitropyridine-2,4-diamine

The title product was prepared according to the procedure used for INTERMEDIATE 94, using 1-(2-methylpropyl)piperidin-4-amine (INTERMEDIATE 87) instead of 1-(4-methoxybenzyl)piperidin-4-amine. $^1$H NMR (600 MHz, CD$_3$OD) δ ppm 7.89 (s, 1H) 4.29-4.41 (m, 1H) 3.55-3.72 (m, 2H) 3.02-3.17 (m, 2H) 2.97 (br. s., 2H) 2.28-2.41 (m, 2H) 2.09-2.20 (m, 1H) 1.80-1.96 (m, 2H) 1.06 (d, J=6.71 Hz, 6H). MS (ESI$^+$) m/z 328 [M+H]$^+$.

Intermediate 105

5-Chloro-N$^4$-[(3S)-1-methylpyrrolidin-3-yl]-3-nitropyridine-2,4-diamine

The title product was prepared according to the procedure used for INTERMEDIATE 94, using (3S)-1-methylpyrrolidin-3-amine (INTERMEDIATE 89) instead of 1-(4-methoxybenzyl)piperidin-4-amine. MS (ESI$^+$) m/z 272 [M+H]$^+$.

Intermediate 106

5-Chloro-N$^4$-[(3S)-1-ethylpyrrolidin-3-yl]-3-nitropyridine-2,4-diamine

The title product was prepared according to the procedure used for INTERMEDIATE 94, using (3S)-1-ethylpyrrolidin-3-amine (INTERMEDIATE 90) instead of 1-(4-methoxybenzyl)piperidin-4-amine. MS (ESI$^+$) m/z 286 [M+H]$^+$.

Intermediate 107

5-Chloro-3-nitro-N$^4$-[(3S)-1-propylpyrrolidin-3-yl]pyridine-2,4-diamine

The title product was prepared according to the procedure used for INTERMEDIATE 94, using (3S)-1-propylpyrrolidin-3-amine (INTERMEDIATE 91) instead of 1-(4-methoxybenzyl)piperidin-4-amine. MS (ESI$^+$) m/z 300 [M+H]$^+$.

Intermediate 108

5-Chloro-N$^4$-[(3S)-1-(1-methylethyl)pyrrolidin-3-yl]-3-nitropyridine-2,4-diamine The title product was prepared according to the procedure used for INTERMEDIATE 94, using (3S)-1-(1-methylethyl)pyrrolidin-3-amine (INTERMEDIATE 92) instead of 1-(4-methoxybenzyl)piperidin-4-amine. MS (ESI$^+$) m/z 300 [M+H]$^+$.

Intermediate 109

5-Chloro-N$^4$-(1-methylpiperidin-4-yl)-3-nitropyridine-2,4-diamine

The title product was prepared according to the procedure used for INTERMEDIATE 94, using 1-methylpiperidin-4-amine instead of 1-(4-methoxybenzyl)piperidin-4-amine. $^1$H NMR (600 MHz, DMSO-d$_6$) δ ppm 7.88 (s, 1H) 7.75 (d, J=7.32 Hz, 1H) 7.57 (s, 2H) 3.72-3.85 (m, 1H) 2.56-2.67 (m, 2H) 2.14 (s, 3H) 1.99 (t, J=10.22 Hz, 2H) 1.86 (dd, J=12.82, 3.66 Hz, 2H) 1.54 (dq, 2H). MS (ESI$^+$) m/z 286 [M+H]$^+$.

Intermediate 110

Methyl (4-{6-chloro-7-[(1-methylpiperidin-4-yl)amino]-3H-imidazo[4,5-b]pyridin-2-yl}phenoxy)acetate The title product was prepared according to the procedure used for INTERMEDIATE 23, using 5-chloro-N$^4$-(1-methylpiperidin-4-yl)-3-nitropyridine-2,4-diamine (INTERMEDIATE 109) and 4-formylphenoxyacetic acid. $^1$H NMR (600 MHz, DMSO-d$_6$) δ ppm 13.18 (s, 1H) 8.11 (d, J=8.8 Hz, 2H) 7.93 (s, 1H) 7.10 (d, J=8.9 Hz, 2H) 5.97 (br. s., 1H) 5.01 (br. s., 1H) 4.90 (s, 2H) 3.72 (s, 3H) 3.19 (br. s., 2H) 2.55 (br. s., 2H) 2.11 (d, J=11.0 Hz, 2H) 1.76-1.90 (m, 2H). MS (ESI$^+$) m/z 430 [M+H]$^+$.

Intermediate 111

5-Bromo-N$^4$-(1-ethylpiperidin-4-yl)-3-nitropyridine-2,4-diamine

The title product was prepared according to the procedure used for INTERMEDIATE 94, using 5-bromo-4-chloro-3-nitropyridin-2-amine (INTERMEDIATE 7) instead of 4,5-dichloro-3-nitropyridine-2-amine and 1-ethylpiperidin-4-amine (INTERMEDIATE 84) instead of 1-(4-methoxybenzyl)piperidin-4-amine. $^1$H NMR (600 MHz, CD$_3$OD) δ ppm (two conformers) 8.04 (s, 2H) 4.11-4.23 (m, 1H) 3.64-3.72 (m, 2H) 3.58-3.66 (m, 2H) 3.38-3.52 (m, 1H) 3.13-3.26 (m, 4H) 2.98-3.15 (m, 4H) 2.29-2.40 (m, 2H) 2.23-2.32 (m, 2H) 1.91-2.04 (m, 2H) 1.77-1.91 (m, 2H) 1.37 (t, J=7.32 Hz, 3H) 1.36 (t, J=7.32 Hz, 3H). MS (ESI$^+$) m/z 346 [M+H]$^+$.

Intermediate 112

5-Bromo-3-nitro-N$^4$-(1-propylpiperidin-4-yl)pyridine-2,4-diamine

The title product was prepared according to the procedure used for INTERMEDIATE 94, using 5-bromo-4-chloro-3-nitropyridin-2-amine (INTERMEDIATE 7) instead of 4,5-dichloro-3-nitropyridine-2-amine and 1-propylpiperidin-4-amine (INTERMEDIATE 88) instead of 1-(4-methoxybenzyl)piperidin-4-amine. $^1$H NMR (600 MHz, CD$_3$OD) δ ppm (two conformers) 8.00 (s, 2H) 4.10-4.29 (m, 2H) 3.49-3.73 (m, 4H) 2.85-3.24 (m, 8H) 2.26-2.40 (m, 2H) 2.21-2.28 (m, 2H) 1.92-2.03 (m, 2H) 1.77-1.94 (m, 2H) 1.73-1.81 (m, 4H) 1.03 (t, J=7.40 Hz, 3H) 1.02 (t, J=7.40 Hz, 3H). MS (ESI$^+$) m/z 358 [M+H]$^+$.

Intermediate 113

5-Bromo-3-nitro-N$^4$-(1-propylpiperidin-4-yl)pyridine-2,4-diamine

The title product was prepared according to the procedure used for INTERMEDIATE 94, using 5-bromo-4-chloro-3-nitropyridin-2-amine (INTERMEDIATE 7) instead of 4,5-dichloro-3-nitropyridine-2-amine and 1-(1-methylethyl)piperidin-4-amine (INTERMEDIATE 85) instead of 1-(4- methoxybenzyl)piperidin-4-amine. $^1$H NMR (600 MHz, CD$_3$OD) δ ppm (major conformer) 8.01 (s, 1H) 4.14-4.27 (m, 1H) 3.45-3.60 (m, 3H) 3.08-3.21 (m, 2H) 2.32-2.43 (m, 2H) 1.76-1.90 (m, 2H) 1.37 (d, J=6.71 Hz, 6H). MS (ESI$^+$) m/z 358 [M+H]$^+$.

Intermediate 114

5-Bromo-N$^4$-[(3S)-1-methylpyrrolidin-3-yl]-3-nitro-pyridine-2,4-diamine

The title product was prepared according to the procedure used for INTERMEDIATE 94, using 5-bromo-4-chloro-3-nitropyridin-2-amine (INTERMEDIATE 7) instead of 4,5-dichloro-3-nitropyridine-2-amine and (3S)-1-methylpyrrolidin-3-amine (INTERMEDIATE 89) instead of 1-(4-methoxybenzyl)piperidin-4-amine. MS (ESI$^+$) m/z 316 [M+H]$^+$.

Intermediate 115

Methyl (4-formyl-3-methylphenoxy)acetate

A mixture of 4-hydroxy-2-methylbenzaldehyde (280 mg, 2.1 mmol), methyl bromoacetate (349 mg, 2.3 mmol, 1.1 eq.) and potassium carbonate (430 mg, 3.1 mmol, 1.5 eq.) in CH$_3$CN (10 mL) were heated at 80° C. for 5 h. The reaction mixture was allowed to cool down to room temperature and EtOAc (50 mL) was added and the resulting organic phase was washed with water (3×10 mL) and brine (19 mL). The organic phase was dried over MgSO$_4$, filtered and evaporated to yield 424 mg (97%) of the title product as yellow solid. $^1$H NMR (600 MHz, CDCl$_3$) δ ppm 10.13 (s, 1H) 7.76 (d, J=8.60 Hz, 1H) 6.83 (dd, J=8.60, 2.50 Hz, 1H) 6.77 (d, J=2.50 Hz, 1H) 4.70 (s, 2H) 3.82 (s, 3H) 2.65 (s, 3H). MS (ESI$^+$) m/z 209 [M+H]$^+$.

Intermediate 116

2-(4-Formyl-3-methylphenoxy)-N-methylacetamide

Methyl (4-formyl-3-methylphenoxy)acetate (INTERMEDIATE 115, 833 mg, 4.0 mmol) was dissolved in MeOH (15 mL) and 9.8 M methylamine in MeOH (2.0 mL, 19.6 mmol) was added. The mixture was stirred at 60° C. for 1.5 h. The solvent and excess methylamine were evaporated to yield a light brown oil. The crude material was dissolved in DCM (20 mL) and 2 M HCl (20 mL) was added and the mixture was stirred at ambient temperature for 23 h. The phases were separated and the aqueous phase was extracted with DCM (3×25 mL). The combined organic phases were washed with 1M NaOH (2×15 mL), water (2×15 mL) and brine (15 mL), dried over MgSO$_4$, filtered and concentrated in vacuo to yield 674 mg (81%) of the title product as beige solid. $^1$H NMR (600 MHz, CDCl$_3$) δ ppm 10.15 (s, 1H) 7.79 (d, J=8.54 Hz, 1H) 6.87 (dd, J=8.54, 2.59 Hz, 1H) 6.78 (d, J=2.59 Hz, 1H) 6.52 (br. s., 1H) 4.56 (s, 2H) 2.93 (d, J=5.04 Hz, 3H) 2.66 (s, 3H). MS (ESI$^+$) m/z 208 [M+H]$^+$.

Intermediate 117

2-(4-Formyl-2-methylphenoxy)-N-methylacetamide

The title product was prepared according to the procedure used for INTERMEDIATE 116, starting from methyl (4-formyl-2-methylphenoxy)acetate, which was prepared according to the procedure for INTERMEDIATE 115 from 4-hydroxy-3-methylbenzaldehyde. $^1$H NMR (600 MHz, CDCl$_3$) δ ppm 9.89 (s, 1H) 7.74-7.75 (m, 1H) 7.71-7.74 (ddq, J=8.32, 2.14, 0.54 Hz, 1H) 6.90 (d, J=8.32 Hz, 1H) 6.46 (br. s., 1H) 4.60 (s, 2H) 2.95 (d, J=5.04 Hz, 3H) 2.35 (s, 3H). (ESI$^+$) m/z 208 [M+H]$^+$.

Intermediate 118

2-(4-Formyl-2-methoxyphenoxy)-N-methylacetamide

The title product was prepared according to the procedure used for INTERMEDIATE 116, starting from methyl (4-formyl-2-methoxyphenoxy)acetate, which was prepared according to the procedure for INTERMEDIATE 115 from vanillin. $^1$H NMR (600 MHz, CDCl$_3$) δ ppm 9.88 (s, 1H) 7.46 (d, J=1.5 Hz, 1H) 7.43 (dd, J=8.2, 1.8 Hz, 1H) 6.89 (d, J=8.2 Hz, 1H) 4.81 (s, 2H) 3.97 (s, 3H) 3.82 (s, 3H). MS (ESI$^+$) m/z 225 [M+H]$^+$.

Intermediate 119

2-[4-(6,7-Dichloro-3H-imidazo[4,5-b]pyridin-2-yl)-3-methylphenoxy]-N-methylacetamide The title product was prepared according to the procedure used for INTERMEDIATE 9, using 2-(4-formyl-3-methylphenoxy)-N-methylacetamide (INTERMEDIATE 116) instead of N-[2-(dimethylamino)ethyl]-2-(4-formylphenoxy)acetamide. $^1$H NMR (600 MHz, DMSO-d$_6$) δ ppm 13.66 (s, 1H) 8.46 (s, 1H) 8.08 (q, J=4.70 Hz, 1H) 7.77 (d, J=8.54 Hz, 1H) 7.02 (d, J=2.44 Hz, 1H) 6.97 (dd, J=8.54, 2.44 Hz, 1H) 4.56 (s, 2H) 2.67 (d, J=4.70 Hz, 3H) 2.63 (s, 3H). MS (ESI$^+$) m/z 365 [M+H]$^+$.

Intermediate 120

2-(4-Formylphenoxy)-N,2-dimethylpropanamide

2-Bromo-2-methyl-propionic acid methyl ester (2.15 g, 11 mmol) in CH$_3$CN (5 mL) was added to a slurry of 4-hydroxybenzaldehyde (1.22 g, 10 mmol) and powdered potassium carbonate (2.073 g, 15 mmol) in CH$_3$CN (25 mL). The mixture was heated at 80° C. More 2-bromo-2-methyl-propionic acid methyl ester (1.07 g, 5.5 mmol) was added after three days and after four days and after five days. The reaction was worked up after six days even though it was not complete (ca. 92% conversion). The solid material was removed by filtration and the remaining solvent was evaporated. The residue was dissolved in EtOAc (60 mL) and the resulting organic phase was washed with 1 M NaOH (2×5 mL), water (2×5 mL) and brine (5 mL). The organic phase was dried over MgSO$_4$ and the solvent was evaporated to yield 2.38 g of 94% pure 2-(4-formyl-phenoxy)-2-methyl-propionic acid methyl ester as colorless oil. $^1$H NMR (600 MHz, CDCl$_3$) δ ppm 9.89 (s, 1H) 7.79 (d, J=8.5 Hz, 2H) 6.91 (d, J=8.9 Hz, 2H) 4.24 (q, J=7.1 Hz, 2H) 1.68 (s, 6H) 1.22 (t, J=7.0 Hz, 3H). MS (ESI$^+$) m/z 237 [M+H]$^+$.

The crude product was dissolved in MeOH (50 mL) and 2M NaOH (8 mL) was added and the mixture was stirred at reflux for 2 h. The reaction mixture was evaporated to a small volume and water (8 mL) was added. The pH was adjusted to weakly acidic with conc. ortho-phosphoric acid and the resulting aqueous phase was extracted with EtOAc (2×25 mL). The combined organic phases were washed with water (2×5 mL) and brine (5 mL), dried over MgSO$_4$, filtered and evaporated to yield 1.952 g (94%) of 2-(4-formylphenoxy)-2-methylpropanoic acid as light yellow gummy oil. $^1$H NMR (600 MHz, CD$_3$OD) δ ppm 9.84 (s, 1H) 7.31 (d, J=8.2 Hz, 2H) 6.88 (d, J=8.5 Hz, 2H) 1.57 (s, 6H). MS (ESI$^+$) m/z 209 [M+H]$^+$.

The crude material from the previous step was dissolved in DCM (40 mL). DMF (30 μL) was added followed by dropwise addition of SOCl$_2$ (2.788 g, 23.44 mmol, 2.5 eq) dissolved in DCM (10 mL). The mixture was stirred at ambient temperature overnight and was then heated to reflux for 1 h. The reaction mixture was allowed to cool down to room temperature and was then chilled in an ice-bath. MeNH$_2$ (9.8 M in MeOH, 6 mL, 58.8 mmol) was added slowly and the mixture was stirred for 1 h. The reaction mixture was treated with 2M HCl (20 mL) and the resulting biphasic system was stirred vigorously at room temperature for 16 h. The phases were separated and the aqueous phase was extracted with DCM (2×30 mL). The combined organic phases were washed with brine (8 mL), dried over MgSO$_4$, filtered and evaporated to yield 1.642 g (79%) of 94% pure title product as beige solid. $^1$H NMR (600 MHz, CDCl$_3$) δ ppm 9.89 (s, 1H) 7.79 (d, J=8.9 Hz, 2H) 6.97 (d, J=8.5 Hz, 2H) 6.51 (br. s., 1H) 2.83 (d, J=4.9 Hz, 3H) 1.58 (s, 6H). MS (ESI$^+$) m/z 222 [M+H]$^+$.

Intermediate 121

2-(2-Fluoro-4-formylphenoxy)-N-methylacetamide

The title product was prepared according to the procedure used for INTERMEDIATE 116, starting from methyl (2-fluoro-4-formylphenoxy)acetate, which was prepared according to the procedure for INTERMEDIATE 115 from 3-fluoro-4-hydroxybenzaldehyde. $^1$H NMR (600 MHz, CDCl$_3$) δ ppm 9.79 (d, J=2.1 Hz, 1H) 7.54-7.60 (m, 2H) 7.01 (t, J=8.2 Hz, 1H) 6.83 (br. s., 1H) 4.53 (s, 2H) 2.82 (d, J=4.9 Hz, 3H). MS (ESI$^+$) m/z 212 [M+H]$^+$.

Intermediate 122

3-(4-Formylphenyl)-N-methylpropanamide

To a solution of SOCl$_2$ (1.782 g, 15 mmol) and DMF (77 μL, 1 mmol) in DCM (30 mL) was added 3-(4-formylphenyl)propanoic acid (1,782 g, 10 mmol) as dry powder. The formed inhomogeneous solution was heated at reflux. After 15 min the reaction mixture had turned homogeneous. The reaction flask was placed in an ice-bath and MeNH$_2$ (9.8 M in MeOH, 3.1 mL, 30 mmol) was slowly added to the reaction mixture. After stirring for 0.5 h at 0° C., 2 M HCl (20 mL) was added and the mixture was stirred at room temperature overnight.

The phases were separated and the aqueous phase was extracted with DCM (2×25 mL). The combined organic phases were washed with 2 M NaOH (10 mL) and brine (10 mL), dried over MgSO$_4$, filtered and evaporated to yield 1.466 g (77%) of title product as white solid. $^1$H NMR (600 MHz, CDCl$_3$) δ ppm 9.98 (s, 1H) 7.81 (d, J=8.2 Hz, 2H) 7.38 (d, J=7.9 Hz, 2H) 5.40 (br. s., 1H) 3.07 (t, J=7.6 Hz, 2H) 2.79 (d, J=4.6 Hz, 3H) 2.50 (t, J=7.6 Hz, 2H). MS (ESI$^+$) m/z 192 [M+H]$^+$.

Intermediate 123

2-(4-Formyl-2,6-dimethylphenoxy)-N-methylacetamide

The title product was prepared according to the procedure used for INTERMEDIATE 116, starting from methyl (4-formyl-2,6-dimethylphenoxy)acetate, which was prepared according to the procedure for INTERMEDIATE 115 from 4-hydroxy-3,5-dimethylbenzaldehyde. $^1$H NMR (600 MHz, CDCl$_3$) δ ppm 9.90 (s, 1H) 7.57-7.59 (m, 2H) 6.84 (br. s., 1H) 4.32 (s, 2H) 2.99 (d, J=4.88 Hz, 3H) 2.33 (s, 6H). MS (ESI$^+$) m/z 222 [M+H]$^+$.

Intermediate 124

2-(4-Formyl-2,5-dimethylphenoxy)-N-methylacetamide

The title product was prepared according to the procedure used for INTERMEDIATE 116, starting from methyl (4-formyl-2,5-dimethylphenoxy)acetate, which was prepared according to the procedure for INTERMEDIATE 115 from 4-hydroxy-2,5-dimethylbenzaldehyde. $^1$H NMR (600 MHz, CDCl$_3$) δ ppm 10.16 (s, 1H) 7.64 (s, 1H) 6.61 (s, 1H) 6.46 (br. s., 1H) 4.57 (s, 2H) 2.95 (d, J=4.88 Hz, 3H) 2.64 (s, 3H) 2.30 (s, 3H). MS (ESI$^+$) m/z 222 [M+H]$^+$.

Intermediate 125

(4-{6-Chloro-7-[(1-methylpiperidin-4-yl)amino]-3H-imidazo[4,5-b]pyridin-2-yl}phenoxy)acetic acid The title product was prepared according to the procedure used for INTERMEDIATE 23, using 5-chloro-N$^4$-(1-methylpiperidin-4-yl)-3-nitropyridine-2,4-diamine (INTERMEDIATE 109) and 4-formylphenoxyacetic acid. $^1$H NMR (600 MHz, DMSO-d$_6$) δ ppm 13.13 (br. s., 1 H) 8.04-8.09 (m, 2H) 7.91 (s, 1H) 7.02-7.06 (m, 2H) 5.83 (d, J=8.70 Hz, 1H) 4.91-5.00 (m, 1H) 4.64 (s, 2H) 2.92-3.03 (m, 2H) 2.36 (s, 3H) 2.28-2.42 (m, 2H) 1.98-2.07 (m, 2H) 1.68-1.79 (m, 2H). MS (ESI$^+$) m/z 416 [M+H]$^+$.

Intermediate 126

2-(2-Fluoro-4-formylphenoxy)-N-(1-methylethyl)acetamide

The title product was prepared according to the procedure used for INTERMEDIATE 116 starting from methyl (2-fluoro-4-formylphenoxy)acetate, which was prepared according to the procedure for INTERMEDIATE 115 from 3-fluoro-4-hydroxybenzaldehyde, and iso-propylamine. $^1$H NMR (600 MHz, CDCl$_3$) δ ppm 9.90 (d, J=2.4 Hz, 1H) 7.65-7.71 (m, 2H) 7.08 (t, J=8.1 Hz, 1H) 6.40 (br. s., 1H) 4.58 (s, 2H) 4.15-4.25 (m, 1H) 1.23 (d, J=6.4 Hz, 6H). MS (ESI$^+$) m/z 240 [M+H]$^+$.

Intermediate 127

2-(4-Formylphenyl)-N-methylacetamide

To a solution of 4-(hydroxymethyl)phenylacetic acid in MeOH (75 mL) was added conc. H$_2$SO$_4$ (ca 10 drops). The mixture was stirred at 55° C. for 1 h and was then allowed to cool to room temperature and solid NaHCO$_3$ was added until neutral pH. The mixture was filtered and the solvent evaporated to furnish 6.2 g of crude material. Further drying in vacuum furnished 5.32 g (98%) of pure methyl [4-(hydroxymethyl)phenyl]acetate. MS (ESI$^+$) m/z 181 [M+H]$^+$.

Methyl [4-(hydroxymethyl)phenyl]acetate (537 mg, 2.98 mmol) was dissolved in MeOH (10 mL). MeNH$_2$ (1 mL, 40% in MeOH, ca 9M, 9 mmol) was added and the mixture was stirred at 27° C. overnight. Additional MeNH$_2$ (1 mL) was added and stirring was continued for another 10 h. The solvent and excess CH$_3$NH$_2$ were removed in vacuum to furnish 520 mg (97%) of 2-[4-(hydroxymethyl)phenyl]-N-methylacetamide as white solid. $^1$H NMR (600 MHz, DMSO-d$_6$) δ ppm 7.90 (br. s., 1H) 7.22 (d, J=8.24 Hz, 2H) 7.19 (d, J=8.24 Hz, 2H) 5.11 (br. s., 1H) 4.45 (s, 2H) 3.35 (s, 2H) 2.56 (d, J=4.58 Hz, 3H). MS (ESI$^+$) m/z 180 [M+H]$^+$.

To a slurry of 2-[4-(hydroxymethyl)phenyl]-N-methylacetamide (312 mg, 1.73 mmol) in CHCl$_3$ (15 mL) was added activated MnO$_2$ (1.66 g, 19.1 mmol). The mixture was stirred at 35° C. for 5 h. Additional MnO$_2$ (150 mg, 1.72 mmol) was added and stirring was continued over the weekend. The mixture was centrifuged and the supernatant was collected. The solid was washed with CHCl$_3$ (10 mL), centrifuged and the supernatants combined and the solvent evaporated to furnish 255 mg (83%) of the title product as white solid. $^1$H NMR (600 MHz, DMSO-d$_6$) δ ppm 9.97 (s, 1H) 8.04 (br. s., 1H) 7.84 (d, J=8.24 Hz, 2H) 7.47 (d, J=8.24 Hz, 2H) 3.51 (s, 2H) 2.58 (d, J=4.58 Hz, 3H). MS (ESI$^+$) m/z 178 [M+H]$^+$.

Intermediate 128

[4-(6-Chloro-7-{[1-(4-methoxybenzyl)piperidin-4-yl]amino}-3H-imidazo[4,5-b]pyridin-2-yl)phenoxy]acetic acid The title product was prepared according to the procedure used for INTERMEDIATE 23, using 5-chloro-N$^4$-[1-(4-methoxybenzyl)piperidin-4-yl]-3-nitropyridine-2,4-diamine (INTERMEDIATE 94) and 4-formylphenoxyacetic acid. $^1$H NMR (600 MHz, DMSO-d$_6$) δ ppm 13.12 (s, 1H) 8.05-8.09 (m, 3H) 7.91 (s, 1H) 7.22-7.26 (m, 2H) 7.10-7.14 (m, 2H) 6.88-6.91 (m, 2H) 5.77 (d, J=9.00 Hz, 1H) 4.91-4.99 (m, 1H) 4.56 (s, 2H) 3.74 (s, 3H) 3.45 (s, 2H) 2.82-2.88 (m, 2H) 2.68 (d, J=4.58 Hz, 3H) 2.08-2.15 (m, 2H) 1.94-2.01 (m, 2H) 1.66 (qd, J=11.55, 3.36 Hz, 2H). MS (ESI$^+$) m/z 522 [M+H]$^+$.

Intermediate 129

5-Chloro-3-nitro-N-[1-(thiophen-2-ylmethyl)piperidin-4-yl]pyridine-2,4-diamine

The title product was prepared according to the procedure used for INTERMEDIATE 94, using 1-(thiophen-2-ylmethyl)piperidin-4-amine (INTERMEDIATE 73) and 4,5-dichloro-3-nitropyridine-2-amine (INTERMEDIATE 3). $^1$H NMR (600 MHz, DMSO-d$_6$) δ ppm 7.87 (s, 1H) 7.73 (d, J=7.32 Hz, 1H) 7.56 (s, 2H) 7.41 (dd, J=4.88, 1.37 Hz, 1H) 6.93-6.97 (m, 2H) 3.76-3.86 (m, 1H) 3.67 (s, 2H) 2.68-2.79 (m, 2H) 2.10 (t, J=10.68 Hz, 2H) 1.84-1.91 (m, 2H) 1.50-1.60 (m, 2H). MS (ESI$^+$) m/z 368 [M+H]$^+$.

Intermediate 130

[4-(6-Chloro-7-{[1-(thiophen-2-ylmethyl)piperidin-4-yl]amino}-3H-imidazo[4,5-b]pyridin-2-yl)phenoxy]acetic acid The title product was prepared according to the procedure used for INTERMEDIATE 23, using 5-chloro-3-nitro-N$^4$-[1-(thiophen-2-ylmethyl)piperidin-4-yl]pyridine-2,4-diamine (INTERMEDIATE 129) and 4-formylphenoxyacetic acid. $^1$H NMR (600 MHz, DMSO-d$_6$) δ ppm 13.12 (br. s., 1H) 12.87 (br. s., 1H) 8.03-8.08 (m, 2H) 7.91 (s, 1H) 7.45 (dd, J=4.96, 1.30 Hz, 1H) 7.05-7.09 (m, 2H) 6.99-7.01 (m, 1H) 6.98 (dd, J=4.96, 3.41 Hz, 1H) 5.83 (d, J=9.00 Hz, 1H) 4.93-5.02 (m, 1H) 4.77 (s, 2H) 3.77 (s, 2H) 2.90-2.99 (m, 2H) 2.22 (t, J=11.14 Hz, 2H) 1.95-2.04 (m, 2H) 1.65-1.75 (m, 2H). MS (ESI$^+$) m/z 498 [M+H]$^+$.

Intermediate 131

(4-{6-Bromo-7-[(1-methylpiperidin-4-yl)amino]-3H-imidazo[4,5-b]pyridin-2-yl}phenoxy)acetic acid The title product was prepared according to the procedure used for INTERMEDIATE 23, using 5-bromo-N$^4$-(1-methylpiperidin-4-yl)-3-nitropyridine-2,4-diamine (INTERMEDIATE 97) and 4-formylphenoxyacetic acid. $^1$H NMR (600 MHz, DMSO-d$_6$) δ ppm 13.16 (br. s., 1H) 8.04-8.10 (m, 2H) 8.01 (s, 1H) 7.99-7.99 (m, 1H) 7.01-7.07 (m, 2H) 5.54 (d, J=8.55 Hz, 1H) 4.91-5.02 (m, 1H) 4.63 (s, 2H) 2.92-3.03 (m, 2H) 2.37 (s, 3H) 2.34-2.46 (m, 2H) 2.01-2.10 (m, 2H) 1.66-1.79 (m, 2H). MS (ESI$^+$) m/z 460 [M+H]$^+$.

Intermediate 132 tert-Butyl [2-(4-formylphenoxy)ethyl]carbamate

4-Hydroxybenzaldehyde (1.22 g, 10 mmol), 2-(boc-amino)ethyl bromide (2.24 g, 10 mmol) and K$_2$CO$_3$ (2.07 g, 15 mmol) were mixed in CH$_3$CN (100 mL). The reaction was stirred at 80° C. More 2-(boc-amino)ethyl bromide (1.24 g, 5.5 mmol) was added after 24 h and the reaction was stirred at 60° C. for another 24 h. The reaction mixture was allowed to cool to room temperature and the solvent was evaporated. EtOAc (100 mL) and water (50 mL) were added. The phases were separated and organic phase was washed with 50 ml 1M Na$_2$CO$_3$ (50 mL), water (2×50 mL) and brine (50 mL), dried over MgSO$_4$, filtered and evaporated to yield 2.56 g (96%) of the title product as yellow oil which crystallized upon standing. $^1$H NMR (600 MHz, CDCl$_3$) δ ppm 9.89 (s, 1H) 7.82-7.85 (m, 2H) 6.98-7.01 (m, 2H) 4.98 (br. s., 1H) 4.11 (t, J=5.19 Hz, 2H) 3.53-3.60 (m, 2H) 1.45 (s, 9H). MS (ESI$^+$) m/z 210 [M+H]$^+$.

Intermediate 133

N-[2-(4-Formylphenoxy)ethyl]acetamide

The product from the previous step, tert-butyl [2-(4-formylphenoxy)ethyl]carbamate (INTERMEDIATE 132, 265 mg, 1.0 mmol), was dissolved in CH$_3$CN (10 mL) and MeOH (81 μL, 2.0 mmol) and NaI (300 mg, 2.0 mmol) were added followed by dropwise addition of acetyl chloride (314 mg, 285 μL, 1.16 mmol). The reaction was stirred at room temperature for 20 min. The reaction mixture was cooled on an ice bath and DIPEA (520 mg, 701 μL, 4.0 mmol) was added dropwise at 0° C. The reaction mixture was allowed to warm to room temperature and was then stirred for 1.5 h. More acetyl chloride (143 μL) and DIPEA (351 μL) were added and the reaction was stirred for 1 h, after which more acetyl chloride (71 μL) and DIPEA (351 μL) were added. The reaction was stirred at room temperature overnight. 1M HCl (16 mL) was added and the mixture was extracted with EtOAc (100+50 mL). The combined organic phases were washed with 1M NaHCO$_3$ (3×20 mL) and brine (20 mL), dried over MgSO$_4$, filtered and evaporated to yield 154 mg of a 80% pure crude material. Purification by flash chromatography (silica, 3% MeOH in DCM) yielded 90 mg (43%) of pure title product as light brown oil. $^1$H NMR (600 MHz, CDCl$_3$) δ ppm 9.89 (s, 1H) 7.82-7.87 (m, 2H) 6.98-7.02 (m, 2H) 5.92 (br. s., 1H) 4.13 (t, J=5.11 Hz, 2H) 3.70 (dt, J=5.80, 5.11 Hz, 2H) 2.03 (s, 3H). MS (ESI$^+$) m/z 208 [M+H]$^+$.

Intermediate 134

2-[4-(2-Aminoethoxy)phenyl]-6-chloro-N-(1-methylpiperidin-4-yl)-3H-imidazo[4,5-b]pyridin-7-amine The title product was prepared according to the procedure used for INTERMEDIATE 23, using 5-chloro-N$^4$-(1-methylpiperidin-4-yl)-3-nitropyridine-2,4-diamine (INTERMEDIATE 109) and tert-butyl [2-(4-formylphenoxy)ethyl]carbamate (INTERMEDIATE 132). The isolated boc-protected product was deprotected with conc. HCl in dioxane at room temperature for 1 h. The reaction mixture was evaporated and dried in vacuum to yield the title product as the hydrochloride salt, white solid. $^1$H NMR (600 MHz, CD$_3$OD) δ ppm 8.23 (s, 1H) 8.19-8.24 (m, 2H) 7.22-7.26 (m, 2H) 5.49 (br. s., 1H) 4.34-4.38 (m, 2H) 3.66-3.71 (m, 2H) 3.41-3.46 (m, 2H) 3.39 (br. s., 2H) 2.98 (s, 3H) 2.44-2.51 (m, 2H) 2.12-2.21 (m, 2H). MS (ESI$^+$) m/z 401 [M+H]$^+$.

Intermediate 135

5-Chloro-N$^4$-[1-(1-methylethyl)piperidin-4-yl]-3-nitropyridine-2,4-diamine

The title product was prepared according to the procedure used for INTERMEDIATE 94, using 1-(1-methylethyl)piperidin-4-amine (INTERMEDIATE 85) and 4,5-dichloro-3-nitropyridine-2-amine (INTERMEDIATE 3). $^1$H NMR (600 MHz, DMSO-d$_6$) δ ppm 7.83 (br. s., 1H) 3.51-4.01 (br. m, 1H) 2.61-2.71 (m, 3H) 2.16 (t, J=10.30 Hz, 2H) 1.70-1.94 (br. m, 2H) 1.34-1.53 (br. m, 2H) 0.93 (d, J=6.56 Hz, 6H). MS (ESI$^+$) m/z 314 [M+H]$^+$.

Intermediate 136

[4-(6-Chloro-7-{[1-(1-methylethyl)piperidin-4-yl]amino}-3H-imidazo[4,5-b]pyridin-2-yl)phenoxy]acetic acid The title product was prepared according to the procedure used for INTERMEDIATE 23, using 5-chloro-N$^4$-[1-(1-methylethyl)piperidin-4-yl]-3-nitropyridine-2,4-diamine (INTERMEDIATE 135) and 4-formylphenoxyacetic acid. $^1$H NMR (600 MHz, DMSO-d$_6$) δ ppm 13.14 (br. s., 1H) 8.04-8.09 (m, 2H) 7.92 (s, 1H) 7.02-7.07 (m, 2H) 5.83 (d, J=8.24 Hz, 1H) 4.91-5.00 (m, 1H) 4.66 (s, 2H) 2.96-3.15 (m, 3H) 2.55-2.70 (m, 2H) 2.07-2.16 (m, 2H) 1.69-1.82 (m, 2H) 1.13 (d, J=6.56 Hz, 6H). MS (ESI$^+$) m/z 444 [M+H]$^+$.

Intermediate 137

2-[4-(2-Aminoethoxy)phenyl]-6-chloro-N-[1-(4-methoxybenzyl)piperidin-4-yl]-3H-imidazo[4,5-b]pyridin-7-amine The title product was prepared according to the procedure used for INTERMEDIATE 23, using 5-chloro-N$^4$-[1-(4-methoxybenzyl)piperidin-4-yl]-3-nitropyridine-2,4-diamine (INTERMEDIATE 94) and tert-butyl [2-(4-formylphenoxy)ethyl]carbamate (INTERMEDIATE 132). The isolated boc-protected product was deprotected with conc. HCl in dioxane at room temperature for 3.5 h. The reaction mixture was evaporated and dried in vacuum to yield the title product as the hydrochloride salt, beige solid. $^1$H NMR (600 MHz, DMSO-d$_6$) δ ppm (free base) 8.08-8.13 (m, 2H) 7.56 (s, 1H) 7.20-7.25 (m, 2H) 6.85-6.93 (m, 4H) 5.02-5.11 (m, 1H) 3.94 (t, J=5.80 Hz, 2H) 3.73 (s, 3H) 3.42 (s, 2H) 2.86 (t, J=5.80 Hz, 2H) 2.74-2.82 (m, 2H) 2.06-2.16 (m, 2H) 1.92-2.02 (m, 2H) 1.42-1.52 (m, 2H). MS (ESI$^+$) m/z 507 [M+H]$^+$.

Intermediate 138

5-Bromo-3-nitro-N$^4$-{1-[4-(1H-1,2,4-triazol-1-yl)benzyl]piperidin-4-yl}pyridine-2,4-diamine The title product was prepared according to the procedure used for INTERMEDIATE 94, using 5-bromo-4-chloro-3-nitropyridin-2-amine (INTERMEDIATE 7) and 1-[4-(1H-1,2,4-triazol-1-yl)benzyl]piperidin-4-amine (INTERMEDIATE 76). $^1$H NMR (600 MHz, DMSO-d$_6$) δ ppm 9.26 (s, 1H) 8.22 (s, 1H) 7.97 (s, 1H) 7.80 (d, J=8.5 Hz, 2H) 7.46 (d, J=8.5 Hz, 2H) 7.43 (s, 2H) 7.14 (d, J=8.9 Hz, 1H) 3.70 (br. s., 1H) 3.52 (s, 2H) 2.71 (br. s., 2H) 2.09 (t, J=10.5 Hz, 2H) 1.87 (d, J=13.7 Hz, 2H) 1.56 (q, J=9.8 Hz, 2H). MS (ESI$^+$) m/z 473 [M+H]$^+$.

Intermediate 139

5-Chloro-3-nitro-N$^4$-{1-[4-(1H-1,2,4-triazol-1-yl)benzyl]piperidin-4-yl}pyridine-2,4-diamine The title product was prepared according to the procedure used for INTERMEDIATE 94, using 4,5-dichloro-3-nitropyridine-2-amine (INTERMEDIATE 3) and 1-[4-(1H-1,2,4-triazol-1-yl)benzyl]piperidin-4-amine (INTERMEDIATE 76). $^1$H NMR (600 MHz, DMSO-d$_6$) δ ppm 9.26 (s, 1H) 8.22 (s, 1H) 7.88 (s, 1H) 7.81 (d, J=8.2 Hz, 2H) 7.77 (d, J=5.8 Hz, 1H) 7.57 (s, 2H) 7.47 (d, J=8.5 Hz, 2H) 3.85 (br. s., 1H) 3.54 (br. s., 2H) 2.72 (br. s., 2H) 2.13 (br. s., 2H) 1.90 (d, J=10.1 Hz, 2H) 1.58 (q, J=10.4 Hz, 2H). MS (ESI$^+$) m/z 429 [M+H]$^+$.

Intermediate 140

1-[(1,3,5-Trimethyl-1H-pyrazol-4-yl)methyl]piperidin-4-amine

The title product was prepared according to the procedure used for INTERMEDIATE 24, using 4-boc-aminopiperidine and 1,3,5-trimethyl-1H-pyrazole-4-carbaldehyde. $^1$H NMR (600 MHz, DMSO-d$_6$) δ ppm 3.59 (s, 3H) 3.12 (s, 2H) 2.65 (d, J=11.6 Hz, 2H) 2.43-2.49 (m, 1H) 2.12 (s, 3H) 2.02 (s, 3H) 1.83 (t, J=10.7 Hz, 2H) 1.61 (d, J=12.2 Hz, 2H) 1.14 (qd, J=11.6, 2.6 Hz, 2H). MS (ESI$^+$) m/z 223 [M+H]$^+$.

Intermediate 141

5-Bromo-3-nitro-N-{1-[(1,3,5-trimethyl-1H-pyrazol-4-yl)methyl]piperidin-4-yl}pyridine-2,4-diamine The title product was prepared according to the procedure used for INTERMEDIATE 94, using 5-bromo-4-chloro-3-nitropyridin-2-amine (INTERMEDIATE 7) and 1-[(1,3,5-trimethyl-1H-pyrazol-4-yl)methyl]piperidin-4-amine (INTERMEDIATE 140). $^1$H NMR (600 MHz, DMSO-d$_6$) δ ppm 7.97 (s, 1H) 7.41 (br. s., 2H) 7.09 (d, J=7.3 Hz, 1H) 3.65 (br. s., 1 H) 3.60 (s, 3H) 3.15 (br. s., 2H) 2.64 (br. s., 2H) 2.12 (s, 3H) 2.03 (s, 3H) 1.95 (br. s., 2H) 1.82 (d, J=11.3 Hz, 2H) 1.47 (q, J=10.4 Hz, 2H). MS (ESI$^+$) m/z 438 [M+H]$^+$.

Intermediate 142

5-Chloro-3-nitro-$N^4$-{1-[(1,3,5-trimethyl-1H-pyrazol-4-yl)methyl]piperidin-4-yl}pyridine-2,4-diamine The title product was prepared according to the procedure used for INTERMEDIATE 94, using 4,5-dichloro-3-nitropyridine-2-amine (INTERMEDIATE 3) and 1-[(1,3,5-trimethyl-1H-pyrazol-4-yl)methyl]piperidin-4-amine (INTERMEDIATE 140). $^1$H NMR (600 MHz, DMSO-d$_6$) δ ppm 7.87 (s, 1H) 7.72 (br. s., 1H) 7.55 (br. s., 2H) 3.79 (br. s., 1H) 3.60 (s, 3H) 3.16 (br. s., 2H) 2.65 (br. s., 2H) 2.13 (s, 3H) 2.04 (s, 3H) 1.97 (br. s., 2H) 1.85 (d, J=9.5 Hz, 2H) 1.48 (q, J=10.1 Hz, 2H). MS (ESI$^+$) m/z 394 [M+H]$^+$.

Intermediate 143

$N^2$-(4-Formylphenyl)-N-methylglycinamide

To a stirred mixture of fluorobenzaldehyde (1.24 g, 10 mmol) and glycine (1.13 g, 15 mmol) was added potassium carbonate (3.46 g, 25 mmol) dissolved in water (10 mL) and the mixture was stirred at 100° C. After 1 h more glycine (375 mg, 5 mmol) and potassium carbonate (691 mg, 5 mmol) were added to the reaction mixture. After 18 h more glycine (375 mg, 5 mmol) and potassium carbonate (691 mg, 5 mmol) were added to the reaction mixture. After stirring for two days at 100° C. the reaction mixture was then allowed to cool down to room temperature. The solid precipitate was collected by filtration and dried under vacuum to afford 499 mg of a brown solid. HPLC revealed that there was still product in the filtrate. The filtrate was extracted with DCM (3×25 mL) and the combined organic phases were dried over MgSO$_4$ and evaporated to yield 112 mg of brown solid. The solids were combined to yield 611 mg (34%) of crude N-(4-formylphenyl)glycine which was taken to the next step without further purification. MS (ESI$^+$) m/z 180 [M+H]$^+$.

The crude N-(4-formylphenyl)glycine was dissolved in MeOH (25 mL) and a catalytic amount of conc. H$_2$SO$_4$ was added. The mixture was stirred at reflux for 18 h. The solvent was evaporated and the residue was partitioned between DCM (35 mL) and sat NaHCO$_3$ (5 mL). The phases were separated and the organic phase was washed with brine (5 mL), dried over Na$_2$SO$_4$, and evaporated to yield 353 mg of a dark brown semi-solid. Purification by flash chromatography (silica, 30-40% EtOAc in n-hexane) yielded 158 mg (8% over two steps) of pure methyl N-(4-formylphenyl)glycinate as light yellow solid. $^1$H NMR (600 MHz, DMSO-d$_6$) δ ppm 9.63 (s, 1H) 7.62 (d, J=8.9 Hz, 2H) 7.14 (t, J=6.4 Hz, 1H) 6.67 (d, J=8.5 Hz, 2H) 4.06 (d, J=6.4 Hz, 2H) 3.66 (s, 3H). MS (ESI$^+$) m/z 194 [M+H]$^+$.

Methyl N-(4-formylphenyl)glycinate (155 mg, 0.80 mmol) was dissolved in MeOH (10 mL) and MeNH$_2$ (ca. 9.8 M in MeOH, 0.50 mL, 4.8 mmol) was slowly added while stirring the solution at room temperature. After 18 h the solvent was evaporated to yield the intermediate N-methyl-$N^2$-{4-[(methylimino)methyl]phenyl}glycinamide as an amber solid. The solid was dissolved in 1 M HCl (10 mL) and the resulting solution was stirred at 60° C. for 15 h. The pH of the reaction mixture was adjusted with 2M NaOH to weakly acidic and then sat. NaHCO$_3$ was added until the pH was approximately 8. The resulting aqueous phase was extracted with DCM (3×15 mL). The combined organic phases were dried over Na$_2$SO$_4$, filtered and evaporated to yield 121 mg (78%) of 94% pure title product as pale yellow solid. $^1$H NMR (600 MHz, DMSO-d$_6$) δ ppm 9.62 (s, 1H) 7.89-7.94 (m, 1H) 7.62 (d, J=8.9 Hz, 2H) 7.07 (t, J=6.0 Hz, 1H) 6.63 (d, J=8.9 Hz, 2H) 3.75 (d, J=6.1 Hz, 2H) 2.61 (d, J=4.9 Hz, 3H). MS (ESI$^+$) m/z 193 [M+H]$^+$.

Intermediate 144

$N^3$-(4-Formylphenyl)-N-methyl-β-alaninamide

The title product was prepared according to the procedure used for INTERMEDIATE 143, using fluorobenzaldehyde and β-alanine. $^1$H NMR (600 MHz, DMSO-d$_6$) δ ppm 9.60 (s, 1H) 7.81-7.87 (m, 1H) 7.60 (d, J=8.9 Hz, 2H) 6.86 (t, J=5.6 Hz, 1H) 6.66 (d, J=8.9 Hz, 2H) 3.35 (q, J=7.0 Hz, 2H) 2.57 (d, J=4.9 Hz, 3H) 2.35 (t, J=7.0 Hz, 2H). MS (ESI$^+$) m/z 207 [M+H]$^+$.

Intermediate 145

Methyl [4-(6-chloro-7-{[1-(4-methoxybenzyl)piperidin-4-yl]amino}-3H-imidazo[4,5-b]pyridin-2-yl)phenoxy]acetate

[4-(6-Chloro-7-{[1-(4-methoxybenzyl)piperidin-4-yl]amino}-3H-imidazo[4,5-b]pyridin-2-yl)phenoxy]acetic acid (INTERMEDIATE 128, 313 mg, 0.60 mmol) was slurried in MeOH (20 mL) and a catalytic amount of H$_2$SO$_4$ was added. The mixture was stirred at reflux for 6 h. The solvent was evaporated and the residue was taken up in DCM (50 mL) and the organic phase was washed with sat. NaHCO$_3$ (5 mL) and brine (5 mL), dried over Na$_2$SO$_4$. The solvent was evaporated to yield 95% pure title product. $^1$H NMR (600 MHz, DMSO-d$_6$) δ ppm 13.14 (br. s., 1H) 8.06 (d, J=8.9 Hz, 2H) 7.91 (s, 1H) 7.26 (br. s., 2H) 7.11 (d, J=9.2 Hz, 2H) 6.91 (d, J=7.3 Hz, 2H) 5.80 (br. s., 1H) 4.97 (br. s., 1H) 4.90 (s, 2H) 3.75 (s, 3H) 3.73 (s, 3H) 3.46 (br. s., 2H) 2.88 (br. s., 2H) 2.14 (br. s., 2H) 1.99 (br. s., 2H) 1.68 (br. s., 2H). MS (ESI$^+$) m/z 536 [M+H]$^+$.

Intermediate 146

2-(4-Formylphenoxy)-N-pyrimidin-2-ylacetamide

The title product was prepared according to the procedure used for INTERMEDIATE 8, using 4-formylphenoxyacetic acid and 2-aminopyrimidine. $^1$H NMR (600 MHz, CDCl$_3$) δ ppm 9.93 (s, 1H) 8.87 (br. s., 1H) 8.68 (d, J=4.88 Hz, 2H) 7.89-7.92 (m, 2H) 7.11-7.15 (m, 2H) 7.11 (t, J=4.88 Hz, 1H) 4.90 (br. s., 2H). MS (ESI$^+$) m/z 258 [M+H]$^+$.

Intermediate 147

2-(4-Formylphenoxy)-N-pyrazin-2-ylacetamide

The title product was prepared according to the procedure used for INTERMEDIATE 8, using 4-formylphenoxyacetic acid and 2-aminopyrazine. $^1$H NMR (600 MHz, CDCl$_3$) δ ppm 9.95 (s, 1H) 9.62 (s, 1H) 8.80 (br. s., 1H) 8.43 (d, J=2.54 Hz, 1H) 8.31 (dd, J=2.54, 1.58 Hz, 1H) 7.90-7.95 (m, 2H) 7.12-7.16 (m, 2H) 4.77 (s, 2H). MS (ESI$^+$) m/z 258 [M+H]$^+$.

Intermediate 148

2-(4-Formylphenoxy)-N-(5-methylisoxazol-3-yl)acetamide

The title product was prepared according to the procedure used for INTERMEDIATE 8, using 4-formylphenoxyacetic acid and 5-methylisoxazol-3-amine. $^1$H NMR (600 MHz, CD$_3$OD) δ ppm 9.87 (s, 1H) 7.91 (d, 2H) 7.19 (d, J=8.85 Hz, 2H) 6.62 (s, 1H) 4.84 (s, 2H) 2.40 (s, 3H). MS (ESI$^+$) m/z 261 [M+H]$^+$.

Intermediate 149

2-(4-Formylphenoxy)-N-isoxazol-3-ylacetamide

The title product was prepared according to the procedure used for INTERMEDIATE 8, using 4-formylphenoxyacetic acid and 3-aminoisoxazole. $^1$H NMR (600 MHz, CDCl$_3$) δ ppm 9.94 (s, 1H) 8.99 (br. s., 1H) 8.35 (dd, J=1.75, 0.61 Hz, 1H) 7.90-7.94 (m, 2H) 7.13 (d, J=1.75 Hz, 1H) 7.09-7.13 (m, 2H) 4.74 (s, 2H). MS (ESI$^+$) m/z 247 [M+H]$^+$.

Intermediate 150

N-(4-Formylphenyl)-N-methylglycine

The title product was prepared according to the first step of the procedure used for INTERMEDIATE 143, using 4-fluorobenzaldehyde and N-methylglycine. $^1$H NMR (600 MHz, DMSO-d$_6$) δ ppm 12.77 (br. s., 1H) 9.69 (s, 1H) 7.69 (d, J=8.85 Hz, 2H) 6.78 (d, J=8.85 Hz, 2H) 4.24 (s, 2H) 3.07 (s, 3H). MS (ESI$^+$) m/z 194 [M+H]$^+$.

Intermediate 151

N$^2$-(4-Formylphenyl)-N$^2$-methyl-N-pyridin-3-yl-glycinamide

The title product was prepared according to the procedure used for INTERMEDIATE 8, using N-(4-formylphenyl)-N-methylglycine (INTERMEDIATE 150) and 3-aminopyridine. MS (ESI$^+$) m/z 270 [M+H]$^+$.

Intermediate 152

N-(5-Chloropyridin-3-yl)-2-(4-formylphenoxy)acetamide

The title product was prepared according to the procedure used for INTERMEDIATE 8, using 4-formylphenoxyacetic acid and 5-chloropyridin-3-amine. MS (ESI$^+$) m/z 291 [M+H]$^+$.

Intermediate 153

2-(4-Formylphenoxy)-N-(3-methylisoxazol-5-yl)acetamide

The title product was prepared according to the procedure used for INTERMEDIATE 8, using 4-formylphenoxyacetic acid and 5-amino-3-methylisoxazole. $^1$H NMR (600 MHz, CD$_3$OD) δ ppm 9.87 (s, 1H) 7.91 (d, J=8.9 Hz, 2H) 7.19 (d, J=8.9 Hz, 2H) 6.28 (s, 1H) 4.87 (s, 2H) 2.25 (s, 3H). MS (ESI$^+$) m/z 261 [M+H]$^+$.

Intermediate 154

2-(4-Formylphenoxy)-N-1,3-thiazol-2-ylacetamide

The title product was prepared according to the procedure used for INTERMEDIATE 8, using 4-formylphenoxyacetic acid and 2-aminothiazole. $^1$H NMR (600 MHz, DMSO-d$_6$) δ ppm 12.43 (br. s., 1H) 9.88 (s, 1H) 7.88 (d, J=8.9 Hz, 2H) 7.51 (d, J=3.7 Hz, 1H) 7.26 (d, J=3.7 Hz, 1H) 7.16 (d, J=8.5 Hz, 2H) 5.01 (s, 2H). MS (ESI$^+$) m/z 263 [M+H]$^+$.

Intermediate 155

N-(5-tert-Butylisoxazol-3-yl)-2-(4-formylphenoxy)acetamide

The title product was prepared according to the procedure used for INTERMEDIATE 8, using 4-formylphenoxyacetic acid and 3-amino-5-tert-butylisoxazole. $^1$H NMR (600 MHz, CD$_3$OD) δ ppm 9.87 (s, 1H) 7.91 (d, J=8.9 Hz, 2H) 7.19 (d, J=8.5 Hz, 2H) 6.60 (s, 1H) 4.85 (s, 2H) 1.35 (s, 9H). MS (ESI$^+$) m/z 303 [M+H]$^+$.

Intermediate 156

2-(4-Formylphenoxy)-N-1,3,4-thiadiazol-2-ylacetamide

The title product was prepared according to the procedure used for INTERMEDIATE 8, using 4-formylphenoxyacetic acid and 1,3,4-thiadiazol-2-amine. $^1$H NMR (600 MHz, DMSO-d$_6$) δ ppm 12.89 (br. s., 1H) 9.88 (s, 1H) 9.21 (s, 1H) 7.86-7.91 (m, 2H) 7.16-7.20 (m, 2H) 5.07 (s, 2H). MS (ESI$^+$) m/z 264 [M+H]$^+$.

Intermediate 157

2-(4-Formylphenoxy)-N-(1-methyl-1H-pyrazol-5-yl)acetamide

The title product was prepared according to the procedure used for INTERMEDIATE 8, using 4-formylphenoxyacetic acid and 1-methyl-1H-pyrazol-5-ylamine. $^1$H NMR (600 MHz, CDCl$_3$) δ ppm 9.95 (s, 1H) 8.24 (br. s., 1H) 7.91-7.95 (m, 2H) 7.50 (d, J=1.98 Hz, 1H) 7.10-7.14 (m, 2H) 6.36 (d, J=1.98 Hz, 1H) 4.79 (s, 2H) 3.81 (s, 3H). MS (ESI$^+$) m/z 260 [M+H]$^+$.

Intermediate 158

2-(4-Formylphenoxy)-N-1H-1,2,4-triazol-3-ylacetamide

The title product was prepared according to the procedure used for INTERMEDIATE 8, using 4-formylphenoxyacetic acid and 3-amino-1,2,4-triazole. $^1$H NMR (600 MHz, DMSO-d$_6$) δ ppm 13.49 (br. s., 1H) 11.75 (br. s., 1H) 9.88 (s, 1H) 9.14 (s, 1H) 7.85-7.91 (m, 2H) 7.14-7.19 (m, 2H) 4.95 (s, 2H). MS (ESI$^+$) m/z 247 [M+H]$^+$.

Intermediate 159

2-(4-Formylphenoxy)-N-pyrimidin-5-ylacetamide

The title product was prepared according to the procedure used for INTERMEDIATE 8, using 4-formylphenoxyacetic acid and 5-aminopyrimidine. MS (ESI$^+$) m/z 258 [M+H]$^+$.

General Procedure A

Example 5

2-(4-{7-[(1-Benzylpiperidin-4-yl)amino]-6-chloro-3H-imidazo[4,5-b]pyridin-2-yl}phenoxy)-N-[2-(dimethylamino)-1,1-dimethylethyl]acetamide 2-[4-(6,7-Dichloro-3H-imidazo[4,5-b]pyridin-2-yl)phenoxy]-N-[2-(dimethylamino)-1,1-dimethylethyl]acetamide (INTERMEDIATE 13, 22 mg, 0.05 mmol) and 1-benzylpiperidin-4-amine (190 mg, 1.0 mmol, 20 eq) were mixed in n-BuOH (0.7 mL) in a microwave vial, which was capped and heated at 160° C. for 9 h. The crude reaction mixture was purified by preparatory RP-HPLC (basic method). The pure fractions were pooled and evaporated to yield 12.6 mg (43%) of pure title product as off-white solid. $^1$H NMR (600 MHz, DMSO-$d_6$) δ ppm 8.07 (d, J=8.9 Hz, 2H) 7.90 (s, 1H) 7.46 (s, 1H) 7.31-7.37 (m, 4H) 7.23-7.29 (m, 1H) 7.09 (d, J=8.9 Hz, 2H) 5.75 (br. s., 1H) 4.90-5.03 (m, 1H) 4.52 (s, 2H) 3.52 (s, 2H) 2.87 (d, J=11.6 Hz, 2H) 2.45 (s, 2H) 2.24 (s, 6H) 2.14 (t, J=11.1 Hz, 2H) 1.98 (d, J=9.5 Hz, 2H) 1.63-1.73 (m, J=11.7, 11.6, 11.6, 3.7 Hz, 2H) 1.27 (s, 6H). MS (ESI$^+$) m/z 590 [M+H]$^+$.

General Procedure B

Example 17

2-(4-{7-[(1-Benzylpiperidin-4-yl)(methyl)amino]-6-chloro-3H-imidazo[4,5-b]pyridin-2-yl}phenoxy)-N-[2-(diethylamino)ethyl]acetamide A 2 mL round bottomed vial was charged with methyl (4-{7-[(1-benzylpiperidin-4-yl)(methyl)amino]-6-chloro-3H-imidazo[4,5-b]pyridin-2-yl}phenoxy)acetate (INTERMEDIATE 23, 26 mg, 0.05 mmol) and N,N-diethylethane-1,2-diamine (29 mg, 0.25 mmol, 5 eq). Methanol (0.75 mL) was added and the vial was capped and the resulting slurry was heated at 60° C. for 28 h. The reaction mixture was purified by preparatory RP-HPLC (basic method). The pure fractions were pooled and evaporated to yield 15.4 mg (51%) of pure title product as off-white solid. $^1$H NMR (600 MHz, DMSO-$d_6$) δ ppm 13.29 (br. s., 1H) 8.10 (d, J=8.9 Hz, 2H) 8.05 (s, 1H) 7.96 (t, J=5.6 Hz, 1H) 7.30-7.35 (m, 4H) 7.22-7.27 (m, 1H) 7.12 (d, J=8.9 Hz, 2H) 4.57 (s, 2H) 3.89 (t, J=11.3 Hz, 1H) 3.47 (s, 2H) 3.17-3.22 (m, 2H) 3.15 (s, 3H) 2.91 (d, J=11.6 Hz, 2H) 2.46 (t, J=6.9 Hz, 2H) 2.46 (q, J=7.0 Hz, 4H) 2.02 (t, J=11.3 Hz, 2H) 1.92 (q, J=11.5 Hz, 2H) 1.83 (d, J=10.7 Hz, 2H) 0.94 (t, J=7.2 Hz, 6H). MS (ESI$^+$) m/z 604 [M+H]$^+$.

General Procedure C

Example 111

2-[4-(6-Bromo-7-{[1-(4-methoxybenzyl)piperidin-4-yl]amino}-3H-imidazo[4,5-b]pyridin-2-yl)phenoxy]-N-methylacetamide 5-Chloro-N$^4$-[1-(4-methoxybenzyl)piperidin-4-yl]-3-nitropyridine-2,4-diamine (INTERMEDIATE 94, 26 mg, 60 µmol) and 2-(4-formylphenoxy)-N-methylacetamide (INTERMEDIATE 14, 12 mg, 60 µmol) was slurried in EtOH (0.5 mL) and Na$_2$S$_2$O$_4$ (31 mg, 18 µmol, 3 eq.) in water (0.2 mL) was added. The mixture was heated at 70° C. for three days. After cooling to room temperature the reaction mixture was diluted with DMSO to about 1.5 mL, filtered and purified by preparatory RP-HPLC (basic method). The pure fractions were pooled and evaporated to yield 9.8 mg (26%) of pure title product as off-white solid. $^1$H NMR (600 MHz, DMSO-$d_6$) δ ppm 13.14 (br. s., 1H) 8.04-8.10 (m, 3H) 8.00 (s, 1H) 7.22-7.26 (m, 2H) 7.10-7.14 (m, 2H) 6.87-6.91 (m, 2H) 5.48 (d, J=8.85 Hz, 1H) 4.92-5.00 (m, 1H) 4.56 (s, 2H) 3.74 (s, 3H) 3.45 (s, 2H) 2.80-2.87 (m, 2H) 2.68 (d, J=4.73 Hz, 3H) 2.10-2.18 (m, 2H) 1.96-2.03 (m, 2H) 1.60-1.69 (m, 2H). MS (ESI$^+$) m/z 579 [M+H]$^+$.

General Procedure D

Example 107

3-[4-(6-Chloro-7-{[1-(4-methoxybenzyl)piperidin-4-yl]amino}-3H-imidazo[4,5-b]pyridin-2-yl)phenyl]-N-[2-(dimethylamino)ethyl]propanamide A 16 mm reaction tube was charged with 3-[4-(6-chloro-7-{[1-(4-methoxybenzyl)piperidin-4-yl]amino}-3H-imidazo[4,5-b]pyridin-2-yl)phenyl]propanoic acid (INTERMEDIATE 93, 26 mg, 0.05 mmol) and DIPEA (13 mg, 0.1 mmol, 17 µL) in pyridine (100 µL), and N,N-dimethylethane-1,2-diamine (18 mg, 0.20 mmol) in pyridine (100 µL) was added to the mixture followed by T3P (50% in EtOAc, 60 µL, 0.1 mmol) in pyridine (750 µL). The reaction mixture was heated at 50° C. for 24 h. The crude reaction mixture was concentrated in vacuo and dissolved in DMSO (ca. 0.8 mL) and purified by preparatory reversed phase HPLC (basic method). The pure fractions were pooled and concentrated to dryness to yield 21.8 mg (74%) of pure title compound as white solid. $^1$H NMR (600 MHz, DMSO-$d_6$) δ ppm 13.16 (br. s., 1H) 8.02 (d, J=8.5 Hz, 2H) 7.92 (s, 1H) 7.75 (t, J=5.5 Hz, 1H) 7.36 (d, J=8.2 Hz, 2 H) 7.23 (d, J=8.5 Hz, 2H) 6.89 (d, J=8.5 Hz, 2H) 5.79 (d, J=8.9 Hz, 1H) 4.90-5.01 (m, 1H) 3.74 (s, 3H) 3.44 (s, 2H) 3.12 (q, J=6.4 Hz, 2H) 2.88 (t, J=7.5 Hz, 2H) 2.85 (d, J=11.3 Hz, 2H) 2.42 (t, J=7.6 Hz, 2H) 2.22 (t, J=6.7 Hz, 2H) 2.11 (s, 6H) 2.10 (t, J=10.8 Hz, 2H) 1.98 (d, J=11.6 Hz, 2H) 1.66 (qd, J=11.7, 3.7 Hz, 2H). MS (ESI$^+$) m/z 590 [M+H]$^+$.

General Procedure E

Example 107

N-{2-[4-(6-Chloro-7-{[1-(4-methoxybenzyl)piperidin-4-yl]amino}-3H-imidazo[4,5-b]pyridin-2-yl)phenoxy]ethyl}-2-methylpropanamide 2-[4-(2-Aminoethoxy)phenyl]-6-chloro-N-[1-(4-methoxybenzyl)piperidin-4-yl]-3H-imidazo[4,5-b]pyridin-7-amine tri-hydrochloride (INTERMEDIATE 282, 31 mg, 0.050 mmol) was slurried in CH$_3$CN (0.5 mL) and DIPEA (33 mg, 0.25 mmol, 44 µL) was added followed by 2-methylpropanoyl chloride (11 mg, 0.10 mmol) dissolved in CH$_3$CN (0.2 mL).

The reaction was stirred at room temperature for 1 h. The reaction mixture was diluted with DMSO to about 1.5 mL, filtered and purified by preparatory RP-HPLC (basic method). The pure fractions were pooled and evaporated to yield 18.9 mg (65%) of pure title product. $^1$H NMR (600 MHz, DMSO-$d_6$) δ ppm 13.10 (br. s., 1H) 8.04-8.08 (m, 2H) 8.00 (t, J=5.57 Hz, 1H) 7.90 (s, 1H) 7.21-7.25 (m, 2H) 7.09-7.13 (m, 2H) 6.88-6.91 (m, 2H) 5.75 (d, J=8.85 Hz, 1H) 4.91-5.00 (m, 1H) 4.07 (t, J=5.80 Hz, 2H) 3.74 (s, 3H) 3.44 (s, 2H) 3.44 (td, J=5.80, 5.57 Hz, 2H) 2.82-2.89 (m, 2H) 2.40 (spt, J=6.84 Hz, 1H) 2.07-2.15 (m, 2H) 1.93-2.01 (m, 2H) 1.61-1.71 (m, 2H) 1.01 (d, J=6.84 Hz, 6H). MS (ESI$^+$) m/z 577 [M+H]$^+$.

Structural formulas and chemical names of some compounds of the invention are shown in Table 1.

TABLE 1

| Ex. | Structural formula (without salt) | Chemical name |
|---|---|---|
| 1 | 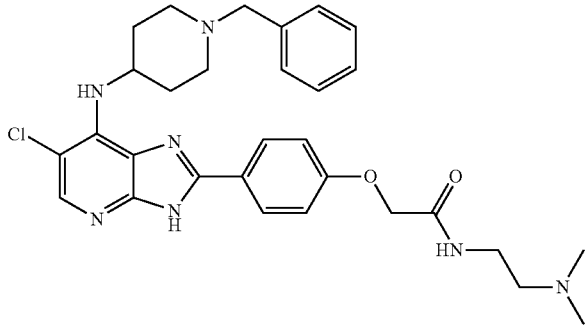 [SMILES: CN(C)CCNC(=O)COc1ccc(-c2nc3c(NC4CCN(Cc5ccccc5)CC4)c(Cl)cnc3[nH]2)cc1] | 2-(4-{7-[(1-benzylpiperidin-4-yl)amino]-6-chloro-3H-imidazo[4,5-b]pyridin-2-yl}phenoxy)-N-[2-(dimethylamino)ethyl]acetamide |
| 2 | 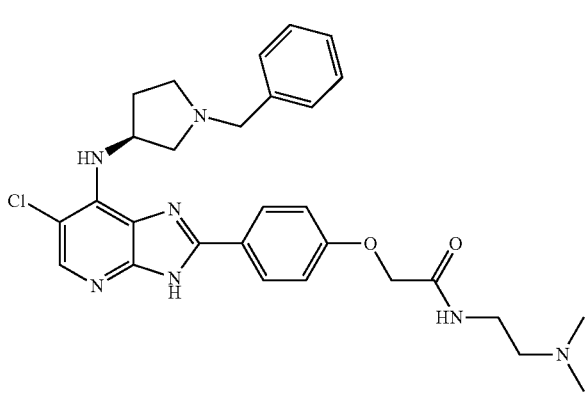 [SMILES: CN(C)CCNC(=O)COc1ccc(-c2nc3c(N[C@H]4CCN(Cc5ccccc5)C4)c(Cl)cnc3[nH]2)cc1] | 2-[4-(7-{[(3S)-1-benzylpyrrolidin-3-yl]amino}-6-chloro-3H-imidazo[4,5-b]pyridin-2-yl)phenoxy]-N-[2-(dimethylamino)ethyl]acetamide |
| 3 | 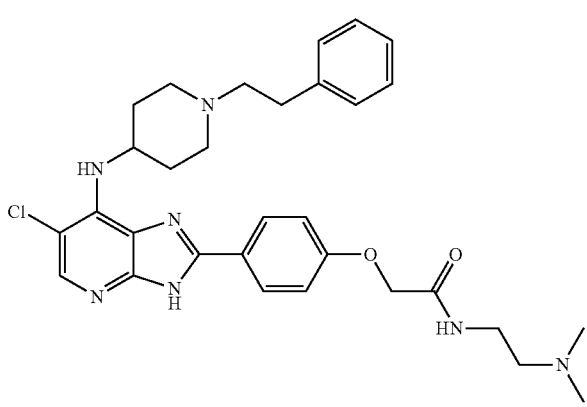 [SMILES: CN(C)CCNC(=O)COc1ccc(-c2nc3c(NC4CCN(CCc5ccccc5)CC4)c(Cl)cnc3[nH]2)cc1] | 2-[4-(6-chloro-7-{[1-(2-phenylethyl)piperidin-4-yl]amino}-3H-imidazo[4,5-b]pyridin-2-yl)phenoxy]-N-[2-(dimethylamino)ethyl]acetamide |
| 4 | 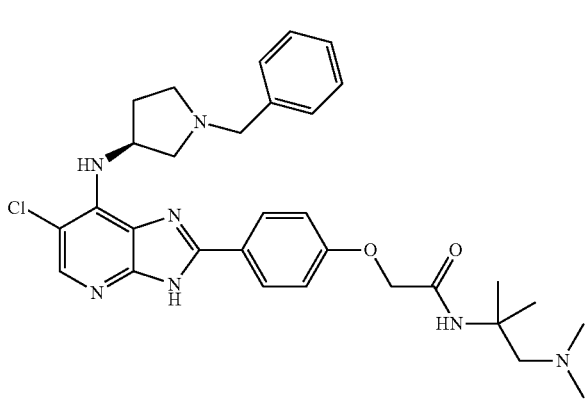 [SMILES: CN(C)CC(C)(C)NC(=O)COc1ccc(-c2nc3c(N[C@H]4CCN(Cc5ccccc5)C4)c(Cl)cnc3[nH]2)cc1] | 2-[4-(7-{[(3S)-1-benzylpyrrolidin-3-yl]amino}-6-chloro-3H-imidazo[4,5-b]pyridin-2-yl)phenoxy]-N-[2-(dimethylamino)-1,1-dimethylethyl]acetamide |

TABLE 1-continued

| Ex. | Structural formula (without salt) | Chemical name |
|---|---|---|
| 5 | | 2-(4-{7-[(1-benzylpiperidin-4-yl)amino]-6-chloro-3H-imidazo[4,5-b]pyridin-2-yl}phenoxy)-N-[2-(dimethylamino)-1,1-dimethylethyl]acetamide |
| 6 | | 2-[4-(6-chloro-7-{[1-(4-fluorobenzyl)piperidin-4-yl]amino}-3H-imidazo[4,5-b]pyridin-2-yl)phenoxy]-N-[2-(dimethylamino)-1,1-dimethylethyl]acetamide |
| 7 | | 2-(4-{7-[(1-benzylpiperidin-3-yl)amino]-6-chloro-3H-imidazo[4,5-b]pyridin-2-yl}phenoxy)-N-[2-(dimethylamino)-1,1-dimethylethyl]acetamide |
| 8 | | 2-{4-[6-chloro-7-({1-[(3-methyl-2-thienyl)methyl]piperidin-4-yl}amino)-3H-imidazo[4,5-b]pyridin-2-yl]phenoxy}-N-[2-(dimethylamino)-1,1-dimethylethyl]acetamide |

TABLE 1-continued

| Ex. | Structural formula (without salt) | Chemical name |
|---|---|---|
| 9 | 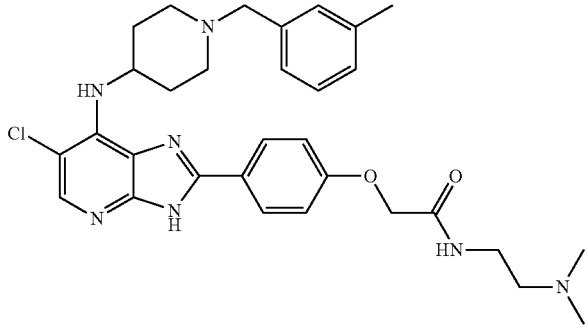 [SMILES: Cc1cccc(CN2CCC(Nc3c(Cl)cnc4[nH]c(-c5ccc(OCC(=O)NCCN(C)C)cc5)nc34)CC2)c1] | 2-[4-(6-chloro-7-{[1-(3-methylbenzyl)piperidin-4-yl]amino}-3H-imidazo[4,5-b]pyridin-2-yl)phenoxy]-N-[2-(dimethylamino)ethyl]acetamide |
| 10 | 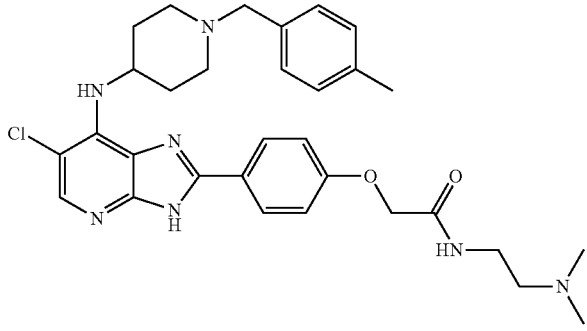 [SMILES: Cc1ccc(CN2CCC(Nc3c(Cl)cnc4[nH]c(-c5ccc(OCC(=O)NCCN(C)C)cc5)nc34)CC2)cc1] | 2-[4-(6-chloro-7-{[1-(4-methylbenzyl)piperidin-4-yl]amino}-3H-imidazo[4,5-b]pyridin-2-yl)phenoxy]-N-[2-(dimethylamino)ethyl]acetamide |
| 11 | 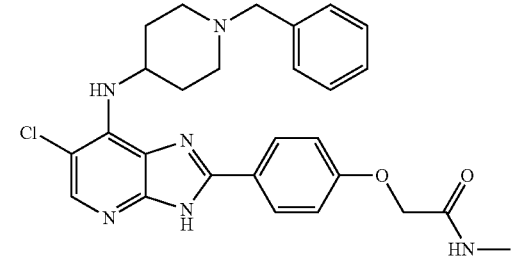 [SMILES: CNC(=O)COc1ccc(-c2nc3c(NC4CCN(Cc5ccccc5)CC4)c(Cl)cnc3[nH]2)cc1] | 2-(4-{7-[(1-benzylpiperidin-4-yl)amino]-6-chloro-3H-imidazo[4,5-b]pyridin-2-yl}phenoxy)-N-methylacetamide |
| 12 | 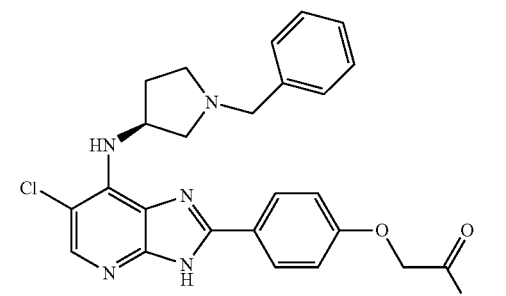 | 2-[4-(7-{[(3S)-1-benzylpyrrolidin-3-yl]amino}-6-chloro-3H-imidazo[4,5-b]pyridin-2-yl)phenoxy]-N-methylacetamide |
| 13 | 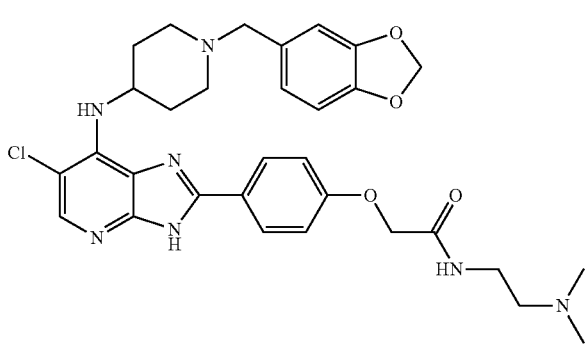 [SMILES: CN(C)CCNC(=O)COc1ccc(-c2nc3c(NC4CCN(Cc5ccc6c(c5)OCO6)CC4)c(Cl)cnc3[nH]2)cc1] | 2-[4-(7-{[1-(1,3-benzodioxol-5-ylmethyl)piperidin-4-yl]amino}-6-chloro-3H-imidazo[4,5-b]pyridin-2-yl)phenoxy]-N-[2-(dimethylamino)ethyl]acetamide |

TABLE 1-continued

| Ex. | Structural formula (without salt) | Chemical name |
|---|---|---|
| 14 | | 2-[4-(6-chloro-7-{[1-(1,3-thiazol-2-ylmethyl)piperidin-4-yl]amino}-3H-imidazo[4,5-b]pyridin-2-yl)phenoxy]-N-[2-(dimethylamino)ethyl]acetamide |
| 15 | | 2-[4-(6-chloro-7-{[1-(thiophen-3-ylmethyl)piperidin-4-yl]amino}-3H-imidazo[4,5-b]pyridin-2-yl)phenoxy]-N-[2-(dimethylamino)ethyl]acetamide |
| 16 | | 2-[4-(7-{[(1-benzylpiperidin-4-yl)methyl]amino}-6-chloro-3H-imidazo[4,5-b]pyridin-2-yl)phenoxy]-N-[2-(dimethylamino)ethyl]acetamide |
| 17 | | 2-(4-{7-[(1-benzylpiperidin-4-yl)(methyl)amino]-6-chloro-3H-imidazo[4,5-b]pyridin-2-yl}phenoxy)-N-[2-(diethylamino)ethyl]acetamide |

TABLE 1-continued

| Ex. | Structural formula (without salt) | Chemical name |
|---|---|---|
| 18 | | 2-(4-{7-[(1-benzylpiperidin-4-yl)(methyl)amino]-6-chloro-3H-imidazo[4,5-b]pyridin-2-yl}phenoxy)-N-[2-(dimethylamino)-2-methylpropyl]acetamide |
| 19 | | 2-(4-{7-[(1-benzylpiperidin-4-yl)(methyl)amino]-6-chloro-3H-imidazo[4,5-b]pyridin-2-yl}phenoxy)-N-methylacetamide |
| 20 | | 2-(4-{7-[(1-benzylpiperidin-4-yl)(methyl)amino]-6-chloro-3H-imidazo[4,5-b]pyridin-2-yl}phenoxy)-N-[2-(dimeethylamino)ethyl]acetamide |
| 21 | | 2-(4-{7-[(1-benzylpiperidin-4-yl)(methyl)amino]-6-chloro-3H-imidazo[4,5-b]pyridin-2-yl}phenoxy)-N-[2-(dimethylamino)-1-methylethyl]acetamide |
| 22 | | 2-[4-(6-chloro-7-{[1-(4-chlorobenzyl)piperidin-4-yl]amino}-3H-imidazo[4,5-b]pyridin-2-yl)phenoxy]-N-[2-(dimethylamino)ethyl]acetamide |

TABLE 1-continued

| Ex. | Structural formula (without salt) | Chemical name |
|---|---|---|
| 23 | | 2-(4-{7-[(1-benzylpiperidin-4-yl)amino]-6-chloro-3H-imidazo[4,5-b]pyridin-2-yl}phenoxy)-N-[2-(dimethylamino)-2-methylpropyl]acetamide |
| 24 | | 2-[4-(7-{[(3R)-1-benzylpyrrolidin-3-yl]amino}-6-chloro-3H-imidazo[4,5-b]pyridin-2-yl)phenoxy]-N-[2-(dimethylamino)-2-methylpropyl]acetamide |
| 25 | | 2-[4-(7-{[(3S)-1-benzylpyrrolidin-3-yl]amino}-6-chloro-3H-imidazo[4,5-b]pyridin-2-yl)phenoxy]-N-[2-(dimethylamino)-2-methylpropyl]acetamide |
| 26 | | 2-[4-(6-chloro-7-{[1-(4-fluorobenzyl)piperidin-4-yl]amino}-3H-imidazo[4,5-b]pyridin-2-yl)phenoxy]-N-[2-(dimethylamino)-2-methylpropyl]acetamide |

TABLE 1-continued

| Ex. | Structural formula (without salt) | Chemical name |
|---|---|---|
| 27 | | 2-[4-(6-chloro-7-{[1-(4-methylbenzyl)piperidin-4-yl]amino}-3H-imidazo[4,5-b]pyridin-2-yl)phenoxy]-N-[2-(dimethylamino)-2-methylpropyl]acetamide |
| 28 | | 2-[4-(6-chloro-7-{[1-(3-methylbenzyl)piperidin-4-yl]amino}-3H-imidazo[4,5-b]pyridin-2-yl)phenoxy]-N-[2-(dimethylamino)-2-methylpropyl]acetamide |
| 29 | | 2-{4-[6-chloro-7-({1-[(5-methylfuran-2-yl)methyl]piperidin-4-yl}amino)-3H-imidazo[4,5-b]pyridin-2-yl]phenoxy}-N-[2-(dimethylamino)ethyl]acetamide |
| 30 | | 2-[4-(7-{[(3R)-1-benzylpyrrolidin-3-yl]amino}-6-chloro-3H-imidazo[4,5-b]pyridin-2-yl)phenoxy]-N-[2-(dimethylamino)ethyl]acetamide |

TABLE 1-continued

| Ex. | Structural formula (without salt) | Chemical name |
|---|---|---|
| 31 | 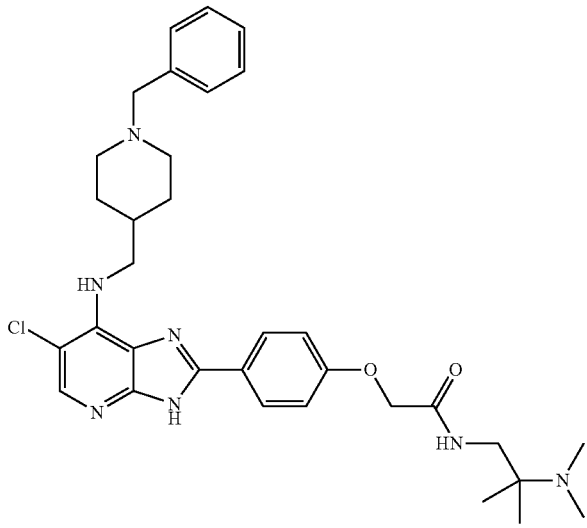 [SMILES: CN(C)C(C)(C)CNC(=O)COc1ccc(-c2nc3c(NCC4CCN(Cc5ccccc5)CC4)c(Cl)cnc3[nH]2)cc1] | 2-[4-(7-{[(1-benzylpiperidin-4-yl)methyl]amino}-6-chloro-3H-imidazo[4,5-b]pyridin-2-yl)phenoxy]-N-[2-(dimeethylamino)-2-methylpropyl]acetamide |
| 32 | 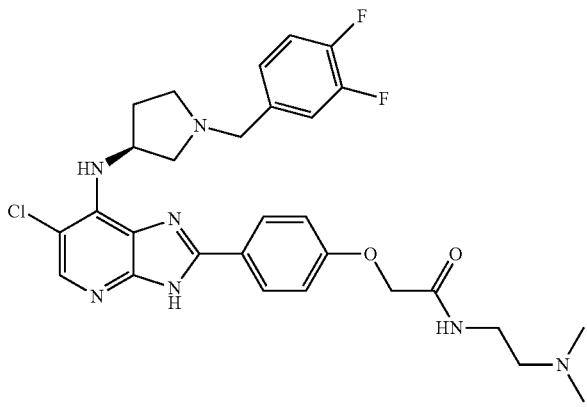 [SMILES: CN(C)CCNC(=O)COc1ccc(-c2nc3c(N[C@H]4CCN(Cc5ccc(F)c(F)c5)C4)c(Cl)cnc3[nH]2)cc1] | 2-[4-(6-chloro-7-{[(3S)-1-(3,4-difluorobenzyl)pyrrolidin-3-yl]amino}-3H-imidazo[4,5-b]pyridin-2-yl)phenoxy]-N-[2-(dimethylamino)ethyl]acetamide |
| 33 | 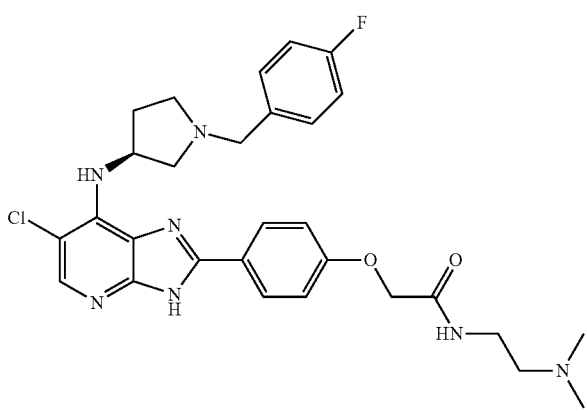 [SMILES: CN(C)CCNC(=O)COc1ccc(-c2nc3c(N[C@H]4CCN(Cc5ccc(F)cc5)C4)c(Cl)cnc3[nH]2)cc1] | 2-[4-(6-chloro-7-{[(3S)-1-(4-fluorobenzyl)pyrrolidin-3-yl]amino}-3H-imidazo[4,5-b]pyridin-2-yl)phenoxy]-N-[2-(dimethylamino)ethyl]acetamide |

TABLE 1-continued

| Ex. | Structural formula (without salt) | Chemical name |
|---|---|---|
| 34 | | 2-[4-(6-chloro-7-{[(3S)-1-(3,4-difluorobenzyl)pyrrolidin-3-yl]amino}-3H-imidazo[4,5-b]pyridin-2-yl)phenoxy]-N-methylacetamide |
| 35 | | 2-[4-(6-chloro-7-{[(3S)-1-(4-fluorobenzyl)pyrrolidin-3-yl]amino}-3H-imidazo[4,5-b]pyridin-2-yl)phenoxy]-N-methylacetamide |
| 36 | | 2-[4-(6-chloro-7-{[(3R)-1-(4-fluorobenzyl)pyrrolidin-3-yl]amino}-3H-imidazo[4,5-b]pyridin-2-yl)phenoxy]-N-[2-(dimethylamino)ethyl]acetamide |
| 37 | | 2-[4-(6-chloro-7-{[(3R)-1-(4-fluorobenzyl)pyrrolidin-3-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 38 | | 2-[4-(7-{[(3R)-1-benzylpyrrolidin-3-yl]amino}-6-chloro-3H-imidazo[4,5-b]pyridin-2-yl)phenoxy]-N-methylacetamide |
| 39 | | 2-[4-(6-chloro-7-{[1-(thiophen-3-ylmethyl)piperidin-4-yl]amino}-3H-imidazo[4,5-b]pyridin-2-yl)phenoxy]-N-meethylacetamide |
| 40 | | 2-[4-(6-chloro-7-{[1-(3-methylbenzyl)piperidin-4-yl]amino}-3H-imidazo[4,5-b]pyridin-2-yl)phenoxy]-N-methylacetamide |
| 41 | | 2-[4-(6-chloro-7-{[(3S)-1-(2-phenylethyl)pyrrolidin-3-yl]amino}-3H-imidazo[4,5-b]pyridin-2-yl)phenoxy]-N-methylacetamide |
| 42 | | 2-{4-[6-chloro-7-({1-[(3-methyl-2-thienyl)methyl]piperidin-4-yl}amino)-3H-imidazo[4,5-b]pyridin-2-yl]phenoxy}-N-methylacetamide |

TABLE 1-continued

| Ex. | Structural formula (without salt) | Chemical name |
|---|---|---|
| 43 | | 2-[4-(6-chloro-7-{[(3S)-1-(4-methoxybenzyl)pyrrolidin-3-yl]amino}-3H-imidazo[4,5-b]pyridin-2-yl)phenoxy]-N-methylacetamide |
| 44 | | 2-[4-(6-chloro-7-{[1-(4-methoxybenzyl)piperidin-4-yl]amino}-3H-imidazo[4,5-b]pyridin-2-yl)phenoxy]-N-methylacetamide |
| 45 | | 2-[4-(7-{[(1,3-benzodioxol-5-ylmethyl)piperidin-4-yl]amino}-6-chloro-3H-imidazo[4,5-b]pyridin-2-yl)phenoxy]-N-methylacetamide |
| 46 | | 2-{4-[6-chloro-7-({1-[(5-methylfuran-2-yl)methyl]piperidin-4-yl}amino)-3H-imidazo[4,5-b]pyridin-2-yl]phenoxy}-N-methylacetamide |
| 47 | | 2-[4-(6-chloro-7-{[(3S)-1-(thiophen-3-ylmethyl)pyrrolidin-3-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 48 | | 2-[4-(6-chloro-7-{[1-(furan-3-ylmethyl)piperidin-4-yl]amino}-3H-imidazo[4,5-b]pyridin-2-yl)phenoxy]-N-methylacetamide |
| 49 | | 2-[4-(7-{[(3S)-1-(1,3-benzodioxol-5-ylmethyl)pyrrolidin-3-yl]amino}-6-chloro-3H-imidazo[4,5-b]pyridin-2-yl)phenoxy]-N-methylacetamide |
| 50 | | 2-[4-(6-chloro-7-{[(3S)-1-(1,3-thiazol-2-ylmethyl)pyrrolidin-3-yl]amino}-3H-imidazo[4,5-b]pyridin-2-yl)phenoxy]-N-methylacetamide |
| 51 | | 2-{4-[6-chloro-7-({(3S)-1-[(3-methyl-2-thienyl)methyl]pyrrolidin-3-yl}amino)-3H-imidazo[4,5-b]pyridin-2-yl]phenoxy}-N-methylacetamide |
| 52 | | 2-{4-[6-chloro-7-({(3S)-1-[4-(trifluoromethyl)benzyl]pyrrolidin-3-yl}amino)-3H-imidazo[4,5-b]pyridin-2-yl]phenoxy}-N-methylacetamide |

TABLE 1-continued

| Ex. | Structural formula (without salt) | Chemical name |
|---|---|---|
| 53 | | 2-[4-(6-chloro-7-{[(3S)-1-(3-methylbenzyl)pyrrolidin-3-yl]amino}-3H-imidazo[4,5-b]pyridin-2-yl)phenoxy]-N-methylacetamide |
| 54 | | 2-[4-(6-chloro-7-{[(3S)-1-(4-methylbenzyl)pyrrolidin-3-yl] amino}-3H-imidazo[4,5-b]pyridin-2-yl)phenoxy]-N-methylacetamide |
| 55 | | 2-[4-(6-chloro-7-{[(3S)-1-(2-thienylmethyl)pyrrolidin-3-yl]amino}-3H-imidazo[4,5-b]pyridin-2-yl)phenoxy]-N-methylacetamide |
| 56 | | 2-(4-{6-chloro-7-[(1-cyclohexylpiperidin-4-yl)amino]-3H-imidazo[4,5-b]pyridin-2-yl}phenoxy)-N-methylacetamide |
| 57 | | 2-[4-(6-chloro-7-{[(3S)-1-(3-methoxybenzyl)pyrrolidin-3-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 58 | | 2-[4-(6-chloro-7-}[(3S)-1-(2-methoxybenzyl)pyrrolidin-3-yl]amino}-3H-imidazo[4,5-b]pyridin-2-yl)phenoxy]-N-methylacetamide |
| 59 | | 2-[4-(6-chloro-7-{[(3S)-1-(2-methylbenzyl)pyrrolidin-3-yl]amino}-3H-imidazo[4,5-b]pyridin-2-yl)phenoxy]-N-methylacetamide |
| 60 | | 2-[4-(6-chloro-7-{[1-(2,4-dimethoxybenzyl)piperidin-4-yl]amino}-3H-imidazo[4,5-b]pyridin-2-yl)phenoxy]-N-methylacetamide |
| 61 | | 2-[4-(6-chloro-7-{[1-(2-methoxybenzyl)piperidin-4-yl]amino}-3H-imidazo[4,5-b]pyridin-2-yl)phenoxy]-N-methylacetamide |
| 62 | | 2-[4-(6-chloro-7-{[1-(3-methoxybenzyl)piperidin-4-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 63 | | 2-(4-{7-[(1-benzylpiperidin-4-yl)amino]-6-chloro-3H-imidazo[4,5-b]pyridin-2-yl}phenoxy)-N,N-dimethylacetamide |
| 64 | | 2-[4-(7-{[(3S)-1-benzylpyrrolidin-3-yl]amino}-6-chloro-3H-imidazo[4,5-b]pyridin-2-yl)phenoxy]-N,N-dimethylacetamide |
| 65 | | 2-[4-(6-chloro-7-{[1-(2,3-dihydro-1,4-benzodioxin-6-ylmethyl)piperidin-4-yl]amino}-3H-imidazo[4,5-b]pyridin-2-yl)phenoxy]-N-methylacetamide |
| 66 | | 2-[4-(6-chloro-7-{[1-(cyclohexylmethyl)piperidin-4-yl]amino}-3H-imidazo[4,5-b]pyridin-2-yl)phenoxy]-N-methylacetamide |
| 67 | | 2-[4-(6-chloro-7-{[1-(2,2-dimethylpropyl)piperidin-4-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 68 | | 2-[4-(6-chloro-7-1[1-(3-hydroxybenzyl)piperidin-4-yl]amino}-3H-imidazo[4,5-b]pyridin-2-yl)phenoxy]-N-methylacetamide |
| 69 | | 2-{4-[6-chloro-7-({1-[4-(difluoromethoxy)benzyl]piperidin-4-yl}amino)-3H-imidazo[4,5-b]pyridin-2-yl]phenoxy}-N-methylacetamide |
| 70 | | 2-[4-(6-chloro-7-{[1-(4-methoxy-3-methylbenzyl)piperidin-4-yl]amino}-3H-imidazo[4,5-b]pyridin-2-yl)phenoxy]-N-methylacetamide |
| 71 | | 2-[4-(6-chloro-7-{[1-(pyridin-4-ylmethyl)piperidin-4-yl]amino}-3H-imidazo[4,5-b]pyridin-2-yl)phenoxy]-N-methylacetamide |
| 72 | | 2-[4-(6-chloro-7-{[1-(pyridin-3-ylmethyl)piperidin-4-yl]amino}-3H-imidazo[4,5-b]pyridin-2-yl)phenoxy]-N-methylacetamide |
| 73 | | 2-{4-[6-chloro-7-({1-[(1-methyl-1H-pyrrol-2-yl)methyl]piperidin-4-yl}amino)-3H-imidazo[4,5-b]pyridin-2-yl]phenoxy}-N-methylacetamide |

TABLE 1-continued

| Ex. | Structural formula (without salt) | Chemical name |
|---|---|---|
| 74 | | 2-{4-[6-chloro-7-({1-[(6-methylpyridin-2-yl)methyl]piperidin-4-yl}amino)-3H-imidazo[4,5-b]pyridin-2-yl]phenoxy}-N-methylacetamide |
| 75 | | 2-[4-(7-{[1-(4-acetamidobenzyl)piperidin-4-yl]amino}-6-chloro-3H-imidazo[4,5-b]pyridin-2-yl)phenoxy]-N-methylacetamide |
| 76 | | 2-[4-(6-chloro-7-{[1-(1,3-thiazol-2-ylmethyl)piperidin-4-yl]amino}-3H-imidazo[4,5-b]pyridin-2-yl)phenoxy]-N-methylacetamide |
| 77 | | 2-[4-(6-chloro-7-{[1-(4-ethoxybenzyl)piperidin-4-yl]amino}-3H-imidazo[4,5-b]pyridin-2-yl)phenoxy]-N-methylacetamide |
| 78 | | 2-[4-(6-chloro-7-{[1-(4-isopropoxybenzyl)piperidin-4-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 79 | | 2-[4-(7-{[(1-benzylpiperidin-4-yl)methyl]amino}-6-chloro-3H-imidazo[4,5-b]pyridin-2-yl)phenoxy]-N-methylacetamide |
| 80 | | 2-[4-(6-chloro-7-{[1-(4-methoxy-3,5-dimethylbenzyl)piperidin-4-yl]amino}-3H-imidazo[4,5-b]pyridin-2-yl)phenoxy]-N-methylacetamide |
| 81 | | 2-[4-(6-chloro-7-{[1-(4-chlorobenzyl)piperidin-4-yl]amino}-3H-imidazo[4,5-b]pyridin-2-yl)phenoxy]-N-methylacetamide |
| 82 | | 2-[4-(6-chloro-7-{[1-(4-methylbeiizyl)piperidin-4-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 83 | | 2-[4-(6-chloro-7-{[1-(4-cyanobenzyl)piperidin-4-yl]amino}-3H-imidazo[4,5-b]pyridin-2-yl)phenoxy]-N-methylacetamide |
| 84 | | 2-[4-(6-chloro-7-{[1-(3-cyanobenzyl)piperidin-4-yl]amino}-3H-imidazo[4,5-b]pyridin-2-yl)phenoxy ]-N-methylacetamide |
| 85 | | 2-[4-(6-chloro-7-{[1-(4-hydroxybenzyl)piperidin-4-yl]amino}-3H-imidazo[4,5-b]pyridin-2-yl)phenoxy]-N-methylacetamide |
| 86 | | 2-{4-[6-chloro-7-(piperidin-4-ylamino)-3H-imidazo[4,5-b]pyridin-2-yl]phenoxy}-N-methylacetamide |
| 87 | | 2-[4-(6-chloro-7-{[1-(4-fluorobenzyl)piperidin-4-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 88 | | 2-[4-(6-chloro-7-{[1-(3,4-difluorobenzyl)piperidin-4-yl]amino}-3H-imidazo[4,5-b]pyridin-2-yl)phenoxy]-N-methylacetamide |
| 89 | | 2-{4-[6-chloro-7-({1-[4-(dimethylamino)benzyl]piperidin-4-yl}amino)-3H-imidazo[4,5-b]pyridin-2-yl]phenoxy}-N-methylacetamide |
| 90 | | 2-{4-[6-chloro-7-({1-[4-(methylsulfonyl)benzyl]piperidin-4-yl}amino)-3H-imidazo[4,5-b]pyridin-2-yl]phenoxy}-N-methylacetamide |
| 91 | | 2-[4-(6-chloro-7-{[1-(2,3-dihydro-1-benzofuran-5-ylmethyl)piperidin-4-yl]amino}-3H-imidazo[4,5-b]pyridin-2-yl)phenoxy]-N-methylacetamide |
| 92 | | 2-(4-{6-chloro-7-[(1-methylpiperidin-4-yl)amino]-3H-imidazo[4,5-b]pyridin-2-yl}phenoxy)-N-methylacetamide |
| 93 | | 2-[4-(6-chloro-7-{[1-(2-thienylmethyl)piperidin-4-yl]amino}-3H-imidazo[4,5-b]pyridin-2-yl)phenoxy]-N-methylacetamide |

TABLE 1-continued

| Ex. | Structural formula (without salt) | Chemical name |
| --- | --- | --- |
| 94 | | 2-[4-(6-chloro-7-{[1-(2-phenylethyl)piperidin-4-yl]amino}-3H-imidazo[4,5-b]pyridin-2-yl)phenoxy]-N-methylacetamide |
| 95 | | 2-{4-[6-chloro-7-({1-[2-(4-methoxyphenyl)ethyl]piperidin-4-yl}amino)-3H-imidazo[4,5-b]pyridin-2-yl]phenoxy}-N-methylacetamide |
| 96 | | 2-[4-(6-chloro-7-{[1-(2-phenoxyethyl)piperidin-4-yl]amino}-3H-imidazo[4,5-b]pyridin-2-yl)phenoxy]-N-methylacetamide |
| 97 | | 2-[4-(6-chloro-7-{[1-(3,4-dimethoxybenzyl)piperidin-4-yl]amino}-3H-imidazo[4,5-b]pyridin-2-yl)phenoxy]-N-methylacetamide |
| 98 | | 2-[4-(6-chloro-7-{[1-(4-hydroxy-3-methoxybenzyl)piperidin-4-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 99 | | 2-{4-[6-chloro-7-({1-[4-(1H-1,2,4-triazol-1-yl)benzyl]piperidin-4-yl}amino)-3H-imidazo[4,5-b]pyridin-2-yl]phenoxy}-N-methylacetamide |
| 100 | | 2-{4-[6-chloro-7-({1-[4-(methylthio)benzyl]piperidin-4-yl}amino)-3H-imidazo[4,5-b]pyridin-2-yl]phenoxy}-N-methylacetamide |
| 101 | | 2-[4-(6-chloro-7-{[1-(4-methoxybenzyl)piperidin-4-yl]amino}-3H-imidazo[4,5-b]pyridin-2-yl)phenoxy]-N-(2-hydroxyethyl)acetamide |
| 102 | | 2-[4-(6-chloro-7-{[1-(4-methoxybenzyl)piperidin-4-yl]amino}-3H-imidazo[4,5-b]pyridin-2-yl)phenoxy]-N-[2-(dimethylamino)ethyl]acetamide |
| 103 | | 2-[4-(6-chloro-7-{[1-(4-methoxybenzyl)pipendin-4-yl]amino}-3H-imidazo[4,5-b]pyridin-2-yl)phenoxy]-N-[2-(dimethylamino)-2-methylpropyl] acetamide |

TABLE 1-continued

| Ex. | Structural formula (without salt) | Chemical name |
|---|---|---|
| 104 | | 2-[4-(6-chloro-7-{[1-(4-methoxybenzyl)piperidin-4-yl]amino}-3H-imidazo[4,5-b]pyridin-2-yl)phenoxy]-N-isopropylacetamide |
| 105 | | 2-[4-(6-chloro-7-{[1-(4-methoxybenzyl)piperidin-4-yl]amino}-3H-imidazo[4,5-b]pyridin-2-yl)phenoxy]-N-(2-isopropoxyethyl)acetamide |
| 106 | | 3-[4-(6-chloro-7-{[1-(4-methoxybenzyl)piperidin-4-yl]amino}-3H-imidazo[4,5-b]pyridin-2-yl)phenyl]-N-methylpropanamide |
| 107 | | 3-[4-(6-chloro-7-{[1-(4-methoxybenzyl)piperidin-4-yl]amino}-3H-imidazo[4,5-b]pyridin-2-yl)phenyl]-N-[2-(dimethylamino)ethyl]propanamide |
| 108 | | 3-[4-(6-chloro-7-{[1-(4-methoxybenzyl)piperidin-4-yl]amino}-3H-imidazo[4,5-b]pyridin-2-yl)phenyl]-N-methoxypropanamide |

TABLE 1-continued

| Ex. | Structural formula (without salt) | Chemical name |
|---|---|---|
| 109 | | 2-(4-{6-chloro-7-[(1-ethylpiperidin-4-yl)amino]-3H-imidazo[4,5-b]pyridin-2-yl}phenoxy)-N-methylacetamide |
| 110 | | 2-[4-(6-chloro-7-{[1-(1-methylethyl)piperidin-4-yl]amino}-3H-imidazo[4,5-b]pyridin-2-yl)phenoxy]-N-methylacetamide |
| 111 | | 2-[4-(6-bromo-7-{[1-(4-methoxybenzyl)piperidin-4-yl]amino}-3H-imidazo[4,5-b]pyridin-2-yl)phenoxy]-N-methylacetamide |
| 112 | | 2-[4-(6-bromo-7-{[1-(2,3-dihydro-1-benzofuran-5-ylmethyl)piperidin-4-yl]amino}-3H-imidazo[4,5-b]pyridin-2-yl)phenoxy]-{V-methylacetamide |
| 113 | | 2-[4-(6-bromo-7-{[1-(thiophen-2-ylmethyl)piperidin-4-yl]amino}-3H-imidazo[4,5-/?]pyridin-2-yl)phenoxy]-N-methylacetamide |

TABLE 1-continued

| Ex. | Structural formula (without salt) | Chemical name |
| --- | --- | --- |
| 114 | | 2-(4-{6-bromo-7-[(1-methylpiperidin-4-yl)amino]-3H-imidazo[4,5-b]pyridin-2-yl}phenoxy)-N-methylacetamide |
| 115 | | 2-[4-(6-bromo-7-{[(3S)-1-(2-methoxybenzyl)pyrrolidin-3-yl]amino}-3H-imidazo[4,5-b]pyridin-2-yl)phenoxy]-N-methylacetamide |
| 116 | | 2-[3-(6-chloro-7-{[1-(4-methoxybenzyl)piperidin-4-yl]amino}-3H-imidazo[4,5-b]pyridin-2-yl)phenoxy]-N-methylacetamide |
| 117 | | 2-(3-{6-chloro-7-[(1-methylpiperidin-4-yl)amino]-3H-imidazo[4,5-b]pyridin-2-yl}phenoxy)-N-methylacetamide |

TABLE 1-continued

| Ex. | Structural formula (without salt) | Chemical name |
|---|---|---|
| 118 | | 2-[3-(6-chloro-7-{[1-(2,3-dihydro-1-benzofuran-5-ylmethyl)piperidin-4-yl]amino}-3H-imidazo[4,5-b]pyridin-2-yl)phenoxy]-N-methylacetamide |
| 119 | | 2-[3-(6-chloro-7-{[1-(thiophen-2-ylmethyl)piperidin-4-yl]amino}-3H-imidazo[4,5-b]pyridin-2-yl)phenoxy]-N-methylacetamide |
| 120 | | 2-[3-(7-{[1-(1,3-benzodioxol-5-ylmethyl)piperidin-4-yl]amino}-6-chloro-3H-imidazo[4,5-b]pyridin-2-yl)phenoxy]-N-methylacetamide |
| 121 | | 2-[3-(6-chloro-7-{[1-(2-phenoxyethyl)piperidin-4-yl] amino}-3H-imidazo[4,5-b]pyridin-2-yl)phenoxy]-N-methylacetamide |

TABLE 1-continued

| Ex. | Structural formula (without salt) | Chemical name |
|---|---|---|
| 122 | | 2-[3-(6-chloro-7-{[(3S)-1-(2-methoxybenzyl)pyrrolidin-3-yl] amino}-3H-imidazo[4,5-b]pyridin-2-yl)phenoxy]-N-methylacetamide |
| 123 | | 2-[3-(7-{[(3S)-1-benzylpyrrolidin-3-yl]amino}-6-chloro-3H-imidazo[4,5-b]pyridin-2-yl)phenoxy]-N-methylacetamide |
| 124 | | 2-(4-{6-chloro-7-[(1-hexylpiperidin-4-yl)amino]-3H-imidazo[4,5-b]pyridin-2-yl}phenoxy)-N-methylacetamide |
| 125 | | 2-[4-(6-chloro-7-{[1-(2-methylpropyl)piperidin-4-yl]amino)-3H-imidazo[4,5-b]pyridin-2-yl)phenoxy ]-N-methylacetamide |
| 126 | | 2-(4-{6-chloro-7-[(1-propylpiperidin-4-yl)amino]-3H-imidazo[4,5-b]pyridin-2-yl}phenoxy)-N-methylacetamide |

TABLE 1-continued

| Ex. | Structural formula (without salt) | Chemical name |
|---|---|---|
| 127 | | 2-(4-{6-chloro-7-[(1,2,2,6,6-pentamethylpiperidin-4-yl)amino]-3H-imidazo[4,5-b]pyridin-2-yl}phenoxy)-N-methylacetamide |
| 128 | | 2-{3-[6-chloro-7-({1-[4-(1H-1,2,4-triazol-1-yl)benzyl]piperidin-4-yl}amino)-3H-imidazo[4,5-b]pyridin-2-yl]phenoxy}-N-methylacetamide |
| 129 | | 2-[4-(6-chloro-7-{[(3S)-1-methylpyrrolidin-3-yl]amino}-3H-imidazo[4,5-b]pyridin-2-yl)phenoxy]-N-methylacetamide |
| 130 | | 2-[3-(6-chloro-7-{[1-(3-thienylmethyl)piperidin-4-yl]amino}-3H-imidazo[4,5-b]pyridin-2-yl)phenoxy]-N-methylacetamide |
| 131 | | 2-[3-(6-chloro-7-{[1-(3-hydroxybenzyl)piperidin-4-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 132 | | 2-[4-(6-chloro-7-{[(3S)-1-ethylpyrrolidin-3-yl]amino}-3H-imidazo[4,5-b]pyridin-2-yl)phenoxy]-N-methylacetamide |
| 133 | | 2-[4-(6-chloro-7-{[(3S)-1-propylpyrrolidin-3-yl]amino}-3H-imidazo[4,5-b]pyridin-2-yl)phenoxy]-N-methylacetamide |
| 134 | | 2-[4-(6-chloro-7-{[(3S)-1-(1-methylethyl)pyrrolidin-3-yl]amino}-3H-imidazo[4,5-b]pyridin-2-yl)phenoxy]-N-methylacetamide |
| 135 | | 2-(4-(6-chloro-7-[(1-methylpiperidin-4-yl)amino]-3H-imidazo[4,5-b]pyridin-2-yl}phenoxy)-N-ethylacetamide |
| 136 | | 2-(4-{6-chloro-7-[(1-methylpiperidin-4-yl)amino]-3H-imidazo[4,5-b]pyridin-2-yl}phenoxy)-N-isopropylacetamide |

TABLE 1-continued

| Ex. | Structural formula (without salt) | Chemical name |
|---|---|---|
| 137 | | 2-(4-{6-chloro-7-[(1-methylpiperidin-4-yl)amino]-3H-imidazo[4,5-b]pyridin-2-yl}phenoxy)-N-cyclopentylacetamide |
| 138 | | 2-(4-{6-bromo-7-[(1-ethylpiperidin-4-yl)amino]-3H-imidazo[4,5-b]pyridin-2-yl}phenoxy)-N-methylacetamide |
| 139 | | 2-(4-{ 6-chloro-7-[(1-methylpiperidin-4-yl)amino]-3H-imidazo[4,5-b]pyridin-2-yl}phenoxy)-N-methoxyacetamide |
| 140 | | 2-(4-{6-bromo-7-[(1-propylpiperidin-4-yl)amino]-3H-imidazo[4,5-b]pyridin-2-yl}phenoxy)-N-methylacetamide |
| 141 | | 2-[4-(6-bromo-7-{[1-(1-methylethyl)piperidin-4-yl]amino}-3H-imidazo[4,5-b]pyridin-2-yl)phenoxy]-N-methylacetamide |

TABLE 1-continued

| Ex. | Structural formula (without salt) | Chemical name |
|---|---|---|
| 142 | | 2-(4-{6-chloro-7-[(1-methylpiperidin-4-yl)amino]-3H-imidazo[4,5-b]pyridin-2-yl}phenoxy)-N-(2-isopropoxyethyl)acetamide |
| 143 | | 2-(4-{6-chloro-7-[(1-methylpiperidin-4-yl)amino]-3H-imidazo[4,5-b]pyridin-2-yl}phenoxy)-N-[2-(dimethylamino)ethyl]acetamide |
| 144 | | 2-[4-(6-bromo-7-{[(3S)-1-methylpyrrolidin-3-yl]amino}-3H-imidazo[4,5-b]pyridin-2-yl)phenoxy]-N-methylacetamide |
| 145 | | 2-(4-{6-chloro-7-[(1-methylpiperidin-4-yl)amino]-3H-imidazo[4,5-b]pyridin-2-yl}phenoxy)-N-(2-cyclohexylethyl)acetamide |

TABLE 1-continued

| Ex. | Structural formula (without salt) | Chemical name |
|---|---|---|
| 146 | | 2-(4-{6-chloro-7-[(1-methylpiperidin-4-yl)amino]-3H-imidazo[4,5-b]pyridin-2-yl}phenoxy)-N-(cyclohexylmethyl)acetamide |
| 147 | | 2-(4-{6-chloro-7-[(1-methylpiperidin-4-yl)amino]-3H-imidazo[4,5-b]pyridin-2-yl}phenoxy)-N-[2-(tetrahydro-2H-pyran-4-yl)ethyl]acetamide |
| 148 | | 2-(4-{6-chloro-7-[(1-methylpiperidin-4-yl)amino]-3H-imidazo[4,5-b]pyridin-2-yl}phenoxy)-N-(tetrahydro-2H-pyran-4-ylmethyl)acetamide |
| 149 | | 2-(4-{6-chloro-7-[(1-methylpiperidin-4-yl)amino]-3H-imidazo[4,5-b]pyridin-2-yl}phenoxy)-N-[2-(1-methylpiperidin-4-yl)ethyl]acetamide bis(trifluoroacetate) |

TABLE 1-continued

| Ex. | Structural formula (without salt) | Chemical name |
|---|---|---|
| 150 | | 2-(4-{6-chloro-7-[(1-methylpiperidin-4-yl)amino]-3H-imidazo[4,5-b]pyridin-2-yl}phenoxy)-N-[(1-methylpiperidin-4-yl)methyl]acetamide |
| 151 | | 2-(4-{6-chloro-7-[(1-methylpiperidin-4-yl)amino]-3H-imidazo[4,5-b]pyridin-2-yl}phenoxy)-N-(piperidin-4-ylmethyl)acetamide |
| 152 | | 2-(4-{6-chloro-7-[(1-methylpiperidin-4-yl)amino]-3H-imidazo[4,5-b]pyridin-2-yl}phenoxy)-N-(2-morpholin-4-ylethyl)acetamide |
| 153 | | 2-(4-{6-chloro-7-[(1-methylpiperidin-4-yl)amino]-3H-imidazo[4,5-b]pyridin-2-yl}phenoxy)-N-(3-morpholin-4-ylpropyl)acetamide |

TABLE 1-continued

| Ex. | Structural formula (without salt) | Chemical name |
|---|---|---|
| 154 | | 2-[4-(6-chloro-7-{[1-(2-methoxyethyl)piperidin-4-yl]amino}-3H-imidazo[4,5-b]pyridin-2-yl)phenoxy]-N-methylacetamide |
| 155 | | 2-(4-{6-chloro-7-[(1-methylpiperidin-4-yl)amino]-3H-imidazo[4,5-b]pyridin-2-yl}phenoxy)-N-(2-piperidin-4-ylethyl)acetamide |
| 156 | | 2-(4-{6-chloro-7-[(1-methylpiperidin-4-yl)amino]-3H-imidazo[4,5-b]pyridin-2-yl}-3-methylphenoxy)-N-methylacetamide |
| 157 | | 2-[4-(6-chloro-7-{[1-(4-methoxybenzyl)piperidin-4-yl]amino}-3H-imidazo[4,5-b]pyridin-2-yl)-3-methylphenoxy]-N-methylacetamide |
| 158 | | 2-(4-{6-bromo-7-[(1-ethylpiperidin-4-yl)amino]-3H-imidazo[4,5-b]pyridin-2-yl}-3-methylphenoxy)-N-methylacetamide |

TABLE 1-continued

| Ex. | Structural formula (without salt) | Chemical name |
|---|---|---|
| 159 | | 2-(4-{6-bromo-7-[(1-methylpiperidin-4-yl)amino]-3H-imidazo[4,5-b]pyridin-2-yl}-3-methylphenoxy)-N-methylacetamide |
| 160 | | 2-[4-(6-bromo-7-{[1-(4-methoxybenzyl)piperidin-4-yl]amino}-3H-imidazo[4,5-b]pyridin-2-yl)-3-methylphenoxy]-N-methylacetamide |
| 161 | | 2-[4-(6-chloro-7-{[1-(4-methoxybenzyl)piperidin-4-yl]amino}-3H-imidazo[4,5-b]pyridin-2-yl)-2-methylphenoxy]-N-methylacetamide |
| 162 | | 2-(4-{6-chloro-7-[(1-methylpiperidin-4-yl)amino]-3H-imidazo[4,5-b]pyridin-2-yl}-2-methylphenoxy)-N-methylacetamide |
| 163 | | 2-(4-{6-bromo-7-[(1-methylpiperidin-4-yl)amino]-3H-imidazo[4,5-b]pyridin-2-yl}-2-methylphenoxy)-N-methylacetamide |
| 164 | | 2-(4-{6-bromo-7-[(1-ethylpiperidin-4-yl)amino]-3H-imidazo[4,5-b]pyridin-2-yl}-2-methylphenoxy)-N-methylacetamide |

TABLE 1-continued

| Ex. | Structural formula (without salt) | Chemical name |
|---|---|---|
| 165 | | 2-(4-{6-bromo-7-[(1-propylpiperidin-4-yl)amino]-3H-imidazo[4,5-b]pyridin-2-yl}-2-methylphenoxy)-N-methylacetamide |
| 166 | | 2-[4-(6-chloro-7-{[(3S)-1-(1-methylethyl)pyrrolidin-3-yl]amino}-3H-imidazo[4,5-b]pyridin-2-yl)-2-methylphenoxy]-N-methylacetamide |
| 167 | | 2-(4-{6-bromo-7-[(1-methylpiperidin-4-yl)amino]-3H-imidazo[4,5-b]pyridin-2-yl}-2-methoxyphenoxy)-N-methylacetamide |
| 168 | | 2-(4-{6-chloro-7-[(1-methylpiperidin-4-yl)amino]-3H-imidazo[4,5-b]pyridin-2-yl}-2-methoxyphenoxy)-N-methylacetamide |
| 169 | | 2-[4-(6-chloro-7-{[1-(4-methoxybenzyl)piperidin-4-yl]amino}-3H-imidazo[4,5-b]pyridin-2-yl)-2-methoxyphenoxy]-N-methylacetamide |

TABLE 1-continued

| Ex. | Structural formula (without salt) | Chemical name |
|---|---|---|
| 170 | | 2-(4-{6-bromo-7-[(1-propylpiperidin-4-yl)amino]-3H-imidazo[4,5-b]pyridin-2-yl}-2-methoxyphenoxy)-N-methylacetamide |
| 171 | | 2-[4-(6-chloro-7-{[(3S)-1-(1-methylethyl)pyrrolidin-3-yl] amino}-3H-imidazo[4,5-b]pyridin-2-yl)-2-methoxyphenoxy]N-methylacetamide |
| 172 | | 2-[4-(6-chloro-7-{[1-(2,3-dihydro-1-benzofuran-5-ylmethyl)piperidin-4-yl]amino}-3H-imidazo[4,5-b]pyridin-2-yl)-3-methylphenoxy]-N-methylacetamide |
| 173 | | 2-(4-{6-chloro-7-[(1-ethylpiperidin-4-yl)amino]-3H-imidazo[4,5-b]pyridin-2-yl}-3-methylphenoxy)-N-methylacetamide |
| 174 | | 2-[4-(6-chloro-7-{[1-(thiophen-3-ylmethyl)piperidin-4-yl]amino}-3H-imidazo[4,5-b]pyridin-2-yl)-3-methylphenoxy]-N-methylacetamide |

TABLE 1-continued

| Ex. | Structural formula (without salt) | Chemical name |
|---|---|---|
| 175 | | 2-[4-(6-chloro-7-{[(3S)-1-(2-methoxybenzyl)pyrrolidin-3-yl]amino}-3H-imidazo[4,5-b]pyridin-2-yl)-2-methylphenoxy]-N-methylacetamide |
| 176 | | 2-[4-(6-chloro-7-{[1-(thiophen-3-ylmethyl)piperidin-4-yl]amino}-3H-imidazo[4,5-b]pyridin-2-yl)-2-methylphenoxy]-N-methylacetami de |
| 177 | | 2-(4-{6-chloro-7-[(1-ethylpiperidin-4-yl)amino]-3H-imidazo[4,5-b]pyridin-2-yl}-2-methylphenoxy)-N-methylacetamide |
| 178 | | 2-[4-(6-chloro-7-{[1-(2-methoxyethyl)piperidin-4-yl]amino}-3H-imidazo[4,5-b]pyridin-2-yl)-2-methylphenoxy]-N-methylacetamide |
| 179 | | 2-(4-{6-bromo-7-[(1-methylpiperidin-4-yl)amino]-3H-imidazo[4,5-b]pyridin-2-yl}phenoxy)-N,2-dimethylpropanamide |

TABLE 1-continued

| Ex. | Structural formula (without salt) | Chemical name |
|---|---|---|
| 180 | | 2-(4-{6-chloro-7-[(1-methylpiperidin-4-yl)amino]-3H-imidazo[4,5-b]pyridin-2-yl}phenoxy)-N,2-dimethylpropanamide |
| 181 | | 2-[4-(6-chloro-7-{[1-(4-methoxybenzyl)piperidin-4-yl]amino}-3H-imidazo[4,5-b]pyridin-2-yl)phenoxy]-N,2-dimethylpropanamide |
| 182 | | 2-(4-{6-bromo-7-[(1-ethylpiperidin-4-yl)amino]-3H-imidazo[4,5-b]pyridin-2-yl}phenoxy)-N,2-dimethylpropanamide |
| 183 | | 2-[4-(6-chloro-7-{[(3S)-1-(1-methylethyl)pyrrolidin-3-yl] amino}-3H-imidazo[4,5-b]pyridin-2-yl)phenoxy]-N,2-dimethylpropanamide |
| 184 | | 2-(4-{6-bromo-7-[(1-methylpiperidin-4-yl)amino]-3H-imidazo[4,5-b]pyridin-2-yl}-2-fluorophenoxy)-N-methylacetamide |
| 185 | | 2-(4-{6-chloro-7-[(1-methylpiperidin-4-yl)amino]-3H-imidazo[4,5-b]pyridin-2-yl}-2-fluorophenoxy)-N-methylacetamide |

TABLE 1-continued

| Ex. | Structural formula (without salt) | Chemical name |
|---|---|---|
| 186 | | 2-[4-(6-chloro-7-{[1-(4-methoxybenzyl)piperidin-4-yl] amino}-3H-imidazo[4,5-b]pyridin-2-yl)-2-fluorophenoxy]-N-methylacetamide |
| 187 | | 2-(4-{6-bromo-7-[(1-ethylpiperidin-4-yl)amino]-3H-imidazo[4,5-b]pyridin-2-yl}-2-fluorophenoxy)-N-methylacetamide |
| 188 | | 2-[4-(6-chloro-7-{[(3S)-1-ethylpyrrolidin-3-yl]amino}-3H-imidazo[4,5-b]pyridin-2-yl)-2-fluorophenoxy]-N-methylacetamide |
| 189 | | 3-(4-{6-bromo-7-[(1-methylpiperidin-4-yl)amino]-3H-imidazo[4,5-b]pyridin-2-yl}phenyl)-N-methylpropanamide |
| 190 | | 3-(4-{6-chloro-7-[(1-methylpiperidin-4-yl)amino]-3H-imidazo[4,5-b]pyridin-2-yl}phenyl)-N-methylpropanamide |

TABLE 1-continued

| Ex. | Structural formula (without salt) | Chemical name |
|---|---|---|
| 191 | | 3-[4-(6-bromo-7-{[1-(1-methylethyl)piperidin-4-yl]amino}-3H-imidazo[4,5-b]pyridin-2-yl)phenyl]-N-methylpropanamide |
| 192 | | 3-(4-{6-bromo-7-[(1-ethylpiperidin-4-yl)amino]-3H-imidazo[4,5-b]pyridin-2-yl}phenyl)-N-methylpropanamide |
| 193 | | 3-[4(6-chloro-7-{[(3S)-1-ethylpyrrolidin-3-yl]amino}-3H-imidazo[4,5-b]pyridin-2-yl)phenyl]-N-methylpropanamide |
| 194 | | 2-[4-(6-chloro-7-{[1-(4-methoxybenzyl)piperidin-4-yl]amino}-3H-imidazo[4,5-b]pyridin-2-yl)-2,6-dimethylphenoxy]-N-methylacetamide |
| 195 | | 2-(4-{6-chloro-7-[(1-methylpiperidin-4-yl)amino]-3H-imidazo[4,5-b]pyridin-2-yl}-2,6-dimethylphenoxy)-N-methylacetamide |

TABLE 1-continued

| Ex. | Structural formula (without salt) | Chemical name |
|---|---|---|
| 196 | | 2-(4-{6-bromo-7-[(1-methylpiperidin-4-yl)amino]-3H-imidazo[4,5-b]pyridin-2-yl}-2,6-dimethylphenoxy)-N-methylacetamide |
| 197 | | 2-[4-(6-bromo-7-{[1-(1-methylethyl)piperidin-4-yl]amino}-3H-imidazo[4,5-b]pyridin-2-yl)-2,6-dimethylphenoxy]-N-methylacetamide |
| 198 | | 2-[4-(6-chloro-7-{[(3S)-1-(1-methylethyl)pyrrolidin-3-yl]amino}-3H-imidazo[4,5-b]pyridin-2-yl)-2,6-dimethylphenoxy]-N-methylacetamide |
| 199 | | 2-[4-(6-bromo-7-{[1-(thiophen-2-ylmethyl)piperidin-4-yl] amino}-3H-imidazo[4,5-b]pyridin-2-yl)-2,6-dimethylphenoxy]-N-methylacetamide |
| 200 | | 2-[4-(6-chloro-7-{[(3S)-1-ethylpyrrolidin-3-yl]amino}-3H-imidazo[4,5-b]pyridin-2-yl)-2,6-dimethylphenoxy]-N-methylacetamide |

TABLE 1-continued

| Ex. | Structural formula (without salt) | Chemical name |
|---|---|---|
| 201 | | 2-[4-(6-chloro-7-{[1-(4-methoxybenzyl)piperidin-4-yl]amino}-3H-imidazo[4,5-b]pyridin-2-yl)-2,5-dimethylphenoxy]-{V-methylacetamide |
| 202 | | 2-(4-{6-chloro-7-[(1-methylpiperidin-4-yl)amino]-3H-imidazo[4,5-b]pyridin-2-yl}-2,5-dimethylphenoxy)-N-methylacetamide |
| 203 | | 2-(4-{6-bromo-7-[(1-methylpiperidin-4-yl)amino]-3H-imidazo[4,5-b]pyridin-2-yl}-2,5-dimethylphenoxy)-N-methylacetamide |
| 204 | | 2-(4-{6-chloro-7-[(1-propylpiperidin-4-yl)amino]-3H-imidazo[4,5-b]pyridin-2-yl}-2,5-dimethylphenoxy)-ALmethylacetamide |
| 205 | | 2-(4-{6-chloro-7-[(1-ethylpiperidin-4-yl)amino]-3H-imidazo[4,5-b]pyridin-2-yl}-2,5-dimethylphenoxy)-N-methylacetamide |
| 206 | | 2-(4-{6-chloro-7-[(1-propylpiperidin-4-yl)amino]-3H-imidazo[4,5-b]pyridin-2-yl}-2-methylphenoxy)-N-methylacetamide |

TABLE 1-continued

| Ex. | Structural formula (without salt) | Chemical name |
|---|---|---|
| 207 | | 2-(4-{6-chloro-7-[(1-ethylpiperidin-4-yl)amino]-3H-imidazo[4,5-b]pyridin-2-yl}-2,6-dimethylphenoxy)-N-methylacetamide |
| 208 | | 2-(4-{6-chloro-7-[(1-methylpiperidin-4-yl)amino]-3H-imidazo[4,5-b]pyridin-2-yl}phenoxy)-N-(4-methylcyclohexyl)acetamide |
| 209 | | N-tert-butyl-2-(4-{6-chloro-7-[(1-methylpiperidin-4-yl)amino]-3H-imidazo[4,5-b]pyridin-2-yl}phenoxy)acetamide |
| 210 | | 2-(4-{6-chloro-7-[(1-methylpiperidin-4-yl)amino]-3H-imidazo[4,5-b]pyridin-2-yl}phenoxy)-N-(1,1-dimethylpropyl)acetamide |
| 211 | | 2-(4-{6-chloro-7-[(1-methylpiperidin-4-yl)amino]-3H-imidazo[4,5-b]pyridin-2-yl}phenoxy)-N-cyclohexylacetamide |

TABLE 1-continued

| Ex. | Structural formula (without salt) | Chemical name |
|---|---|---|
| 212 | | 3-(4-{6-chloro-7-[(1-ethylpiperidin-4-yl)amino]-3H-imidazo[4,5-b]pyridin-2-yl}phenyl)-N-methylpropanamide |
| 213 | | 3-[4-(6-chloro-7-{[1-(1-methylethyl)piperidin-4-yl]amino}-3H-imidazo[4,5-b]pyridin-2-yl)phenyl]-N-methylpropanamide |
| 214 | | 2-(4-{6-chloro-7-[(1-ethylpiperidin-4-yl)amino]-3H-imidazo[4,5-b]pyridin-2-yl}-2-fluorophenoxy)-N-methylacetamide |
| 215 | | 2-[4-(6-chloro-7-{[1-(1-methylethyl)piperidin-4-yl]amino}-3H-imidazo[4,5-b]pyridin-2-yl)-2-fluorophenoxy]-N-methylacetamide |
| 216 | | 2-(4-{6-chloro-7-[(1-ethylpiperidin-4-yl)amino]-3H-imidazo[4,5-b]pyridin-2-yl}phenoxy)-N,2-dimethylpropanamide |

TABLE 1-continued

| Ex. | Structural formula (without salt) | Chemical name |
|---|---|---|
| 217 | | 2-[4-(6-chloro-7-{[1-(1-methylethyl)piperidin-4-yl]amino}-3H-imidazo[4,5-b]pyridin-2-yl)phenoxy]-N,2-dimethylpropanamide |
| 218 | | 2-(4-{6-chloro-7-[(1-ethylpiperidin-4-yl)amino]-3H-imidazo[4,5-b]pyridin-2-yl}-2-methoxyphenoxy)-N-methylacetamide |
| 219 | | 2-[4-(6-chloro-7-{[1-(1-methylethyl)piperidin-4-yl]amino}-3H-imidazo[4,5-b]pyridin-2-yl)-2-methoxyphenoxy]-N-methylacetamide |
| 220 | | 2-(4-{6-chloro-7-[(1-methylpiperidin-4-yl)amino]-3H-imidazo[4,5-b]pyridin-2-yl}phenoxy)-N-propylacetamide |
| 221 | | 2-(4-{6-chloro-7-[(1-methylpiperidin-4-yl)amino]-3H-imidazo[4,5-b]pyridin-2-yl}phenoxy)-N-(2-methylpropyl)acetamide |

TABLE 1-continued

| Ex. | Structural formula (without salt) | Chemical name |
|---|---|---|
| 222 | | 2-(4-{6-chloro-7-[(1-methylpiperidin-4-yl)amino]-3H-imidazo[4,5-b]pyridin-2-yl}phenoxy)-N-(tetrahydrofuran-2-ylmethyl)acetamide |
| 223 | | 2-(4-(6-chloro-7-[(1-methylpiperidin-4-yl)amino]-3H-imidazo[4,5-b]pyridin-2-yl}phenoxy)-N-[1-(methoxymethyl)propyl]acetamide |
| 224 | | 2-(4-{6-chloro-7-[(1-methylpiperidin-4-yl)amino]-3H-imidazo[4,5-b]pyridin-2-yl}phenoxy)-N-(2-methoxy-1-methylethyl)acetamide |
| 225 | | N-benzyl-2-(4-{6-chloro-7-[(1-methylpiperidin-4-yl)amino]-3H-imidazo[4,5-6]pyridin-2-yl}phenoxy)acetamide |

TABLE 1-continued

| Ex. | Structural formula (without salt) | Chemical name |
|---|---|---|
| 226 | | 2-(4-{6-chloro-7-[(1-methylpiperidin-4-yl)amino]-3H-imidazo[4,5-b]pyridin-2-yl}phenoxy)-N-(1-phenylethyl)acetamide |
| 227 | | 2-(4-{6-chloro-7-[(1-methylpiperidin-4-yl)amino]-3H-imidazo[4,5-b]pyridin-2-yl}phenoxy)-N-cycloheptylacetamide |
| 228 | | 2-(4-{6-bromo-7-[(1-methylpiperidin-4-yl)amino]-3H-imidazo[4,5-b]pyridin-2-yl}-2-fluorophenoxy)-N-(1-methylethyl)acetamide |
| 229 | | 2-(4-{6-chloro-7-[(1-methylpiperidin-4-yl)amino]-3H-imidazo[4,5-b]pyridin-2-yl}-2-fluorophenoxy)-N-(1-methylethyl)acetamide |
| 230 | | 2-(4-{6-chloro-7-[(1-ethylpiperidin-4-yl)amino]-3H-imidazo[4,5-b]pyridin-2-yl}-2-fluorophenoxy)-N-(1-methylethyl)acetamide |

TABLE 1-continued

| Ex. | Structural formula (without salt) | Chemical name |
|---|---|---|
| 231 | | 2-[4-(6-chloro-7-{[1-(1-methylethyl)piperidin-4-yl]amino}-3H-imidazo[4,5-b]pyridin-2-yl)-2-fluorophenoxy]-N-(1-methylethyl)acetamide |
| 232 | | 2-(4-{6-chloro-7-[(1-methylpiperidin-4-yl)amino]-3H-imidazo[4,5-b]pyridin-2-yl}phenyl)-N-methylacetamide |
| 233 | | 2-[4-(6-chloro-7-{[1-(4-methoxybenzyl)piperidin-4-yl]amino}-3H-imidazo[4,5-b]pyridin-2-yl)phenyl]-N-methylacetamide |
| 234 | | 2-[4-(6-chloro-7-{[1-(4-methoxybenzyl)piperidin-4-yl]amino}-3H-imidazo[4,5-b]pyridin-2-yl)phenoxy]-N-cyclopentylacetamide |
| 235 | | 2-[4-(6-chloro-7-{[1-(4-methoxybenzyl)piperidin-4-yl]amino}-3H-imidazo[4,5-b]pyridin-2-yl)phenoxy]-N-(cyclohexylmethyl)acetamide |

TABLE 1-continued

| Ex. | Structural formula (without salt) | Chemical name |
|---|---|---|
| 236 | | 2-[4-(6-chloro-7-{[1-(4-methoxybenzyl)piperidin-4-yl]amino}-3H-imidazo[4,5-b]pyridin-2-yl)phenoxy]-N-cycloheptylacetamide |
| 237 | | 2-[4-(6-chloro-7-{[1-(4-methoxybenzyl)piperidin-4-yl]amino}-3H-imidazo[4,5-b]pyridin-2-yl)phenoxy]-N-(2-cyclohexylethyl)acetamide |
| 238 | | 2-[4-(6-chloro-7-{[1-(4-methoxybenzyl)piperidin-4-yl]amino}-3H-imidazo[4,5-b]pyridin-2-yl)phenoxy]-N-[2-(tetrahydro-2H-pyran-4-yl)ethyl] acetamide |
| 239 | | 2-(4-{6-chloro-7-[(1-methylpiperidin-4-yl)amino]-3H-imidazo[4,5-b]pyridin-2-yl}phenoxy)-N-(4-methoxybenzyl)acetamide |
| 240 | | 2-(4-{6-chloro-7-[(1-methylpiperidin-4-yl)amino]-3H-imidazo[4,5-b]pyridin-2-yl}phenoxy)-N-(furan-2-ylmethyl)acetamide |

TABLE 1-continued

| Ex. | Structural formula (without salt) | Chemical name |
|---|---|---|
| 241 | 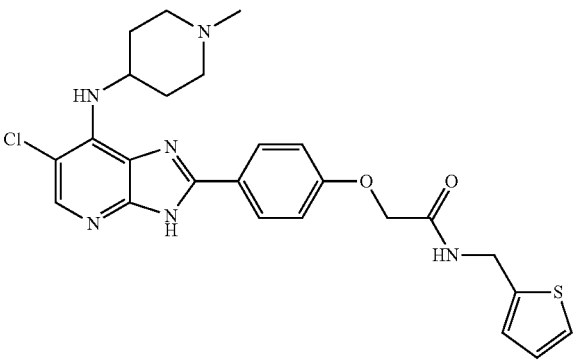 [SMILES: CN1CCC(Nc2c(Cl)cnc3[nH]c(-c4ccc(OCC(=O)NCc5ccco5)cc4)nc23)CC1] | 2-(4-(6-chloro-7-[(1-methylpiperidin-4-yl)amino]-3H-imidazo[4,5-b]pyridin-2-yl}phenoxy)-N-(thiophen-2-ylmethyl)acetamide |
| 242 | 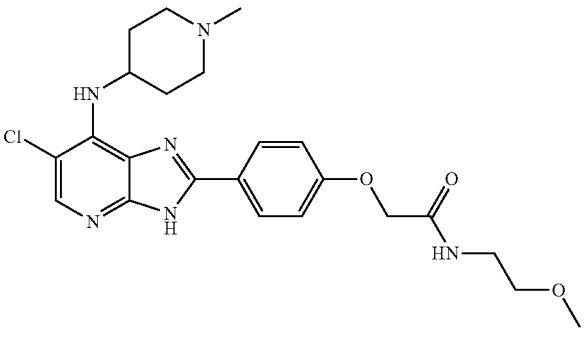 [SMILES: COCCNC(=O)COc1ccc(-c2nc3c(NC4CCN(C)CC4)c(Cl)cnc3[nH]2)cc1] | 2-(4-{6-chloro-7-[(1-methylpiperidin-4-yl)amino]-3H-imidazo[4,5-b]pyridin-2-yl}phenoxy)-N-(2-methoxyethyl)acetamide |
| 243 | 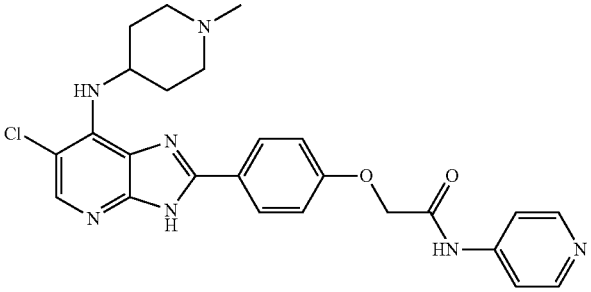 [SMILES: CN1CCC(Nc2c(Cl)cnc3[nH]c(-c4ccc(OCC(=O)Nc5ccncc5)cc4)nc23)CC1] | 2-(4-{6-chloro-7-[(1-methylpiperidin-4-yl)amino]-3H-imidazo[4,5-b]pyridin-2-yl}phenoxy)-N-pyridin-4-ylacetamide |
| 244 | 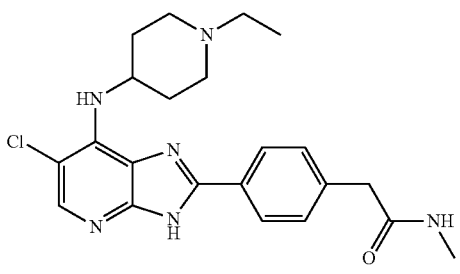 [SMILES: CCN1CCC(Nc2c(Cl)cnc3[nH]c(-c4ccc(CC(=O)NC)cc4)nc23)CC1] | 2-(4-{6-chloro-7-[(1-ethylpiperidin-4-yl)amino]-3H-imidazo[4,5-b]pyridin-2-yl}phenyl)-N-methylacetamide |
| 245 | 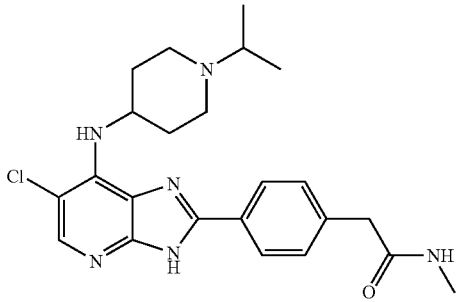 [SMILES: CNC(=O)Cc1ccc(-c2nc3c(NC4CCN(C(C)C)CC4)c(Cl)cnc3[nH]2)cc1] | 2-[4-(6-chloro-7-{[1-(1-methylethyl)piperidin-4-yl]amino}-3H-imidazo[4,5-b]pyridin-2-yl)phenyl]-N-methylacetamide |

TABLE 1-continued

| Ex. | Structural formula (without salt) | Chemical name |
|---|---|---|
| 246 | | 2-(4-{6-chloro-7-[(1-propylpiperidin-4-yl)amino]-3H-imidazo[4,5-b] pyridin-2-yl}phenyl)-N-methylacetamide |
| 247 | | 2-(4-{6-bromo-7-[(1-propylpiperidin-4-yl)amino]3H-imidazo[4,5-b]pyridin-2-yl}phenyl)-N-methylacetamide |
| 248 | | 2-[4-(6-bromo-7-{[1-(1-methylethyl)piperidin-4-yl]amino}-3H-imidazo[4,5-b]pyridin-2-yl)phenyl]-N-methylacetamide |
| 249 | | 2-(4-{6-bromo-7-[(1-methylpiperidin-4-yl)amino]-3H-imidazo[4,5-b]pyridin-2-yl}phenyl)-N-methylacetamide |
| 250 | | 2-[4-(6-chloro-7-{[1-(thiophen-2-ylmethyl)piperidin-4-yl] amino}-3H-imidazo[4,5-b]pyridin-2-yl)phenoxy]-N-cyclopentylacetamide |

TABLE 1-continued

| Ex. | Structural formula (without salt) | Chemical name |
|---|---|---|
| 251 | | 2-[4-(6-chloro-7-{[1-(thiophen-2-ylmethyl)piperidin-4-yl]amino}-3H-imidazo[4,5-b]pyridin-2-yl)phenoxy]-N-cyclohexylacetamide |
| 252 | | 2-(4-{6-bromo-7-[(1-methylpiperidin-4-yl)amino]-3H-imidazo[4,5-b]pyridin-2-yl}phenoxy)-N-(1-methylethyl)acetamide |
| 253 | | 2-(4-{6-bromo-7-[(1-methylpiperidin-4-yl)amino]-3H-imidazo[4,5-b]pyridin-2-yl}phenoxy)-N-propylacetamide |
| 254 | | 2-(4-{6-bromo-7-[(1-methylpiperidin-4-yl)amino]-3H-imidazo[4,5-b]pyridin-2-yl}phenoxy)-N-[1-(methoxymethyl)propyl]acetamide |
| 255 | | 2-(4-{6-bromo-7-[(1-methylpiperidin-4-yl)amino]-3H-imidazo[4,5-b]pyridin-2-yl}phenoxy)-N-(2-methylpropyl)acetamide |

TABLE 1-continued

| Ex. | Structural formula (without salt) | Chemical name |
| --- | --- | --- |
| 256 | | 2-(4-{6-bromo-7-[(1-methylpiperidin-4-yl)amino]-3H-imidazo[4,5-b]pyridin-2-yl}phenoxy)-N-tert-butylacetamide |
| 257 | | 2-(4-{6-bromo-7-[(1-methylpiperidin-4-yl)amino]-3H-imidazo[4,5-b]pyridin-2-yl}phenoxy)-N-(1,1-dimethylpropyl)acetamide |
| 258 | | 2-(4-{6-bromo-7-[(1-methylpiperidin-4-yl)amino]-3H-imidazo[4,5-b]pyridin-2-yl}phenoxy)-N-cyclohexylacetamide |
| 259 | | 2-(4-{6-bromo-7-[(1-methylpiperidin-4-yl)amino]-3H-imidazo[4,5-b]pyridin-2-yl}phenoxy)-N-cyclopentylacetamide |
| 260 | | 2-(4-{6-bromo-7-[(1-methylpiperidin-4-yl)amino]-3H-imidazo[4,5-b]pyridin-2-yl}phenoxy)-N-ethylacetamide |

TABLE 1-continued

| Ex. | Structural formula (without salt) | Chemical name |
|---|---|---|
| 261 | | 2-(4-{6-chloro-7-[(1-methylpiperidin-4-yl)amino]-3H-imidazo[4,5-b]pyridin-2-yl}phenoxy)-N-(tetrahydro-2H-thiopyran-4-yl)acetamide |
| 262 | | 2-(4-{6-chloro-7-[(1-methylpiperidin-4-yl)amino]-3H-imidazo[4,5-b]pyridin-2-yl}phenoxy)-N-(tetrahydro-2H-pyran-4-yl)acetamide |
| 263 | | 2-(4-{6-chloro-7-[(1-methylpiperidin-4-yl)amino]-3H-imidazo[4,5-b]pyridin-2-yl}phenoxy)-N-(2,2,2-trifluoroethyl)acetamide |
| 264 | | N-{2-[4-(6-chloro-7-{[1-(4-methoxybenzyl)piperidin-4-yl]amino}-3H-imidazo[4,5-b]pyridin-2-yl)phenoxy] ethyl}acetamide |
| 265 | | N-[2-(4-{6-chloro-7-[(1-methylpiperidin-4-yl)amino]-3H-imidazo[4,5-b]pyridin-2-yl}phenoxy)ethyl] acetamide |

TABLE 1-continued

| Ex. | Structural formula (without salt) | Chemical name |
| --- | --- | --- |
| 266 | | N-[2-(4-{6-bromo-7-[(1-methylpiperidin-4-yl)amino]-3H-imidazo[4,5-b]pyridin-2-yl}phenoxy)ethyl] acetamide |
| 267 | | N-{2-[4-(6-chloro-7-{[1-(1-methylethyl)piperidin-4-yl]amino}-3H-imidazo[4,5-b]pyridin-2-yl)phenoxy] ethyl}acetamide |
| 268 | | N-[2-(4-{6-chloro-7-[(1-methylpiperidin-4-yl)amino]-3H-imidazo[4,5-b]pyridin-2-yl}phenoxy)ethyl]cyclohexanecarboxamide |
| 269 | | N-[2-(4-{6-chloro-7-[(1-methylpiperidin-4-yl)amino]-3H-imidazo[4,5-b]pyridin-2-yl}phenoxy)ethyl]-2,2-dimethylpropanamide |

TABLE 1-continued

| Ex. | Structural formula (without salt) | Chemical name |
|---|---|---|
| 270 | | 2-(4-{6-bromo-7-[(1-methylpiperidin-4-yl)amino]-3H-imidazo[4,5-b]pyridin-2-yl}phenoxy)-N-pyridin-4-ylacetamide |
| 271 | | 2-[4-(6-chloro-7-{[1-(1-methylethyl)piperidin-4-yl]amino}-3H-imidazo[4,5-b]pyridin-2-yl)phenoxy]-N-cyclohexylacetamide |
| 272 | | N-[2-(4-{6-chloro-7-[(1-methylpiperidin-4-yl)amino]-3H-imidazo[4,5-b]pyridin-2-yl}phenoxy)ethyl]pyridine-4-carboxamide |
| 273 | | N-[2-(4-{6-chloro-7-[(1-methylpiperidin-4-yl)amino]-3H-imidazo[4,5-b]pyridin-2-yl}phenoxy)ethyl]pyridine-3-carboxamide |

TABLE 1-continued

| Ex. | Structural formula (without salt) | Chemical name |
|---|---|---|
| 274 | | N-[2-(4-{6-chloro-7-[(1-methylpiperidin-4-yl)amino]-3H-imidazo[4,5-b]pyridin-2-yl}phenoxy)ethyl]-2-methoxyacetamide |
| 275 | | N-[2-(4-{6-chloro-7-[(1-methylpiperidin-4-yl)amino]-3H-imidazo[4,5-b]pyridin-2-yl}phenoxy)ethyl]cyclopentanecarboxamide |
| 276 | | N-[2-(4-{6-chloro-7-[(1-methylpiperidin-4-yl)amino]-3H-imidazo[4,5-b]pyridin-2-yl}phenoxy)ethyl]-2-methylpropanamide |
| 277 | | N-[2-(4-{6-chloro-7-[(1-methylpiperidin-4-yl)amino]-3H-imidazo[4,5-b]pyridin-2-yl}phenoxy)ethyl]cyclopropanecarboxamide |

TABLE 1-continued

| Ex. | Structural formula (without salt) | Chemical name |
|---|---|---|
| 278 | | N-[2-(4-(6-chloro-7-[(1-ethylpiperidin-4-yl)amino]-3H-imidazo[4,5-b]pyridin-2-yl}phenoxy)ethyl] acetamide |
| 279 | | N-{2-[4-(6-chloro-7-{[1-(thiophen-2-ylmethyl)piperidin-4-yl]amino}-3H-imidazo[4,5-b]pyridin-2-yl)phenoxy]ethyl}acetamide |
| 280 | | N-{2-[4-(6-chloro-7-{[1-(4-methoxybenzyl)piperidin-4-yl]amino}-3H-imidazo[4,5-b]pyridin-2-yl)phenoxy]ethyl}propanamide |
| 281 | | N-{2-[4-(6-chloro-7-{[1-(4-methoxybenzyl)piperidin-4-yl]amino}-3H-imid azo[4,5-b]pyridin-2-yl)phenoxy]ethyl}cyclopentanecarboxamide |
| 282 | | N-{2-[4-(6-chloro-7-{[1-(4-methoxybenzyl)piperidin-4-yl]amino}-3H-imidazo[4,5-b]pyridin-2-yl)phenoxy]ethyl}-2-methylpropanamide |

TABLE 1-continued

| Ex. | Structural formula (without salt) | Chemical name |
| --- | --- | --- |
| 283 | | N-{2-[4-(6-chloro-7-{[1-(4-methoxybenzyl)piperidin-4-yl]amino}-3H-imidazo[4,5-b]pyridin-2-yl)phenoxy] ethyl}pyridine-4-carboxamide |
| 284 | | 2-{4-[6-Bromo-7-({1-[4-(1H-1,2,4-triazol-1-yl)benzyl]piperidin-4-yl}amino)-3H-imidazo[4,5-b]pyridin-2-yl]phenoxy}-N-methylacetamide |
| 285 | | N-(2-{4-[6-chloro-7-({1-[4-(1H-1,2,4-triazol-1-yl)benzyl]piperidin-4-yl}amino)-3H-imidazo[4,5-b]pyridin-2-yl]phenoxy}ethyl)acetamide |
| 286 | | N-(2-{4-[6-bromo-7-({1-[4-(1H-1,2,4-triazol-1-yl)benzyl]piperidin-4-yl}amino)-3H-imidazo[4,5-b]pyridin-2-yl]phenoxy}ethyl)acetamide |
| 287 | | 2-{4-[6-chloro-7-({1-[(1,3,5-trimethyl-1H-pyrazol-4-yl)methyl]piperidin-4-yl}amino)-3H-imidazo[4,5-b]pyridin-2-yl]phenoxy}-N-methylacetamide |

TABLE 1-continued

| Ex. | Structural formula (without salt) | Chemical name |
|---|---|---|
| 288 | | 2-{4-[6-bromo-7-({1-[(1,3,5-trimethyl-1H-pyrazol-4-yl)methyl]piperidin-4-yl}amino)-3H-imidazo[4,5-b]pyridin-2-yl]phenoxy}-N-methylacetamide |
| 289 | | 2-[4-(6-chloro-7-{[1-(4-methoxybenzyl)piperidin-4-yl]amino}-3H-imidazo[4,5-b]pyridin-2-yl)phenoxy]-N-pyridin-3-ylacetamide |
| 290 | | 2-[4-(6-chloro-7-{[1-(4-methoxybenzyl)piperidin-4-yl]amino}-3H-imidazo[4,5-b]pyridin-2-yl)phenoxy]-N-(1-methyl-1H-pyrazol-5-yl)acetamide |
| 291 | | 2-(4-{6-chloro-7-[(1-methylpiperidin-4-yl)amino]-3H-imidazo[4,5-b]pyridin-2-yl}phenoxy)-N-pyridin-3-ylacetamide |
| 292 | | 2-(4-{6-chloro-7-[(1-methylpiperidin-4-yl)amino]-3H-imidazo[4,5-b]pyridin-2-yl}phenoxy)-N-pyrazin-2-ylacetamide |

TABLE 1-continued

| Ex. | Structural formula (without salt) | Chemical name |
|---|---|---|
| 293 | | N²-(4-{6-bromo-7-[(1-methylpiperidin-4-yl)amino]-3H-imidazo[4,5-b]pyridin-2-yl}phenyl)-N-methylglycinamide |
| 294 | | N²-(4-(6-chloro-7-[(1-methylpiperidin-4-yl)amino]-3H-imidazo[4,5-b]pyridin-2-yl}phenyl)-N-methylglycinamide |
| 295 | | N²-[4-(6-chloro-7-{[1-(1-methylethyl)piperidin-4-yl]amino}-3H-imidazo[4,5-b]pyridin-2-yl)phenyl]-N-methylglycinamide |
| 296 | | N²-[4-(6-chloro-7-{[1-(4-methoxybenzyl)piperidin-4-yl]amino}-3H-imidazo[4,5-b]pyridin-2-yl)phenyl]-N-methylglycinamide |
| 297 | | N²-(4-{6-chloro-7-[(1-ethylpiperidin-4-yl)amino]-3H-imidazo[4,5-b]pyridin-2-yl}phenyl)-N-methylglycinamide |

TABLE 1-continued

| Ex. | Structural formula (without salt) | Chemical name |
|---|---|---|
| 298 | | 2-(4-{6-chloro-7-[(1-methylpiperidin-4-yl)amino]-3H-imidazo[4,5-b]pyridin-2-yl}phenoxy)-N-pyridin-2-ylacetamide |
| 299 | | 2-(4-{6-chloro-7-[(1-methylpiperidin-4-yl)amino]-3H-imidazo[4,5-b]pyridin-2-yl}phenoxy)-N-isoxazol-3-ylacetamide |
| 300 | | 2-(4-{6-chloro-7-[(1-methylpiperidin-4-yl)amino]-3H-imidazo[4,5-b]pyridin-2-yl}phenoxy)-N-(pyridin-4-ylmethyl)acetamide |
| 301 | | N$^3$-(4-{6-bromo-7-[(1-methylpiperidin-4-yl)amino]-3H-imidazo[4,5-b]pyridin-2-yl}phenyl)-N-methyl-b-alaninamide |
| 302 | | N$^3$-(4-{6-chloro-7-[(1-methylpiperidin-4-yl)amino]-3H-imidazo[4,5-b]pyridin-2-yl}phenyl)-N-methyl-b-alaninamide |

TABLE 1-continued

| Ex. | Structural formula (without salt) | Chemical name |
|---|---|---|
| 303 | | $N^3$-[4-(6-chloro-7-{[1-(1-methylethyl)piperidin-4-yl]amino}-3H-imidazo[4,5-b]pyridin-2-yl)phenyl]-N-methyl-b-alaninamide |
| 304 | | $N^3$-[4-(6-chloro-7-{[1-(4-methoxybenzyl)piperidin-4-yl]amino}-3H-imidazo[4,5-b]pyridin-2-yl)phenyl]-N-methyl-b-alaninamide |
| 305 | | $N^3$-(4-{6-chloro-7-[(1-ethylpiperidin-4-yl)amino]-3H-imidazo[4,5-b]pyridin-2-yl}phenyl)-N-methyl-b-alaninamide |
| 306 | | 2-[4-(6-chloro-7-{[1-(4-methoxybenzyl)piperidin-4-yl]amino}-3H-imidazo[4,5-b]pyridin-2-yl)phenoxy]-N-(pyridin-4-ylmethyl)acetamide |
| 307 | | 2-[4-(6-chloro-7-{[1-(4-methoxybenzyl)piperidin-4-yl]amino}-3H-imidazo[4,5-b]pyridin-2-yl)phenoxy]-N-pyrimidin-2-ylacetamide |

TABLE 1-continued

| Ex. | Structural formula (without salt) | Chemical name |
| --- | --- | --- |
| 308 | | 2-(4-{6-chloro-7-[(1-methylpiperidin-4-yl)amino]-3H-imidazo[4,5-b]pyridin-2-yl}phenoxy)-N-pyrimidin-2-ylacetamide |
| 309 | | 2-[4-(6-chloro-7-{[1-(thiophen-2-ylmethyl)piperidin-4-yl]amino}-3H-imidazo[4,5-b]pyridin-2-yl)phenoxy]-N-pyrimidin-2-ylacetamide |
| 310 | | 2-(4-{6-chloro-7-[(1-methylpiperidin-4-yl)amino]-3H-imidazo[4,5-b]pyridin-2-yl}phenoxy)-N-pyrazin-2-ylacetamide |
| 311 | | 2-(4-{6-bromo-7-[(1-methylpiperidin-4-yl)amino]-3H-imidazo[4,5-b]pyridin-2-yl}phenoxy)-N-pyrazin-2-ylacetamide |
| 312 | | 2-[4-(6-chloro-7-{[1-(1-methylethyl)piperidin-4-yl]amino}-3H-imidazo[4,5-b]pyridin-2-yl)phenoxy]-N-pyrazin-2-ylacetamide |

TABLE 1-continued

| Ex. | Structural formula (without salt) | Chemical name |
|---|---|---|
| 313 | | 2-[4-(6-chloro-7-{[1-(thiophen-3-ylmethyl)piperidin-4-yl]amino}-3H-imidazo[4,5-b]pyridin-2-yl)phenoxy]-N-pyrazin-2-ylacetamide |
| 314 | | 2-[4-(6-chloro-7-{[1-(2,3-dihydro-1-benzofuran-5-ylmethyl)piperidin-4-yl]amino}-3H-imidazo[4,5-b]pyridin-2-yl)phenoxy]-N-pyrazin-2-ylacetamide |
| 315 | | 2-(4-{5-chloro-4-[(1-methylpiperidin-4-yl)amino]-1H-pyrrolo[2,3-b]pyridin-2-yl}phenoxy)-N-(5-methylisoxazol-3-yl)acetamide |
| 316 | | N$^2$-(4-{6-chloro-7-[(1-methylpiperidin-4-yl)amino]-3H-imidazo[4,5-b]pyridin-2-yl}phenyl)-N2-methyl-N-pyridin-3-ylglycinamide |
| 317 | | 2-(4-{6-chloro-7-[(1-methylpiperidin-4-yl)amino]-3H-imidazo[4,5-b]pyridin-2-yl}phenoxy)-N-(5-chloropyridin-3-yl)acetamide |

TABLE 1-continued

| Ex. | Structural formula (without salt) | Chemical name |
|---|---|---|
| 318 | | 2-[4-(6-chloro-7-{[1-(4-methoxybenzyl)piperidin-4-yl]amino}-3H-imidazo[4,5-b]pyridin-2-yl)phenoxy]-N-isoxazol-3-ylacetamide |
| 319 | | 2-(4-{6-bromo-7-[(1-methylpiperidin-4-yl)amino]-3H-imidazo[4,5-b]pyridin-2-yl}phenoxy)-N-isoxazol-3-ylacetamide |
| 320 | | 2-[4-(6-chloro-7-{[1-(1-methylethyl)piperidin-4-yl]amino}-3H-imidazo[4,5-b]pyridin-2-yl)phenoxy]-N-isoxazol-3-ylacetamide |
| 321 | | 2-[4-(6-chloro-7-{[1-(thiophen-3-ylmethyl)piperidin-4-yl]amino}-3H-imidazo[4,5-b]pyridin-2-yl)phenoxy]-N-isoxazol-3-ylacetamide |
| 322 | | 2-(4-{6-chloro-7-[(1-propylpiperidin-4-yl)amino]-3H-imidazo[4,5-b]pyridin-2-yl}phenoxy)-N-isoxazol-3-ylacetamide |

TABLE 1-continued

| Ex. | Structural formula (without salt) | Chemical name |
| --- | --- | --- |
| 323 | | 2-[4-(6-chloro-7-{[1-(4-methoxybenzyl)piperidin-4-yl]amino}-3H-imidazo[4,5-b]pyridin-2-yl)phenoxy]-N-pyrazin-2-ylacetamide |
| 324 | | 2-(4-{6-chloro-7-[(1-methylpiperidin-4-yl)amino]-3H-imidazo[4,5-b]pyridin-2-yl}phenoxy)-N-(1-methyl-1H-pyrazol-5-yl)acetamide |
| 325 | | 2-[4-(6-chloro-7-{[1-(4-methoxybenzyl)piperidin-4-yl]amino}-3H-imidazo[4,5-b]pyridin-2-yl)phenoxy]-N-1H-1,2,4-triazol-3-ylacetamide |
| 326 | | 2-(4-{6-chloro-7-[(1-methylpiperidin-4-yl)amino]-3H-imidazo[4,5-b]pyridin-2-yl}phenoxy)-N-1H-1,2,4-triazol-3-ylacetamide |
| 327 | | 2-(4-{6-chloro-7-[(1-methylpiperidin-4-yl)amino]-3H-imidazo[4,5-b]pyridin-2-yl}phenoxy)-N-1,3,4-thiadiazol-2-ylacetamide |

TABLE 1-continued

| Ex. | Structural formula (without salt) | Chemical name |
|---|---|---|
| 328 | | 2-(4-{6-chloro-7-[(1-methylpiperidin-4-yl)amino]-3H-imidazo[4,5-b]pyridin-2-yl}phenoxy)-N-(3-methylisoxazol-5-yl)acetamide |
| 329 | | 2-(4-{6-chloro-7-[(1-methylpiperidin-4-yl)amino]-3H-imidazo[4,5-b]pyridin-2-yl}phenoxy)-N-1,3-thiazol-2-ylacetamide |
| 330 | | N-(5-tert-butylisoxazol-3-yl)-2-(4-{6-chloro-7-[(1-methylpiperidin-4-yl)amino]-3H-imidazo[4,5-b]pyridin-2-yl}phenoxy)acetamide |
| 331 | | 2-(4-{6-chloro-7-[(1-niethylpiperidin-4-yl)amino]-3H-imidazo[4,5-b]pyridin-2-yl}phenoxy)-N-pyrimidin-5-ylacetamide |

The compounds exemplified in Table 1 have been prepared by the General Procedures A to D (GP A to D) outlined herein above. In Table 2, analytical data for the exemplified compounds are shown together with the preparation methods.

TABLE 2

| Ex. | MS (ESI)+ m/z [M + H]+ | $^1H$ NMR (600 MHz, DMSO-$d_6$) δ ppm (unless otherwise stated) | GP |
|---|---|---|---|
| 1 | 562 | 8.05-8.09 (m, 2 H) 8.01 (t, J = 5.57 Hz, 1 H) 7.90 (s, 1 H) 7.32-7.36 (m, 4 H) 7.24-7.28 (m, 1 H) 7.09-7.13 (m, 2 H) 5.74 (d, J = 7.48 Hz, 1 H) 4.92-5.01 (m, | A |

TABLE 2-continued

| Ex. | MS (ESI)+ m/z [M + H]+ | $^1H$ NMR (600 MHz, DMSO-d$_6$) δ ppm (unless otherwise stated) | GP |
|---|---|---|---|
| | | 1 H) 4.57 (s, 2 H) 3.52 (s, 2 H) 3.24 (td, J = 6.64, 5.57 Hz, 2 H) 2.84-2.90 (m, 2 H) 2.32 (t, J = 6.64 Hz, 2 H) 2.15 (s, 6 H) 2.11-2.18 (m, 2 H) 1.95-2.01 (m, 2 H) 1.63-1.72 (m, 2 H). | |
| 2 | 548 | 8.04-8.08 (m, 2 H) 8.03 (t, J = 5.80 Hz, 1 H) 7.92 (s, 1 H) 7.32-7.36 (m, 2 H) 7.28-7.32 (m, 2 H) 7.20-7.24 (m, 1 H) 7.09-7.12 (m, 2 H) 5.82 (d, J = 8.39 Hz, 1 H) 5.48-5.57 (m, 1 H) 4.56 (s, 2 H) 3.65 (d, J = 13.12 Hz, 1 H) 3.60 (d, J = 12.97 Hz, 1 H) 3.24 (td, J = 6.71, 5.80 Hz, 2 H) 2.90 (dd, J = 9.38, 6.64 Hz, 1 H) 2.76 (td, J = 8.62, 5.49 Hz, 1 H) 2.51-2.58 (m, 2 H) 2.32-2.39 (m, 1 H) 2.32 (t, J = 6.71 Hz, 2 H) 2.15 (s, 6 H) 1.81-1.89 (m, 1 H). | A |
| 3 | 576 | 8.08 (d, J = 9.2 Hz, 2 H) 8.00 (t, J = 5.6 Hz, 1 H) 7.91 (s, 1 H) 7.23-7.31 (m, 4 H) 7.19 (t, J = 7.2 Hz, 1 H) 7.11 (d, J = 8.9 Hz, 2 H) 5.79 (d, J = 8.9 Hz, 1 H) 4.91-4.99 (m, 1 H) 4.56 (s, 2 H) 3.23 (q, J = 6.4 Hz, 2 H) 3.01 (d, J = 11.0 Hz, 2 H) 2.77 (dd, J = 8.2, 7.6 Hz, 2 H) 2.57 (dd, J = 8.2, 7.6 Hz, 2 H) 2.31 (t, J = 6.6 Hz, 2 H) 2.15-2.20 (m, 2 H) 2.14 (s, 6 H) 2.00 (d, J = 10.4 Hz, 2 H) 1.67 (qd, J = 11.7, 3.7 Hz, 2 H). | A |
| 4 | 576 | 8.06 (d, J = 8.9 Hz, 2 H) 7.92 (s, 1 H) 7.46 (s, 1 H) 7.34 (d, J = 6.7 Hz, 2 H) 7.30 (t, J = 7.5 Hz, 2 H) 7.22 (t, J = 7.2 Hz, 1 H) 7.08 (d, J = 8.9 Hz, 2 H) 5.81 (br. s., 1 H) 5.53 (br. s., 1 H) 4.51 (s, 2 H) 3.65 (d, J = 13.1 Hz, 1 H) 3.60 (d, J = 13.1 Hz, 1 H) 2.90 (dd, J = 9.3, 6.6 Hz, 1 H) 2.76 (td, J = 8.7, 5.5 Hz, 1 H) 2.51-2.57 (m, 2 H) 2.44 (s, 2 H) 2.31-2.40 (m, 1 H) 2.23 (s, 6 H) 1.81-1.89 (m, 1 H) 1.27 (s, 6 H). | A |
| 5 | 590 | 8.07 (d, J = 8.9 Hz, 2 H) 7.90 (s, 1 H) 7.46 (s, 1 H) 7.31-7.37 (m, 4 H) 7.23-7.29 (m, 1 H) 7.09 (d, J = 8.9 Hz, 2 H) 5.75 (br. s., 1 H) 4.90-5.03 (m, 1 H) 4.52 (s, 2 H) 3.52 (s, 2 H) 2.87 (d, J = 11.6 Hz, 2 H) 2.45 (s, 2 H) 2.24 (s, 6 H) 2.14 (t, J = 11.1 Hz, 2 H) 1.98 (d, J = 9.5 Hz, 2 H) 1.63-1.73 (m, J = 11.7, 11.6, 11.6, 3.7 Hz, 2 H) 1.27 (s, 6 H). | A |
| 6 | 608 | 13.09 (br. s., 1 H) 8.04-8.09 (m, 2 H) 7.90 (s, 1 H) 7.45 (s, 1 H) 7.33-7.39 (m, 2 H) 7.13-7.19 (m, 2 H) 7.07-7.11 (m, 2 H) 5.74 (br. s., 1 H) 4.91-5.02 (m, 1 H) 4.52 (s, 2 H) 3.50 (s, 2 H) 2.82-2.89 (m, 2 H) 2.44 (s, 2 H) 2.24 (s, 6 H) 2.10-2.18 (m, 2 H) 1.95-2.02 (m, 2 H) 1.62-1.72 (m, 2 H) 1.27 (s, 6 H). | A |
| 7 | 590 | 8.09 (d, J = 8.9 Hz, 2 H) 7.93 (s, 1 H) 7.46 (s, 1 H) 7.36 (d, J = 7.0 Hz, 2 H) 7.23 (t, J = 7.3 Hz, 2 H) 7.18 (t, J = 7.3 Hz, 1 H) 7.09 (d, J = 8.9 Hz, 2 H) 5.91 (d, J = 8.9 Hz, 1 H) 5.17 (br. s., 1 H) 4.51 (s, 2 H) 3.50-3.58 (m, 2 H) 2.71 (br. s., 1 H) 2.43 (s, 2 H) 2.40-2.48 (m, 2 H) 2.22 (s, 6 H) 1.79 (br. s., 1 H) 1.64-1.74 (m, 2 H) 1.53-1.63 (m, 1 H) 1.27 (s, 6 H). | A |
| 8 | 610 | 8.07 (d, J = 8.8 Hz, 2 H) 7.90 (s, 1 H) 7.46 (s, 1 H) 7.31 (d, J = 5.2 Hz, 1 H) 7.09 (d, J = 8.9 Hz, 2 H) 6.83 (d, J = 5.2 Hz, 1 H) 5.80 (d, J = 7.6 Hz, 1 H) 4.91-5.03 (m, 1 H) 4.52 (s, 2 H) 3.63 (s, 2 H) 2.94 (d, J = 11.3 Hz, 2 H) 2.44 (s, 2 H) 2.23 (s, 6 H) 2.18 (s, 3 H) 2.19 (t, J = 11.1 Hz, 2 H) 1.98 (d, J = 12.2 Hz, 2 H) 1.68 (qd, J = 11.8, 2.9 Hz, 2 H) 1.27 (s, 6 H). | A |
| 9 | 576 | 8.07 (d, J = 8.9 Hz, 2 H) 8.01 (t, J = 5.6 Hz, 1 H) 7.90 (s, 1 H) 7.22 (t, J = 7.5 Hz, 1 H) 7.14 (s, 1 H) 7.09-7.13 (m, 3 H) 7.06 (d, J = 7.3 Hz, 1 H) 5.73 (br. s., 1 H) 4.91-5.03 (m, 1 H) 4.57 (s, 2 H) 3.47 (s, 2 H) 3.24 (q, J = 6.4 Hz, 2 H) 2.86 (d, J = 11.9 Hz, 2 H) 2.32 (t, J = 6.7 Hz, 2 H) 2.31 (s, 3 H) 2.15 (s, 6 H) 2.10-2.15 (m, 2 H) 1.98 (d, J = 9.8 Hz, 2 H) 1.67 (dq, J = 11.7, 3.8 Hz, 2 H). | A |
| 10 | 576 | 13.12 (br. s., 1 H) 8.05-8.09 (m, 2 H) 8.01 (t, J = 5.65 Hz, 1 H) 7.91 (s, 1 H) 7.19-7.23 (m, 2 H) 7.12-7.16 (m, 2 H) 7.10-7.13 (m, 2 H) 5.76 (d, J = 8.54 Hz, 1 H) 4.91-5.00 (m, 1 H) 4.57 (s, 2 H) 3.46 (s, 2 H) 3.24 (td, J = 6.71, 5.65 Hz, 2 H) 2.82-2.89 (m, 2 H) 2.32 (t, J = 6.71 Hz, 2 H) 2.29 (s, 3 H) 2.15 (s, 6 H) 2.12 (td, J = 11.70, 1.83 Hz, 2 H) 1.94-2.00 (m, 2 H) 1.67 (qd, J = 11.70, 3.43 Hz, 2 H). | A |
| 11 | 505 | 8.08 (br. s., 1 H) 8.07 (d, J = 9.2 Hz, 2 H) 7.91 (s, 1 H) 7.21-7.37 (m, 5 H) 7.12 (d, J = 8.9 Hz, 2 H) 5.77 (d, J = 8.9 Hz, 1 H) 4.90-5.02 (m, 1 H) 4.56 (s, 2 H) 3.53 (s, 2 H) 2.87 (d, J = 11.9 Hz, 2 H) 2.68 (d, J = 4.6 Hz, 3 H) 2.12-2.19 (m, 2 H) 1.98 (d, J = 11.9 Hz, 2 H) 1.68 (qd, J = 11.8, 11.6, 3.7 Hz, 2 H). | A |
| 12 | 491 | 8.09 (q, J = 4.6 Hz, 1 H) 8.06 (d, J = 8.9 Hz, 2 H) 7.93 (s, 1 H) 7.33-7.35 (m, 2 H) 7.31 (t, J = 7.5 Hz, 2 H) 7.22 (t, J = 7.3 Hz, 1 H) 7.11 (d, J = 8.9 Hz, 2 H) 5.84 (d, J = 8.5 Hz, 1 H) 5.48-5.56 (m, 1 H) 4.55 (s, 2 H) 3.66 (d, J = 13.1 Hz, 1 H) 3.60 (d, J = 13.1 Hz, 1 H) 2.91 (dd, J = 9.3, 6.6 Hz, 1 H) 2.76 (td, J = 8.7, 5.5 Hz, 1 H) 2.68 (d, J = 4.6 Hz, 3 H) 2.51-2.57 (m, 2 H) 2.31-2.40 (m, 1 H) 1.82-1.89 (m, 1H). | A |
| 13 | 606 | 13.07 (br. s., 1 H) 8.05-8.09 (m, 2 H) 8.01 (t, J = 5.65 Hz, 1 H) 7.91 (s, 1 H) 7.10-7.13 (m, 2 H) 6.88 (d, J = 1.53 Hz, 1 H) 6.85 (d, J = 7.93 Hz, 1 H) 6.78 (dd, J = 7.83, 1.53 Hz, 1 H) 5.99 (s, 2 H) 5.77 (d, J = 8.70 Hz, 1 H) 4.91-5.00 (m, 1 H) 4.57 (s, 2 H) 3.42 (s, 2 H) 3.24 (td, J = 6.64, 5.65 Hz, 2 H) 2.83-2.89 (m, 2 H) 2.32 (t, J = 6.64 Hz, 2 H) 2.15 (s, 6 H) 2.08-2.15 (m, 2 H) 1.95-2.01 (m, 2 H) 1.67 (qd, J = 11.72, 3.74 Hz, 2 H). | A |
| 14 | 569 | 8.08 (d, J = 8.9 Hz, 2 H) 8.01 (t, J = 5.8 Hz, 1 H) 7.91 (s, 1 H) 7.73 (d, J = 3.1 Hz, 1 H) 7.67 (d, J = 3.4 Hz, 1 H) 7.11 (d, J = 8.9 Hz, 2 H) 5.85 (d, J = 9.2 Hz, 1 H) 4.95-5.04 (m, 1 H) 4.57 (s, 2 H) 3.89 (s, 2 H) 3.24 (q, J = 6.5 Hz, 2 H) 2.97 (d, J = 11.9 Hz, 2 H) 2.34 (t, J = 11.9, 2.1 Hz, 2 H) 2.32 (t, J = 6.7 Hz, 2 H) 2.15 (s, 6 H) 2.01 (d, J = 10.1 Hz, 2 H) 1.74 (qd, J = 11.8, 3.7 Hz, 2 H). | A |
| 15 | 568 | 13.10 (br. s., 1 H) 8.04-8.09 (m, 2 H) 8.01 (t, J = 5.73 Hz, 1 H) 7.91 (s, 1 H) 7.50 (dd, J = 4.91, 2.92 Hz, 1 H) 7.32 (d, J = 2.92 Hz, 1 H) 7.09-7.13 (m, 2 H) 7.07 (dd, J = 4.91, 1.09 Hz, 1 H) 5.78 (d, J = 8.85 Hz, 1 H) 4.91-4.99 (m, 1 H) 4.57 (s, 2 H) 3.53 (s, 2 H) 3.24 (td, J = 6.67, 5.73 Hz, 2 H) 2.84-2.92 (m, 2 H) 2.32 (t, J = 6.67 Hz, | A |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| | | 2 H) 2.15 (s, 6 H) 2.09-2.15 (m, 2 H) 1.94-2.01 (m, 2 H) 1.67 (qd, J = 11.65, 3.51 Hz, 2 H). | |
| 16 | 576 | 8.07 (d, J = 8.9 Hz, 2 H) 8.00 (t, J = 5.6 Hz, 1 H) 7.88 (s, 1 H) 7.24-7.31 (m, 4 H) 7.21 (t, J = 7.0 Hz, 1 H) 7.10 (d, J = 8.9 Hz, 2 H) 6.46 (t, J = 6.3 Hz, 1 H) 4.56 (s, 2 H) 3.98 (t, J = 6.4 Hz, 2 H) 3.40 (s, 2 H) 3.23 (q, J = 6.4 Hz, 2 H) 2.79 (d, J = 11.3 Hz, 2 H) 2.31 (t, J = 6.7 Hz, 2 H) 2.14 (s, 6 H) 1.85 (t, J = 10.7 Hz, 2 H) 1.74 (br. s., 1 H) 1.72 (d, J = 11.0 Hz, 2 H) 1.27 (qd, J = 11.9, 2.4 Hz, 2 H). | B |
| 17 | 604 | 13.29 (br. s., 1 H) 8.10 (d, J = 8.9 Hz, 2 H) 8.05 (s, 1 H) 7.96 (t, J = 5.6 Hz, 1 H) 7.30-7.35 (m, 4 H) 7.22-7.27 (m, 1 H) 7.12 (d, J = 8.9 Hz, 2 H) 4.57 (s, 2 H) 3.89 (t, J = 11.3 Hz, 1 H) 3.47 (s, 2 H) 3.17-3.22 (m, 2 H) 3.15 (s, 3 H) 2.91 (d, J = 11.6 Hz, 2 H) 2.46 (t, J = 6.9 Hz, 2 H) 2.46 (q, J = 7.0 Hz, 4 H) 2.02 (t, J = 11.3 Hz, 2 H) 1.92 (q, J = 11.5 Hz, 2 H) 1.83 (d, J = 10.7 Hz, 2 H) 0.94 (t, J = 7.2 Hz, 6 H). | B |
| 18 | 604 | 13.30 (br. s., 1 H) 8.10 (d, J = 8.5 Hz, 2 H) 8.05 (s, 1 H) 7.58 (t, J = 5.3 Hz, 1 H) 7.29-7.35 (m, 4 H) 7.22-7.27 (m, 1 H) 7.11 (d, J = 8.9 Hz, 2 H) 4.65 (s, 2 H) 3.90 (t, J = 11.1 Hz, 1 H) 3.47 (s, 2 H) 3.15 (s, 3 H) 3.13 (d, J = 5.5 Hz, 2 H) 2.91 (d, J = 11.0 Hz, 2 H) 2.12 (s, 6 H) 2.02 (t, J = 11.0 Hz, 2 H) 1.92 (dq, J = 11.4, 2.9 Hz, 2 H) 1.83 (d, J = 10.4 Hz, 2 H) 0.90 (s, 6 H). | B |
| 19 | 519 | 13.29 (br. s., 1 H) 8.10 (d, J = 8.5 Hz, 2 H) 8.09 (t, J = 4.9 Hz, 1 H) 8.05 (s, 1 H) 7.29-7.37 (m, 4 H) 7.22-7.27 (m, 1 H) 7.12 (d, J = 8.9 Hz, 2 H) 4.56 (s, 2 H) 3.88 (t, J = 11.1 Hz, 1 H) 3.47 (s, 2 H) 3.15 (s, 3 H) 2.90 (d, J = 10.7 Hz, 2 H) 2.67 (d, J = 4.6 Hz, 3 H) 2.02 (t, J = 11.3 Hz, 2 H) 1.92 (qd, J = 12.2, 2.1 Hz, 2 H) 1.82 (d, J = 11.6 Hz, 2 H). | B |
| 20 | 576 | 13.30 (br. s., 1 H) 8.10 (d, J = 8.5 Hz, 2 H) 8.05 (s, 1 H) 8.02 (t, J = 5.6 Hz, 1 H) 7.29-7.36 (m, 4 H) 7.22-7.27 (m, 1 H) 7.12 (d, J = 8.9 Hz, 2 H) 4.57 (s, 2 H) 3.89 (t, J = 11.0 Hz, 1 H) 3.47 (s, 2 H) 3.24 (td, J = 6.7, 5.8 Hz, 2 H) 3.15 (s, 3 H) 2.90 (d, J = 11.0 Hz, 2 H) 2.32 (t, J = 6.7 Hz, 2 H) 2.15 (s, 6 H) 2.02 (t, J = 10.8 Hz, 2 H) 1.92 (qd, J = 11.6, 2.4 Hz, 2 H) 1.83 (d, J = 11.0 Hz, 2 H). | B |
| 21 | 590 | 13.30 (br. s., 1 H) 8.10 (d, J = 8.9 Hz, 2 H) 8.05 (s, 1 H) 7.85 (d, J = 8.2 Hz, 1 H) 7.29-7.35 (m, 4 H) 7.21-7.27 (m, 1 H) 7.12 (d, J = 8.9 Hz, 2 H) 4.55 (s, 2 H) 3.94-4.03 (m, 1 H) 3.89 (t, J = 11.3 Hz, 1 H) 3.47 (s, 2 H) 3.15 (s, 3 H) 2.91 (d, J = 11.0 Hz, 2 H) 2.30 (dd, J = 12.1, 7.8 Hz, 1 H) 2.13 (s, 6 H) 2.14 (dd, J = 12.1, 6.7 Hz, 1 H) 2.02 (t, J = 10.8 Hz, 2 H) 1.92 (dq, J = 11.7, 3.1 Hz, 2 H) 1.83 (d, J = 11.0 Hz, 2 H) 1.07 (d, J = 6.7 Hz, 3 H). | A |
| 22 | 596 | 13.12 (br. s., 1 H) 8.07 (d, J = 8.9 Hz, 2 H) 8.01 (t, J = 5.6 Hz, 1 H) 7.91 (s, 1 H) 7.40 (d, J = 8.5 Hz, 2 H) 7.36 (d, J = 8.5 Hz, 2 H) 7.11 (d, J = 9.2 Hz, 2 H) 5.78 (d, J = 8.9 Hz, 1 H) 4.90-5.02 (m, 1 H) 4.57 (s, 2 H) 3.51 (s, 2 H) 3.24 (q, J = 6.4 Hz, 2 H) 2.85 (d, J = 11.3 Hz, 2 H) 2.32 (t, J = 6.6 Hz, 2 H) 2.15 (s, 6 H) 2.12-2.19 (m, 2 H) 1.98 (d, J = 9.5 Hz, 2 H) 1.68 (dq, J = 11.6, 3.5 Hz, 2 H). | A |
| 23 | 590 | 8.05-8.09 (m, 2 H) 7.89 (s, 1 H) 7.57 (t, J = 5.42 Hz, 1 H) 7.31-7.36 (m, 4 H) 7.23-7.29 (m, 1 H) 7.08-7.13 (m, 2 H) 5.73 (br. s., 1 H) 4.93-5.02 (m, 1 H) 4.65 (s, 2 H) 3.52 (s, 2 H) 3.13 (d, J = 5.42 Hz, 2 H) 2.84-2.90 (m, 2 H) 2.13 (s, 6 H) 2.11-2.17 (m, 2 H) 1.96-2.01 (m, 2 H) 1.67 (qd, J = 11.65, 3.51 Hz, 2 H) 0.91 (s, 6 H). | A |
| 24 | 576 | 8.04-8.08 (m, 2 H) 7.92 (s, 1 H) 7.57 (t, J = 5.49 Hz, 1 H) 7.32-7.36 (m, 2 H) 7.28-7.32 (m, 2 H) 7.20-7.24 (m, 1 H) 7.07-7.12 (m, 2 H) 5.82 (d, J = 7.48 Hz, 1 H) 5.49-5.56 (m, 1 H) 4.65 (s, 2 H) 3.65 (d, J = 13.12 Hz, 1 H) 3.60 (d, J = 13.12 Hz, 1 H) 3.13 (d, J = 5.49 Hz, 2 H) 2.90 (dd, J = 9.50, 6.56 Hz, 1 H) 2.76 (td, J = 8.70, 5.49 Hz, 1 H) 2.55 (dd, J = 9.50, 4.65 Hz, 1 H) 2.49-2.53 (m, 1 H) 2.31-2.39 (m, 1 H) 2.12 (s, 6 H) 1.81-1.89 (m, 1 H) 0.90 (s, 6 H). | A |
| 25 | 576 | 13.11 (br. s., 1 H) 8.04-8.08 (m, 2 H) 7.92 (s, 1 H) 7.57 (t, J = 5.49 Hz, 1 H) 7.32-7.35 (m, 2 H) 7.28-7.32 (m, 2 H) 7.20-7.24 (m, 1 H) 7.07-7.12 (m, 2 H) 5.81 (d, J = 7.63 Hz, 1 H) 5.49-5.56 (m, 1 H) 4.65 (s, 2 H) 3.65 (d, J = 13.12 Hz, 1 H) 3.60 (d, J = 13.12 Hz, 1 H) 3.13 (d, J = 5.49 Hz, 2 H) 2.90 (dd, J = 9.46, 6.56 Hz, 1 H) 2.76 (td, J = 8.66, 5.42 Hz, 1 H) 2.55 (dd, J = 9.46, 4.58 Hz, 1 H) 2.49-2.53 (m, 1 H) 2.31-2.39 (m, 1 H) 2.12 (s, 6 H) 1.81-1.89 (m, 1 H) 0.91 (s, 6 H). | A |
| 26 | 608 | 13.11 (br. s., 1 H) 8.05-8.09 (m, 2 H) 7.90 (s, 1 H) 7.57 (t, J = 5.49 Hz, 1 H) 7.33-7.38 (m, 2 H) 7.13-7.18 (m, 2 H) 7.09-7.13 (m, 2 H) 5.77 (d, J = 8.24 Hz, 1 H) 4.92-5.01 (m, 1 H) 4.65 (s, 2 H) 3.50 (s, 2 H) 3.13 (d, J = 5.49 Hz, 2 H) 2.82-2.89 (m, 2 H) 2.13 (s, 6 H) 2.11-2.17 (m, 2H) 1.95-2.01 (m, 2H) 1.63-1.72 (m, 2 H) 0.91 (s, 6 H). | A |
| 27 | 604 | 13.06 (br. s., 1 H) 8.05-8.09 (m, 2 H) 7.90 (s, 1 H) 7.57 (t, J = 5.42 Hz, 1 H) 7.19-7.23 (m, 2 H) 7.12-7.16 (m, 2 H) 7.09-7.13 (m, 2 H) 5.76 (d, J = 8.70 Hz, 1 H) 4.91-5.00 (m, 1 H) 4.65 (s, 2 H) 3.46 (s, 2 H) 3.13 (d, J = 5.42 Hz, 2 H) 2.83-2.89 (m, 2 H) 2.29 (s, 3 H) 2.13 (s, 6 H) 2.08-2.15 (m, 2 H) 1.94-2.00 (m, 2 H) 1.66 (qd, J = 11.70, 3.81 Hz, 2 H) 0.91 (s, 6 H). | A |
| 28 | 604 | 8.05-8.10 (m, 2 H) 7.89 (s, 1 H) 7.57 (t, J = 5.49 Hz, 1 H) 7.21 (t, J = 7.48 Hz, 1 H) 7.14 (br. s., 1 H) 7.10-7.13 (m, 2 H) 7.09-7.12 (m, 2 H) 7.06 (d, J = 7.48 Hz, 1 H) 5.71 (br. s., 1 H) 4.92-5.02 (m, 1 H) 4.65 (s, 2 H) 3.47 (s, 2 H) 3.13 (d, J = 5.49 Hz, 2 H) 2.82-2.90 (m, 2 H) 2.31 (s, 3 H) 2.13 (s, 6 H) 2.09-2.16 (m, 2 H) 1.95-2.01 (m, 2 H) 1.67 (qd, J = 11.67, 3.74 Hz, 2 H) 0.91 (s, 6 H). | A |
| 29 | 566 | 8.04-8.08 (m, 2 H) 8.01 (t, J = 5.65 Hz, 1 H) 7.91 (s, 1 H) 7.09-7.12 (m, 2 H) 6.15 (d, J = 2.97 Hz, 1 H) 6.00 (dq, J = 2.97, 1.07 Hz, 1 H) 5.78 (d, J = 8.85 Hz, 1 H) | A |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| 30 | 548 | 4.88-4.97 (m, 1 H) 4.57 (s, 2 H) 3.45 (s, 2 H) 3.24 (td, J = 6.71, 5.65 Hz, 2 H) 2.84-2.91 (m, 2 H) 2.32 (t, J = 6.71 Hz, 2 H) 2.25 (d, J = 1.07 Hz, 3 H) 2.15 (s, 6 H) 2.11-2.19 (m, 2 H) 1.94-2.00 (m, 2 H) 1.66 (qd, J = 11.76, 3.59 Hz, 2 H). 13.11 (br. s., 1 H) 8.04-8.08 (m, 2 H) 8.02 (t, J = 5.65 Hz, 1 H) 7.92 (s, 1 H) 7.32-7.36 (m, 2 H) 7.29-7.33 (m, 2 H) 7.20-7.24 (m, 1 H) 7.09-7.12 (m, 2 H) 5.83 (d, J = 8.70 Hz, 1 H) 5.49-5.56 (m, 1 H) 4.56 (s, 2 H) 3.65 (d, J = 13.12 Hz, 1 H) 3.60 (d, J = 13.12 Hz, 1 H) 3.24 (td, J = 6.71, 5.65 Hz, 2 H) 2.91 (dd, J = 9.34, 6.71 Hz, 1 H) 2.76 (td, J = 8.58, 5.57 Hz, 1 H) 2.55 (dd, J = 9.34, 4.50 Hz, 1 H) 2.49-2.54 (m, 1 H) 2.32-2.39 (m, 1 H) 2.32 (t, J = 6.71 Hz, 2 H) 2.15 (s, 6 H) 1.82-1.89 (m, 1 H). | A |
| 31 | 604 | 12.94 (br. s., 1 H) 8.05-8.09 (m, 2 H) 7.88 (s, 1 H) 7.55 (t, J = 5.49 Hz, 1 H) 7.27-7.31 (m, 2 H) 7.24-7.27 (m, 2 H) 7.20-7.23 (m, 1 H) 7.08-7.12 (m, 2 H) 6.47 (t, J = 6.56 Hz, 1 H) 4.64 (s, 2 H) 3.97 (t, J = 6.41 Hz, 2 H) 3.40 (s, 2 H) 3.12 (d, J = 5.49 Hz, 2 H) 2.76-2.82 (m, 2 H) 2.11 (s, 6 H) 1.80-1.88 (m, 2 H) 1.71-1.78 (m, 1 H) 1.69-1.75 (m, 2 H) 1.22-1.32 (m, 2 H) 0.89 (s, 6 H). | A |
| 32 | 584 | 8.04-8.08 (m, 2 H) 8.02 (t, J = 5.80 Hz, 1 H) 7.92 (s, 1 H) 7.39 (ddd, J = 11.60, 7.93, 1.98 Hz, 1 H) 7.35 (dt, J = 10.80, 8.41 Hz, 1 H) 7.16-7.20 (m, 1 H) 7.08-7.12 (m, 2 H) 5.83 (d, J = 7.93 Hz, 1 H) 5.50-5.58 (m, 1 H) 4.56 (s, 2 H) 3.65 (d, J = 13.43 Hz, 1 H) 3.59 (d, J = 13.43 Hz, 1 H) 3.24 (td, J = 6.71, 5.80 Hz, 2 H) 2.91 (dd, J = 9.46, 6.56 Hz, 1 H) 2.76 (td, J = 8.66, 5.26 Hz, 1 H) 2.57 (dd, J = 9.46, 4.58 Hz, 1 H) 2.48-2.54 (m, 1 H) 2.32-2.40 (m, 1 H) 2.32 (t, J = 6.71 Hz, 2 H) 2.15 (s, 6 H) 1.82-1.89 (m, 1 H). | A |
| 33 | 566 | 8.04-8.08 (m, 2 H) 8.02 (t, J = 5.72 Hz, 1 H) 7.92 (s, 1 H) 7.35-7.39 (m, 2 H) 7.10-7.15 (m, 2 H) 7.09-7.12 (m, 2 H) 5.82 (d, J = 8.55 Hz, 1 H) 5.49-5.56 (m, 1 H) 4.56 (s, 2 H) 3.64 (d, J = 12.97 Hz, 1 H) 3.58 (d, J = 12.97 Hz, 1 H) 3.24 (td, J = 6.71, 5.72 Hz, 2 H) 2.90 (dd, J = 9.38, 6.49 Hz, 1 H) 2.74 (td, J = 8.62, 5.34 Hz, 1 H) 2.55 (dd, J = 9.38, 4.65 Hz, 1 H) 2.47-2.53 (m, 1 H) 2.31-2.39 (m, 1 H) 2.32 (t, J = 6.71 Hz, 2 H) 2.15 (s, 6 H) 1.81-1.89 (m, 1 H). | A |
| 34 | 527 | 13.14 (br. s., 1 H) 8.08 (q, J = 4.58 Hz, 1 H) 8.05-8.08 (m, 2 H) 7.93 (s, 1 H) 7.39 (ddd, J = 11.75, 8.24, 1.98 Hz, 1 H) 7.35 (dt, J = 10.83, 8.39 Hz, 1 H) 7.16-7.20 (m, 1 H) 7.09-7.13 (m, 2 H) 5.86 (d, J = 8.55 Hz, 1 H) 5.50-5.58 (m, 1 H) 4.55 (s, 2 H) 3.66 (d, J = 13.43 Hz, 1 H) 3.59 (d, J = 13.43 Hz, 1 H) 2.91 (dd, J = 9.38, 6.64 Hz, 1 H) 2.76 (td, J = 8.66, 5.72 Hz, 1 H) 2.68 (d, J = 4.58 Hz, 3 H) 2.57 (dd, J = 9.38, 4.65 Hz, 1 H) 2.50-2.54 (m, 1 H) 2.32-2.40 (dddd, J = 13.58, 8.39, 8.39, 5.65 Hz, 1 H) 1.82-1.90 (m, 1 H). | A |
| 35 | 509 | 13.13 (br. s., 1 H) 8.09 (q, J = 4.58 Hz, 1 H) 8.04-8.08 (m, 2 H) 7.93 (s, 1 H) 7.35-7.39 (m, 2 H) 7.11-7.15 (m, 2 H) 7.09-7.13 (m, 2 H) 5.83 (d, J = 8.54 Hz, 1 H) 5.49-5.56 (m, 1 H) 4.55 (s, 2 H) 3.64 (d, J = 12.97 Hz, 1 H) 3.58 (d, J = 12.97 Hz, 1 H) 2.91 (dd, J = 9.42, 6.56 Hz, 1 H) 2.74 (td, J = 8.70, 5.49 Hz, 1 H) 2.68 (d, J = 4.58 Hz, 3 H) 2.55 (dd, J = 9.42, 4.50 Hz, 1 H) 2.47-2.53 (m, 1 H) 2.35 (dddd, J = 13.41, 8.37, 8.20, 5.57 Hz, 1 H) 1.81-1.89 (m, 1 H). | A |
| 36 | 566 | 13.08 (br. s., 1 H) 8.04-8.08 (m, 2 H) 8.02 (t, J = 5.72 Hz, 1 H) 7.92 (s, 1 H) 7.34-7.39 (m, 2 H) 7.11-7.15 (m, 2 H) 7.09-7.12 (m, 2 H) 5.83 (d, J = 8.09 Hz, 1 H) 5.49-5.56 (m, 1 H) 4.56 (s, 2 H) 3.64 (d, J = 12.97 Hz, 1 H) 3.58 (d, J = 12.97 Hz, 1 H) 3.24 (td, J = 6.71, 5.72 Hz, 2 H) 2.90 (dd, J = 9.38, 6.71 Hz, 1 H) 2.74 (td, J = 8.62, 5.49 Hz, 1 H) 2.55 (dd, J = 9.38, 4.65 Hz, 1 H) 2.47-2.53 (m, 1 H) 2.32-2.39 (m, 1 H) 2.32 (t, J = 6.71 Hz, 2 H) 2.15 (s, 6 H) 1.82-1.88 (m, 1 H). | A |
| 37 | 509 | 13.14 (br. s., 1 H) 8.09 (q, J = 4.73 Hz, 1 H) 8.04-8.08 (m, 2 H) 7.93 (s, 1 H) 7.35-7.39 (m, 2 H) 7.11-7.15 (m, 2 H) 7.09-7.13 (m, 2 H) 5.83 (d, J = 8.55 Hz, 1 H) 5.49-5.56 (m, 1 H) 4.55 (s, 2 H) 3.64 (d, J = 13.12 Hz, 1 H) 3.58 (d, J = 13.12 Hz, 1 H) 2.90 (dd, J = 9.38, 6.64 Hz, 1 H) 2.74 (td, J = 8.58, 5.57 Hz, 1 H) 2.68 (d, J = 4.73 Hz, 3 H) 2.55 (dd, J = 9.38, 4.58 Hz, 1 H) 2.48-2.53 (m, 1 H) 2.35 (dddd, J = 13.43, 8.54, 5.65 Hz, 1 H) 1.81-1.88 (m, 1 H). | A |
| 38 | 491 | 13.13 (br. s., 1 H) 8.09 (q, J = 4.58 Hz, 1 H) 8.04-8.08 (m, 2 H) 7.92 (s, 1 H) 7.32-7.36 (m, 2 H) 7.28-7.33 (m, 2 H) 7.20-7.24 (m, 1 H) 7.09-7.13 (m, 2 H) 5.83 (d, J = 8.55 Hz, 1 H) 5.48-5.56 (m, 1 H) 4.55 (s, 2 H) 3.66 (d, J = 13.12 Hz, 1 H) 3.60 (d, J = 13.12 Hz, 1 H) 2.91 (dd, J = 9.54, 6.49 Hz, 1 H) 2.76 (td, J = 8.55, 5.65 Hz, 1 H) 2.68 (d, J = 4.58 Hz, 3 H) 2.55 (dd, J = 9.54, 4.50 Hz, 1 H) 2.50-2.54 (m, 1 H) 2.31-2.39 (m, 1 H) 1.82-1.89 (m, 1 H). | A |
| 39 | 511 | 8.06-8.09 (m, 1 H) 8.05-8.08 (m, 2 H) 7.90 (s, 1 H) 7.50 (dd, J = 4.9, 2.9 Hz, 1 H) 7.31-7.34 (m, J = 2.9, 1.2, 0.7, 0.7 Hz, 1 H) 7.09-7.14 (m, 2 H) 7.07 (dd, J = 4.9, 1.2 Hz, 1 H) 5.76 (d, J = 8.8 Hz, 1 H) 4.90-4.99 (m, 1 H) 4.56 (s, 2 H) 3.53 (s, 2 H) 2.85-2.91 (m, 2 H) 2.68 (d, J = 4.7 Hz, 3 H) 2.13 (td, J = 11.6, 1.5 Hz, 2 H) 1.94-2.01 (m, 2 H) 1.67 (dddd, J = 11.8, 11.6, 3.6 Hz, 2 H). | A |
| 40 | 519 | 13.12 (br. s., 1 H) 8.08 (br. s., 1 H) 8.07 (d, J = 8.9 Hz, 2 H) 7.91 (s, 1 H) 7.22 (t, J = 7.5 Hz, 1 H) 7.15 (s, 1 H) 7.12 (br. s., 1 H) 7.12 (d, J = 8.9 Hz, 2 H) 7.07 (d, J = 7.3 Hz, 1 H) 5.78 (d, J = 8.9 Hz, 1 H) 4.92-5.01 (m, 1 H) 4.56 (s, 2 H) 3.48 (s, 2 H) 2.87 (d, J = 11.3 Hz, 2 H) 2.68 (d, J = 4.9 Hz, 3 H) 2.31 (s, 3 H) 2.14 (t, J = 11.4 Hz, 2 H) 1.98 (d, J = 10.7 Hz, 2 H) 1.68 (qd, J = 11.7, 3.7 Hz, 2 H). | A |
| 41 | 505 | 13.16 (br. s., 1 H) 8.09 (d, J = 8.9 Hz, 2 H) 8.08 (br. s., 1 H) 7.94 (s, 1 H) 7.23-7.29 (m, 4 H) 7.18-7.19 (m, 1 H) 7.18 (t, J = 7.0 Hz, 1 H) 7.16 (s, 1 H) 7.18 (d, J = 7.0 Hz, 0 H) 7.11 (d, J = 8.9 Hz, 2 H) 5.77 (d, J = 8.5 Hz, 1 H) 5.53-5.61 (m, 1 H) 4.55 (s, 2 H) 2.88 (dd, J = 9.3, 6.6 Hz, 1 H) 2.83 (td, J = 8.7, 5.2 Hz, 1 H) 2.76 (t, J = 7.5 Hz, 2 H) 2.67 (d, J = 4.6 Hz, 3 H) 2.64-2.71 (m, 2 H) 2.30-2.38 (m, 1 H) 1.78-1.85 (m, 1 H). | A |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| 42 | 525 | 13.12 (br. s., 1 H) 8.08 (d, J = 9.2 Hz, 2 H) 8.06 (br. s., 1 H) 7.91 (s, 1 H) 7.31 (d, J = 4.9 Hz, 1 H) 7.11 (d, J = 8.9 Hz, 2 H) 6.84 (d, J = 5.2 Hz, 1 H) 5.82 (d, J = 8.9 Hz, 1 H) 4.56 (s, 2 H) 3.64 (s, 2 H) 2.94 (d, J = 11.3 Hz, 1 H) 2.68 (d, J = 4.9 Hz, 3 H) 2.18 (s, 3 H) 2.17-2.23 (m, 2 H) 1.98 (d, J = 10.7 Hz, 2 H) 1.68 (qd, J = 11.6, 3.8 Hz, 2 H). | A |
| 43 | 521 | 13.15 (br. s., 1 H) 8.09 (d, J = 4.6 Hz, 1 H) 8.06 (d, J = 8.9 Hz, 2 H) 7.93 (s, 1 H) 7.24 (d, J = 8.2 Hz, 2 H) 7.11 (d, J = 8.9 Hz, 2 H) 6.86 (d, J = 8.5 Hz, 2 H) 5.83 (d, J = 7.6 Hz, 1 H) 5.47-5.59 (m, 1 H) 4.55 (s, 2 H) 3.71 (s, 3 H) 3.49-3.64 (m, 1 H) 2.88 (br. s., 1 H) 2.75 (br. s., 1 H) 2.68 (d, J = 4.9 Hz, 3 H) 2.52-2.58 (m, 1 H) 2.31-2.38 (m, 1 H) 1.79-1.89 (m, 1 H). | A |
| 44 | 535 | 13.11 (br. s., 1 H) 8.08 (br. s., 1 H) 8.07 (d, J = 8.9 Hz, 2 H) 7.91 (s, 1 H) 7.24 (d, J = 8.5 Hz, 2 H) 7.12 (d, J = 8.9 Hz, 2 H) 6.89 (d, J = 8.5 Hz, 2 H) 5.77 (d, J = 9.2 Hz, 1 H) 4.89-5.01 (m, 1 H) 4.56 (s, 2 H) 3.74 (s, 3 H) 3.44 (s, 2 H) 2.85 (d, J = 11.3 Hz, 2 H) 2.68 (d, J = 4.9 Hz, 3 H) 2.12 (t, J = 10.8 Hz, 2 H) 1.97 (d, J = 10.1 Hz, 2 H) 1.66 (qd, J = 11.5, 3.5 Hz, 2 H). | A |
| 45 | 549 | 8.05-8.09 (m, 3 H) 7.91 (s, 1 H) 7.10-7.14 (m, 2 H) 6.89 (d, J = 1.53 Hz, 1 H) 6.85 (d, J = 7.85 Hz, 1 H) 6.78 (dd, J = 7.85, 1.53 Hz, 1 H) 5.99 (s, 2 H) 5.76 (d, J = 9.00 Hz, 1 H) 4.90-5.00 (m, 1 H) 4.56 (s, 2 H) 3.43 (s, 2 H) 2.81-2.90 (m, 2 H) 2.68 (d, J = 4.73 Hz, 3 H) 2.12 (td, J = 11.86, 1.91 Hz, 2 H) 1.94-2.01 (m, 2 H) 1.67 (qd, J = 11.80, 3.74 Hz, 2 H). | A |
| 46 | 509 | $^1$H NMR (600 MHz, CD$_3$OD) δ ppm 8.04-8.08 (m, 2 H) 7.89 (s, 1 H) 7.12-7.16 (m, 2 H) 6.20 (d, J = 3.0 Hz, 1 H) 5.98 (dq, J = 3.0, 1.0 Hz, 1 H) 5.02-5.10 (m, 1 H) 4.60 (s, 2 H) 3.58 (s, 2 H) 2.98-3.04 (m, 2 H) 2.85 (s, 3 H) 2.33-2.39 (m, 2 H) 2.29 (d, J = 1.0 Hz, 3 H) 2.14-2.21 (m, 2 H) 1.66-1.74 (m, 2 H). | A |
| 47 | 497 | 13.11 (br. s., 1 H) 8.09 (q, J = 4.7 Hz, 1 H) 8.05-8.08 (m, 2 H) 7.92 (s, 1 H) 7.46 (dd, J = 4.9, 3.0 Hz, 1 H) 7.32 (dq, J = 3.0, 1.2 Hz, 1 H) 7.09-7.13 (m, 2 H) 7.09 (dd, J = 4.9, 1.2 Hz, 1 H) 5.82 (d, J = 8.4 Hz, 1 H) 5.48-5.56 (m, 1 H) 4.55 (s, 2 H) 3.65 (d, J = 13.2 Hz, 1 H) 3.61 (d, J = 13.2 Hz, 1 H) 2.90 (d, J = 9.4, 6.7 Hz, 1 H) 2.76 (td, J = 8.5, 5.3 Hz, 1 H) 2.68 (d, J = 4.7 Hz, 3 H) 2.56 (dd, J = 9.4, 4.7 Hz, 1 H) 2.51 (td, J = 8.5, 6.3 Hz, 1 H) 2.31-2.38 (m, J = 13.7, 8.5, 8.5, 5.0 Hz, 1 H) 1.80-1.87 (m, 1 H). | A |
| 48 | 495 | 8.05-8.10 (m, 3 H) 7.91 (s, 1 H) 7.62 (t, J = 1.68 Hz, 1 H) 7.57-7.58 (m, 1 H) 7.10-7.13 (m, 2 H) 6.45 (dd, J = 1.68, 0.76 Hz, 1 H) 5.76 (d, J = 8.70 Hz, 1 H) 4.90-4.99 (m, 1 H) 4.56 (s, 2 H) 3.37 (s, 2 H) 2.85-2.92 (m, 2 H) 2.68 (d, J = 4.73 Hz, 3 H) 2.08-2.15 (m, 2 H) 1.94-2.02 (m, 2 H) 1.66 (qd, J = 11.70, 3.59 Hz, 2 H). | A |
| 49 | 535 | 13.03 (br. s., 1 H) 8.08 (q, J = 4.58 Hz, 1 H) 8.05-8.08 (m, 2 H) 7.93 (s, 1 H) 7.09-7.13 (m, 2 H) 6.90 (d, J = 1.53 Hz, 1 H) 6.81-6.83 (m, J = 7.93 Hz, 1 H) 6.78 (dd, J = 7.93, 1.53 Hz, 1 H) 5.95-5.97 (m, 2 H) 5.82 (d, J = 8.55 Hz, 1 H) 5.49-5.56 (m, 1 H) 4.55 (s, 2 H) 3.55 (d, J = 12.97 Hz, 1 H) 3.51 (d, J = 12.97 Hz, 1 H) 2.86 (dd, J = 9.41, 6.64 Hz, 1 H) 2.74 (td, J = 8.62, 5.26 Hz, 1 H) 2.68 (d, J = 4.58 Hz, 3 H) 2.55 (dd, J = 9.41, 4.50 Hz, 1 H) 2.47 (td, J = 8.62, 6.79 Hz, 1 H) 2.31-2.38 (dtd, J = 13.43, 8.55, 5.19 Hz, 1 H) 1.80-1.87 (m, 1 H). | A |
| 50 | 498 | 8.09 (br. s., 1 H) 8.08 (d, J = 8.8 Hz, 2 H) 7.94 (s, 1 H) 7.70 (d, J = 3.1 Hz, 1 H) 7.65 (d, J = 3.1 Hz, 1 H) 7.11 (d, J = 9.2 Hz, 2 H) 5.88 (d, J = 8.5 Hz, 1 H) 5.52-5.60 (m, 1 H) 4.55 (s, 2 H) 4.01 (s, 2 H) 3.05 (dd, J = 9.3, 6.6 Hz, 1 H) 2.94 (td, J = 8.7, 5.5 Hz, 1 H) 2.72 (dd, J = 9.6, 4.4 Hz, 1 H) 2.68 (d, J = 4.6 Hz, 3 H) 2.65-2.70 (m, 1 H) 2.38 (dddd, J = 13.5, 8.4, 8.3, 5.5 Hz, 1 H) 1.87-1.96 (m, 1 H). | A |
| 51 | 511 | 8.09 (br. s., 1 H) 8.08 (d, J = 8.9 Hz, 2 H) 7.92 (s, 1 H) 7.28 (d, J = 4.9 Hz, 1 H) 7.10 (d, J = 8.9 Hz, 2 H) 6.80 (d, J = 4.9 Hz, 1 H) 5.81 (d, J = 8.5 Hz, 1 H) 5.52 (br. s., 1 H) 4.55 (s, 2 H) 3.74 (s, 3 H) 2.93 (dd, J = 9.3, 6.6 Hz, 1 H) 2.84 (td, J = 8.5, 5.5 Hz, 1 H) 2.68 (d, J = 4.6 Hz, 3 H) 2.62 (dd, J = 9.3, 4.4 Hz, 1 H) 2.53-2.57 (m, 1 H) 2.30-2.39 (m, 1 H) 2.16 (s, 3 H) 1.80-1.91 (m, 1 H). | A |
| 52 | 559 | 8.09 (br. s., 1 H) 8.07 (d, J = 8.9 Hz, 2 H) 7.93 (s, 1 H) 7.67 (d, J = 7.9 Hz, 2 H) 7.58 (d, J = 8.2 Hz, 2 H) 7.11 (d, J = 8.9 Hz, 2 H) 5.86 (d, J = 8.5 Hz, 1 H) 5.51-5.62 (m, 1 H) 4.55 (s, 2 H) 3.76 (d, J = 13.7 Hz, 1 H) 3.70 (d, J = 13.7 Hz, 1 H) 2.94 (dd, J = 9.3, 6.6 Hz, 1 H) 2.78 (td, J = 8.5, 5.5 Hz, 1 H) 2.68 (d, J = 4.6 Hz, 3 H) 2.60 (dd, J = 9.5, 4.6 Hz, 1 H) 2.52-2.56 (m, 1 H) 2.33-2.41 (m, 1 H) 1.82-1.92 (m, 1 H). | A |
| 53 | 505 | 8.09 (d, J = 4.6 Hz, 1 H) 8.06 (d, J = 8.9 Hz, 2 H) 7.93 (s, 1 H) 7.18 (t, J = 7.5 Hz, 1 H) 7.14 (s, 1 H) 7.12 (d, J = 7.3 Hz, 1 H) 7.11 (d, J = 8.9 Hz, 2 H) 7.03 (d, J = 7.3 Hz, 1 H) 5.82 (d, J = 8.2 Hz, 1 H) 5.49-5.58 (m, 1 H) 4.55 (s, 2 H) 3.60 (d, J = 13.1 Hz, 1 H) 3.57 (d, J = 13.1 Hz, 1 H) 2.87 (dd, J = 9.3, 6.6 Hz, 1 H) 2.76 (td, J = 8.6, 5.6 Hz, 1 H) 2.68 (d, J = 4.9 Hz, 3 H) 2.55 (dd, J = 9.6, 4.4 Hz, 1 H) 2.47-2.52 (m, 1 H) 2.31-2.40 (m, 1 H) 2.27 (s, 3 H) 1.81-1.89 (m, 1 H). | A |
| 54 | 505 | 13.12 (br. s., 1 H) 8.09 (q, J = 4.7 Hz, 1 H) 8.04-8.08 (m, 2 H) 7.92 (s, 1 H) 7.19-7.23 (m, 2 H) 7.09-7.13 (m, 4 H) 5.81 (d, J = 8.5 Hz, 1 H) 5.48-5.55 (m, 1 H) 4.55 (s, 2 H) 3.59 (d, J = 13.0 Hz, 1 H) 3.56 (d, J = 13.0 Hz, 1 H) 2.86 (dd, J = 9.4, 6.6 Hz, 1 H) 2.75 (td, J = 8.6, 5.3 Hz, 1 H) 2.68 (d, J = 4.7 Hz, 3 H) 2.54 (dd, J = 9.4, 4.6 Hz, 1 H) 2.48 (td, J = 8.6, 6.6 Hz, 1 H) 2.31-2.38 (m, 1 H) 2.26 (s, 3 H) 1.80-1.87 (m, 1 H). | A |
| 55 | 497 | 8.08-8.11 (m, 1 H) 8.07 (d, J = 8.9 Hz, 2 H) 7.93 (s, 1 H) 7.40 (dd, J = 4.9, 1.2 Hz, 1 H) 7.11 (d, J = 8.9 Hz, 2 H) 6.96 (dd, J = 3.4, 1.2 Hz, 1 H) 6.94 (dd, J = 5.2, 3.4 Hz, 1 H) 5.83 (d, J = 8.5 Hz, 1 H) 5.48-5.58 (m, 1 H) 4.55 (s, 2 H) 3.84 (s, 2 H) 2.94 (dd, J = 9.3, 6.6 Hz, 1 H) 2.82 (td, J = 8.7, 5.5 Hz, 1 H) 2.68 (d, J = 4.9 Hz, 3 H) | A |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| | | 2.60 (dd, J = 9.5, 4.6 Hz, 1 H) 2.56 (td, J = 8.2, 6.7 Hz, 1 H) 2.30-2.41 (m, 1 H) 1.81-1.93 (m, 1 H). | |
| 56 | 497 | 8.07 (d, J = 8.9 Hz, 2 H) 8.06 (br. s., 1 H) 7.91 (s, 1 H) 7.12 (d, J = 8.9 Hz, 2 H) 5.70 (d, J = 8.9 Hz, 1 H) 4.83-4.95 (m, 1 H) 4.55 (s, 2 H) 2.88 (d, J = 11.6 Hz, 2 H) 2.67 (d, J = 4.6 Hz, 3 H) 2.36 (td, J = 11.9, 2.1 Hz, 2 H) 2.26-2.33 (m, 1 H) 2.00 (d, J = 10.7 Hz, 2 H) 1.72-1.82 (m, 4 H) 1.62-1.65 (m, 1 H) 1.59 (td, J = 11.4, 2.9 Hz, 2 H) 1.17-1.28 (m, 4H) 1.05-1.14 (m, 1 H). | A |
| 57 | 521 | 13.14 (br. s., 1 H) 8.09 (q, J = 4.6 Hz, 1 H) 8.04-8.08 (m, 2 H) 7.93 (s, 1 H) 7.21 (t, J = 7.9 Hz, 1 H) 7.08-7.13 (m, 2 H) 6.89-6.91 (m, 1 H) 6.89-6.92 (m, 1 H) 6.77-6.80 (m, 1 H) 5.83 (d, J = 8.5 Hz, 1 H) 5.49-5.57 (m, 1 H) 4.55 (s, 2 H) 3.72 (s, 3 H) 3.62 (d, J = 13.3 Hz, 1 H) 3.59 (d, J = 13.3 Hz, 1 H) 2.87 (dd, J = 9.5, 6.6 Hz, 1 H) 2.78 (td, J = 8.5, 5.5 Hz, 1 H) 2.68 (d, J = 4.6 Hz, 3 H) 2.57 (dd, J = 9.5, 4.3 Hz, 1 H) 2.47-2.53 (m, 1 H) 2.32-2.39 (m, 1 H) 1.82-1.89 (m, 1 H). | A |
| 58 | 521 | 12.96 (br. s., 1 H) 8.09 (q, J = 4.6 Hz, 1 H) 8.05-8.09 (m, 2 H) 7.93 (s, 1 H) 7.36 (dd, J = 7.5, 1.8 Hz, 1 H) 7.21 (ddd, J = 8.2, 7.5, 1.8 Hz, 1 H) 7.09-7.13 (m, 2 H) 6.96 (dd, J = 8.2, 0.8 Hz, 1 H) 6.90 (td, J = 7.5, 0.8 Hz, 1 H) 5.84 (d, J = 8.5 Hz, 1 H) 5.48-5.56 (m, 1 H) 4.55 (s, 2 H) 3.76 (s, 3 H) 3.64 (d, J = 13.9 Hz, 1 H) 3.61 (d, J = 13.9 Hz, 1 H) 2.93 (dd, J = 9.5, 6.6 Hz, 1 H) 2.79 (td, J = 8.5, 5.5 Hz, 1 H) 2.68 (d, J = 4.6 Hz, 3 H) 2.59 (dd, J = 9.5, 4.6 Hz, 1 H) 2.53 (td, J = 8.5, 6.7 Hz, 1 H) 2.30-2.38 (m, 1 H) 1.80-1.88 (m, 1 H). | A |
| 59 | 505 | 13.15 (s, 1 H) 8.09 (d, J = 4.6 Hz, 1 H) 8.06 (d, J = 8.9 Hz, 2 H) 7.93 (s, 1 H) 7.28 (dd, J = 7.0, 1.8 Hz, 1 H) 7.08-7.18 (m, 5 H) 5.80 (d, J = 8.5 Hz, 1 H) 5.47-5.56 (m, 1 H) 4.55 (s, 2 H) 3.64 (d, J = 13.1 Hz, 1 H) 3.58 (d, J = 13.4 Hz, 1 H) 2.91 (dd, J = 9.2, 6.4 Hz, 1 H) 2.73-2.80 (m, 1 H) 2.68 (d, J = 4.6 Hz, 3 H) 2.57 (dd, J = 9.5, 4.3 Hz, 1 H) 2.47-2.53 (m, 1 H) 2.36 (s, 3 H) 2.30-2.38 (m, 1 H) 1.80-1.90 (m, 1 H). | A |
| 60 | 565 | 13.12 (br. s., 1 H) 8.08 (br. s., 1 H) 8.07 (d, J = 8.9 Hz, 2 H) 7.91 (s, 1 H) 7.20 (d, J = 8.2 Hz, 1 H) 7.12 (d, J = 8.9 Hz, 2 H) 6.55 (d, J = 2.4 Hz, 1 H) 6.51 (dd, J = 8.2, 2.4 Hz, 1 H) 5.77 (d, J = 8.9 Hz, 1 H) 4.89-4.99 (m, 1 H) 4.56 (s, 2 H) 3.78 (s, 3 H) 3.75 (s, 3 H) 3.44 (s, 2 H) 2.87 (d, J = 11.6 Hz, 2 H) 2.68 (d, J = 4.6 Hz, 3 H) 2.15 (t, J = 11.1 Hz, 2 H) 1.97 (d, J = 11.3 Hz, 2 H) 1.66 (dq, J = 11.8, 2.9 Hz, 2 H). | A |
| 61 | 535 | 13.12 (br. s., 1 H) 8.04-8.10 (m, 3 H) 7.91 (s, 1 H) 7.34 (dd, J = 7.4, 1.8 Hz, 1 H) 7.24 (ddd, J = 8.2, 7.4, 1.8 Hz, 1 H) 7.10-7.14 (m, 2 H) 6.99 (dd, J = 8.2, 1.0 Hz, 1 H) 6.94 (td, J = 7.4, 1.0 Hz, 1 H) 5.79 (d, J = 8.9 Hz, 1 H) 4.92-5.00 (m, 1 H) 4.56 (s, 2 H) 3.79 (s, 3 H) 3.52 (s, 2 H) 2.86-2.93 (m, 2 H) 2.68 (d, J = 4.7 Hz, 3 H) 2.15-2.23 (m, 2 H) 1.95-2.02 (m, 2 H) 1.69 (qd, J = 11.7, 3.1 Hz, 2 H). | A |
| 62 | 535 | 13.10 (br. s., 1 H) 8.05-8.09 (m, 3 H) 7.91 (s, 1 H) 7.25 (t, J = 8.0 Hz, 1 H) 7.10-7.14 (m, 2 H) 6.89-6.92 (m, 2 H) 6.82 (ddd, J = 8.2, 2.5, 0.8 Hz, 1 H) 5.78 (d, J = 9.0 Hz, 1 H) 4.92-5.01 (m, 1 H) 4.56 (s, 2 H) 3.75 (s, 3 H) 3.50 (s, 2 H) 2.84-2.90 (m, 2 H) 2.68 (d, J = 4.7 Hz, 3 H) 2.15 (td, J = 11.7, 1.5 Hz, 2 H) 1.95-2.03 (m, 2 H) 1.64-1.75 (m, 2 H). | A |
| 63 | 519 | 13.11 (br. s., 1 H) 8.04 (d, J = 9.16 Hz, 2 H) 7.91 (s, 1 H) 7.30-7.39 (m, 4 H) 7.25 (q, 1 H) 7.07 (d, J = 8.85 Hz, 2 H) 5.77 (d, J = 8.85 Hz, 1 H) 4.92-5.01 (m, 1 H) 4.91 (s, 2 H) 3.52 (s, 2 H) 3.02 (s, 3 H) 2.88-2.92 (m, 2 H) 2.87 (s, 3 H) 2.15 (td, J = 12.05, 2.44 Hz, 2 H) 1.99 (d, J = 12.82 Hz, 2 H) 1.68 (qd, J = 11.80, 3.66 Hz, 2H). | A |
| 64 | 505 | 13.13 (br. s., 1 H) 8.03 (d, J = 9.16 Hz, 2 H) 7.92 (s, 1 H) 7.32-7.37 (m, 2 H) 7.30 (t, J = 7.63 Hz, 2 H) 7.23 (t, 1 H) 7.06 (d, J = 8.85 Hz, 2 H) 5.83 (d, J = 8.55 Hz, 1 H) 5.44-5.58 (m, 1 H) 4.90 (s, 2 H) 3.61 (q, 2 H) 3.02 (s, 3 H) 2.90 (dd, 1 H) 2.86 (s, 3 H) 2.69-2.79 (m, 1 H) 2.53-2.59 (m, 1 H) 2.50-2.53 (m, 1 H) 2.26-2.41 (m, 1 H) 1.76-1.91 (m, 1 H). | A |
| 65 | 563 | 13.09 (br. s., 1 H) 8.04-8.10 (m, 3 H) 7.91 (s, 1 H) 7.10-7.14 (m, 2 H) 6.81 (d, J = 1.9 Hz, 1 H) 6.80 (d, J = 8.2 Hz, 1 H) 6.77 (dd, J = 8.2, 1.9 Hz, 1 H) 5.77 (d, J = 8.9 Hz, 1 H) 4.91-5.00 (m, 1 H) 4.56 (s, 2 H) 4.19-4.25 (m, 4 H) 3.39 (s, 2 H) 2.82-2.88 (m, 2 H) 2.68 (d, J = 4.6 Hz, 3 H) 2.07-2.15 (m, 2 H) 1.94-2.01 (m, 2 H) 1.62-1.71 (m, 2 H). | A |
| 66 | 511 | 13.09 (br. s., 1 H) 8.07 (d, J = 8.9 Hz, 2 H) 8.06 (br. s., 1 H) 7.90 (s, 1 H) 7.11 (d, J = 8.9 Hz, 2 H) 5.73 (d, J = 7.9 Hz, 1 H) 4.88-4.99 (m, 1 H) 4.55 (s, 2 H) 2.67 (d, J = 4.6 Hz, 3 H) 2.12 (t, J = 7.3 Hz, 2 H) 2.04 (t, J = 10.8 Hz, 2 H) 1.98 (d, J = 11.0 Hz, 2 H) 1.75 (d, J = 11.6 Hz, 2 H) 1.60-1.70 (m, 5 H) 1.44-1.56 (m, 1 H) 1.09-1.27 (m, 3 H) 0.84 (qd, J = 11.4, 1.7 Hz, 2 H). | A |
| 67 | 485 | 13.06 (br. s., 1 H) 8.08 (br. s., 1 H) 8.08 (d, J = 8.8 Hz, 2 H) 7.91 (s, 1 H) 7.12 (d, J = 9.2 Hz, 2 H) 5.75 (d, J = 8.9 Hz, 1 H) 4.89-5.00 (m, 1 H) 4.55 (s, 2 H) 2.83 (d, J = 11.6 Hz, 2 H) 2.67 (d, J = 4.9 Hz, 3 H) 2.42 (td, J = 11.6, 1.8 Hz, 2 H) 2.11 (s, 2 H) 1.93 (d, J = 10.7 Hz, 2 H) 1.71 (qd, J = 11.6, 3.5 Hz, 2 H) 0.87 (s, 9 H). | A |
| 68 | 521 | 13.12 (s, 1 H) 9.30 (s, 1 H) 8.08 (br. s., 1 H) 8.07 (d, J = 8.9 Hz, 2 H) 7.91 (s, 1 H) 7.12 (d, J = 9.2 Hz, 2 H) 7.11 (t, J = 7.9 Hz, 1 H) 6.76 (s, 1 H) 6.74 (d, J = 7.6 Hz, 1 H) 6.64 (dd, J = 7.9, 1.5 Hz, 1 H) 5.78 (d, J = 8.9 Hz, 1 H) 4.90-5.01 (m, 1 H) 4.56 (s, 2 H) 3.43 (br. s., 2 H) 2.86 (d, J = 10.7 Hz, 2 H) 2.68 (d, J = 4.6 Hz, 3 H) 2.13 (t, J = 11.3 Hz, 2 H) 1.98 (d, J = 10.4 Hz, 2 H) 1.67 (qd, J = 10.8, 2.0 Hz, 2 H). | A |
| 69 | 571 | $^1$H NMR (600 MHz, CD$_3$OD) δ ppm 8.07 (d, J = 9.2 Hz, 2 H) 7.90 (s, 1 H) 7.46 (d, J = 8.5 Hz, 2 H) 7.17 (d, J = 8.2 Hz, 2 H) 7.15 (d, J = 9.2 Hz, 2 H) 6.84 (t, J = 73.9 Hz, 1 H) 5.12 (br. s., 1 H) 4.61 (s, 2 H) 3.78 (br. s., 2 H) 3.11 (br. s., 2 H) 2.85 (s, 3 H) 2.54 (br. s., 2 H) 2.24 (d, J = 11.6 Hz, 2 H) 1.69-1.82 (m, 2 H). | |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| 70 | 549 | 8.08 (br. s., 1 H) 8.07 (d, J = 9.2 Hz, 2 H) 7.91 (s, 1 H) 7.12 (d, J = 8.9 Hz, 2 H) 7.07-7.11 (m, 2 H) 6.87 (d, J = 7.9 Hz, 1 H) 5.76 (d, J = 9.2 Hz, 1 H) 4.91-5.00 (m, 1 H) 4.56 (s, 2 H) 3.76 (s, 3 H) 3.40 (s, 2 H) 2.85 (d, J = 11.9 Hz, 2 H) 2.68 (d, J = 4.6 Hz, 3 H) 2.14 (s, 3 H) 2.10 (td, J = 11.6, 1.5 Hz, 2 H) 1.97 (d, J = 10.1 Hz, 2 H) 1.66 (qd, J = 11.7, 3.4 Hz, 2 H). | A |
| 71 | 506 | 13.09 (br. s., 1 H) 8.52-8.54 (m, 2 H) 8.05-8.10 (m, 3 H) 7.91 (s, 1 H) 7.34-7.37 (m, 2 H) 7.10-7.13 (m, 2 H) 5.79 (d, J = 8.9 Hz, 1 H) 4.93-5.02 (m, 1 H) 4.56 (s, 2 H) 3.57 (s, 2 H) 2.83-2.89 (m, 2 H) 2.68 (d, J = 4.6 Hz, 3 H) 2.17-2.24 (m, 2 H) 1.97-2.03 (m, 2 H) 1.72 (qd, J = 11.8, 3.5 Hz, 2 H). | A |
| 72 | 506 | 13.11 (br. s., 1 H) 8.53 (dd, J = 2.2, 0.8 Hz, 1 H) 8.48 (dd, J = 4.8, 1.7 Hz, 1 H) 8.05-8.10 (m, 3 H) 7.91 (s, 1 H) 7.74 (ddd, J = 7.8, 2.2, 1.7 Hz, 1 H) 7.38 (ddd, J = 7.8, 4.8, 0.8 Hz, 1 H) 7.10-7.14 (m, 2 H) 5.78 (d, J = 9.0 Hz, 1 H) 4.93-5.01 (m, 1 H) 4.56 (s, 2 H) 3.57 (s, 2 H) 2.83-2.90 (m, 2 H) 2.68 (d, J = 4.6 Hz, 3 H) 2.15-2.22 (m, 2 H) 1.95-2.02 (m, 2 H) 1.63-1.73 (m, 2 H). | A |
| 73 | 508 | 8.05-8.10 (m, 3 H) 7.90 (s, 1 H) 7.10-7.14 (m, 2 H) 6.66 (dd, J = 2.6, 1.9 Hz, 1 H) 5.89 (dd, J = 3.4, 1.9 Hz, 1 H) 5.87 (dd, J = 3.4, 2.6 Hz, 1 H) 5.75 (d, J = 8.9 Hz, 1 H) 4.92-5.01 (m, 1 H) 4.56 (s, 2 H) 3.61 (s, 3 H) 3.43 (s, 2 H) 2.84-2.91 (m, 2 H) 2.68 (d, J = 4.6 Hz, 3 H) 2.05-2.13 (m, 2 H) 1.94-2.01 (m, 2 H) 1.63 (qd, J = 11.7, 3.6 Hz, 2 H). | A |
| 74 | 520 | 13.10 (br. s., 1 H) 8.05-8.10 (m, 3 H) 7.91 (s, 1 H) 7.66 (t, J = 7.6 Hz, 1 H) 7.26 (d, J = 7.6 Hz, 1 H) 7.11-7.14 (m, 2 H) 7.12 (d, J = 7.6 Hz, 1 H) 5.79 (d, J = 8.9 Hz, 1 H) 4.93-5.01 (m, 1 H) 4.56 (s, 2 H) 3.60 (s, 2 H) 2.86-2.93 (m, 2 H) 2.68 (d, J = 4.7 Hz, 3 H) 2.45 (s, 3 H) 2.20-2.28 (m, 2 H) 1.96-2.03 (m, 2 H) 1.66-1.76 (m, 2 H). | A |
| 75 | 562 | 9.91 (br. s., 1 H) 8.09 (br. s., 1 H) 8.07 (d, J = 8.9 Hz, 2 H) 7.91 (s, 1 H) 7.53 (d, J = 7.9 Hz, 2 H) 7.24 (d, J = 7.3 Hz, 2 H) 7.12 (d, J = 8.9 Hz, 2 H) 5.79 (d, J = 6.7 Hz, 1 H) 4.89-5.03 (m, 1 H) 4.56 (s, 2 H) 3.46 (br. s., 2 H) 2.80-2.94 (m, 2 H) 2.68 (d, J = 4.6 Hz, 3 H) 2.13 (br. s., 2 H) 2.03 (s, 3 H) 1.98 (d, J = 9.5 Hz, 2 H) 1.59-1.75 (m, 2 H). | A |
| 76 | 512 | 13.13 (s, 1 H) 8.09-8.10 (m, 1 H) 8.08 (d, J = 8.9 Hz, 2 H) 7.91 (s, 1 H) 7.73 (d, J = 2.7 Hz, 1 H) 7.67 (d, J = 2.7 Hz, 1 H) 7.12 (d, J = 8.9 Hz, 2 H) 5.87 (d, J = 9.2 Hz, 1 H) 4.94-5.04 (m, 1 H) 4.56 (s, 2 H) 3.90 (br. s., 2 H) 2.98 (d, J = 11.0 Hz, 2 H) 2.67 (d, J = 4.6 Hz, 3 H) 2.35 (t, J = 11.6 Hz, 2 H) 2.01 (d, J = 11.3 Hz, 2 H) 1.74 (qd, J = 12.1, 2.3 Hz, 2 H). | A |
| 77 | 549 | 13.09 (br. s., 1 H) 8.08 (br. s., 1 H) 8.07 (d, J = 8.9 Hz, 2 H) 7.91 (s, 1 H) 7.22 (d, J = 8.5 Hz, 2 H) 7.12 (d, J = 8.9 Hz, 2 H) 6.87 (d, J = 8.5 Hz, 2 H) 5.76 (d, J = 9.2 Hz, 1 H) 4.90-5.01 (m, 1 H) 4.56 (s, 2 H) 4.00 (q, J = 7.0 Hz, 2 H) 3.44 (s, 2 H) 2.85 (d, J = 11.3 Hz, 1 H) 2.68 (d, J = 4.6 Hz, 3 H) 2.11 (td, J = 11.6, 1.5 Hz, 2 H) 1.97 (d, J = 10.1 Hz, 2 H) 1.66 (qd, J = 11.6, 3.7 Hz, 2 H) 1.31 (t, J = 7.0 Hz, 3 H). | A |
| 78 | 563 | 13.12 (br. s., 1 H) 8.08 (br. s., 1 H) 8.07 (d, J = 8.9 Hz, 2 H) 7.91 (s, 1 H) 7.21 (d, J = 8.5 Hz, 2 H) 7.12 (d, J = 9.2 Hz, 2 H) 6.86 (d, J = 8.9 Hz, 2 H) 5.77 (d, J = 8.9 Hz, 1 H) 4.89-5.02 (m, 1 H) 4.56 (s, 2 H) 4.57 (spt, J = 6.1 Hz, 1 H) 3.43 (s, 2 H) 2.86 (d, J = 11.3 Hz, 2 H) 2.68 (d, J = 4.6 Hz, 3 H) 2.12 (t, J = 11.6 Hz, 2 H) 1.98 (d, J = 11.6 Hz, 2 H) 1.66 (qd, J = 11.4, 2.9 Hz, 2 H) 1.25 (d, J = 6.1 Hz, 6 H). | A |
| 79 | 519 | 13.04 (br. s., 1 H) 8.04-8.10 (m, 3 H) 7.88 (s, 1 H) 7.27-7.31 (m, 1 H) 7.24-7.27 (m, 2 H) 7.19-7.24 (m, 1 H) 7.09-7.12 (m, 2 H) 6.45 (t, J = 6.3 Hz, 1 H) 4.54 (s, 2 H) 3.98 (t, J = 6.5 Hz, 2 H) 3.40 (s, 2 H) 2.76-2.81 (m, 2 H) 2.67 (d, J = 4.7 Hz, 3 H) 1.81-1.89 (m, 2 H) 1.71-1.78 (m, 1 H) 1.68-1.75 (m, 2 H) 1.21-1.32 (m, 2 H). | A |
| 80 | 563 | 13.12 (br. s., 1 H) 8.08 (br. s., 1 H) 8.07 (d, J = 8.9 Hz, 2 H) 7.91 (s, 1 H) 7.12 (d, J = 8.9 Hz, 2 H) 6.97 (s, 2 H) 5.77 (d, J = 8.9 Hz, 1 H) 4.88-5.03 (m, 1 H) 4.56 (s, 2 H) 3.63 (s, 3 H) 3.38 (br. s., 2 H) 2.85 (d, J = 10.4 Hz, 2 H) 2.68 (d, J = 4.9 Hz, 3 H) 2.21 (s, 6 H) 2.12 (t, J = 11.4 Hz, 2 H) 1.98 (d, J = 10.7 Hz, 2 H) 1.67 (qd, J = 11.6, 3.8 Hz, 2 H). | A |
| 81 | 539 | 13.10 (br. s., 1 H) 8.07 (d, J = 8.9 Hz, 2 H) 8.08 (br. s., 1 H) 7.91 (s, 1 H) 7.40 (d, J = 8.5 Hz, 2 H) 7.36 (d, J = 8.5 Hz, 2 H) 7.12 (d, J = 9.2 Hz, 2 H) 5.78 (d, J = 8.9 Hz, 1 H) 4.91-5.02 (m, 1 H) 4.56 (s, 2 H) 3.52 (s, 2 H) 2.85 (d, J = 11.6 Hz, 2 H) 2.68 (d, J = 4.9 Hz, 3 H) 2.16 (t, J = 10.8 Hz, 2 H) 1.98 (d, J = 10.1 Hz, 2 H) 1.68 (qd, J = 11.7, 3.5 Hz, 2 H). | A |
| 82 | 519 | 13.10 (br. s., 1 H) 8.07 (d, J = 8.9 Hz, 2 H) 8.08 (br. s., 1 H) 7.91 (s, 1 H) 7.21 (d, J = 7.9 Hz, 2 H) 7.14 (d, J = 7.9 Hz, 2 H) 7.12 (d, J = 8.9 Hz, 2 H) 5.76 (d, J = 8.9 Hz, 1 H) 4.90-5.01 (m, 1 H) 4.56 (s, 2 H) 3.47 (s, 2 H) 2.85 (d, J = 11.6 Hz, 2 H) 2.68 (d, J = 4.9 Hz, 3 H) 2.29 (s, 3 H) 2.13 (t, J = 10.8 Hz, 2 H) 1.97 (d, J = 10.7 Hz, 2 H) 1.66 (qd, J = 11.6, 3.1 Hz, 2 H). | A |
| 83 | 530 | 13.12 (br. s., 1 H) 8.03-8.10 (m, 3 H) 7.91 (s, 1 H) 7.79-7.84 (m, 2 H) 7.53-7.57 (m, 2 H) 7.09-7.14 (m, 2 H) 5.79 (d, J = 8.9 Hz, 1 H) 4.93-5.02 (m, 1 H) 4.56 (s, 2 H) 3.62 (s, 2 H) 2.82-2.89 (m, 2 H) 2.68 (d, J = 4.7 Hz, 3 H) 2.17-2.24 (m, 2 H) 1.96-2.03 (m, 2 H) 1.70 (qd, J = 11.6, 3.6 Hz, 2 H). | A |
| 84 | 530 | 13.12 (br. s., 1 H) 8.04-8.10 (m, 3 H) 7.91 (s, 1 H) 7.78 (t, J = 1.6 Hz, 1 H) 7.74 (ddd, J = 7.7, 1.6, 1.2 Hz, 1 H) 7.69 (ddd, J = 7.7, 1.6, 1.2 Hz, 1 H) 7.57 (t, J = 7.7 Hz, 1 H) 7.10-7.14 (m, 2 H) 5.79 (d, J = 8.7 Hz, 1 H) 4.93-5.01 (m, 1 H) 4.56 (s, 2 H) 3.60 (s, 2 H) 2.83-2.89 (m, 2 H) 2.68 (d, J = 4.6 Hz, 3 H) 2.16-2.23 (m, 2 H) 1.96-2.02 (m, 2 H) 1.66-1.75 (m, 2 H). | C |
| 85 | 521 | 13.12 (s, 1 H) 9.25 (s, 1 H) 8.05-8.10 (m, 3 H) 7.91 (s, 1 H) 7.10-7.14 (m, 2 H) 7.09-7.12 (m, 2 H) 6.69-6.74 (m, 2 H) 5.76 (d, J = 9.0 Hz, 1 H) 4.90-4.99 (m, | A |

TABLE 2-continued

| Ex. | MS (ESI)+ m/z [M + H]+ | 1H NMR (600 MHz, DMSO-d6) δ ppm (unless otherwise stated) | GP |
|---|---|---|---|
|  |  | 1 H) 4.56 (s, 2 H) 3.39 (s, 2 H) 2.81-2.89 (m, 2 H) 2.68 (d, J = 4.6 Hz, 3 H) 2.05-2.14 (m, 2 H) 1.93-2.01 (m, 2 H) 1.60-1.70 (m, 2 H). |  |
| 86 | 415 | 8.07-8.11 (m, 2 H) 8.07 (q, J = 4.7 Hz, 1 H) 7.91 (s, 1 H) 7.08-7.13 (m, 2 H) 5.71 (d, J = 8.4 Hz, 1 H) 4.96-5.05 (m, 1 H) 4.55 (s, 2 H) 2.97-3.04 (m, 2 H) 2.67 (d, J = 4.7 Hz, 3 H) 2.63 (td, J = 12.0, 2.0 Hz, 2 H) 1.91-1.99 (m, 2 H) 1.47 (qd, J = 11.6, 3.9 Hz, 2 H). | A |
| 87 | 523 | 13.12 (br. s., 1 H) 8.04-8.10 (m, 3 H) 7.34-7.39 (m, 2 H) 7.13-7.18 (m, 2 H) 7.10-7.14 (m, 2 H) 5.77 (d, J = 8.7 Hz, 1 H) 4.92-5.01 (m, 1 H) 4.56 (s, 2 H) 3.51 (s, 2 H) 2.82-2.89 (m, 2 H) 2.68 (d, J = 4.6 Hz, 3 H) 2.15 (td, J = 11.8, 2.0 Hz, 2 H) 1.95-2.02 (m, 2 H) 1.67 (qd, J = 11.8, 3.7 Hz, 2 H). | A |
| 88 | 541 | 13.11 (br. s., 1 H) 8.04-8.10 (m, 3 H) 7.91 (s, 1 H) 7.39 (dt, J = 10.8, 8.4 Hz, 1 H) 7.37 (ddd, J = 11.8, 8.0, 2.0 Hz, 1 H) 7.16-7.21 (m, 2 H) 7.09-7.13 (m, 2 H) 5.78 (d, J = 8.9 Hz, 1 H) 4.93-5.01 (m, 1 H) 4.56 (s, 2 H) 3.52 (s, 2 H) 2.83-2.88 (m, 2 H) 2.68 (d, J = 4.6 Hz, 3 H) 2.18 (td, J = 11.6, 2.0 Hz, 2 H) 1.96-2.02 (m, 2 H) 1.69 (qd, J = 11.6, 3.7 Hz, 2 H). | A |
| 89 | 548 | 13.12 (s, 1 H) 8.04-8.10 (m, 3 H) 7.91 (s, 1 H) 7.12-7.15 (m, 2 H) 7.10-7.14 (m, 2 H) 6.67-6.72 (m, 2 H) 5.77 (d, J = 8.2 Hz, 1 H) 4.91-4.99 (m, 1 H) 4.56 (s, 2 H) 3.40 (br. s., 2 H) 2.87 (s, 6 H) 2.82-2.92 (m, 2 H) 2.68 (d, J = 4.7 Hz, 3 H) 2.02-2.20 (m, 2 H) 1.93-2.03 (m, 2 H) 1.60-1.71 (m, 2 H). | A |
| 90 | 583 | 13.10 (br. s., 1 H) 8.07 (br. s., 1 H) 8.07 (d, J = 8.9 Hz, 2 H) 7.91 (s, 1 H) 7.90 (d, J = 8.2 Hz, 2 H) 7.62 (d, J = 8.5 Hz, 2 H) 7.12 (d, J = 8.9 Hz, 2 H) 5.80 (d, J = 8.9 Hz, 1 H) 4.94-5.02 (m, 1 H) 4.56 (s, 2 H) 3.64 (s, 2 H) 3.20 (s, 3 H) 2.87 (d, J = 11.9 Hz, 2 H) 2.68 (d, J = 4.6 Hz, 3 H) 2.21 (t, J = 11.6 Hz, 2 H) 2.00 (d, J = 8.9 Hz, 2 H) 1.71 (qd, J = 11.7, 3.7 Hz, 2 H). | A |
| 91 | 547 | 13.12 (s, 1 H) 8.07 (br. s., 1 H) 8.07 (d, J = 8.9 Hz, 2 H) 7.91 (s, 1 H) 7.18 (s, 1 H) 7.12 (d, J = 9.2 Hz, 2 H) 7.02 (d, J = 7.9 Hz, 1 H) 6.70 (d, J = 8.2 Hz, 1 H) 5.76 (d, J = 8.9 Hz, 1 H) 4.89-5.01 (m, 1 H) 4.56 (s, 2 H) 4.50 (t, J = 8.7 Hz, 2 H) 3.42 (br. s., 2 H) 3.16 (t, J = 8.9 Hz, 2 H) 2.86 (d, J = 10.7 Hz, 2 H) 2.68 (d, J = 4.6 Hz, 3 H) 2.11 (t, J = 11.7 Hz, 2 H) 1.98 (d, J = 11.3 Hz, 2 H) 1.66 (qd, J = 11.4, 3.1 Hz, 2 H). | A |
| 92 | 429 | 13.08 (br. s., 1 H) 8.08 (d, J = 8.8 Hz, 2 H) 8.06 (br. s., 1 H) 7.91 (s, 1 H) 7.12 (d, J = 8.9 Hz, 2 H) 5.76 (d, J = 8.9 Hz, 1 H) 4.85-4.97 (m, 1 H) 4.55 (s, 2 H) 2.81 (d, J = 11.6 Hz, 2 H) 2.67 (d, J = 4.9 Hz, 3 H) 2.21 (s, 3 H) 2.07 (td, J = 11.6, 2.7 Hz, 2 H) 1.94-2.01 (m, 2 H) 1.68 (qd, J = 11.7, 3.7 Hz, 2 H). | A |
| 93 | 511 | 13.07 (br. s., 1 H) 8.08 (br. s., 1 H) 8.07 (d, J = 8.9 Hz, 2 H) 7.91 (s, 1 H) 7.44 (dd, J = 4.6, 1.8 Hz, 1 H) 7.11 (d, J = 8.9 Hz, 2 H) 6.99 (s, 1 H) 6.98 (t, J = 3.1 Hz, 1 H) 5.82 (d, J = 8.9 Hz, 1 H) 4.90-5.03 (m, 1 H) 4.56 (s, 2 H) 3.74 (s, 2 H) 2.93 (d, J = 11.6 Hz, 2 H) 2.68 (d, J = 4.9 Hz, 3 H) 2.19 (t, J = 10.8 Hz, 2 H) 1.98 (d, J = 11.0 Hz, 2 H) 1.69 (qd, J = 11.6, 3.8 Hz, 2 H). | A |
| 94 | 519 | 13.09 (br. s., 1 H) 8.08 (d, J = 8.9 Hz, 2 H) 8.06 (br. s., 1 H) 7.91 (s, 1 H) 7.24-7.31 (m, 4 H) 7.16-7.21 (m, 1 H) 7.12 (d, J = 8.9 Hz, 2 H) 5.78 (d, J = 8.9 Hz, 1 H) 4.90-5.01 (m, 1 H) 4.55 (s, 2 H) 3.00 (d, J = 11.6 Hz, 2 H) 2.77 (t, J = 8.2 Hz, 2 H) 2.67 (d, J = 4.6 Hz, 3 H) 2.57 (t, J = 8.2 Hz, 2 H) 2.16 (t, J = 10.7 Hz, 2 H) 2.00 (d, J = 10.1 Hz, 2 H) 1.67 (qd, J = 11.6, 3.5 Hz, 2 H). | A |
| 95 | 549 | 13.11 (br. s., 1 H) 8.08 (d, J = 8.9 Hz, 2 H) 8.06 (br. s., 1 H) 7.91 (s, 1 H) 7.16 (d, J = 8.5 Hz, 2 H) 7.12 (d, J = 9.2 Hz, 2 H) 6.84 (d, J = 8.9 Hz, 2 H) 5.78 (d, J = 8.9 Hz, 1 H) 4.90-5.00 (m, 1 H) 4.55 (s, 2 H) 3.72 (s, 3 H) 2.99 (d, J = 11.6 Hz, 2 H) 2.70 (t, J = 8.2 Hz, 2 H) 2.67 (d, J = 4.6 Hz, 3 H) 2.52 (t, J = 8.2 Hz, 2 H) 2.15 (t, J = 11.0 Hz, 2 H) 2.00 (d, J = 11.6 Hz, 2 H) 1.67 (qd, J = 11.7, 3.5 Hz, 2 H). | A |
| 96 | 535 | 13.10 (br. s., 1 H) 8.08 (d, J = 8.8 Hz, 2 H) 8.07 (br. s., 1 H) 7.91 (s, 1 H) 7.29 (d, J = 7.3 Hz, 1 H) 7.28 (d, J = 7.3 Hz, 1 H) 7.11 (d, J = 9.2 Hz, 2 H) 6.96 (d, J = 7.9 Hz, 2 H) 6.93 (t, J = 7.3 Hz, 1 H) 5.79 (d, J = 8.9 Hz, 1 H) 4.90-5.00 (m, 1 H) 4.55 (s, 2 H) 4.10 (t, J = 5.8 Hz, 2 H) 3.01 (d, J = 11.9 Hz, 2 H) 2.76 (t, J = 6.0 Hz, 2 H) 2.67 (d, J = 4.6 Hz, 3 H) 2.26 (td, J = 11.7, 1.7 Hz, 2 H) 2.00 (d, J = 10.4 Hz, 2 H) 1.69 (qd, J = 11.6, 3.5 Hz, 2 H). | A |
| 97 | 565 | 13.06 (br. s., 1 H) 8.04-8.10 (m, 3 H) 7.91 (s, 1 H) 7.10-7.14 (m, 2 H) 6.92 (d, J = 1.9 Hz, 1 H) 6.90 (d, J = 8.2 Hz, 1 H) 6.83 (dd, J = 8.2, 1.9 Hz, 1 H) 5.78 (d, J = 9.0 Hz, 1 H) 4.92-5.01 (m, 1 H) 4.56 (s, 2 H) 3.75 (s, 3 H) 3.73 (s, 3 H) 3.45 (s, 2 H) 2.83-2.91 (m, 2 H) 2.68 (d, J = 4.6 Hz, 3 H) 2.09-2.17 (m, 2 H) 1.95-2.01 (m, 2 H) 1.64-1.74 (m, 2 H). | A |
| 98 | 551 | 13.10 (br. s., 1 H) 8.80 (s, 1 H) 8.05-8.10 (m, 3 H) 7.91 (s, 1 H) 7.10-7.14 (m, 2 H) 6.87 (d, J = 1.6 Hz, 1 H) 6.72 (d, J = 7.9 Hz, 1 H) 6.70 (dd, J = 7.9, 1.6 Hz, 1 H) 5.77 (d, J = 7.9 Hz, 1 H) 4.92-5.01 (m, 1 H) 4.56 (s, 2 H) 3.76 (s, 3 H) 3.41 (s, 2 H) 2.84-2.89 (m, 2 H) 2.68 (d, J = 4.7 Hz, 3 H) 2.08-2.14 (m, 2 H) 1.94-2.01 (m, 2 H) 1.62-1.72 (m, 2 H). | A |
| 99 | 572 | 13.10 (br. s., 1 H) 9.27 (s, 1 H) 8.23 (s, 1 H) 8.08 (br. s., 1 H) 8.07 (d, J = 8.9 Hz, 2 H) 7.91 (s, 1 H) 7.83 (d, J = 8.5 Hz, 2 H) 7.52 (d, J = 8.5 Hz, 2 H) 7.11 (d, J = 9.2 Hz, 2 H) 5.78 (d, J = 8.9 Hz, 1 H) 4.93-5.03 (m, 1 H) 4.56 (s, 2 H) 3.59 (s, 2 H) 2.89 (d, J = 11.3 Hz, 2 H) 2.68 (d, J = 4.6 Hz, 3 H) 2.19 (t, J = 11.6 Hz, 2 H) 2.00 (d, J = 9.8 Hz, 2 H) 1.70 (qd, J = 11.8, 3.8 Hz, 2 H). | A |
| 100 | 551 | 13.10 (br. s., 1 H) 8.08 (br. s., 1 H) 8.07 (d, J = 8.9 Hz, 2 H) 7.91 (s, 1 H) 7.27 (d, J = 8.2 Hz, 2 H) 7.23 (d, J = 8.2 Hz, 2 H) 7.12 (d, J = 8.9 Hz, 2 H) 5.77 (d, J = 8.9 Hz, 1 H) 4.91-5.01 (m, 1 H) 4.56 (s, 2 H) 3.48 (s, 2 H) 2.86 (d, J = 11.3 Hz, 2 H) 2.68 (d, J = 4.9 Hz, 3 H) 2.46 (s, 3 H) 2.14 (t, J = 10.8 Hz, 2 H) 1.98 (d, J = 11.6 Hz, 2 H) 1.67 (qd, J = 11.6, 3.2 Hz, 2 H). | B |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| 101 | 565 | 13.10 (br. s., 1 H) 8.07 (d, J = 8.9 Hz, 2 H) 8.06 (br. s., 1 H) 7.90 (s, 1 H) 7.24 (d, J = 8.5 Hz, 2 H) 7.12 (d, J = 8.9 Hz, 2 H) 6.89 (d, J = 8.5 Hz, 2 H) 5.76 (d, J = 8.9 Hz, 1 H) 4.91-5.01 (m, 1 H) 4.74 (t, J = 5.5 Hz, 1 H) 4.58 (s, 2 H) 3.74 (s, 3 H) 3.45 (q, J = 6.1 Hz, 2 H) 3.44 (s, 2 H) 3.23 (q, J = 6.1 Hz, 2 H) 2.85 (d, J = 11.6 Hz, 2 H) 2.12 (t, J = 11.6 Hz, 2 H) 1.97 (d, J = 9.8 Hz, 2 H) 1.66 (qd, J = 11.6, 3.7 Hz, 2 H). | B |
| 102 | 592 | 13.11 (br. s., 1 H) 8.07 (d, J = 8.9 Hz, 2 H) 8.01 (t, J = 5.6 Hz, 1 H) 7.91 (s, 1 H) 7.23 (d, J = 8.5 Hz, 2 H) 7.12 (d, J = 8.9 Hz, 2 H) 6.89 (d, J = 8.5 Hz, 2 H) 5.77 (d, J = 9.2 Hz, 1 H) 4.90-5.02 (m, 1 H) 4.57 (s, 2 H) 3.74 (s, 3 H) 3.44 (s, 2 H) 3.24 (q, J = 6.4 Hz, 2 H) 2.85 (d, J = 11.9 Hz, 2 H) 2.32 (t, J = 6.7 Hz, 2 H) 2.15 (s, 6 H) 2.11 (t, J = 10.8 Hz, 2 H) 1.97 (d, J = 10.1 Hz, 2 H) 1.66 (qd, J = 11.7, 3.7 Hz, 2 H). | B |
| 103 | 620 | 13.10 (br. s., 1 H) 8.07 (d, J = 8.9 Hz, 2 H) 7.90 (s, 1 H) 7.57 (t, J = 5.3 Hz, 1 H) 7.23 (d, J = 8.5 Hz, 2 H) 7.11 (d, J = 9.2 Hz, 2 H) 6.89 (d, J = 8.5 Hz, 2 H) 5.77 (d, J = 8.9 Hz, 1 H) 4.90-5.01 (m, 1 H) 4.65 (s, 2 H) 3.74 (s, 3 H) 3.44 (s, 2 H) 3.13 (d, J = 5.5 Hz, 2 H) 2.85 (d, J = 11.6 Hz, 2 H) 2.13 (s, 6 H) 2.10 (t, J = 11.5 Hz, 2 H) 1.97 (d, J = 10.7 Hz, 2 H) 1.66 (qd, J = 11.6, 3.1 Hz, 2 H) 0.91 (s, 6 H). | B |
| 104 | 563 | 13.09 (br. s., 1 H) 8.06 (d, J = 8.9 Hz, 2 H) 7.93 (d, J = 7.9 Hz, 1 H) 7.90 (s, 1 H) 7.23 (d, J = 8.9 Hz, 2 H) 7.11 (d, J = 9.2 Hz, 2 H) 6.89 (d, J = 8.9 Hz, 2 H) 5.76 (d, J = 8.9 Hz, 1 H) 4.89-5.02 (m, 1 H) 4.53 (s, 2 H) 3.96 (dq, J = 14.3, 6.4 Hz, 1 H) 3.74 (s, 3 H) 3.44 (s, 2 H) 2.85 (d, J = 11.6 Hz, 2 H) 2.11 (t, J = 11.0 Hz, 2 H) 1.97 (d, J = 10.7 Hz, 2 H) 1.66 (qd, J = 11.6, 3.8 Hz, 2 H) 1.11 (d, J = 6.1 Hz, 6 H). | B |
| 105 | 607 | 13.10 (br. s., 1 H) 8.08 (t, J = 5.8 Hz, 1 H) 8.07 (d, J = 8.9 Hz, 2 H) 7.90 (s, 1 H) 7.23 (d, J = 8.9 Hz, 2 H) 7.11 (d, J = 8.9 Hz, 2 H) 6.89 (d, J = 8.5 Hz, 2 H) 5.76 (d, J = 9.2 Hz, 1 H) 4.90-5.01 (m, 1 H) 4.58 (s, 2 H) 3.74 (s, 3 H) 3.53 (spt, J = 6.1 Hz, 1 H) 3.44 (s, 2 H) 3.41 (t, J = 6.0 Hz, 2 H) 3.28 (q, J = 5.8 Hz, 2 H) 2.85 (d, J = 11.3 Hz, 2 H) 2.11 (t, J = 11.0 Hz, 2 H) 1.97 (d, J = 11.6 Hz, 2 H) 1.66 (qd, J = 11.6, 3.4 Hz, 2 H) 1.07 (d, J = 6.1 Hz, 6 H). | D |
| 106 | 533 | 13.17 (br. s., 1 H) 8.02 (d, J = 8.2 Hz, 2 H) 7.92 (s, 1 H) 7.76 (q, J = 4.4 Hz, 1 H) 7.36 (d, J = 8.2 Hz, 2 H) 7.24 (d, J = 8.5 Hz, 2 H) 6.89 (d, J = 8.5 Hz, 2 H) 5.80 (d, J = 8.9 Hz, 1 H) 4.89-5.01 (m, 1 H) 3.74 (s, 3 H) 3.45 (s, 2 H) 2.88 (t, J = 7.3 Hz, 2 H) 2.85 (d, J = 11.3 Hz, 2 H) 2.56 (d, J = 4.6 Hz, 3 H) 2.41 (t, J = 7.6 Hz, 2 H) 2.11 (t, J = 10.8 Hz, 2 H) 1.98 (d, J = 10.7 Hz, 2 H) 1.66 (qd, J = 11.7, 3.7 Hz, 2 H). | D |
| 107 | 590 | 13.16 (br. s., 1 H) 8.02 (d, J = 8.5 Hz, 2 H) 7.92 (s, 1 H) 7.75 (t, J = 5.5 Hz, 1 H) 7.36 (d, J = 8.2 Hz, 2 H) 7.23 (d, J = 8.5 Hz, 2 H) 6.89 (d, J = 8.5 Hz, 2 H) 5.79 (d, J = 8.9 Hz, 1 H) 4.90-5.01 (m, 1 H) 3.74 (s, 3 H) 3.44 (s, 2 H) 3.12 (q, J = 6.4 Hz, 2 H) 2.88 (t, J = 7.5 Hz, 2 H) 2.85 (d, J = 11.3 Hz, 2 H) 2.42 (t, J = 7.6 Hz, 2 H) 2.22 (t, J = 6.7 Hz, 2 H) 2.11 (s, 6 H) 2.10 (t, J = 10.8 Hz, 2 H) 1.98 (d, J = 11.6 Hz, 2 H) 1.66 (qd, J = 11.7, 3.7 Hz, 2 H). | D |
| 108 | 549 | 10.99 (s, 1 H) 8.03 (d, J = 8.2 Hz, 2 H) 7.92 (s, 1 H) 7.36 (d, J = 8.2 Hz, 2 H) 7.24 (d, J = 8.9 Hz, 2 H) 6.89 (d, J = 8.5 Hz, 2 H) 5.81 (d, J = 8.9 Hz, 1 H) 4.89-5.03 (m, 1 H) 3.74 (s, 3 H) 3.54 (s, 3 H) 3.44 (s, 2 H) 2.89 (t, J = 7.6 Hz, 2 H) 2.85 (d, J = 11.9 Hz, 2 H) 2.30 (t, J = 7.6 Hz, 2 H) 2.11 (t, J = 11.0 Hz, 2 H) 1.97 (d, J = 10.4 Hz, 2 H) 1.66 (qd, J = 11.7, 3.7 Hz, 2 H). | A |
| 109 | 443 | 13.09 (br. s., 1 H) 8.06-8.09 (m, 2 H) 8.06 (t, J = 4.73 Hz, 1 H) 7.91 (s, 1 H) 7.10-7.14 (m, 2 H) 5.75 (d, J = 8.70 Hz, 1 H) 4.89-4.97 (m, 1 H) 4.55 (s, 2 H) 2.88-2.96 (m, 2 H) 2.67 (d, J = 4.73 Hz, 3 H) 2.36 (q, J = 7.17 Hz, 2 H) 2.05 (td, J = 11.73, 1.90 Hz, 2 H) 1.96-2.02 (m, 2H) 1.65 (qd, J = 11.73, 3.60 Hz, 2 H) 1.03 (t, J = 7.17 Hz, 3 H). | A |
| 110 | 457 | 13.10 (br. s., 1 H) 8.06-8.09 (m, 2 H) 8.06 (t, J = 4.58 Hz, 1 H) 7.91 (s, 1 H) 7.10-7.14 (m, 2 H) 5.71 (d, J = 8.85 Hz, 1 H) 4.85-4.94 (m, 1 H) 4.55 (s, 2 H) 2.82-2.88 (m, 2 H) 2.72 (spt, J = 6.56 Hz, 1 H) 2.67 (d, J = 4.58 Hz, 3 H) 2.28 (td, J = 11.50, 2.13 Hz, 2 H) 1.96-2.04 (m, 2 H) 1.61 (qd, J = 11.50, 3.82 Hz, 2 H) 1.01 (d, J = 6.56 Hz, 6 H). | C |
| 111 | 579 | 13.14 (br. s., 1 H) 8.04-8.10 (m, 3 H) 8.00 (s, 1 H) 7.22-7.26 (m, 2 H) 7.10-7.14 (m, 2 H) 6.87-6.91 (m, 2 H) 5.48 (d, J = 8.85 Hz, 1 H) 4.92-5.00 (m, 1 H) 4.56 (s, 2 H) 3.74 (s, 3 H) 3.45 (s, 2 H) 2.80-2.87 (m, 2 H) 2.68 (d, J = 4.73 Hz, 3 H) 2.10-2.18 (m, 2 H) 1.96-2.03 (m, 2 H) 1.60-1.69 (m, 2 H). | C |
| 112 | 591 | 13.13 (br. s., 1 H) 8.04-8.10 (m, 3 H) 8.00 (s, 1 H) 7.18 (br. s., 1 H) 7.10-7.14 (m, 2 H) 7.02 (dd, J = 8.08, 1.76 Hz, 1 H) 6.70 (d, J = 8.08 Hz, 1 H) 5.47 (d, J = 8.54 Hz, 1 H) 4.92-5.00 (m, 1 H) 4.56 (s, 2 H) 4.50 (t, J = 8.70 Hz, 2 H) 3.42 (s, 2 H) 3.16 (t, J = 8.70 Hz, 2 H) 2.80-2.88 (m, 2 H) 2.68 (d, J = 4.73 Hz, 3 H) 2.10-2.17 (m, 2 H) 1.96-2.02 (m, 2 H) 1.60-1.68 (m, 2 H). | C |
| 113 | 555 | 13.13 (br. s., 1 H) 8.04-8.10 (m, 3 H) 8.00 (s, 1 H) 7.44 (dd, J = 4.58, 1.68 Hz, 1 H) 7.09-7.13 (m, 2 H) 6.97-7.00 (m, 2 H) 5.53 (d, J = 8.55 Hz, 1 H) 4.94-5.02 (m, 1 H) 4.56 (s, 2 H) 3.75 (s, 2 H) 2.88-2.95 (m, 2 H) 2.68 (d, J = 4.73 Hz, 3 H) 2.17-2.24 (m, 2 H) 1.97-2.03 (m, 2 H) 1.63-1.72 (m, 2 H). | C |
| 114 | 473 | 13.14 (br. s., 1 H) 8.06-8.10 (m, 2 H) 8.07 (q, J = 4.58 Hz, 1 H) 8.01 (s, 1 H) 7.10-7.14 (m, 2 H) 5.47 (d, J = 8.70 Hz, 1 H) 4.88-4.97 (m, 1 H) 4.55 (s, 2 H) 2.75-2.83 (m, 2 H) 2.67 (d, J = 4.58 Hz, 3 H) 2.21 (s, 3 H) 2.05-2.13 (m, 2 H) 1.95-2.02 (m, 2 H) 1.61-1.71 (m, 2 H). | C |
| 115 | 565 | 13.16 (br. s., 1 H) 8.09 (q, J = 4.70 Hz, 1 H) 8.05-8.09 (m, 2 H) 8.02 (s, 1 H) 7.37 (dd, J = 7.45, 1.77 Hz, 1 H) 7.21 (ddd, J = 8.09, 7.45, 1.77 Hz, 1 H) 7.09-7.13 (m, 2 H) 6.96 (dd, J = 8.09, 1.00 Hz, 1 H) 6.90 (td, J = 7.45, 1.00 Hz, 1 H) 5.60 (d, J = 8.54 Hz, 1 H) 5.50-5.57 (m, 1 H) 4.55 (s, 2 H) 3.77 (s, 3 H) 3.65 (d, J = 13.89 Hz, 1 H) 3.62 (d, J = 13.89 Hz, 1 H) 2.88 (dd, J = 9.54, 6.22 Hz, 1 H) 2.83 (td, J = 8.60, 5.20 Hz, 1 H) 2.68 (d, J = 4.70 Hz, 3 H) 2.61 (dd, J = 9.54, 4.02 Hz, 1 | A |

TABLE 2-continued

| Ex. | MS (ESI)+ m/z [M + H]+ | 1H NMR (600 MHz, DMSO-d6) δ ppm (unless otherwise stated) | GP |
|---|---|---|---|
| | | H) 2.46-2.51 (m, 1 H) 2.36 (dddd, J = 12.80, 8.60, 5.20 Hz, 1 H) 1.80 (dddd, J = 12.80, 8.60, 6.38, 4.12 Hz, 1 H). | |
| 116 | 535 | 13.26 (br. s., 1 H) 8.06-8.11 (m, 1 H) 7.94 (s, 1 H) 7.73-7.77 (m, 2 H) 7.47 (t, J = 8.2 Hz, 1 H) 7.24 (d, J = 8.5 Hz, 2 H) 7.06-7.09 (m, 1 H) 6.88 (d, J = 8.5 Hz, 2 H) 5.86 (d, J = 8.9 Hz, 1 H) 4.91-5.02 (m, 1 H) 4.57 (s, 2 H) 3.74 (s, 3 H) 3.45 (s, 2 H) 2.86 (d, J = 11.3 Hz, 2 H) 2.69 (d, J = 4.6 Hz, 3 H) 2.13 (t, J = 10.8 Hz, 2 H) 1.98 (d, J = 10.4 Hz, 2 H) 1.67 (qd, J = 11.7, 3.4 Hz, 2 H). | A |
| 117 | 429 | 13.23 (br. s., 1 H) 8.04-8.09 (m, 1 H) 7.95 (s, 1 H) 7.74-7.78 (m, 2 H) 7.47 (t, J = 8.2 Hz, 1 H) 7.06 (ddd, J = 8.5, 2.3, 1.3 Hz, 1 H) 5.85 (d, J = 8.9 Hz, 1 H) 4.88-4.97 (m, 1 H) 4.56 (s, 2 H) 2.81 (d, J = 11.6 Hz, 2 H) 2.67 (d, J = 4.9 Hz, 3 H) 2.22 (s, 3 H) 2.08 (td, J = 11.3, 2.1 Hz, 2 H) 1.94-2.00 (m, 2 H) 1.69 (qd, J = 11.6, 3.5 Hz, 2 H). | A |
| 118 | 547 | 13.25 (br. s., 1 H) 8.05-8.12 (m, 1 H) 7.94 (s, 1 H) 7.72-7.80 (m, 2 H) 7.47 (t, J = 8.1 Hz, 1 H) 7.18 (s, 1 H) 7.05-7.11 (m, 1 H) 7.02 (d, J = 8.2 Hz, 1 H) 6.69 (d, J = 8.2 Hz, 1 H) 5.85 (d, J = 8.9 Hz, 1 H) 4.92-5.02 (m, 1 H) 4.57 (s, 2 H) 4.50 (t, J = 8.7 Hz, 2 H) 3.42 (s, 2 H) 3.16 (t, J = 8.7 Hz, 2 H) 2.87 (d, J = 11.6 Hz, 2 H) 2.69 (d, J = 4.6 Hz, 3 H) 2.13 (t, J = 10.8 Hz, 2 H) 1.98 (d, J = 9.5 Hz, 2 H) 1.67 (qd, J = 11.4, 3.2 Hz, 2 H). | A |
| 119 | 511 | 13.27 (br. s., 1 H) 8.05-8.11 (m, 1 H) 7.95 (s, 1 H) 7.73-7.77 (m, 2 H) 7.47 (t, J = 8.2 Hz, 1 H) 7.43 (dd, J = 4.9, 1.2 Hz, 1 H) 7.07 (ddd, J = 8.2, 2.4, 0.9 Hz, 1 H) 6.99 (dd, J = 3.4, 0.9 Hz, 1 H) 6.97 (dd, J = 4.9, 3.4 Hz, 1 H) 5.91 (d, J = 8.9 Hz, 1 H) 4.94-5.03 (m, 1 H) 4.57 (s, 2 H) 3.74 (s, 2 H) 2.94 (d, J = 11.3 Hz, 2 H) 2.69 (d, J = 4.6 Hz, 3 H) 2.20 (t, J = 10.8 Hz, 2 H) 1.99 (d, J = 10.7 Hz, 2 H) 1.70 (qd, J = 11.7, 3.5 Hz, 2 H). | A |
| 120 | 549 | 13.24 (br. s., 1 H) 8.05-8.11 (m, 1 H) 7.95 (s, 1 H) 7.74-7.78 (m, 2 H) 7.47 (t, J = 8.2 Hz, 1 H) 7.06-7.09 (m, 1 H) 6.89 (d, J = 1.2 Hz, 1 H) 6.85 (d, J = 7.9 Hz, 1 H) 6.79 (dd, J = 7.9, 1.5 Hz, 1 H) 5.99 (s, 2 H) 5.87 (d, J = 8.9 Hz, 1 H) 4.93-5.02 (m, 1 H) 4.57 (s, 2 H) 3.43 (s, 2 H) 2.86 (d, J = 11.0 Hz, 2 H) 2.69 (d, J = 4.6 Hz, 3 H) 2.14 (t, J = 10.8 Hz, 2 H) 1.98 (d, J = 10.1 Hz, 2 H) 1.68 (qd, J = 11.6, 3.5 Hz, 2 H). | A |
| 121 | 535 | 13.25 (br. s., 1 H) 8.03-8.09 (m, 1 H) 7.95 (s, 1 H) 7.75-7.78 (m, 2 H) 7.46 (t, J = 8.1 Hz, 1 H) 7.28 (dd, J = 8.8, 7.3 Hz, 2 H) 7.06 (dd, J = 7.6, 2.1 Hz, 1 H) 6.96 (d, J = 7.6 Hz, 2 H) 6.90-6.94 (m, 1 H) 5.87 (d, J = 8.2 Hz, 1 H) 4.89-5.02 (m, 1 H) 4.56 (s, 2 H) 4.10 (t, J = 6.0 Hz, 2 H) 3.02 (d, J = 11.9 Hz, 2 H) 2.77 (t, J = 6.0 Hz, 2 H) 2.67 (d, J = 4.6 Hz, 3 H) 2.27 (t, J = 10.8 Hz, 2 H) 2.00 (d, J = 10.4 Hz, 2 H) 1.70 (qd, J = 11.7, 3.4 Hz, 2 H). | A |
| 122 | 521 | 13.25 (br. s., 1 H) 8.06-8.13 (m, 1 H) 7.96 (s, 1 H) 7.73-7.78 (m, 2 H) 7.46 (t, J = 8.2 Hz, 1 H) 7.36 (dd, J = 7.6, 1.5 Hz, 1 H) 7.20 (td, J = 7.8, 1.5 Hz, 1 H) 7.05-7.09 (m, 1 H) 6.95 (d, J = 7.6 Hz, 1 H) 6.89 (td, J = 7.3, 0.9 Hz, 1 H) 5.89 (d, J = 8.2 Hz, 1 H) 5.49-5.57 (m, 1 H) 4.56 (s, 2 H) 3.76 (s, 3 H) 3.64 (s, 2 H) 2.91 (dd, J = 9.5, 6.7 Hz, 1 H) 2.81 (td, J = 8.5, 5.2 Hz, 1 H) 2.68 (d, J = 4.9 Hz, 3 H) 2.62 (dd, J = 9.5, 4.3 Hz, 1 H) 2.51-2.54 (m, 1 H) 2.35 (dddd, J = 13.4, 8.4, 8.2, 5.2 Hz, 1 H) 1.79-1.91 (m, 1 H). | A |
| 23 | 491 | 13.25 (br. s., 1 H) 8.06-8.15 (m, 1 H) 7.96 (s, 1 H) 7.72-7.79 (m, 2 H) 7.46 (t, J = 8.1 Hz, 1 H) 7.34 (d, J = 7.0 Hz, 2 H) 7.30 (t, J = 7.6 Hz, 2 H) 7.22 (t, J = 7.3 Hz, 1 H) 7.07 (ddd, J = 7.8, 2.0, 0.6 Hz, 1 H) 5.89 (d, J = 8.2 Hz, 1 H) 5.49-5.57 (m, 1 H) 4.56 (s, 2 H) 3.64 (dd, J = 23.2, 13.1 Hz, 2 H) 2.89 (dd, J = 9.5, 6.4 Hz, 1 H) 2.77 (td, J = 8.6, 5.3 Hz, 1 H) 2.68 (d, J = 4.9 Hz, 3 H) 2.59 (dd, J = 9.5, 4.3 Hz, 1 H) 2.47-2.53 (m, 1 H) 2.36 (dddd, J = 13.4, 8.5, 8.2, 5.3 Hz, 1 H) 1.83-1.90 (m, 1 H). | A |
| 124 | 499 | 13.10 (br. s., 1 H) 8.04-8.10 (m, 3 H) 7.91 (s, 1 H) 7.10-7.14 (m, 2 H) 5.75 (d, J = 8.85 Hz, 1 H) 4.89-4.97 (m, 1 H) 4.55 (s, 2 H) 2.86-2.94 (m, 2 H) 2.67 (d, J = 4.73 Hz, 3 H) 2.27-2.33 (m, 2 H) 2.01-2.09 (m, 2 H) 1.95-2.01 (m, 2 H) 1.61-1.70 (m, 2 H) 1.40-1.47 (m, 2 H) 1.21-1.35 (m, 6 H) 0.84-0.90 (m, 3 H). | A |
| 125 | 471 | 13.11 (br. s., 1 H) 8.03-8.10 (m, 3 H) 7.91 (s, 1 H) 7.09-7.14 (m, 2H) 5.76 (d, J = 9.00 Hz, 1 H) 4.89-4.98 (m, 1 H) 4.55 (s, 2 H) 2.83-2.90 (m, 2 H) 2.67 (d, J = 4.73 Hz, 3 H) 2.08 (d, J = 7.32 Hz, 2 H) 2.02-2.08 (m, 2 H) 1.95-2.02 (m, 2 H) 1.73-1.82 (m, 1 H) 1.63-1.72 (m, 2 H) 0.88 (d, J = 6.56 Hz, 6 H). | C |
| 126 | 457 | 13.09 (br. s., 1 H) 8.04-8.10 (m, 3 H) 7.91 (s, 1 H) 7.09-7.14 (m, 2 H) 5.74 (d, J = 8.39 Hz, 1 H) 4.88-4.98 (m, 1 H) 4.55 (s, 2 H) 2.86-2.94 (m, 2 H) 2.67 (d, J = 4.58 Hz, 3 H) 2.24-2.30 (m, 2 H) 2.03-2.10 (m, 2 H) 1.95-2.02 (m, 2 H) 1.61-1.70 (m, 2 H) 1.42-1.50 (m, 2 H) 0.87 (t, J = 7.32 Hz, 3 H). | A |
| 127 | 485 | 13.12 (br. s., 1 H) 8.08 (d, J = 8.54 Hz, 2 H) 8.06 (br. s., 1 H) 7.91 (s, 1 H) 7.09 (d, J = 8.85 Hz, 2 H) 5.65 (d, J = 9.46 Hz, 1 H) 5.50-5.60 (m, 1 H) 4.55 (s, 2 H) 2.66 (d, J = 4.58 Hz, 3 H) 2.22 (s, 3 H) 1.84 (dd, J = 12.05, 3.51 Hz, 2 H) 1.53 (t, J = 11.90 Hz, 2 H) 1.18 (s, 6 H) 1.10 (s, 6 H). | A |
| 128 | 572 | 13.26 (br. s., 1 H) 9.27 (s, 1 H) 8.22 (s, 1 H) 8.09 (q, J = 4.2 Hz, 1 H) 7.95 (s, 1 H) 7.82 (d, J = 8.5 Hz, 2 H) 7.74-7.78 (m, 2 H) 7.53 (d, J = 8.5 Hz, 2 H) 7.47 (t, J = 7.9 Hz, 1 H) 7.05-7.10 (m, 1 H) 5.89 (d, J = 8.9 Hz, 1 H) 4.94-5.05 (m, 1 H) 4.58 (s, 2 H) 3.60 (s, 2 H) 2.90 (d, J = 11.9 Hz, 2 H) 2.69 (d, J = 4.9 Hz, 3 H) 2.21 (t, J = 10.7 Hz, 2 H) 2.01 (d, J = 10.7 Hz, 2 H) 1.72 (qd, J = 11.6, 3.5 Hz, 2 H). | A |
| 129 | 415 | 13.15 (br. s., 1 H) 8.05-8.13 (m, 3 H) 7.93 (s, 1 H) 7.09-7.14 (m, 2 H) 5.77 (d, J = 8.70 Hz, 1 H) 5.52-5.60 (m, 1 H) 4.55 (s, 2 H) 2.71-2.78 (m, 2 H) 2.67 (d, | C |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| | | J = 4.73 Hz, 3 H) 2.59 (dd, J = 9.46, 4.12 Hz, 1 H) 2.31-2.41 (m, 2 H) 2.28 (s, 3 H) 1.76-1.85 (m, 1 H). | |
| 130 | 511 | 13.18 (br. s., 1 H) 8.08 (q, J = 4.5 Hz, 1 H) 7.94 (s, 1 H) 7.73-7.77 (m, 2 H) 7.48 (dd, J = 4.9, 3.0 Hz, 1 H) 7.46 (t, J = 8.2 Hz, 1 H) 7.34 (d, J = 1.8 Hz, 1 H) 7.08 (dd, J = 4.9, 1.2 Hz, 1 H) 7.07 (dd, J = 8.9, 2.1 Hz, 1 H) 5.85 (d, J = 7.0 Hz, 1 H) 4.91-5.01 (m, 1 H) 4.57 (s, 2 H) 3.53 (s, 2 H) 2.88 (d, J = 11.6 Hz, 2 H) 2.69 (d, J = 4.6 Hz, 3 H) 2.14 (td, J = 11.6, 1.8 Hz, 2 H) 1.99 (d, J = 11.6 Hz, 2 H) 1.63-1.73 (m, J = 11.7, 11.6, 11.6, 3.5 Hz, 2 H). | A |
| 131 | 521 | 13.25 (br. s., 1 H) 9.28 (s, 1 H) 8.08 (q, J = 4.2 Hz, 1 H) 7.94 (s, 1 H) 7.74-7.79 (m, 2 H) 7.47 (t, J = 8.2 Hz, 1 H) 7.10 (t, J = 7.8 Hz, 1 H) 7.05-7.08 (m, 1 H) 6.72-6.78 (m, 2 H) 6.63 (dd, J = 8.1, 1.7 Hz, 1 H) 5.85 (d, J = 7.6 Hz, 1 H) 4.92-5.03 (m, 1 H) 4.57 (s, 2 H) 3.43 (s, 2 H) 2.87 (d, J = 11.6 Hz, 2 H) 2.69 (d, J = 4.6 Hz, 3 H) 2.15 (t, J = 10.8 Hz, 2 H) 1.99 (d, J = 9.8 Hz, 2 H) 1.68 (qd, J = 11.4, 2.9 Hz, 2 H). | A |
| 132 | 429 | 13.14 (br. s., 1 H) 8.07-8.11 (m, 2 H) 8.06-8.10 (m, 1 H) 7.93 (s, 1 H) 7.09-7.13 (m, 2 H) 5.77 (d, J = 8.39 Hz, 1 H) 5.51-5.59 (m, 1 H) 4.55 (s, 2 H) 2.81 (dd, J = 9.50, 6.62 Hz, 1 H) 2.76 (td, J = 8.58, 5.11 Hz, 1 H) 2.67 (d, J = 4.58 Hz, 3 H) 2.61 (dd, J = 9.50, 4.26 Hz, 1 H) 2.45 (q, J = 7.17 Hz, 2 H) 2.41 (td, J = 8.58, 6.33 Hz, 1 H) 2.34 (dtd, J = 13.20, 8.50, 5.11 Hz, 1 H) 1.76-1.84 (m, 1 H) 1.04 (t, J = 7.17 Hz, 3 H). | C |
| 133 | 443 | 13.15 (br. s., 1 H) 8.07-8.11 (m, 2 H) 8.05-8.10 (m, 1 H) 7.93 (s, 1 H) 7.09-7.13 (m, 2 H) 5.77 (d, J = 8.70 Hz, 1 H) 5.50-5.58 (m, 1 H) 4.55 (s, 2 H) 2.81 (dd, J = 9.45, 6.56 Hz, 1 H) 2.75 (td, J = 8.50, 5.14 Hz, 1 H) 2.67 (d, J = 4.73 Hz, 3 H) 2.59 (dd, J = 9.45, 4.22 Hz, 1 H) 2.42 (td, J = 8.50, 6.55 Hz, 1 H) 2.35-2.40 (m, 2 H) 2.33 (dtd, J = 13.30, 8.50, 5.14 Hz, 1 H) 1.76-1.84 (m, 1 H) 1.46 (s × t, J = 7.39 Hz, 2 H) 0.88 (t, J = 7.40 Hz, 3 H). | C |
| 134 | 443 | 13.15 (br. s., 1 H) 8.08-8.11 (m, 2 H) 8.08 (q, J = 4.73 Hz, 1 H) 7.93 (s, 1 H) 7.09-7.14 (m, 2 H) 5.79 (d, J = 8.39 Hz, 1 H) 5.50-5.57 (m, 1 H) 4.55 (s, 2 H) 2.93 (dd, J = 9.38, 6.71 Hz, 1 H) 2.78 (td, J = 8.58, 5.42 Hz, 1 H) 2.67 (d, J = 4.73 Hz, 3 H) 2.62 (dd, J = 9.38, 4.60 Hz, 1 H) 2.52 (td, J = 8.58, 6.66 Hz, 1 H) 2.40 (spt, J = 6.28 Hz, 1 H) 2.32 (dtd, J = 13.10, 8.53, 5.42 Hz, 1 H) 1.76-1.84 (m, 1 H) 1.05 (d, J = 6.26 Hz, 3 H) 1.02 (d, J = 6.26 Hz, 3 H). | C |
| 135 | 443 | 13.11 (br. s., 1 H) 8.13 (t, J = 5.6 Hz, 1 H) 8.08 (d, J = 8.9 Hz, 2 H) 7.91 (s, 1 H) 7.12 (d, J = 8.9 Hz, 2 H) 5.77 (d, J = 8.9 Hz, 1 H) 4.87-4.96 (m, 1 H) 4.54 (s, 2 H) 3.17 (quin, J = 6.9 Hz, 2 H) 2.81 (d, J = 11.9 Hz, 2 H) 2.21 (s, 3 H) 2.07 (td, J = 11.7, 2.0 Hz, 2 H) 1.97 (d, J = 9.8 Hz, 2 H) 1.68 (qd, J = 11.6, 3.8 Hz, 2 H) 1.05 (t, J = 7.2 Hz, 3 H). | B |
| 136 | 457 | 13.10 (br. s., 1 H) 8.07 (d, J = 8.9 Hz, 2 H) 7.92 (d, J = 8.2 Hz, 1 H) 7.91 (s, 1 H) 7.11 (d, J = 9.2 Hz, 2 H) 5.75 (d, J = 8.9 Hz, 1 H) 4.86-4.98 (m, 1 H) 4.52 (s, 2 H) 3.95 (s × t, J = 6.8 Hz, 1 H) 2.81 (d, J = 11.6 Hz, 2 H) 2.21 (s, 3 H) 2.07 (td, J = 11.6, 1.8 Hz, 2 H) 1.97 (d, J = 11.3 Hz, 2 H) 1.63-1.73 (m, J = 11.8, 11.6, 11.6, 3.7 Hz, 2 H) 1.10 (d, J = 6.7 Hz, 6 H). | B |
| 137 | 483 | 13.10 (br. s., 1 H) 8.07 (d, J = 8.9 Hz, 2 H) 8.01 (d, J = 7.3 Hz, 1 H) 7.91 (s, 1 H) 7.11 (d, J = 8.9 Hz, 2 H) 5.76 (d, J = 8.5 Hz, 1 H) 4.86-4.98 (m, 1 H) 4.53 (s, 2 H) 4.08 (s × t, J = 7.0 Hz, 1 H) 2.81 (d, J = 11.6 Hz, 2 H) 2.21 (s, 3 H) 2.06 (td, J = 11.6, 1.8 Hz, 2 H) 1.97 (d, J = 9.8 Hz, 2 H) 1.78-1.86 (m, 2 H) 1.68 (qd, J = 11.3, 3.4 Hz, 2 H) 1.61-1.66 (m, 2 H) 1.47-1.56 (m, 2 H) 1.40-1.47 (m, 2 H). | B |
| 138 | 487 | 13.14 (br. s., 1 H) 8.06-8.10 (m, 2 H) 8.06 (q, J = 4.73 Hz, 1 H) 8.01 (s, 1 H) 7.10-7.14 (m, 2 H) 5.46 (d, J = 8.70 Hz, 1 H) 4.89-4.98 (m, 1 H) 4.55 (s, 2 H) 2.85-2.94 (m, 2 H) 2.67 (d, J = 4.73 Hz, 3 H) 2.36 (q, J = 7.17 Hz, 2 H) 2.04-2.12 (m, 2 H) 1.98-2.04 (m, 2 H) 1.58-1.68 (m, 2 H) 1.03 (t, J = 7.17 Hz, 3 H). | C |
| 139 | 445 | 13.12 (br. s., 1 H) 11.48 (br. s., 1 H) 8.08 (d, J = 8.8 Hz, 2 H) 7.91 (s, 1 H) 7.12 (d, J = 8.5 Hz, 2 H) 5.77 (d, J = 8.9 Hz, 1 H) 4.84-4.98 (m, 1 H) 4.57 (s, 2 H) 3.64 (s, 3 H) 2.81 (d, J = 11.9 Hz, 2 H) 2.21 (s, 3 H) 2.07 (td, J = 11.3, 1.5 Hz, 2 H) 1.97 (d, J = 11.9 Hz, 2 H) 1.68 (qd, J = 11.9, 11.6, 3.7 Hz, 2 H). | B |
| 140 | 501 | 13.14 (br. s., 1 H) 8.06-8.09 (m, 2 H) 8.06 (q, J = 4.58 Hz, 1 H) 8.01 (s, 1 H) 7.10-7.14 (m, 2 H) 5.47 (d, J = 9.00 Hz, 1 H) 4.90-4.98 (m, 1 H) 4.55 (s, 2 H) 2.84-2.91 (m, 2 H) 2.67 (d, J = 4.58 Hz, 3 H) 2.25-2.30 (m, 2 H) 2.05-2.12 (m, 2 H) 1.97-2.04 (m, 2 H) 1.59-1.69 (m, 2 H) 1.46 (s × t, J = 7.39 Hz, 2 H) 0.87 (t, J = 7.40 Hz, 3 H). | C |
| 141 | 501 | 13.15 (br. s., 1 H) 8.06-8.09 (m, 2 H) 8.06 (q, J = 4.58 Hz, 1 H) 8.01 (s, 1 H) 7.10-7.14 (m, 2 H) 5.43 (d, 1 H) 4.86-4.95 (m, 1 H) 4.55 (s, 2 H) 2.80-2.86 (m, 2 H) 2.73 (spt, J = 6.56 Hz, 1 H) 2.67 (d, J = 4.58 Hz, 3 H) 2.30 (td, J = 11.29, 1.98 Hz, 2 H) 1.99-2.05 (m, 2 H) 1.54-1.65 (m, 2 H) 1.01 (d, J = 6.56 Hz, 6 H). | C |
| 142 | 501 | 13.12 (br. s., 1 H) 8.07-8.07 (m, 1 H) 8.07 (d, J = 9.2 Hz, 2 H) 7.91 (s, 1 H) 7.11 (d, J = 8.9 Hz, 2 H) 5.77 (d, J = 8.9 Hz, 1 H) 4.86-4.96 (m, 1 H) 4.58 (s, 2 H) 3.53 (spt, J = 6.1 Hz, 1 H) 3.40 (t, J = 6.0 Hz, 2 H) 3.27 (q, J = 6.0 Hz, 2 H) 2.81 (d, J = 11.6 Hz, 2 H) 2.21 (s, 3 H) 2.06 (td, J = 11.6, 1.8 Hz, 2 H) 1.97 (d, J = 11.9 Hz, 2 H) 1.68 (qd, J = 11.6, 3.8 Hz, 2 H) 1.07 (d, J = 6.1 Hz, 6 H). | B |
| 143 | 486 | 13.12 (br. s., 1 H) 8.07 (d, J = 9.2 Hz, 2 H) 8.00 (t, J = 5.6 Hz, 1 H) 7.91 (s, 1 H) 7.12 (d, J = 9.2 Hz, 2 H) 5.77 (d, J = 8.9 Hz, 1 H) 4.86-4.97 (m, 1 H) 4.56 (s, 2 H) 3.23 (dd, J = 12.5, 5.8 Hz, 2 H) 2.81 (d, J = 11.3 Hz, 2 H) 2.31 (t, J = 6.7 Hz, 2 H) 2.21 (s, 3 H) 2.15 (s, 6 H) 2.06 (td, J = 11.7, 2.0 Hz, 2 H) 1.97 (d, J = 11.0 Hz, 2 H) 1.68 (qd, J = 11.6, 3.7 Hz, 2 H). | B |

TABLE 2-continued

| Ex. | MS (ESI)+ m/z [M + H]+ | 1H NMR (600 MHz, DMSO-d6) δ ppm (unless otherwise stated) | GP |
|---|---|---|---|
| 144 | 459 | 13.18 (br. s., 1 H) 8.08-8.11 (m, 2 H) 8.08 (q, J = 4.73 Hz, 1 H) 8.02 (s, 1 H) 7.09-7.13 (m, 2 H) 5.54-5.61 (m, 1 H) 5.53 (d, J = 8.70 Hz, 1 H) 4.55 (s, 2 H) 2.74-2.80 (m, 1 H) 2.71 (dd, J = 9.54, 6.18 Hz, 1 H) 2.67 (d, J = 4.73 Hz, 3 H) 2.61 (dd, J = 9.54, 3.43 Hz, 1 H) 2.30-2.42 (m, 2 H) 2.28 (s, 3 H) 1.72-1.80 (m, 1 H). | C |
| 145 | 525 | 13.12 (br. s., 1 H) 8.06-8.10 (m, 2 H) 8.04 (t, J = 5.79 Hz, 1 H) 7.91 (s, 1 H) 7.08-7.12 (m, 2 H) 5.77 (d, J = 8.85 Hz, 1 H) 4.86-4.95 (m, 1 H) 4.55 (s, 2 H) 3.15 (td, J = 6.96, 5.79 Hz, 2 H) 2.78-2.84 (m, 2 H) 2.21 (s, 3 H) 2.02-2.10 (m, 2 H) 1.94-2.00 (m, 2 H) 1.52-1.73 (m, 7 H) 1.32 (q, J = 6.96 Hz, 2 H) 1.04-1.23 (m, 4 H) 0.78-0.88 (m, 2 H). | B |
| 146 | 511 | 13.11 (br. s., 1 H) 8.05-8.09 (m, 3 H) 7.91 (s, 1 H) 7.08-7.13 (m, 2 H) 5.77 (d, J = 8.70 Hz, 1 H) 4.87-4.95 (m, 1 H) 4.57 (s, 2 H) 2.98 (t, J = 6.41 Hz, 2 H) 2.78-2.84 (m, 2 H) 2.21 (s, 3 H) 2.02-2.10 (m, 2 H) 1.94-2.00 (m, 2 H) 1.64-1.72 (m, 2 H) 1.55-1.68 (m, 5 H) 1.38-1.46 (m, 1 H) 1.05-1.20 (m, 3 H) 0.79-0.90 (m, 2 H). | B |
| 147 | 527 | 13.13 (s, 1 H) 8.06-8.10 (m, 2 H) 8.05-8.09 (m, 1 H) 7.91 (s, 1 H) 7.09-7.13 (m, 2 H) 5.77 (d, J = 8.70 Hz, 1 H) 4.87-4.95 (m, 1 H) 4.57 (s, 2 H) 3.77 (ddd, J = 11.42, 4.40, 1.47 Hz, 2 H) 3.18 (td, J = 11.42, 2.10 Hz, 2 H) 3.17 (q, J = 6.60 Hz, 2 H) 2.77-2.85 (m, 2 H) 2.21 (s, 3 H) 2.02-2.11 (m, 2 H) 1.93-2.00 (m, 2 H) 1.63-1.73 (m, 2 H) 1.49-1.56 (m, 2 H) 1.35-1.44 (m, 1 H) 1.36 (q, J = 6.60 Hz, 2 H) 1.05-1.13 (m, J = 12.80, 11.42, 11.42, 4.40 Hz, 2 H). | B |
| 148 | 513 | 13.11 (br. s., 1 H) 8.14 (t, J = 6.04 Hz, 1 H) 8.05-8.09 (m, 2 H) 7.91 (s, 1 H) 7.09-7.13 (m, 2 H) 5.77 (d, J = 8.85 Hz, 1 H) 4.87-4.95 (m, 1 H) 4.58 (s, 2 H) 3.81 (ddd, J = 11.70, 4.36, 1.85 Hz, 2 H) 3.22 (td, J = 11.70, 2.10 Hz, 2 H) 3.03 (t, J = 6.40 Hz, 2 H) 2.78-2.84 (m, 2 H) 2.21 (s, 3 H) 2.06 (td, J = 11.64, 1.75 Hz, 2 H) 1.93-2.00 (m, 2 H) 1.62-1.73 (m, 3 H) 1.47-1.53 (m, 2 H) 1.08-1.17 (dtd, J = 13.00, 11.70, 4.40 Hz, 2 H). | B |
| 149 | 540 | 1H NMR (600 MHz, CD3OD) δ ppm 8.16-8.20 (m, 2 H) 7.78 (s, 1 H) 7.02-7.06 (m, 2 H) 4.82-4.88 (m, 1 H) 4.58 (s, 2 H) 3.32 (t, J = 7.02 Hz, 2 H) 2.84-2.92 (m, 2 H) 2.74-2.79 (m, 2 H) 2.32 (s, 3 H) 2.26-2.33 (m, 2 H) 2.13 (s, 3 H) 2.09-2.16 (m, 2 H) 1.86-1.94 (m, 2 H) 1.66-1.72 (m, 2 H) 1.53-1.64 (m, 2 H) 1.44-1.50 (m, 2 H) 1.15-1.26 (m, 3 H). | B |
| 150 | 526 | 13.09 (br. s., 1 H) 8.11 (t, J = 6.03 Hz, 1 H) 8.05-8.09 (m, 2 H) 7.91 (s, 1 H) 7.08-7.13 (m, 2 H) 5.76 (d, J = 8.54 Hz, 1 H) 4.87-4.95 (m, 1 H) 4.57 (s, 2 H) 3.02 (t, J = 6.41 Hz, 2 H) 2.78-2.85 (m, 2 H) 2.67-2.73 (m, 2 H) 2.21 (s, 3 H) 2.10 (s, 3 H) 2.06 (td, J = 11.75, 2.04 Hz, 2 H) 1.94-2.00 (m, 2 H) 1.75 (td, J = 11.70, 2.37 Hz, 2 H) 1.63-1.72 (m, J = 11.86, 11.70, 11.70, 3.97 Hz, 2 H) 1.51-1.58 (m, 2 H) 1.33-1.42 (m, 1 H) 1.06-1.15 (m, J = 12.17, 12.17, 11.70, 3.74 Hz, 2 H). | B |
| 151 | 512 | 8.08 (t, J = 6.18 Hz, 1 H) 8.05-8.08 (m, 2 H) 7.91 (s, 1 H) 7.08-7.13 (m, 2 H) 5.75 (d, J = 8.85 Hz, 1 H) 4.87-4.95 (m, 1 H) 4.57 (s, 2 H) 2.99 (t, J = 6.18 Hz, 2 H) 2.84-2.90 (m, 2 H) 2.78-2.84 (m, 2 H) 2.35 (td, J = 11.98, 1.98 Hz, 2 H) 2.21 (s, 3 H) 2.06 (td, J = 11.71, 1.91 Hz, 2H) 1.93-2.00 (m, 2H) 1.63-1.72 (m, 2 H) 1.47-1.53 (m, 2 H) 1.45-1.51 (m, 1 H) 0.91-1.00 (m, 2 H). | B |
| 152 | 528 | 13.12 (br. s., 1 H) 8.06-8.10 (m, 2 H) 7.99 (t, J = 5.79 Hz, 1 H) 7.91 (s, 1 H) 7.10-7.14 (m, 2 H) 5.77 (d, J = 8.85 Hz, 1 H) 4.86-4.95 (m, 1 H) 4.57 (s, 2 H) 3.51-3.57 (m, 4 H) 3.27 (td, J = 6.69, 5.79 Hz, 2 H) 2.77-2.85 (m, 2 H) 2.38 (t, J = 6.69 Hz, 2 H) 2.32-2.39 (m, 4 H) 2.21 (s, 3 H) 2.06 (td, J = 11.70, 2.20 Hz, 2 H) 1.94-2.00 (m, 2 H) 1.63-1.72 (m, 2 H). | B |
| 153 | 542 | 13.11 (br. s., 1 H) 8.12 (t, J = 5.80 Hz, 1 H) 8.06-8.10 (m, 2 H) 7.91 (s, 1 H) 7.09-7.14 (m, 2 H) 5.76 (d, J = 8.54 Hz, 1 H) 4.87-4.95 (m, 1 H) 4.56 (s, 2 H) 3.49-3.57 (m, 4 H) 3.18 (td, J = 6.90, 5.80 Hz, 2 H) 2.78-2.85 (m, 2 H) 2.25-2.34 (m, 4 H) 2.24 (t, J = 7.10 Hz, 2 H) 2.21 (s, 3 H) 2.03-2.10 (m, 2 H) 1.94-2.00 (m, 2 H) 1.63-1.72 (m, 2 H) 1.59 (tt, J = 7.10, 6.90 Hz, 2 H). | B |
| 154 | 473 | 13.11 (br. s., 1 H) 8.06-8.09 (m, 2 H) 8.06 (t, J = 4.73 Hz, 1 H) 7.91 (s, 1 H) 7.10-7.14 (m, 2 H) 5.76 (d, J = 9.00 Hz, 1 H) 4.88-4.97 (m, 1 H) 4.55 (s, 2 H) 3.45 (t, J = 5.90 Hz, 2 H) 3.25 (s, 3 H) 2.90-2.96 (m, 2 H) 2.67 (d, J = 4.73 Hz, 3 H) 2.51 (t, J = 5.90 Hz, 2 H) 2.16 (td, J = 11.60, 1.68 Hz, 2 H) 1.94-2.00 (m, 2 H) 1.61-1.70 (m, 2 H). | A |
| 155 | 526 | 8.06-8.10 (m, 2 H) 8.06 (t, J = 5.81 Hz, 1 H) 7.91 (s, 1 H) 7.07-7.13 (m, 2 H) 5.75 (d, J = 8.70 Hz, 1 H) 4.87-4.95 (m, 1 H) 4.55 (s, 2 H) 3.16 (td, J = 7.00, 5.81 Hz, 2 H) 2.82-2.87 (m, 2 H) 2.79-2.84 (m, 2 H) 2.35 (td, J = 11.98, 2.35 Hz, 2 H) 2.21 (s, 3 H) 2.06 (td, J = 11.71, 2.23 Hz, 2 H) 1.93-2.01 (m, 2 H) 1.62-1.72 (m, 2 H) 1.51-1.57 (m, 2 H) 1.33 (q, J = 7.00 Hz, 2 H) 1.22-1.30 (m, 1 H) 0.94 (qd, J = 11.98, 3.89 Hz, 2 H). | B followed by BOC de-protection |
| 156 | 443 | 12.91 (br. s., 1 H) 8.05 (q, J = 4.72 Hz, 1 H) 7.93 (s, 1 H) 7.75 (d, J = 8.60 Hz, 1 H) 6.99 (d, J = 2.67 Hz, 1 H) 6.93 (dd, J = 8.60, 2.67 Hz, 1 H) 5.77 (d, J = 8.70 Hz, 1 H) 4.88-4.96 (m, 1 H) 4.54 (s, 2 H) 2.75-2.82 (m, 2 H) 2.68 (d, J = 4.72 Hz, 3 H) 2.17 (s, 3 H) 1.91-2.00 (m, 4 H) 1.64-1.73 (m, 2 H). | C |
| 157 | 549 | 12.90 (br. s., 1 H) 8.06 (q, J = 4.58 Hz, 1 H) 7.92 (s, 1 H) 7.75 (d, J = 8.62 Hz, 1 H) 7.19-7.23 (m, 2 H) 6.98 (d, J = 2.67 Hz, 1 H) 6.93 (dd, J = 8.62, 2.67 Hz, 1 H) 6.86-6.90 (m, 2 H) 5.76 (d, J = 8.70 Hz, 1 H) 4.91-5.00 (m, 1 H) 4.54 (s, 2 H) 3.74 (s, 3 H) 3.40 (s, 2 H) 2.79-2.86 (m, 2 H) 2.68 (d, J = 4.58 Hz, 3 H) 2.65 (s, 3 H) 1.98-2.05 (m, 2 H) 1.92-1.98 (m, 2 H) 1.62-1.72 (m, 2 H). | C |
| 158 | 501 | 12.94 (br. s., 1 H) 8.05 (q, J = 4.60 Hz, 1 H) 8.02 (s, 1 H) 7.75 (d, J = 8.62 Hz, 1 H) 6.99 (d, J = 2.67 Hz, 1 H) 6.93 (dd, J = 8.62, 2.67 Hz, 1 H) 5.47 (d, J = 9.00 Hz, 1 H) 4.90-4.98 (m, 1 H) 4.54 (s, 2 H) 2.84-2.91 (m, 2 H) 2.67 (s, 3 H) 2.67 (d, | C |

TABLE 2-continued

| Ex. | MS (ESI)+ m/z [M + H]+ | 1H NMR (600 MHz, DMSO-d6) δ ppm (unless otherwise stated) | GP |
|---|---|---|---|
| | | J = 4.60 Hz, 3 H) 2.32 (q, J = 7.17 Hz, 2 H) 1.94-2.02 (m, 4 H) 1.59-1.69 (m, 2 H) 1.00 (t, J = 7.17 Hz, 3 H). | |
| 159 | 487 | 12.94 (br. s., 1 H) 8.05 (q, J = 4.60 Hz, 1 H) 8.02 (s, 1 H) 7.75 (d, J = 8.60 Hz, 1 H) 6.99 (d, J = 2.59 Hz, 1 H) 6.93 (dd, J = 8.60, 2.59 Hz, 1 H) 5.48 (d, J = 8.85 Hz, 1 H) 4.88-4.96 (m, 1 H) 4.54 (s, 2 H) 2.73-2.81 (m, 2 H) 2.67 (s, 3 H) 2.67 (d, J = 4.60 Hz, 3 H) 2.17 (s, 3 H) 1.93-2.02 (m, 4 H) 1.62-1.71 (m, 2 H). | C |
| 160 | 593 | 12.94 (br. s., 1 H) 8.06 (q, J = 4.73 Hz, 1 H) 8.02 (s, 1 H) 7.75 (d, J = 8.60 Hz, 1 H) 7.19-7.24 (m, 2 H) 6.98 (d, J = 2.59 Hz, 1 H) 6.93 (dd, J = 8.60, 2.59 Hz, 1 H) 6.86-6.91 (m, 2 H) 5.48 (d, J = 9.00 Hz, 1 H) 4.91-5.00 (m, 1 H) 4.54 (s, 2 H) 3.74 (s, 3 H) 3.40 (s, 2 H) 2.77-2.85 (m, 2 H) 2.68 (d, J = 4.73 Hz, 3 H) 2.65 (s, 3 H) 2.00-2.07 (m, 2 H) 1.94-2.00 (m, 2 H) 1.60-1.70 (m, 2 H). | C |
| 161 | 549 | 13.06 (br. s., 1 H) 7.95 (dq, J = 2.30, 0.86 Hz, 1 H) 7.92 (dd, J = 8.63, 2.30 Hz, 1 H) 7.90 (s, 1 H) 7.90 (q, J = 4.65 Hz, 1 H) 7.21-7.25 (m, 2 H) 6.99 (d, J = 8.63 Hz, 1 H) 6.87-6.91 (m, 2 H) 5.77 (d, J = 8.85 Hz, 1 H) 4.89-4.98 (m, 1 H) 4.58 (s, 2 H) 3.74 (s, 3 H) 3.46 (s, 2 H) 2.83-2.89 (m, 2 H) 2.69 (d, J = 4.65 Hz, 3 H) 2.32 (s, 3 H) 2.08-2.16 (m, 2 H) 1.95-2.01 (m, 2 H) 1.66 (dd, J = 11.90, 3.74 Hz, 2 H). | C |
| 162 | 443 | 13.06 (br. s., 1 H) 7.97 (dq, J = 2.30, 0.81 Hz, 1 H) 7.93 (dd, J = 8.61, 2.30 Hz, 1 H) 7.90 (s, 1 H) 7.89 (q, J = 4.70 Hz, 1 H) 7.00 (d, J = 8.61 Hz, 1 H) 5.77 (d, J = 8.70 Hz, 1 H) 4.87-4.95 (m, 1 H) 4.57 (s, 2 H) 2.78-2.85 (m, 2 H) 2.68 (d, J = 4.70 Hz, 3 H) 2.32 (s, 3 H) 2.21 (s, 3 H) 2.06 (td, J = 11.60, 1.83 Hz, 2 H) 1.94-2.01 (m, 2 H) 1.63-1.73 (m, 2 H). | C |
| 163 | 487 | 13.09 (br. s., 1 H) 8.00 (s, 1 H) 7.97 (dq, J = 2.31, 0.76 Hz, 1 H) 7.93 (dd, J = 8.60, 2.23 Hz, 1 H) 7.89 (q, J = 4.69 Hz, 1 H) 7.00 (d, J = 8.60 Hz, 1 H) 5.48 (d, J = 8.85 Hz, 1 H) 4.88-4.97 (m, 1 H) 4.57 (s, 2 H) 2.75-2.84 (m, 2 H) 2.68 (d, J = 4.73 Hz, 3 H) 2.32 (s, 3 H) 2.21 (s, 3 H) 2.05-2.14 (m, 2 H) 1.96-2.03 (m, 2 H) 1.61-1.71 (m, 2 H). | C |
| 164 | 501 | 13.09 (br. s., 1 H) 8.00 (s, 1 H) 7.97 (dq, J = 2.30, 0.75 Hz, 1 H) 7.93 (dd, J = 8.60, 2.30 Hz, 1 H) 7.89 (q, J = 4.69 Hz, 1 H) 7.00 (d, J = 8.60 Hz, 1 H) 5.47 (d, J = 8.70 Hz, 1 H) 4.90-4.98 (m, 1 H) 4.57 (s, 2 H) 2.87-2.94 (m, 2 H) 2.68 (d, J = 4.69 Hz, 3 H) 2.37 (q, J = 7.17 Hz, 2 H) 2.32 (s, 3 H) 2.05-2.12 (m, 2 H) 1.98-2.05 (m, 2 H) 1.64 (qd, J = 11.47, 3.59 Hz, 2 H) 1.03 (t, J = 7.17 Hz, 3 H). | C |
| 165 | 515 | 13.09 (br. s., 1 H) 8.00 (s, 1 H) 7.97 (dq, J = 2.30, 0.77 Hz, 1 H) 7.93 (dd, J = 8.57, 2.30 Hz, 1 H) 7.89 (q, J = 4.73 Hz, 1 H) 7.00 (d, J = 8.57 Hz, 1 H) 5.47 (d, J = 8.70 Hz, 1 H) 4.90-4.99 (m, 1 H) 4.57 (s, 2 H) 2.85-2.92 (m, 2 H) 2.68 (d, J = 4.73 Hz, 3 H) 2.32 (s, 3 H) 2.25-2.30 (m, 2 H) 2.05-2.12 (m, 2 H) 1.98-2.04 (m, 2 H) 1.60-1.68 (m, 2 H) 1.42-1.50 (m, 2 H) 0.88 (t, J = 7.32 Hz, 3 H). | C |
| 166 | 457 | 13.09 (br. s., 1 H) 7.97 (d, J = 2.20 Hz, 1 H) 7.93 (dd, J = 8.64, 2.20 Hz, 1 H) 7.92 (s, 1 H) 7.89 (q, J = 4.68 Hz, 1 H) 6.98 (d, J = 8.64 Hz, 1 H) 5.77 (d, J = 8.55 Hz, 1 H) 5.47-5.54 (m, 1 H) 4.57 (s, 2 H) 2.96 (dd, J = 9.31, 6.76 Hz, 1 H) 2.77 (td, J = 8.66, 5.26 Hz, 1 H) 2.68 (d, J = 4.68 Hz, 3 H) 2.60 (dd, J = 9.31, 4.73 Hz, 1 H) 2.53 (td, J = 8.46, 6.34 Hz, 1 H) 2.37-2.45 (m, 1 H) 2.32 (s, 3 H) 2.28-2.36 (m, 1 H) 1.76-1.84 (m, 1 H) 1.05 (d, J = 6.26 Hz, 3 H) 1.03 (d, J = 6.26 Hz, 3 H). | C |
| 167 | 503 | 13.17 (br. s., 1 H) 8.01 (s, 1 H) 7.89 (q, J = 4.1 Hz, 1 H) 7.81 (d, J = 2.1 Hz, 1 H) 7.68 (dd, J = 8.4, 2.0 Hz, 1 H) 7.06 (d, J = 8.5 Hz, 1 H) 5.56 (d, J = 8.5 Hz, 1 H) 4.89-4.99 (m, 1 H) 4.53 (s, 2 H) 3.91 (s, 3 H) 2.82 (d, J = 11.0 Hz, 2 H) 2.67 (d, J = 4.9 Hz, 3 H) 2.19 (s, 3 H) 2.07 (t, J = 11.0 Hz, 2 H) 2.00 (d, J = 11.3 Hz, 2 H) 1.67 (qd, J = 11.6, 3.5 Hz, 2 H). | C |
| 168 | 459 | 13.15 (br. s., 1 H) 7.91 (s, 1 H) 7.89 (q, J = 4.6 Hz, 1 H) 7.82 (d, J = 1.8 Hz, 1 H) 7.68 (dd, J = 8.4, 2.0 Hz, 1 H) 7.06 (d, J = 8.5 Hz, 1 H) 5.85 (d, J = 8.5 Hz, 1 H) 4.88-4.98 (m, 1 H) 4.53 (s, 2 H) 3.91 (s, 3 H) 2.84 (d, J = 11.6 Hz, 2 H) 2.67 (d, J = 4.6 Hz, 3 H) 2.19 (s, 3 H) 2.05 (td, J = 11.6, 1.8 Hz, 2 H) 1.98 (d, J = 11.9 Hz, 2 H) 1.69 (qd, J = 11.7, 3.8 Hz, 2 H). | C |
| 169 | 565 | 13.13 (br. s., 1 H) 7.90 (s, 1 H) 7.89 (br. s., 1 H) 7.80 (d, J = 2.1 Hz, 1 H) 7.67 (dd, J = 8.4, 2.0 Hz, 1 H) 7.22 (d, J = 8.9 Hz, 2 H) 7.05 (d, J = 8.5 Hz, 1 H) 6.89 (d, J = 8.5 Hz, 2 H) 5.81 (br. s., 1 H) 4.88-5.02 (m, 1 H) 4.54 (s, 2 H) 3.90 (s, 3 H) 3.74 (s, 3 H) 3.43 (s, 2 H) 2.87 (d, J = 11.3 Hz, 2 H) 2.68 (d, J = 4.6 Hz, 3 H) 2.10 (t, J = 11.6 Hz, 2 H) 2.00 (d, J = 11.7 Hz, 2 H) 1.66 (qd, J = 11.7, 3.7 Hz, 2 H). | C |
| 170 | 531 | 13.17 (br. s., 1 H) 8.01 (s, 1 H) 7.89 (q, J = 4.9 Hz, 1 H) 7.81 (d, J = 2.1 Hz, 1 H) 7.68 (dd, J = 8.4, 2.0 Hz, 1 H) 7.06 (d, J = 8.5 Hz, 1 H) 5.54 (d, J = 8.9 Hz, 1 H) 4.87-5.03 (m, 1 H) 4.53 (s, 2 H) 3.90 (s, 3 H) 2.91 (d, J = 11.6 Hz, 2 H) 2.67 (d, J = 4.6 Hz, 3 H) 2.25 (t, J = 7.6 Hz, 2 H) 2.06 (t, J = 11.6 Hz, 2 H) 2.02 (d, J = 12.2 Hz, 2 H) 1.65 (qd, J = 11.6, 3.5 Hz, 2 H) 1.45 (s × t, J = 7.4 Hz, 2 H) 0.87 (t, J = 7.3 Hz, 3 H). | C |
| 171 | 473 | 13.18 (br. s., 1 H) 7.94 (s, 1 H) 7.90 (q, J = 4.6 Hz, 1 H) 7.78 (d, J = 1.8 Hz, 1 H) 7.70 (dd, J = 8.4, 2.0 Hz, 1 H) 7.05 (d, J = 8.5 Hz, 1 H) 5.81 (d, J = 8.2 Hz, 1 H) 5.44-5.55 (m, 1 H) 4.53 (s, 2 H) 3.89 (s, 3 H) 2.95 (dd, J = 9.3, 6.9 Hz, 1 H) 2.79 (td, J = 8.6, 5.0 Hz, 1 H) 2.67 (d, J = 4.6 Hz, 3 H) 2.64 (dd, J = 9.5, 4.6 Hz, 1 H) 2.51-2.54 (m, 1 H) 2.40 (spt, J = 6.3 Hz, 1 H) 2.27-2.35 (m, 1 H) 1.78-1.87 (m, 1 H) 1.04 (d, J = 6.4 Hz, 3 H) 1.02 (d, J = 6.1 Hz, 3 H). | C |
| 172 | 561 | 12.89 (br. s., 1 H) 8.06 (q, J = 4.73 Hz, 1 H) 7.92 (s, 1 H) 7.75 (d, J = 8.60 Hz, 1 H) 7.15 (br. s., 1 H) 6.97-7.01 (m, 2 H) 6.93 (d, J = 8.60, 2.52 Hz, 1 H) 6.68 (d, J = 8.09 Hz, 1 H) 5.75 (d, J = 8.55 Hz, 1 H) 4.91-4.99 (m, 1 H) 4.54 (s, 2 H) 4.50 (t, J = 8.70 Hz, 2 H) 3.38 (s, 2 H) 3.16 (t, J = 8.70 Hz, 2 H) 2.80-2.86 (m, 2 H) 2.68 (d, J = 4.73 Hz, 3 H) 2.65 (s, 3 H) 1.98-2.05 (m, 2 H) 1.92-1.98 (m, 2 H) 1.61-1.71 (m, 2 H). | A |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| 173 | 457 | 12.90 (br. s., 1 H) 8.05 (q, J = 4.60 Hz, 1 H) 7.93 (s, 1 H) 7.75 (d, J = 8.60 Hz, 1 H) 6.98 (d, J = 2.59 Hz, 1 H) 6.93 (dd, J = 8.60, 2.59 Hz, 1 H) 5.75 (d, J = 8.70 Hz, 1 H) 4.90-4.98 (m, 1 H) 4.53 (s, 2 H) 2.86-2.92 (m, 2 H) 2.67 (s, 3 H) 2.67 (d, J = 4.60 Hz, 3 H) 2.32 (q, J = 7.17 Hz, 2 H) 1.92-2.00 (m, 4 H) 1.61-1.71 (m, 2 H) 1.00 (t, J = 7.17 Hz, 3 H). | A |
| 174 | 525 | 12.88 (br. s., 1 H) 8.06 (q, J = 4.73 Hz, 1 H) 7.92 (s, 1 H) 7.75 (d, J = 8.60 Hz, 1 H) 7.49 (dd, J = 4.98, 2.95 Hz, 1 H) 7.29-7.31 (m, 1 H) 7.05 (dd, J = 4.98, 1.15 Hz, 1 H) 6.98 (d, J = 2.59 Hz, 1 H) 6.93 (dd, J = 8.60, 2.59 Hz, 1 H) 5.77 (d, J = 8.85 Hz, 1 H) 4.90-4.99 (m, 1 H) 4.54 (s, 2 H) 3.49 (s, 2 H) 2.82-2.88 (m, 2 H) 2.68 (d, J = 4.73 Hz, 3 H) 2.64 (s, 3 H) 1.99-2.07 (m, 2 H) 1.92-1.98 (m, 2 H) 1.68 (qd, J = 11.75, 3.66 Hz, 2 H). | A |
| 175 | 535 | 13.05 (br. s., 1 H) 7.94-7.96 (m, 1 H) 7.91 (s, 1 H) 7.91 (dd, J = 8.60, 2.20 Hz, 1 H) 7.90 (q, J = 4.73 Hz, 1 H) 7.36 (dd, J = 7.52, 1.72 Hz, 1 H) 7.20 (ddd, J = 7.83, 7.52, 1.72 Hz, 1 H) 6.97 (d, J = 8.60 Hz, 1 H) 6.95 (dd, J = 7.83, 0.98 Hz, 1 H) 6.89 (td, J = 7.52, 0.98 Hz, 1 H) 5.73-5.83 (m, 1 H) 5.49-5.57 (m, 1 H) 4.57 (s, 2 H) 3.76 (s, 3 H) 3.65 (d, J = 14.00 Hz, 1 H) 3.62 (d, J = 14.00 Hz, 1 H) 2.92 (m, J = 9.45, 6.54 Hz, 1 H) 2.80 (td, J = 8.40, 5.56 Hz, 1 H) 2.69 (d, J = 4.73 Hz, 3 H) 2.59 (dd, J = 9.45, 4.46 Hz, 1 H) 2.52 (td, J = 8.40, 6.30 Hz, 1 H) 2.32 (s, 3 H) 2.29-2.38 (m, 1 H) 1.80-1.87 (m, 1 H). | A |
| 176 | 525 | 13.03 (br. s., 1 H) 7.94 (d, J = 2.19 Hz, 1 H) 7.91 (dd, J = 8.57, 2.19 Hz, 1 H) 7.90 (s, 1 H) 7.90 (q, J = 4.73 Hz, 1 H) 7.49 (dd, J = 4.88, 2.86 Hz, 1 H) 7.32-7.34 (m, 1 H) 7.08 (dd, J = 4.88, 0.97 Hz, 1 H) 6.99 (d, J = 8.57 Hz, 1 H) 5.78 (d, J = 9.00 Hz, 1 H) 4.89-4.98 (m, 1 H) 4.58 (s, 2 H) 3.55 (s, 2 H) 2.85-2.91 (m, 2 H) 2.69 (d, J = 4.73 Hz, 3 H) 2.32 (s, 3 H) 2.10-2.17 (m, 2 H) 1.95-2.01 (m, 2 H) 1.67 (qd, J = 11.65, 3.66 Hz, 2 H). | A |
| 177 | 457 | 13.07 (br. s., 1 H) 7.97 (d, J = 1.98 Hz, 1 H) 7.93 (dd, J = 8.70, 1.98 Hz, 1 H) 7.90 (s, 1 H) 7.89 (q, J = 4.65 Hz, 1 H) 7.00 (d, J = 8.70 Hz, 1 H) 5.76 (d, J = 8.70 Hz, 1 H) 4.89-4.97 (m, 1 H) 4.57 (s, 2 H) 2.89-2.96 (m, 2 H) 2.68 (d, J = 4.65 Hz, 3 H) 2.37 (q, J = 7.17 Hz, 2 H) 2.31 (s, 3 H) 2.02-2.09 (m, 2 H) 1.96-2.03 (m, 2 H) 1.61-1.70 (m, 2 H) 1.03 (t, J = 7.17 Hz, 3 H). | A |
| 178 | 487 | 13.07 (s, 1 H) 7.97 (d, J = 2.06 Hz, 1 H) 7.93 (dd, J = 8.65, 2.06 Hz, 1 H) 7.90 (s, 1 H) 7.89 (q, J = 4.65 Hz, 1 H) 6.99 (d, J = 8.65 Hz, 1 H) 5.77 (d, J = 8.85 Hz, 1 H) 4.88-4.96 (m, 1 H) 4.57 (s, 2 H) 3.46 (t, J = 5.87 Hz, 2 H) 3.25 (s, 3 H) 2.91-2.97 (m, 2 H) 2.68 (d, J = 4.65 Hz, 3 H) 2.52 (t, J = 5.87 Hz, 2 H) 2.32 (s, 3 H) 2.13-2.21 (m, 2 H) 1.94-2.01 (m, 2 H) 1.61-1.70 (m, 2 H). | A |
| 179 | 501 | 13.15 (br. s., 1 H) 8.09 (q, J = 4.3 Hz, 1 H) 8.04 (d, J = 8.9 Hz, 2 H) 8.01 (s, 1 H) 7.00 (d, J = 8.9 Hz, 2 H) 5.48 (d, J = 8.9 Hz, 1 H) 4.85-4.97 (m, 1 H) 2.78 (d, J = 11.6 Hz, 2 H) 2.64 (d, J = 4.6 Hz, 3 H) 2.21 (s, 3 H) 2.09 (t, J = 10.7 Hz, 2 H) 1.98 (d, J = 11.6 Hz, 2 H) 1.66 (qd, J = 11.4, 3.7 Hz, 2 H) 1.47 (s, 6 H). | C |
| 180 | 457 | 13.13 (br. s., 1 H) 8.09 (q, J = 4.5 Hz, 1 H) 8.04 (d, J = 8.9 Hz, 2 H) 7.92 (s, 1 H) 7.00 (d, J = 8.5 Hz, 2 H) 5.77 (d, J = 8.9 Hz, 1 H) 4.84-4.96 (m, 1 H) 2.81 (d, J = 11.6 Hz, 2 H) 2.64 (d, J = 4.6 Hz, 3 H) 2.21 (s, 3 H) 2.07 (t, J = 11.1 Hz, 2 H) 1.96 (d, J = 11.0 Hz, 2 H) 1.68 (qd, J = 11.7, 3.7 Hz, 2 H) 1.47 (s, 6 H). | C |
| 181 | 563 | 13.13 (br. s., 1 H) 8.10 (q, J = 4.5 Hz, 1 H) 8.03 (d, J = 8.9 Hz, 2 H) 7.91 (s, 1 H) 7.23 (d, J = 8.5 Hz, 2 H) 7.00 (d, J = 8.9 Hz, 2 H) 6.89 (d, J = 8.5 Hz, 2 H) 5.76 (d, J = 8.5 Hz, 1 H) 4.89-5.02 (m, 1 H) 3.74 (s, 3 H) 3.45 (s, 2 H) 2.85 (d, J = 11.6 Hz, 2 H) 2.65 (d, J = 4.9 Hz, 3 H) 2.12 (t, J = 10.7 Hz, 2 H) 1.97 (d, J = 10.7 Hz, 2 H) 1.66 (qd, J = 11.6, 3.5 Hz, 2 H) 1.48 (s, 6 H). | C |
| 182 | 515 | 13.16 (br. s., 1 H) 8.09 (q, J = 4.4 Hz, 1 H) 8.04 (d, J = 8.9 Hz, 2 H) 8.01 (s, 1 H) 7.00 (d, J = 8.9 Hz, 2 H) 5.47 (d, J = 8.9 Hz, 1 H) 4.88-4.98 (m, 1 H) 2.89 (d, J = 10.7 Hz, 2 H) 2.64 (d, J = 4.6 Hz, 3 H) 2.37 (q, J = 7.0 Hz, 2 H) 2.08 (t, J = 11.3 Hz, 2 H) 2.01 (d, J = 11.0 Hz, 2 H) 1.63 (qd, J = 11.4, 3.5 Hz, 2 H) 1.47 (s, 6 H) 1.02 (t, J = 7.2 Hz, 3 H). | C |
| 183 | 471 | 13.16 (br. s., 1 H) 8.09 (q, J = 4.5 Hz, 1 H) 8.05 (d, J = 8.8 Hz, 2 H) 7.93 (s, 1 H) 6.98 (d, J = 8.9 Hz, 2 H) 5.78 (d, J = 8.2 Hz, 1 H) 5.53 (br. s., 1 H) 2.91 (dd, J = 9.5, 6.7 Hz, 1 H) 2.78 (td, J = 8.5, 5.5 Hz, 1 H) 2.64 (d, J = 4.6 Hz, 3 H) 2.62 (dd, J = 9.3, 4.7 Hz, 1 H) 2.51-2.53 (m, 1 H) 2.40 (quin, J = 6.3 Hz, 1 H) 2.31 (dddd, J = 13.3, 8.5, 8.3, 5.3 Hz, 1 H) 1.75-1.82 (m, 1 H) 1.47 (s, 6 H) 1.04 (d, J = 6.1 Hz, 3 H) 1.02 (d, J = 6.4 Hz, 3 H). | C |
| 184 | 491 | 13.24 (br. s., 1 H) 8.03 (s, 1 H) 8.02 (q, J = 4.3 Hz, 1 H) 7.94 (dd, J = 12.4, 2.0 Hz, 1 H) 7.91 (dd, J = 8.5, 1.8 Hz, 1 H) 7.26 (t, J = 8.7 Hz, 1 H) 5.55 (d, J = 8.9 Hz, 1 H) 4.84-4.95 (m, 1 H) 4.66 (s, 2 H) 2.80 (d, J = 12.2 Hz, 2 H) 2.66 (d, J = 4.9 Hz, 3 H) 2.22 (s, 3 H) 2.09 (t, J = 11.0 Hz, 2 H) 1.99 (d, J = 10.4 Hz, 2 H) 1.67 (qd, J = 11.6, 3.8 Hz, 2 H). | C |
| 185 | 447 | 13.21 (br. s., 1 H) 8.02 (q, J = 4.9 Hz, 1 H) 7.93 (s, 1 H) 7.94 (dd, J = 12.4, 2.0 Hz, 1 H) 7.91 (dd, J = 8.5, 1.8 Hz, 1 H) 7.26 (t, J = 8.7 Hz, 1 H) 5.84 (d, J = 8.9 Hz, 1 H) 4.84-4.93 (m, 1 H) 4.66 (s, 2 H) 2.82 (d, J = 11.9 Hz, 2 H) 2.66 (d, J = 4.6 Hz, 3 H) 2.21 (s, 3 H) 2.06 (t, J = 10.8 Hz, 2 H) 1.97 (d, J = 11.3 Hz, 2 H) 1.69 (td, J = 11.6, 3.7 Hz, 2 H). | C |
| 186 | 553 | 13.21 (br. s., 1 H) 8.03 (q, J = 4.4 Hz, 1 H) 7.92 (s, 1 H) 7.93 (dd, J = 12.2, 1.8 Hz, 1 H) 7.90 (dd, J = 8.5, 1.8 Hz, 1 H) 7.25 (t, J = 8.7 Hz, 1 H) 7.23 (d, J = 8.5 Hz, 2 H) 6.89 (d, J = 8.9 Hz, 2 H) 5.82 (d, J = 7.9 Hz, 1 H) 4.87-4.98 (m, 1 H) 4.66 (s, 2 H) 3.74 (s, 3 H) 3.45 (s, 2 H) 2.86 (d, J = 11.6 Hz, 2 H) 2.67 (d, J = 4.6 Hz, 3 H) 2.11 (t, J = 10.8 Hz, 2 H) 1.97 (d, J = 10.4 Hz, 2 H) 1.66 (qd, J = 11.7, 3.5 Hz, 2 H). | C |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| 187 | 505 | 13.24 (br. s., 1 H) 8.03 (s, 1 H) 8.02 (q, J = 4.9 Hz, 1 H) 7.94 (dd, J = 12.4, 2.0 Hz, 1 H) 7.91 (dd, J = 8.5, 1.5 Hz, 1 H) 7.25 (t, J = 8.7 Hz, 1 H) 5.53 (d, J = 8.9 Hz, 1 H) 4.86-4.97 (m, 1 H) 4.66 (s, 2 H) 2.90 (d, J = 11.3 Hz, 2 H) 2.66 (d, J = 4.9 Hz, 3 H) 2.36 (q, J = 7.1 Hz, 2 H) 2.07 (t, J = 11.4 Hz, 2 H) 2.01 (d, J = 11.3 Hz, 2 H) 1.64 (qd, J = 11.3, 3.1 Hz, 2 H) 1.03 (t, J = 7.2 Hz, 3 H). | C |
| 188 | 447 | 13.25 (br. s., 1 H) 8.03 (q, J = 4.6 Hz, 1 H) 7.95 (s, 1 H) 7.96 (dd, J = 12.5, 2.1 Hz, 1 H) 7.92 (dd, J = 8.7, 1.4 Hz, 1 H) 7.23 (t, J = 8.7 Hz, 1 H) 5.83 (d, J = 8.2 Hz, 1 H) 5.48-5.57 (m, 1 H) 4.65 (s, 2 H) 2.81 (dd, J = 9.5, 6.7 Hz, 2 H) 2.76 (td, J = 8.6, 5.0 Hz, 1 H) 2.67 (d, J = 4.6 Hz, 3 H) 2.61 (dd, J = 9.5, 4.3 Hz, 1 H) 2.45 (q, J = 7.3 Hz, 2 H) 2.39-2.44 (m, 1 H) 2.30-2.38 (m, 1 H) 1.76-1.85 (m, 1 H) 1.04 (t, J = 7.2 Hz, 3 H). | C |
| 189 | 471 | 13.21 (br. s., 1 H) 8.04 (d, J = 8.2 Hz, 2 H) 8.02 (s, 1 H) 7.75 (q, J = 4.6 Hz, 1 H) 7.36 (d, J = 8.5 Hz, 2 H) 5.51 (d, J = 8.9 Hz, 1 H) 4.88-4.98 (m, 1 H) 2.87 (t, J = 7.8 Hz, 2 H) 2.79 (d, J = 11.6 Hz, 2 H) 2.56 (d, J = 4.6 Hz, 3 H) 2.40 (t, J = 7.8 Hz, 2 H) 2.21 (s, 3 H) 2.09 (t, J = 10.7 Hz, 2 H) 1.99 (d, J = 11.6 Hz, 2 H) 1.66 (qd, J = 11.5, 3.8 Hz, 2 H). | C |
| 190 | 427 | 13.19 (s, 1 H) 8.03 (d, J = 8.2 Hz, 2 H) 7.93 (s, 1 H) 7.75 (q, J = 4.0 Hz, 1 H) 7.36 (d, J = 8.2 Hz, 2 H) 5.81 (d, J = 8.9 Hz, 1 H) 4.87-4.98 (m, 1 H) 2.87 (t, J = 7.6 Hz, 2 H) 2.81 (d, J = 11.9 Hz, 2 H) 2.56 (d, J = 4.6 Hz, 3 H) 2.41 (t, J = 7.8 Hz, 2 H) 2.21 (s, 3 H) 2.06 (t, J = 10.8 Hz, 2 H) 1.97 (d, J = 10.4 Hz, 2 H) 1.68 (qd, J = 11.6, 3.5 Hz, 2 H). | C |
| 191 | 499 | 13.22 (s, 1 H) 8.03 (d, J = 8.5 Hz, 2 H) 8.03 (s, 1 H) 7.75 (q, J = 4.1 Hz, 1 H) 7.36 (d, J = 8.5 Hz, 2 H) 5.48 (d, J = 8.9 Hz, 1 H) 4.87-4.97 (m, 1 H) 2.87 (t, J = 7.6 Hz, 2 H) 2.84 (d, J = 10.7 Hz, 2 H) 2.69-2.78 (m, 1 H) 2.56 (d, J = 4.6 Hz, 3 H) 2.40 (t, J = 7.6 Hz, 2 H) 2.30 (t, J = 10.5 Hz, 2 H) 2.03 (d, J = 10.4 Hz, 2 H) 1.60 (qd, J = 11.1, 2.3 Hz, 2 H) 1.01 (d, J = 6.4 Hz, 6 H). | C |
| 192 | 485 | 13.21 (br. s., 1 H) 8.03 (d, J = 8.2 Hz, 2 H) 8.02 (s, 1 H) 7.75 (q, J = 4.0 Hz, 1 H) 7.35 (d, J = 8.2 Hz, 2 H) 5.49 (d, J = 8.5 Hz, 1 H) 4.89-5.01 (m, 1 H) 2.90 (d, J = 11.6 Hz, 2 H) 2.87 (t, J = 7.8 Hz, 2 H) 2.56 (d, J = 4.6 Hz, 3 H) 2.40 (t, J = 7.8 Hz, 2 H) 2.36 (q, J = 7.3 Hz, 2 H) 2.07 (t, J = 11.0 Hz, 2 H) 2.01 (d, J = 10.7 Hz, 2 H) 1.64 (qd, J = 11.5, 3.5 Hz, 2 H) 1.03 (t, J = 7.2 Hz, 3 H). | C |
| 193 | 427 | 13.22 (br. s., 1 H) 8.05 (d, J = 8.2 Hz, 2 H) 7.95 (s, 1 H) 7.76 (q, J = 4.3 Hz, 1 H) 7.35 (d, J = 7.9 Hz, 2 H) 5.81 (d, J = 8.5 Hz, 1 H) 5.50-5.59 (m, 1 H) 2.87 (t, J = 7.8 Hz, 2 H) 2.82 (dd, J = 9.5, 6.7 Hz, 1 H) 2.76 (td, J = 8.4, 5.2 Hz, 1 H) 2.61 (dd, J = 9.5, 4.3 Hz, 1 H) 2.56 (d, J = 4.6 Hz, 3 H) 2.45 (q, J = 7.5 Hz, 2 H) 2.42-2.43 (m, 1 H) 2.40 (t, J = 7.8 Hz, 2 H) 2.30-2.38 (m, 1 H) 1.76-1.86 (m, 1 H) 1.04 (t, J = 7.3 Hz, 3 H). | C |
| 194 | 563 | 13.09 (br. s., 1 H) 8.20 (q, J = 4.66 Hz, 1 H) 7.91 (s, 1 H) 7.82 (s, 2 H) 7.21-7.25 (m, 2 H) 6.87-6.91 (m, 2 H) 5.79 (d, J = 7.48 Hz, 1 H) 4.87-4.96 (m, 1 H) 4.26 (s, 2 H) 3.74 (s, 3 H) 3.47 (s, 2 H) 2.83-2.89 (m, 2 H) 2.73 (d, J = 4.66 Hz, 3 H) 2.31 (s, 6 H) 2.08-2.15 (m, 2 H) 1.95-2.01 (m, 2 H) 1.62-1.71 (m, 2 H). | C |
| 195 | 457 | 13.11 (br. s., 1 H) 8.19 (q, J = 4.73 Hz, 1 H) 7.92 (s, 1 H) 7.84 (s, 2 H) 5.81 (d, J = 8.54 Hz, 1 H) 4.86-4.95 (m, 1 H) 4.25 (s, 2 H) 2.78-2.86 (m, 2 H) 2.72 (d, J = 4.73 Hz, 3 H) 2.31 (s, 6 H) 2.21 (s, 3 H) 2.02-2.10 (m, 2 H) 1.94-2.01 (m, 2 H) 1.69 (qd, J = 11.60, 3.66 Hz, 2 H). | C |
| 196 | 501 | 13.13 (br. s., 1 H) 8.19 (q, J = 4.70 Hz, 1 H) 8.01 (s, 1 H) 7.85 (s, 2 H) 5.51 (d, J = 8.39 Hz, 1 H) 4.87-4.97 (m, 1 H) 4.25 (s, 2 H) 2.76-2.84 (m, 2 H) 2.72 (d, J = 4.70 Hz, 3 H) 2.31 (s, 6 H) 2.21 (s, 3 H) 2.04-2.12 (m, 2 H) 1.96-2.03 (m, 2 H) 1.63-1.71 (m, 2 H). | C |
| 197 | 530 | 13.14 (br. s., 1 H) 8.19 (q, J = 4.73 Hz, 1 H) 8.01 (s, 1 H) 7.85 (s, 2 H) 5.52 (d, J = 8.85 Hz, 1 H) 4.89-4.98 (m, 1 H) 4.25 (s, 2 H) 2.81-2.87 (m, 2 H) 2.75 (spt, J = 6.56 Hz, 1 H) 2.72 (d, J = 4.73 Hz, 3 H) 2.33 (td, J = 11.14, 2.29 Hz, 2 H) 2.30 (s, 6 H) 1.98-2.05 (m, 2 H) 1.61 (qd, J = 11.32, 3.43 Hz, 2 H) 1.01 (d, J = 6.56 Hz, 6 H). | C |
| 198 | 471 | 13.13 (br. s., 1 H) 8.19 (q, J = 4.67 Hz, 1 H) 7.94 (s, 1 H) 7.84 (s, 2 H) 5.80 (d, J = 8.55 Hz, 1 H) 5.44-5.52 (m, 1 H) 4.25 (s, 2 H) 2.98 (dd, J = 9.30, 6.79 Hz, 1 H) 2.77 (td, J = 8.63, 5.69 Hz, 1 H) 2.72 (d, J = 4.67 Hz, 3 H) 2.59 (dd, J = 9.30, 4.72 Hz, 1 H) 2.55 (td, J = 8.63, 6.35 Hz, 1 H) 2.42 (spt, J = 6.26 Hz, 1 H) 2.31 (s, 6 H) 2.27-2.35 (m, 1 H) 1.77-1.85 (m, 1 H) 1.05 (d, J = 6.26 Hz, 3 H) 1.03 (d, J = 6.26 Hz, 3 H). | C |
| 199 | 583 | 13.12 (br. s., 1 H) 8.19 (q, J = 4.73 Hz, 1 H) 8.01 (s, 1 H) 7.82 (s, 2 H) 7.42-7.45 (m, 1 H) 6.97-7.00 (m, 2 H) 5.57 (d, J = 8.70 Hz, 1 H) 4.89-4.98 (m, 1 H) 4.26 (s, 2 H) 3.78 (s, 2 H) 2.88-2.94 (m, 2 H) 2.73 (d, J = 4.73 Hz, 3 H) 2.31 (s, 6 H) 2.18-2.25 (m, 2 H) 1.98-2.04 (m, 2 H) 1.64-1.73 (m, 2 H). | C |
| 200 | 457 | 13.13 (br. s., 1 H) 8.19 (q, J = 4.73 Hz, 1 H) 7.94 (s, 1 H) 7.83 (s, 2 H) 5.78 (d, J = 8.54 Hz, 1 H) 5.48-5.56 (m, 1 H) 4.25 (s, 2 H) 2.84 (dd, J = 9.35, 6.65 Hz, 1 H) 2.76 (td, J = 8.64, 5.47 Hz, 1 H) 2.72 (d, J = 4.73 Hz, 3 H) 2.59 (dd, J = 9.35, 4.20 Hz, 1 H) 2.40-2.49 (m, 3 H) 2.31-2.38 (m, 1 H) 2.31 (s, 6 H) 1.76-1.84 (m, 1 H) 1.04 (t, J = 7.25 Hz, 3 H). | C |
| 201 | 563 | 12.84 (br. s., 1 H) 7.91 (s, 1 H) 7.88 (q, J = 4.73 Hz, 1 H) 7.65 (s, 1 H) 7.19-7.23 (m, 2 H) 6.86-6.90 (m, 2 H) 6.84 (s, 1 H) 5.73 (d, J = 7.17 Hz, 1 H) 4.91-5.00 (m, 1 H) 4.56 (s, 2 H) 3.74 (s, 3 H) 3.40 (s, 2 H) 2.79-2.85 (m, 2 H) 2.70 (d, J = 4.73 Hz, 3 H) 2.62 (s, 3 H) 2.27 (s, 3 H) 1.98-2.05 (m, 2 H) 1.91-1.98 (m, 2 H) 1.61-1.70 (m, 2 H). | C |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| 202 | 457 | 12.86 (br. s., 1 H) 7.92 (s, 1 H) 7.87 (q, J = 4.73 Hz, 1 H) 7.64 (s, 1 H) 6.85 (s, 1 H) 5.76 (d, J = 9.00 Hz, 1 H) 4.88-4.97 (m, 1 H) 4.56 (s, 2 H) 2.75-2.82 (m, 2 H) 2.69 (d, J = 4.73 Hz, 3 H) 2.64 (s, 3 H) 2.27 (s, 3 H) 2.16 (s, 3 H) 1.90-2.00 (m, 4 H) 1.64-1.73 (m, 2 H). | C |
| 203 | 501 | 12.89 (s, 1 H) 8.01 (s, 1 H) 7.87 (q, J = 4.73 Hz, 1 H) 7.64 (s, 1 H) 6.85 (s, 1 H) 5.47 (d, J = 9.00 Hz, 1 H) 4.88-4.97 (m, 1 H) 4.56 (s, 2 H) 2.73-2.81 (m, 2 H) 2.69 (d, J = 4.73 Hz, 3 H) 2.64 (s, 3 H) 2.27 (s, 3 H) 2.17 (s, 3 H) 1.92-2.03 (m, 4 H) 1.61-1.71 (m, 2 H). | C |
| 204 | 485 | 12.86 (s, 1 H) 7.92 (s, 1 H) 7.87 (q, J = 4.73 Hz, 1 H) 7.65 (s, 1 H) 6.85 (s, 1 H) 5.74 (d, J = 9.00 Hz, 1 H) 4.90-4.98 (m, 1 H) 4.56 (s, 2 H) 2.83-2.91 (m, 2 H) 2.69 (d, J = 4.73 Hz, 3 H) 2.64 (s, 3 H) 2.27 (s, 3 H) 2.20-2.25 (m, 2 H) 1.91-2.00 (m, 4 H) 1.61-1.71 (m, 2 H) 1.44 (sxt, J = 7.36 Hz, 2 H) 0.86 (t, J = 7.36 Hz, 3 H). | C |
| 205 | 471 | 12.86 (s, 1 H) 7.92 (s, 1 H) 7.87 (q, J = 4.65 Hz, 1 H) 7.65 (s, 1 H) 6.85 (s, 1 H) 5.75 (d, J = 9.00 Hz, 1 H) 4.90-4.98 (m, 1 H) 4.55 (s, 2 H) 2.85-2.92 (m, 2 H) 2.69 (d, J = 4.65 Hz, 3 H) 2.64 (s, 3 H) 2.32 (q, J = 7.17 Hz, 2 H) 2.27 (s, 3 H) 1.92-1.99 (m, 4 H) 1.60-1.70 (m, 2 H) 1.00 (t, J = 7.17 Hz, 3 H). | C |
| 206 | 471 | 13.07 (s, 1 H) 7.96 (dq, J = 2.26, 0.85 Hz, 1 H) 7.93 (dd, J = 8.62, 2.26 Hz, 1 H) 7.90 (s, 1 H) 7.89 (q, J = 4.73 Hz, 1 H) 7.00 (d, J = 8.62 Hz, 1 H) 5.76 (d, J = 8.85 Hz, 1 H) 4.89-4.98 (m, 1 H) 4.57 (s, 2 H) 2.87-2.94 (m, 2 H) 2.68 (d, J = 4.73 Hz, 3 H) 2.32 (s, 3 H) 2.25-2.30 (m, 2 H) 2.03-2.10 (m, 2 H) 1.96-2.02 (m, 2 H) 1.61-1.70 (m, 2 H) 1.46 (sxt, J = 7.35 Hz, 2 H) 0.88 (t, J = 7.35 Hz, 3 H). | C |
| 207 | 471 | 13.11 (br. s., 1 H) 8.19 (q, J = 4.73 Hz, 1 H) 7.92 (s, 1 H) 7.84 (s, 2 H) 5.81 (d, J = 8.70 Hz, 1 H) 4.88-4.97 (m, 1 H) 4.25 (s, 2 H) 2.88-2.96 (m, 2 H) 2.72 (d, J = 4.73 Hz, 3 H) 2.37 (q, J = 7.17 Hz, 2 H) 2.31 (s, 6 H) 2.02-2.09 (m, 2 H) 1.96-2.02 (m, 2 H) 1.66 (qd, J = 11.57, 3.43 Hz, 2 H) 1.03 (t, J = 7.17 Hz, 3 H). | C |
| 208 | 511 | Mixture of cis and trans isomers: 13.11 (s, 2 H) 8.06-8.09 (m, 2 H) 8.05-8.08 (m, 2 H) 7.91 (s, 1 H) 7.90 (d, J = 8.24 Hz, 1 H) 7.82 (d, J = 7.63 Hz, 1 H) 7.08-7.13 (m, 4 H) 5.77 (d, J = 8.70 Hz, 1 H) 5.77 (d, J = 8.70 Hz, 1 H) 4.86-4.95 (m, 2 H) 4.60 (s, 2 H) 4.53 (s, 2 H) 3.78-3.85 (m, 1 H) 3.52-3.61 (m, 1 H) 2.77-2.86 (m, 4 H) 2.21 (s, 6 H) 2.02-2.11 (m, 4 H) 1.93-2.01 (m, 4 H) 1.72-1.79 (m, 2 H) 1.63-1.73 (m, 6 H) 1.57-1.64 (m, 2 H) 1.48-1.57 (m, 1 H) 1.42-1.52 (m, 3 H) 1.21-1.36 (m, 6 H) 0.93-1.01 (m, 2 H) 0.90 (d, J = 6.71 Hz, 3 H) 0.86 (d, J = 6.56 Hz, 3 H). | D |
| 209 | 471 | 13.10 (br. s., 1 H) 8.04-8.09 (m, 2 H) 7.91 (s, 1 H) 7.52 (s, 1 H) 7.07-7.12 (m, 2 H) 5.76 (d, J = 8.85 Hz, 1 H) 4.87-4.96 (m, 1 H) 4.49 (s, 2 H) 2.77-2.85 (m, 2 H) 2.21 (s, 3 H) 2.06 (td, J = 11.76, 2.27 Hz, 2 H) 1.93-2.01 (m, 2 H) 1.63-1.72 (m, 2 H) 1.30 (s, 9 H). | D |
| 210 | 485 | 13.11 (s, 1 H) 8.04-8.09 (m, 2 H) 7.91 (s, 1 H) 7.37 (s, 1 H) 7.07-7.12 (m, 2 H) 5.77 (d, J = 8.85 Hz, 1 H) 4.87-4.96 (m, 1 H) 4.51 (s, 2 H) 2.78-2.85 (m, 2 H) 2.21 (s, 3 H) 2.03-2.11 (m, 2 H) 1.94-2.00 (m, 2 H) 1.67 (q, J = 7.48 Hz, 2 H) 1.63-1.72 (m, 2 H) 1.24 (s, 6 H) 0.79 (t, J = 7.48 Hz, 3 H). | D |
| 211 | 497 | Mixture of conformers: 13.10 (br. s., 1 H) 8.05-8.09 (m, 2 H) 7.91 (s, 1 H) 7.91 (d, J = 8.09 Hz, 1 H) 7.09-7.13 (m, 2 H) 5.76 (d, J = 8.85 Hz, 1 H) 4.87-4.96 (m, 1 H) 4.54 (s, 2 H) 3.58-3.67 (m, 1 H) 2.77-2.85 (m, 2 H) 2.21 (s, 3 H) 2.02-2.11 (m, 2H) 1.93-2.01 (m, 2H) 1.63-1.77 (m, 6 H) 1.53-1.60 (m, 1 H) 1.20-1.33 (m, 4 H) 1.07-1.20 (m, 1 H). | D |
| 212 | 441 | 13.17 (br. s., 1 H) 8.03 (d, J = 8.2 Hz, 2 H) 7.93 (s, 1 H) 7.76 (q, J = 4.0 Hz, 1 H) 7.35 (d, J = 8.2 Hz, 2 H) 5.79 (d, J = 8.9 Hz, 1 H) 4.86-5.00 (m, 1 H) 2.92 (d, J = 11.9 Hz, 2 H) 2.87 (t, J = 7.8 Hz, 2 H) 2.56 (d, J = 4.6 Hz, 3 H) 2.40 (t, J = 7.8 Hz, 2 H) 2.36 (q, J = 7.0 Hz, 2 H) 2.04 (t, J = 11.7 Hz, 2 H) 1.99 (d, J = 11.6 Hz, 2 H) 1.65 (qd, J = 11.6, 3.7 Hz, 2 H) 1.03 (t, J = 7.3 Hz, 3 H). | C |
| 213 | 455 | 13.18 (br. s., 1 H) 8.03 (d, J = 8.2 Hz, 2 H) 7.93 (s, 1 H) 7.75 (q, J = 4.1 Hz, 1 H) 7.35 (d, J = 8.2 Hz, 2 H) 5.75 (d, J = 8.9 Hz, 1 H) 4.85-4.96 (m, 1 H) 2.87 (t, J = 7.6 Hz, 2 H) 2.85 (d, J = 11.8 Hz, 2 H) 2.72 (spt, J = 6.5 Hz, 1 H) 2.56 (d, J = 4.6 Hz, 3 H) 2.40 (t, J = 7.8 Hz, 2 H) 2.28 (td, J = 11.5, 1.7 Hz, 2 H) 2.00 (d, J = 10.4 Hz, 2 H) 1.62 (qd, J = 11.5, 3.7 Hz, 2 H) 1.01 (d, J = 6.7 Hz, 6 H). | C |
| 214 | 461 | 13.20 (br. s., 1 H) 8.02 (q, J = 4.6 Hz, 1 H) 7.93 (s, 1 H) 7.93 (dd, J = 12.2, 2.1 Hz, 1 H) 7.90 (dd, J = 8.7, 1.7 Hz, 1 H) 7.25 (t, J = 8.7 Hz, 1 H) 5.81 (d, J = 8.9 Hz, 1 H) 4.86-4.96 (m, 1 H) 4.65 (s, 2 H) 2.93 (d, J = 11.6 Hz, 2 H) 2.66 (d, J = 4.6 Hz, 3 H) 2.36 (q, J = 7.0 Hz, 2 H) 2.04 (td, J = 11.7, 1.8 Hz, 2 H) 1.99 (d, J = 11.6 Hz, 2 H) 1.65 (qd, J = 11.7, 3.8 Hz, 2 H) 1.03 (t, J = 7.2 Hz, 3 H). | C |
| 215 | 475 | 13.21 (br. s., 1 H) 8.01 (q, J = 4.6 Hz, 1 H) 7.94 (dd, J = 12.2, 1.8 Hz, 1 H) 7.93 (s, 1 H) 7.90 (dd, J = 8.5, 1.2 Hz, 1 H) 7.25 (t, J = 8.7 Hz, 1 H) 5.78 (d, J = 8.5 Hz, 1 H) 4.82-4.93 (m, 1 H) 4.66 (s, 2 H) 2.85 (d, J = 11.9 Hz, 2 H) 2.73 (spt, J = 6.6 Hz, 1 H) 2.66 (d, J = 4.9 Hz, 3 H) 2.28 (td, J = 11.5, 2.0 Hz, 2 H) 2.00 (d, J = 9.8 Hz, 2 H) 1.62 (qd, J = 11.6, 3.7 Hz, 2 H) 1.01 (d, J = 6.7 Hz, 6 H). | C |
| 216 | 471 | 13.14 (br. s., 1 H) 8.09 (q, J = 4.6 Hz, 1 H) 8.04 (d, J = 8.9 Hz, 2 H) 7.92 (s, 1 H) 7.00 (d, J = 8.9 Hz, 2 H) 5.75 (d, J = 8.9 Hz, 1 H) 4.87-4.98 (m, 1 H) 2.91 (d, J = 11.3 Hz, 2 H) 2.64 (d, J = 4.6 Hz, 3 H) 2.36 (q, J = 7.3 Hz, 2 H) 2.05 (td, J = 11.6, 1.5 Hz, 2 H) 1.99 (d, J = 11.9 Hz, 2 H) 1.65 (qd, J = 11.7, 3.7 Hz, 2 H) 1.47 (s, 6 H) 1.02 (t, J = 7.2 Hz, 3 H). | C |
| 217 | 485 | 13.13 (br. s., 1 H) 8.09 (q, J = 4.5 Hz, 1 H) 8.03 (d, J = 8.9 Hz, 2 H) 7.91 (s, 1 H) 7.00 (d, J = 8.9 Hz, 2 H) 5.70 (d, J = 8.9 Hz, 1 H) 4.84-4.93 (m, 1 H) 2.84 (d, J = 11.6 Hz, 2 H) 2.72 (spt, J = 6.5 Hz, 1 H) 2.64 (d, J = 4.6 Hz, 3 H) 2.27 (td, | C |

TABLE 2-continued

| Ex. | MS (ESI)+ m/z [M + H]+ | 1H NMR (600 MHz, DMSO-d6) δ ppm (unless otherwise stated) | GP |
|---|---|---|---|
| | | J = 11.3, 1.8 Hz, 2 H) 2.00 (d, J = 10.1 Hz, 2 H) 1.61 (qd, J = 11.5, 3.8 Hz, 2 H) 1.47 (s, 6 H) 1.00 (d, J = 6.7 Hz, 6 H). | |
| 218 | 473 | 13.15 (br. s., 1 H) 7.92 (s, 1 H) 7.89 (q, J = 4.6 Hz, 1 H) 7.82 (d, J = 2.1 Hz, 1 H) 7.68 (dd, J = 8.4, 2.0 Hz, 1 H) 7.05 (d, J = 8.5 Hz, 1 H) 5.84 (d, J = 8.5 Hz, 1 H) 4.90-5.01 (m, 1 H) 4.53 (s, 2 H) 3.90 (s, 3 H) 2.94 (d, J = 11.6 Hz, 2 H) 2.67 (d, J = 4.6 Hz, 3 H) 2.34 (q, J = 7.3 Hz, 2 H) 2.04 (t, J = 10.7 Hz, 2 H) 2.00 (d, J = 11.1 Hz, 2 H) 1.66 (qd, J = 11.7, 4.0 Hz, 2 H) 1.02 (t, J = 7.2 Hz, 3 H). | C |
| 219 | 487 | 13.15 (s, 1 H) 7.91 (s, 1 H) 7.89 (q, J = 4.6 Hz, 1 H) 7.83 (d, J = 1.8 Hz, 1 H) 7.67 (dd, J = 8.4, 2.0 Hz, 1 H) 7.05 (d, J = 8.5 Hz, 1 H) 5.81 (d, J = 8.5 Hz, 1 H) 4.88-4.97 (m, 1 H) 4.53 (s, 2 H) 3.90 (s, 3 H) 2.86 (d, J = 11.9 Hz, 2 H) 2.73 (spt, J = 6.6 Hz, 1 H) 2.67 (d, J = 4.6 Hz, 3 H) 2.30 (td, J = 11.5, 1.5 Hz, 2 H) 2.02 (d, J = 10.7 Hz, 2 H) 1.62 (qd, J = 11.6, 3.7 Hz, 2 H) 0.99 (d, J = 6.4 Hz, 6 H). | C |
| 220 | 457 | 13.11 (br. s., 1 H) 8.11 (t, J = 5.65 Hz, 1 H) 8.05-8.09 (m, 2 H) 7.91 (s, 1 H) 7.09-7.14 (m, 2 H) 5.77 (d, J = 8.54 Hz, 1 H) 4.87-4.95 (m, 1 H) 4.56 (s, 2 H) 3.10 (td, J = 7.27, 5.65 Hz, 2 H) 2.77-2.85 (m, 2 H) 2.21 (s, 3 H) 2.07 (td, J = 11.64, 2.06 Hz, 2 H) 1.93-2.00 (m, 2 H) 1.63-1.72 (m, 2 H) 1.42-1.49 (m, 2 H) 0.84 (t, J = 7.40 Hz, 3 H). | D |
| 221 | 471 | 13.11 (br. s., 1 H) 8.10 (t, J = 6.03 Hz, 1 H) 8.05-8.09 (m, 2 H) 7.91 (s, 1 H) 7.09-7.13 (m, 2 H) 5.77 (d, J = 8.70 Hz, 1 H) 4.87-4.96 (m, 1 H) 4.58 (s, 2 H) 2.97 (t, J = 6.49 Hz, 2 H) 2.77-2.85 (m, 2 H) 2.21 (s, 3 H) 2.03-2.10 (m, 2 H) 1.93-2.00 (m, 2 H) 1.71-1.78 (m, 1 H) 1.63-1.72 (m, 2 H) 0.83 (d, J = 6.71 Hz, 6 H). | D |
| 222 | 499 | 13.12 (br. s., 1 H) 8.12 (t, J = 5.95 Hz, 1 H) 8.05-8.10 (m, 2 H) 7.91 (s, 1 H) 7.09-7.14 (m, 2 H) 5.76 (d, J = 8.70 Hz, 1 H) 4.87-4.95 (m, 1 H) 4.56-4.63 (m, 2 H) 3.85-3.91 (m, 1 H) 3.74 (ddd, J = 8.10, 7.10, 6.20 Hz, 1 H) 3.61 (ddd, J = 7.35, 6.45 Hz, 1 H) 3.17-3.25 (m, 2 H) 2.78-2.85 (m, 2 H) 2.21 (s, 3 H) 2.06 (td, J = 11.60, 1.68 Hz, 2 H) 1.93-2.00 (m, 2 H) 1.73-1.89 (m, 3 H) 1.68 (qd, J = 11.70, 3.51 Hz, 2 H) 1.47-1.55 (m, 1 H). | D |
| 223 | 501 | 13.11 (br. s., 1 H) 8.05-8.09 (m, 2 H) 7.91 (s, 1 H) 7.86 (d, J = 8.70 Hz, 1 H) 7.09-7.13 (m, 2 H) 5.77 (d, J = 8.85 Hz, 1 H) 4.87-4.95 (m, 1 H) 4.55-4.62 (m, 2 H) 3.84-3.91 (m, 1 H) 3.34 (dd, J = 9.71, 6.11 Hz, 1 H) 3.28 (dd, J = 9.71, 5.35 Hz, 1 H) 3.25 (s, 3 H) 2.78-2.85 (m, 2 H) 2.21 (s, 3 H) 2.05 (td, J = 11.71, 2.21 Hz, 2 H) 1.93-2.00 (m, 2 H) 1.63-1.72 (m, 2 H) 1.49-1.58 (m, 1 H) 1.34-1.44 (m, 1 H) 0.83 (t, J = 7.40 Hz, 3 H). | D |
| 224 | 487 | 13.11 (br. s., 1 H) 8.05-8.10 (m, 3 H) 7.91 (s, 1 H) 7.08-7.13 (m, 2H) 5.76 (d, J = 8.09 Hz, 1 H) 4.87-4.96 (m, 1 H) 4.60 (s, 2 H) 3.36-3.41 (m, 1 H) 3.24 (s, 3 H) 3.13-3.22 (m, 2 H) 2.78-2.84 (m, 2 H) 2.21 (s, 3 H) 2.06 (td, J = 11.56, 1.60 Hz, 2 H) 1.93-2.00 (m, 2 H) 1.63-1.72 (m, 2 H) 1.03 (d, J = 6.26 Hz, 3 H). | D |
| 225 | 505 | 13.12 (br. s., 1 H) 8.68 (t, J = 6.18 Hz, 1 H) 8.06-8.10 (m, 2 H) 7.91 (s, 1 H) 7.28-7.33 (m, 2H) 7.24-7.28 (m, 2 H) 7.21-7.25 (m, 1 H) 7.11-7.15 (m, 2 H) 5.77 (d, J = 8.85 Hz, 1 H) 4.87-4.96 (m, 1 H) 4.66 (s, 2 H) 4.36 (d, J = 6.10 Hz, 2 H) 2.78-2.85 (m, 2 H) 2.21 (s, 3 H) 2.07 (td, J = 11.67, 1.83 Hz, 2 H) 1.94-2.01 (m, 2 H) 1.64-1.73 (m, 2 H). | D |
| 226 | 519 | 13.11 (br. s., 1 H) 8.54 (d, J = 8.09 Hz, 1 H) 8.04-8.09 (m, 2 H) 7.91 (s, 1 H) 7.29-7.35 (m, 4 H) 7.20-7.25 (m, 1 H) 7.08-7.12 (m, 2 H) 5.77 (d, J = 8.70 Hz, 1 H) 4.99-5.05 (m, 1 H) 4.87-4.96 (m, 1 H) 4.58-4.66 (m, 2 H) 2.78-2.85 (m, 2 H) 2.21 (s, 3 H) 2.07 (td, J = 11.63, 1.91 Hz, 2 H) 1.93-2.01 (m, 2 H) 1.63-1.73 (m, 2 H) 1.41 (d, J = 7.02 Hz, 3 H). | D |
| 227 | 511 | 13.10 (br. s., 1 H) 8.04-8.09 (m, 2 H) 7.96 (d, J = 8.09 Hz, 1 H) 7.91 (s, 1 H) 7.08-7.12 (m, 2 H) 5.75 (d, J = 7.78 Hz, 1 H) 4.87-4.95 (m, 1 H) 4.53 (s, 2 H) 3.78-3.85 (m, 1 H) 2.78-2.84 (m, 2 H) 2.21 (s, 3 H) 2.06 (td, J = 11.60, 1.83 Hz, 2 H) 1.94-2.00 (m, 2 H) 1.73-1.80 (m, 2 H) 1.63-1.72 (m, 2 H) 1.44-1.64 (m, 8 H) 1.35-1.44 (m, 2 H). | D |
| 228 | 519 | 13.23 (br. s., 1 H) 8.03 (s, 1 H) 7.92-7.96 (m, 2 H) 7.90 (dd, J = 8.5, 2.1 Hz, 1 H) 7.24 (t, J = 8.7 Hz, 1 H) 5.54 (d, J = 8.9 Hz, 1 H) 4.84-4.94 (m, 1 H) 4.63 (s, 2 H) 3.88-3.98 (m, 1 H) 2.80 (d, J = 11.3 Hz, 2 H) 2.21 (s, 3 H) 2.08 (t, J = 11.0 Hz, 2 H) 1.99 (d, J = 10.4 Hz, 2 H) 1.67 (qd, J = 11.5, 3.7 Hz, 2 H) 1.09 (d, J = 6.4 Hz, 6 H). | C |
| 229 | 475 | 13.19 (br. s., 1 H) 7.94 (d, J = 7.6 Hz, 1 H) 7.93 (s, 1 H) 7.93 (dd, J = 12.4, 2.0 Hz, 1 H) 7.90 (dd, J = 8.7, 1.7 Hz, 1 H) 7.23 (t, J = 8.7 Hz, 1 H) 5.82 (d, J = 7.9 Hz, 1 H) 4.84-4.94 (m, 1 H) 4.62 (s, 2 H) 3.88-3.99 (m, 1 H) 2.82 (d, J = 11.9 Hz, 2 H) 2.21 (s, 3 H) 2.06 (td, J = 11.6, 1.8 Hz, 2 H) 1.97 (d, J = 10.7 Hz, 2 H) 1.68 (qd, J = 11.6, 4.0 Hz, 2 H) 1.09 (d, J = 6.7 Hz, 6 H). | C |
| 230 | 489 | 13.20 (br. s., 1 H) 7.93 (s, 1 H) 7.91-7.95 (m, 2 H) 7.90 (dd, J = 8.5, 1.5 Hz, 1 H) 7.23 (t, J = 8.7 Hz, 1 H) 5.82 (d, J = 8.2 Hz, 1 H) 4.86-4.96 (m, 1 H) 4.62 (s, 2 H) 3.88-3.99 (m, 1 H) 2.92 (d, J = 11.6 Hz, 2 H) 2.36 (q, J = 7.0 Hz, 2 H) 2.04 (td, J = 11.6, 1.8 Hz, 2 H) 1.99 (d, J = 11.3 Hz, 2 H) 1.66 (qd, J = 11.6, 3.7 Hz, 2 H) 1.09 (d, J = 6.7 Hz, 6 H) 1.02 (t, J = 7.2 Hz, 3 H). | C |
| 231 | 503 | 13.19 (br. s., 1 H) 7.93 (s, 1 H) 7.92-7.95 (m, 2 H) 7.89 (dd, J = 8.5, 1.5 Hz, 1 H) 7.23 (t, J = 8.7 Hz, 1 H) 5.79 (d, J = 8.5 Hz, 1 H) 4.83-4.93 (m, 1 H) 4.63 (s, 2 H) 3.87-3.99 (m, 1 H) 2.85 (d, J = 11.9 Hz, 2 H) 2.73 (spt, J = 6.6 Hz, 1 H) 2.28 (td, J = 11.6, 2.1 Hz, 2 H) 2.00 (d, J = 11.0 Hz, 2 H) 1.62 (qd, J = 11.5, 3.5 Hz, 2 H) 1.09 (d, J = 6.4 Hz, 6 H) 1.00 (d, J = 6.4 Hz, 6 H). | C |
| 232 | 413 | 13.21 (br. s., 1 H) 8.05 (d, J = 8.5 Hz, 2 H) 7.97 (q, J = 4.2 Hz, 1 H) 7.93 (s, 1 H) 7.40 (d, J = 8.2 Hz, 2 H) 5.82 (d, J = 8.9 Hz, 1 H) 4.87-4.97 (m, 1 H) 3.47 (s, 2 H) | C |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| | | 2.81 (d, J = 11.3 Hz, 2 H) 2.59 (d, J = 4.9 Hz, 3 H) 2.21 (s, 3 H) 2.02-2.11 (m, 2 H) 1.97 (dd, J = 11.3, 1.8 Hz, 2 H) 1.68 (dq, J = 11.8, 11.6, 3.7 Hz, 2 H). | |
| 233 | 519 | 13.20 (br. s., 1 H) 8.04 (d, J = 8.2 Hz, 2 H) 7.95-8.00 (m, 1 H) 7.93 (s, 1 H) 7.40 (d, J = 8.2 Hz, 2 H) 7.24 (d, J = 8.5 Hz, 2 H) 6.89 (d, J = 8.5 Hz, 2 H) 5.82 (d, J = 8.9 Hz, 1 H) 4.92-5.01 (m, 1 H) 3.74 (s, 3 H) 3.47 (s, 2 H) 3.45 (s, 2 H) 2.86 (d, J = 11.6 Hz, 2 H) 2.60 (d, J = 4.6 Hz, 3 H) 2.12 (td, J = 11.8, 2.0 Hz, 2 H) 1.98 (dd, J = 11.9, 2.4 Hz, 2 H) 1.67 (qd, J = 11.6, 3.4 Hz, 2 H). | C |
| 234 | 589 | 13.11 (br. s., 1 H) 8.04-8.08 (m, 2 H) 8.01 (d, J = 7.63 Hz, 1 H) 7.91 (s, 1 H) 7.21-7.26 (m, 2 H) 7.08-7.13 (m, 2 H) 6.87-6.91 (m, 2 H) 5.76 (d, J = 9.16 Hz, 1 H) 4.91-5.00 (m, 1 H) 4.54 (s, 2 H) 4.09 (s × t, J = 6.99 Hz, 1 H) 3.74 (s, 3 H) 3.44 (s, 2 H) 2.81-2.89 (m, 2 H) 2.08-2.15 (m, 2 H) 1.94-2.01 (m, 2 H) 1.79-1.86 (m, 2 H) 1.60-1.71 (m, 4 H) 1.48-1.56 (m, 2 H) 1.41-1.49 (m, 2 H). | D |
| 235 | 617 | 13.11 (br. s., 1 H) 8.04-8.10 (m, 3 H) 7.91 (s, 1 H) 7.21-7.25 (m, 2H) 7.08-7.13 (m, 2 H) 6.87-6.91 (m, 2 H) 5.77 (d, J = 9.00 Hz, 1 H) 4.91-4.99 (m, 1 H) 4.58 (s, 2 H) 3.74 (s, 3 H) 3.44 (s, 2 H) 2.99 (t, J = 6.41 Hz, 2 H) 2.81-2.89 (m, 2 H) 2.07-2.14 (m, 2 H) 1.94-2.01 (m, 2 H) 1.54-1.71 (m, 7 H) 1.38-1.47 (m, 1 H) 1.05-1.20 (m, 3 H) 0.80-0.90 (m, 2 H). | D |
| 236 | 617 | 13.10 (br. s., 1 H) 8.03-8.08 (m, 2 H) 7.96 (d, J = 8.09 Hz, 1 H) 7.90 (s, 1 H) 7.21-7.25 (m, 2 H) 7.07-7.13 (m, 2 H) 6.87-6.92 (m, 2 H) 5.76 (d, J = 8.85 Hz, 1 H) 4.90-5.00 (m, 1 H) 4.54 (s, 2 H) 3.78-3.86 (m, 1 H) 3.74 (s, 3 H) 3.44 (s, 2 H) 2.81-2.90 (m, 2 H) 2.07-2.15 (m, 2 H) 1.93-2.02 (m, 2 H) 1.73-1.81 (m, 2 H) 1.44-1.72 (m, 10 H) 1.36-1.44 (m, 2 H). | D |
| 237 | 631 | 13.12 (s, 1 H) 8.05-8.09 (m, 2 H) 8.05 (t, J = 5.86 Hz, 1 H) 7.91 (s, 1 H) 7.21-7.25 (m, 2 H) 7.08-7.12 (m, 2 H) 6.87-6.91 (m, 2 H) 5.77 (d, J = 8.85 Hz, 1 H) 4.91-4.99 (m, 1 H) 4.56 (s, 2 H) 3.74 (s, 3 H) 3.44 (s, 2 H) 3.16 (td, J = 7.10, 5.86 Hz, 2 H) 2.81-2.89 (m, 2 H) 2.07-2.15 (m, 2 H) 1.94-2.01 (m, 2 H) 1.58-1.71 (m, 6 H) 1.52-1.58 (m, 1 H) 1.32 (q, J = 7.10 Hz, 2 H) 1.03-1.25 (m, 4 H) 0.78-0.88 (m, 2 H). | D |
| 238 | 633 | 13.12 (br. s., 1 H) 8.05-8.10 (m, 3 H) 7.91 (s, 1 H) 7.21-7.25 (m, 2 H) 7.09-7.13 (m, 2 H) 6.87-6.91 (m, 2 H) 5.76 (d, J = 8.85 Hz, 1 H) 4.91-4.99 (m, 1 H) 4.57 (s, 2 H) 3.74-3.79 (m, 2 H) 3.74 (s, 3 H) 3.44 (s, 2 H) 3.15-3.21 (m, 4 H) 2.82-2.89 (m, 2 H) 2.08-2.15 (m, 2 H) 1.94-2.01 (m, 2 H) 1.61-1.71 (m, 2 H) 1.50-1.56 (m, 2 H) 1.36-1.44 (m, 1 H) 1.34-1.39 (m, 2 H) 1.05-1.14 (m, 2H). | D |
| 239 | 535 | 13.12 (br. s., 1 H) 8.60 (t, J = 6.10 Hz, 1 H) 8.06-8.09 (m, 2 H) 7.91 (s, 1 H) 7.17-7.20 (m, 2 H) 7.11-7.14 (m, 2 H) 6.84-6.88 (m, 2 H) 5.77 (d, J = 8.55 Hz, 1 H) 4.87-4.96 (m, 1 H) 4.63 (s, 2 H) 4.28 (d, J = 5.95 Hz, 2 H) 3.71 (s, 3 H) 2.78-2.84 (m, 2 H) 2.21 (s, 3 H) 2.07 (td, J = 11.64, 2.06 Hz, 2 H) 1.94-2.00 (m, 2 H) 1.63-1.73 (m, 2 H). | D |
| 240 | 495 | 13.12 (br. s., 2 H) 8.63 (t, J = 5.80 Hz, 1 H) 8.05-8.10 (m, 2 H) 7.91 (s, 1 H) 7.57 (dd, J = 1.83, 0.86 Hz, 1 H) 7.09-7.14 (m, 2 H) 6.39 (dd, J = 3.20, 1.83 Hz, 1 H) 6.24 (dq, J = 3.20, 0.86 Hz, 1 H) 5.76 (d, J = 8.85 Hz, 1 H) 4.87-4.96 (m, 1 H) 4.62 (s, 2 H) 4.35 (d, J = 5.80 Hz, 2 H) 2.77-2.85 (m, 2 H) 2.21 (s, 3 H) 2.02-2.11 (m, 2 H) 1.93-2.01 (m, 2 H) 1.63-1.73 (m, 2 H). | D |
| 241 | 511 | 13.12 (br. s., 1 H) 8.78 (t, J = 6.03 Hz, 1 H) 8.05-8.09 (m, 2 H) 7.91 (s, 1 H) 7.39 (dd, J = 5.04, 1.33 Hz, 1 H) 7.10-7.14 (m, 2 H) 6.97-6.99 (ddt, J = 3.41, 1.33, 0.88, 0.88 Hz, 1 H) 6.95 (dd, J = 5.04, 3.41 Hz, 1 H) 5.77 (d, J = 8.85 Hz, 1 H) 4.87-4.95 (m, 1 H) 4.62 (s, 2 H) 4.51 (d, J = 6.03 Hz, 2 H) 2.78-2.85 (m, 2 H) 2.21 (s, 3 H) 2.07 (td, J = 11.48, 1.75 Hz, 2 H) 1.94-2.00 (m, 2 H) 1.63-1.72 (m, 2 H). | D |
| 242 | 473 | 13.12 (br. s., 1 H) 8.15 (t, J = 5.57 Hz, 1 H) 8.05-8.10 (m, 2 H) 7.91 (s, 1 H) 7.09-7.14 (m, 2 H) 5.77 (d, J = 8.85 Hz, 1 H) 4.87-4.95 (m, 1 H) 4.57 (s, 2 H) 3.39 (t, J = 5.95 Hz, 2 H) 3.31 (td, J = 5.95, 5.57 Hz, 2 H) 3.25 (s, 3 H) 2.77-2.85 (m, 2 H) 2.21 (s, 3 H) 2.06 (td, J = 11.70, 1.53 Hz, 2 H) 1.94-2.00 (m, 2 H) 1.68 (qd, J = 11.70, 3.66 Hz, 2 H) | D |
| 243 | 492 | 13.13 (br. s., 1 H) 10.53 (s, 1 H) 8.44-8.47 (m, 2 H) 8.07-8.11 (m, 2 H) 7.91 (s, 1 H) 7.61-7.65 (m, 2 H) 7.14-7.19 (m, 2 H) 5.76 (d, J = 9.00 Hz, 1 H) 4.87-4.95 (m, 1 H) 4.86 (s, 2 H) 2.77-2.84 (m, 2 H) 2.21 (s, 3 H) 2.07 (td, J = 11.60, 1.53 Hz, 2 H) 1.93-2.00 (m, 2 H) 1.63-1.72 (m, 2 H). | D |
| 244 | 427 | 13.21 (br. s., 1 H) 8.05 (d, J = 8.2 Hz, 2 H) 7.97 (q, J = 4.6 Hz, 1 H) 7.93 (s, 1 H) 7.40 (d, J = 8.5 Hz, 2 H) 5.81 (d, J = 8.9 Hz, 1 H) 4.88-4.98 (m, 1 H) 3.46 (s, 2 H) 2.92 (d, J = 11.6 Hz, 2 H) 2.59 (d, J = 4.9 Hz, 3 H) 2.36 (q, J = 7.2 Hz, 2 H) 2.05 (td, J = 11.9, 2.1 Hz, 2H) 1.99 (d, J = 11.3 Hz, 2 H) 1.66 (dq, J = 11.9, 11.6, 3.7 Hz, 2 H) 1.03 (t, J = 7.2 Hz, 3 H). | C |
| 245 | 441 | 13.21 (s, 1 H) 8.05 (d, J = 8.2 Hz, 2 H) 7.97 (q, J = 4.5 Hz, 1 H) 7.93 (s, 1 H) 7.40 (d, J = 8.2 Hz, 2 H) 5.77 (d, J = 8.9 Hz, 1 H) 4.78-5.03 (m, 1 H) 3.46 (s, 2 H) 2.85 (d, J = 11.3 Hz, 2 H) 2.73 (spt, 1 H) 2.59 (d, J = 4.6 Hz, 3 H) 2.29 (td, J = 11.7, 1.8 Hz, 2 H) 2.01 (d, J = 11.0 Hz, 2 H) 1.62 (qd, J = 11.5, 3.5 Hz, 2 H) 1.01 (d, J = 6.4 Hz, 6 H). | C |
| 246 | 441 | 13.21 (br. s., 1 H) 8.05 (d, J = 8.5 Hz, 2 H) 7.97 (q, J = 4.3 Hz, 1 H) 7.93 (s, 1 H) 7.40 (d, J = 8.2 Hz, 2 H) 5.81 (d, J = 9.2 Hz, 1 H) 4.88-4.99 (m, 1 H) 3.46 (s, 2 H) 2.90 (d, J = 11.6 Hz, 2 H) 2.59 (d, J = 4.6 Hz, 3 H) 2.27 (t, J = 2 H) 2.06 (td, J = 11.7, 1.7 Hz, 2 H) 1.99 (d, J = 11.3 Hz, 2 H) 1.66 (qd, J = 11.7, 3.4 Hz, 2 H) 1.46 (s × t, J = 7.4 Hz, 2 H) 0.87 (t, J = 7.3 Hz, 3 H). | C |
| 247 | 485 | 13.24 (br. s., 1 H) 8.05 (d, J = 8.2 Hz, 2 H) 8.03 (s, 1 H) 7.93-7.99 (m, 1 H) 7.40 (d, J = 8.2 Hz, 2 H) 5.52 (d, J = 8.5 Hz, 1 H) 4.89-5.00 (m, 1 H) 3.46 (s, 2 H) | C |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
|  |  | 2.88 (d, J = 11.6 Hz, 2 H) 2.59 (d, J = 4.9 Hz, 3 H) 2.27 (t, 2 H) 2.08 (t, J = 11.3 Hz, 2 H) 2.01 (dd, J = 12.2, 2.7 Hz, 2 H) 1.65 (qd, J = 11.5, 3.7 Hz, 2 H) 1.46 (s × t, J = 7.4, 7.2 Hz, 2 H) 0.87 (t, J = 7.3 Hz, 3 H). |  |
| 248 | 485 | 13.23 (br. s., 1 H) 8.05 (d, J = 8.2 Hz, 2 H) 8.03 (s, 1 H) 7.96 (q, J = 4.4 Hz, 1 H) 7.40 (d, J = 8.2 Hz, 2 H) 5.48 (d, J = 8.5 Hz, 1 H) 4.84-4.99 (m, 1 H) 3.46 (s, 2 H) 2.84 (d, J = 11.9 Hz, 2 H) 2.73 (spt, 1 H) 2.59 (d, J = 4.6 Hz, 3 H) 2.30 (td, J = 11.4, 2.0 Hz, 2 H) 2.02 (dd, J = 12.4, 2.6 Hz, 2 H) 1.60 (qd, J = 11.5, 3.8 Hz, 2 H) 1.01 (d, J = 6.7 Hz, 6 H). | C |
| 249 | 457 | 13.24 (br. s., 1 H) 8.06 (d, J = 8.2 Hz, 2 H) 8.03 (s, 1 H) 7.93-8.00 (m, 1 H) 7.40 (d, J = 8.2 Hz, 2 H) 5.53 (d, J = 8.5 Hz, 1 H) 4.87-4.99 (m, 1 H) 3.47 (s, 2 H) 2.79 (d, J = 11.6 Hz, 2 H) 2.59 (d, J = 4.6 Hz, 3 H) 2.21 (s, 3 H) 2.09 (td, J = 11.6, 1.8 Hz, 2 H) 1.99 (d, J = 11.3 Hz, 2 H) 1.60-1.72 (m, J = 11.6, 11.4, 11.4, 3.7 Hz, 2 H). | C |
| 250 | 565 | 13.10 (br. s., 1 H) 8.03-8.09 (m, 2 H) 8.02 (d, J = 7.48 Hz, 1 H) 7.91 (s, 1 H) 7.44 (dd, J = 4.04, 2.21 Hz, 1 H) 7.07-7.12 (m, 2 H) 6.97-7.00 (m, 2 H) 5.81 (d, J = 9.00 Hz, 1 H) 4.93-5.01 (m, 1 H) 4.54 (s, 2 H) 4.09 (s × t, J = 7.02 Hz, 1 H) 3.74 (s, 2 H) 2.90-2.96 (m, 2 H) 2.15-2.21 (m, 2 H) 1.96-2.02 (m, 2 H) 1.79-1.86 (m, 2 H) 1.65-1.74 (m, 2 H) 1.61-1.70 (m, 2 H) 1.47-1.56 (m, 2 H) 1.41-1.48 (m, 2 H). | D |
| 251 | 579 | 13.10 (br. s., 1 H) 8.04-8.08 (m, 2 H) 7.92 (d, J = 8.09 Hz, 1 H) 7.90 (s, 1 H) 7.44 (dd, J = 4.04, 2.21 Hz, 1 H) 7.07-7.12 (m, 2 H) 6.97-7.00 (m, 2 H) 5.80 (br. s., 1 H) 4.92-5.02 (m, 1 H) 4.54 (s, 2 H) 3.74 (s, 2 H) 3.59-3.67 (m, 1 H) 2.89-2.96 (m, 2 H) 2.14-2.22 (m, 2 H) 1.95-2.02 (m, 2 H) 1.63-1.78 (m, 6 H) 1.53-1.60 (m, 1 H) 1.21-1.33 (m, 4 H) 1.07-1.18 (m, 1 H). | D |
| 252 | 501 | 13.14 (br. s., 1 H) 8.05-8.09 (m, 2 H) 8.01 (s, 1 H) 7.92 (d, J = 7.78 Hz, 1 H) 7.10-7.14 (m, 2 H) 5.48 (d, J = 8.85 Hz, 1 H) 4.88-4.97 (m, 1 H) 4.53 (s, 2 H) 3.91-4.00 (m, 1 H) 2.74-2.84 (m, 2 H) 2.21 (s, 3 H) 2.05-2.12 (m, 2 H) 1.96-2.02 (m, 2 H) 1.61-1.70 (m, 2 H) 1.10 (d, J = 6.71 Hz, 6 H). | D |
| 253 | 501 | 13.14 (br. s., 1 H) 8.11 (t, J = 5.91 Hz, 1 H) 8.06-8.10 (m, 2 H) 8.01 (s, 1 H) 7.10-7.14 (m, 2 H) 5.48 (d, J = 8.85 Hz, 1 H) 4.88-4.97 (m, 1 H) 4.56 (s, 2 H) 3.10 (td, J = 6.80, 5.91 Hz, 2 H) 2.75-2.83 (m, 2 H) 2.21 (s, 3 H) 2.05-2.13 (m, 2 H) 1.96-2.02 (m, 2 H) 1.62-1.70 (m, 2 H) 1.41-1.49 (m, J = 7.44, 7.44, 7.44, 6.80, 6.80 Hz, 2 H) 0.84 (t, J = 7.44 Hz, 3 H). | D |
| 254 | 545 | 13.14 (br. s., 1 H) 8.05-8.10 (m, 2 H) 8.01 (s, 1 H) 7.86 (d, J = 8.70 Hz, 1 H) 7.08-7.13 (m, 2 H) 5.48 (d, J = 8.39 Hz, 1 H) 4.88-4.97 (m, 1 H) 4.55-4.62 (m, 2 H) 3.84-3.92 (m, 1 H) 3.34 (dd, J = 9.60, 6.26 Hz, 1 H) 3.28 (dd, J = 9.60, 5.34 Hz, 1 H) 3.25 (s, 3 H) 2.76-2.84 (m, 2 H) 2.21 (s, 3 H) 2.04-2.12 (m, 2 H) 1.95-2.02 (m, 2 H) 1.61-1.70 (m, 2 H) 1.49-1.58 (m, 1 H) 1.34-1.43 (m, 1 H) 0.83 (t, J = 7.40 Hz, 3 H). | D |
| 255 | 515 | 13.13 (br. s., 1 H) 8.10 (t, J = 6.56 Hz, 1 H) 8.05-8.09 (m, 2 H) 8.01 (s, 1 H) 7.10-7.14 (m, 2 H) 5.48 (d, J = 8.85 Hz, 1 H) 4.88-4.97 (m, 1 H) 4.58 (s, 2 H) 2.97 (t, J = 6.49 Hz, 2 H) 2.76-2.82 (m, 2 H) 2.21 (s, 3 H) 2.05-2.12 (m, 2 H) 1.96-2.02 (m, 2 H) 1.70-1.78 (m, 1 H) 1.61-1.70 (m, 2 H) 0.83 (d, J = 6.71 Hz, 6 H). | D |
| 256 | 515 | 13.13 (br. s., 1 H) 8.05-8.09 (m, 2 H) 8.01 (s, 1 H) 7.52 (s, 1 H) 7.07-7.12 (m, 2 H) 5.48 (d, J = 8.70 Hz, 1 H) 4.88-4.97 (m, 1 H) 4.49 (s, 2 H) 2.76-2.82 (m, 2 H) 2.21 (s, 3 H) 2.05-2.12 (m, 2 H) 1.96-2.02 (m, 2 H) 1.62-1.70 (m, 2 H) 1.30 (s, 9 H). | D |
| 257 | 529 | 13.13 (br. s., 1 H) 8.04-8.09 (m, 2 H) 8.00 (s, 1 H) 7.37 (s, 1 H) 7.07-7.11 (m, 2 H) 5.48 (d, J = 8.54 Hz, 1 H) 4.88-4.96 (m, 1 H) 4.51 (s, 2 H) 2.75-2.83 (m, 2 H) 2.21 (s, 3 H) 2.05-2.12 (m, 2 H) 1.96-2.02 (m, 2 H) 1.67 (q, J = 7.48 Hz, 2 H) 1.62-1.69 (m, 2 H) 1.24 (s, 6 H) 0.79 (t, J = 7.48 Hz, 3 H). | D |
| 258 | 541 | 13.13 (br. s., 1 H) 8.05-8.09 (m, 2 H) 8.01 (s, 1 H) 7.91 (d, J = 8.24 Hz, 1 H) 7.09-7.13 (m, 2 H) 5.48 (d, J = 9.00 Hz, 1 H) 4.88-4.96 (m, 1 H) 4.54 (s, 2 H) 3.58-3.67 (m, 1 H) 2.75-2.84 (m, 2 H) 2.21 (s, 3 H) 2.05-2.13 (m, 2 H) 1.95-2.02 (m, 2 H) 1.62-1.78 (m, 6 H) 1.53-1.60 (m, 1 H) 1.19-1.32 (m, 4 H) 1.07-1.18 (m, 1 H). | D |
| 259 | 527 | 13.12 (br. s., 1 H) 8.05-8.10 (m, 2 H) 8.00 (s, 1 H) 8.01 (d, J = 7.30 Hz, 1 H) 7.08-7.13 (m, 2 H) 5.47 (d, J = 8.85 Hz, 1 H) 4.88-4.97 (m, 1 H) 4.53 (s, 2 H) 4.04-4.12 (m, 1 H) 2.75-2.83 (m, 2 H) 2.21 (s, 3 H) 2.05-2.13 (m, 2 H) 1.96-2.02 (m, 2 H) 1.78-1.86 (m, 2 H) 1.61-1.70 (m, 4 H) 1.47-1.55 (m, 2 H) 1.39-1.49 (m, 2 H). | D |
| 260 | 487 | 13.14 (br. s., 1 H) 8.13 (t, J = 5.95 Hz, 1 H) 8.06-8.10 (m, 2 H) 8.01 (s, 1 H) 7.10-7.15 (m, 2 H) 5.48 (d, J = 8.70 Hz, 1 H) 4.88-4.97 (m, 1 H) 4.54 (s, 2 H) 3.17 (qd, J = 7.20, 5.95 Hz, 2 H) 2.74-2.83 (m, 2 H) 2.21 (s, 3 H) 2.05-2.13 (m, 2 H) 1.95-2.02 (m, 2 H) 1.62-1.70 (m, 2 H) 1.05 (t, J = 7.20 Hz, 3 H). | D |
| 261 | 515 | 13.09 (br. s., 1 H) 8.10 (d, J = 8.24 Hz, 1 H) 8.05-8.08 (m, 2 H) 7.91 (s, 1 H) 7.09-7.13 (m, 2 H) 5.76 (d, J = 8.85 Hz, 1 H) 4.87-4.95 (m, 1 H) 4.55 (s, 2 H) 3.70 (tdt, J = 10.99, 8.24, 3.51 Hz, 1 H) 2.77-2.84 (m, 2 H) 2.60-2.71 (m, 4 H) 2.21 (s, 3 H) 2.03-2.11 (m, 2 H) 1.93-2.03 (m, 4 H) 1.68 (qd, J = 11.65, 3.97 Hz, 2 H) 1.55-1.64 (m, 2 H). | D |
| 262 | 499 | 13.10 (br. s., 1 H) 8.05-8.10 (m, 3 H) 7.91 (s, 1 H) 7.10-7.14 (m, 2 H) 5.76 (d, J = 9.00 Hz, 1 H) 4.87-4.96 (m, 1 H) 4.56 (s, 2 H) 3.83-3.91 (m, 1 H) 3.80-3.86 (m, 2 H) 3.35 (td, J = 11.67, 2.14 Hz, 2 H) 2.77-2.85 (m, 2 H) 2.21 (s, 3 H) 2.02-2.11 (m, 2H) 1.94-2.00 (m, 2H) 1.63-1.73 (m, 4H) 1.46-1.55 (m, 2 H). | D |

TABLE 2-continued

| Ex. | MS (ESI)+ m/z [M + H]+ | $^1H$ NMR (600 MHz, DMSO-d$_6$) δ ppm (unless otherwise stated) | GP |
|---|---|---|---|
| 263 | 497 | 13.12 (br. s., 1 H) 8.81 (t, J = 6.50 Hz, 1 H) 8.05-8.10 (m, 2 H) 7.91 (s, 1 H) 7.10-7.14 (m, 2 H) 5.77 (d, J = 8.85 Hz, 1 H) 4.87-4.95 (m, 1 H) 4.70 (s, 2 H) 3.98 (qd, J = 9.69, 6.50 Hz, 2 H) 2.77-2.85 (m, 2 H) 2.21 (s, 3 H) 2.07 (td, J = 11.67, 1.83 Hz, 2 H) 1.94-2.00 (m, 2 H) 1.63-1.73 (m, 2 H). | D |
| 264 | 549 | 13.10 (br. s., 1 H) 8.13 (t, J = 5.72 Hz, 1 H) 8.03-8.08 (m, 2 H) 7.90 (s, 1 H) 7.22-7.26 (m, 2 H) 7.09-7.13 (m, 2 H) 6.87-6.92 (m, 2 H) 5.75 (d, J = 9.00 Hz, 1 H) 4.92-5.00 (m, 1 H) 4.07 (t, J = 5.72 Hz, 2 H) 3.74 (s, 3 H) 3.44 (s, 2 H) 3.44 (q, J = 5.72 Hz, 2 H) 2.82-2.89 (m, 2 H) 2.07-2.15 (m, 2 H) 1.94-2.01 (m, 2 H) 1.84 (s, 3 H) 1.66 (qd, J = 11.65, 3.66 Hz, 2 H). | C |
| 265 | 443 | 13.10 (br. s., 1 H) 8.13 (t, J = 5.72 Hz, 1 H) 8.04-8.09 (m, 2 H) 7.91 (s, 1 H) 7.09-7.13 (m, 2 H) 5.75 (d, J = 8.85 Hz, 1 H) 4.87-4.95 (m, 1 H) 4.06 (t, J = 5.72 Hz, 2 H) 3.43 (q, J = 5.72 Hz, 2 H) 2.78-2.84 (m, 2 H) 2.21 (s, 3 H) 2.03-2.10 (m, 2 H) 1.94-2.00 (m, 2 H) 1.84 (s, 3 H) 1.63-1.72 (m, 2 H). | C |
| 266 | 487 | 13.13 (br. s., 1 H) 8.13 (t, J = 5.72 Hz, 1 H) 8.05-8.10 (m, 2 H) 8.00 (s, 1 H) 7.09-7.13 (m, 2 H) 5.47 (d, J = 8.70 Hz, 1 H) 4.88-4.96 (m, 1 H) 4.06 (t, J = 5.72 Hz, 2 H) 3.43 (q, J = 5.72 Hz, 2 H) 2.75-2.83 (m, 2 H) 2.21 (s, 3 H) 2.05-2.12 (m, 2 H) 1.96-2.02 (m, 2 H) 1.84 (s, 3 H) 1.61-1.70 (m, 2 H). | C |
| 267 | 471 | 13.10 (br. s., 1 H) 8.12 (t, J = 5.72 Hz, 1 H) 8.04-8.09 (m, 2 H) 7.91 (s, 1 H) 7.08-7.13 (m, 2 H) 5.70 (d, J = 8.85 Hz, 1 H) 4.85-4.94 (m, 1 H) 4.06 (t, J = 5.72 Hz, 2 H) 3.43 (q, J = 5.72 Hz, 2 H) 2.82-2.88 (m, 2 H) 2.72 (spt, J = 6.56 Hz, 1 H) 2.28 (td, J = 11.56, 1.91 Hz, 2 H) 1.96-2.04 (m, 2 H) 1.84 (s, 3 H) 1.56-1.66 (m, 2 H) 1.01 (d, J = 6.56 Hz, 6 H). | C |
| 268 | 511 | 13.10 (br. s., 1 H) 8.04-8.08 (m, 2 H) 7.94 (t, J = 5.57 Hz, 1 H) 7.91 (s, 1 H) 7.08-7.13 (m, 2 H) 5.75 (d, J = 9.00 Hz, 1 H) 4.86-4.96 (m, 1 H) 4.05 (t, J = 5.85 Hz, 2 H) 3.42 (td, J = 5.85, 5.57 Hz, 2 H) 2.77-2.85 (m, 2 H) 2.21 (s, 3 H) 2.12 (tt, J = 11.60, 3.28 Hz, 1 H) 2.03-2.09 (m, 2 H) 1.93-2.01 (m, 2 H) 1.63-1.73 (m, 6 H) 1.56-1.63 (m, 1 H) 1.28-1.37 (m, 2 H) 1.09-1.25 (m, 3 H). | E |
| 269 | 485 | 13.10 (br. s., 1 H) 8.04-8.08 (m, 2 H) 7.91 (s, 1 H) 7.69 (t, J = 5.57 Hz, 1 H) 7.09-7.13 (m, 2 H) 5.76 (d, J = 8.70 Hz, 1 H) 4.87-4.95 (m, 1 H) 4.07 (t, J = 6.18 Hz, 2 H) 3.43 (td, J = 6.18, 5.57 Hz, 2 H) 2.78-2.84 (m, 2 H) 2.21 (s, 3 H) 2.02-2.10 (m, 2 H) 1.94-2.00 (m, 2 H) 1.63-1.73 (m, 2 H) 1.09 (s, 9 H). | E |
| 270 | 536 | 13.16 (br. s., 1 H) 10.53 (s, 1 H) 8.44-8.47 (m, 2 H) 8.07-8.11 (m, 2 H) 8.01 (s, 1 H) 7.61-7.65 (m, 2 H) 7.15-7.19 (m, 2 H) 5.47 (d, J = 8.70 Hz, 1 H) 4.88-4.96 (m, 1 H) 4.86 (s, 2 H) 2.75-2.82 (m, 2 H) 2.21 (s, 3 H) 2.05-2.13 (m, 2 H) 1.96-2.02 (m, 2 H) 1.61-1.70 (m, 2 H). | D |
| 271 | 525 | 13.10 (br. s., 1 H) 8.04-8.09 (m, 2 H) 7.91 (s, 1 H) 7.91 (d, J = 7.77 Hz, 1 H) 7.08-7.13 (m, 2 H) 5.71 (d, J = 8.70 Hz, 1 H) 4.85-4.94 (m, 1 H) 4.54 (s, 2 H) 3.58-3.67 (m, 1 H) 2.81-2.88 (m, 2 H) 2.72 (spt, J = 6.59 Hz, 1 H) 2.28 (td, J = 11.56, 2.21 Hz, 2 H) 1.97-2.04 (m, 2 H) 1.65-1.77 (m, 4 H) 1.56-1.65 (m, 2 H) 1.53-1.59 (m, 1 H) 1.19-1.32 (m, 4 H) 1.06-1.17 (m, 1 H) 1.01 (d, J = 6.56 Hz, 6 H). | D |
| 272 | 506 | 13.10 (br. s., 1 H) 9.04 (t, J = 5.42 Hz, 1 H) 8.71-8.75 (m, 2 H) 8.05-8.09 (m, 2 H) 7.91 (s, 1 H) 7.75-7.79 (m, 2 H) 7.12-7.16 (m, 2 H) 5.75 (d, J = 8.85 Hz, 1 H) 4.87-4.95 (m, 1 H) 4.23 (t, J = 5.80 Hz, 2 H) 3.69 (td, J = 5.80, 5.42 Hz, 2 H) 2.77-2.84 (m, 2 H) 2.21 (s, 3 H) 2.06 (td, J = 11.47, 1.93 Hz, 2 H) 1.94-2.00 (m, 2 H) 1.63-1.72 (m, 2 H). | E |
| 273 | 506 | 13.10 (br. s., 1 H) 9.02 (dd, J = 2.28, 0.80 Hz, 1 H) 8.95 (t, J = 5.51 Hz, 1 H) 8.71 (dd, J = 4.80, 1.69 Hz, 1 H) 8.21 (ddd, J = 7.95, 2.28, 1.69 Hz, 1 H) 8.05-8.10 (m, 2 H) 7.90 (s, 1 H) 7.51 (ddd, J = 7.95, 4.80, 0.80 Hz, 1 H) 7.12-7.17 (m, 2 H) 5.75 (d, J = 8.55 Hz, 1 H) 4.86-4.95 (m, 1 H) 4.23 (t, J = 5.80 Hz, 2 H) 3.69 (td, J = 5.80, 5.51 Hz, 2 H) 2.77-2.84 (m, 2 H) 2.21 (s, 3 H) 2.06 (td, J = 11.62, 1.60 Hz, 2 H) 1.93-2.00 (m, 2 H) 1.67 (qd, J = 11.62, 3.74 Hz, 2 H). | E |
| 274 | 473 | 13.10 (br. s., 1 H) 8.04-8.09 (m, 2 H) 7.99 (t, J = 5.82 Hz, 1 H) 7.91 (s, 1 H) 7.09-7.13 (m, 2 H) 5.75 (d, J = 9.16 Hz, 1 H) 4.87-4.95 (m, 1 H) 4.11 (t, J = 6.00 Hz, 2 H) 3.83 (s, 2 H) 3.50 (td, J = 6.00, 5.82 Hz, 2 H) 3.31 (s, 3 H) 2.77-2.84 (m, 2 H) 2.21 (s, 3 H) 2.06 (td, J = 11.56, 1.75 Hz, 2 H) 1.93-2.00 (m, 2 H) 1.63-1.73 (m, 2 H). | E |
| 275 | 497 | 13.10 (br. s., 1 H) 8.05-8.09 (m, 2 H) 8.02 (t, J = 5.57 Hz, 1 H) 7.91 (s, 1 H) 7.09-7.13 (m, 2 H) 5.75 (d, J = 8.85 Hz, 1 H) 4.87-4.95 (m, 1 H) 4.07 (t, J = 5.80 Hz, 2 H) 3.44 (td, J = 5.80, 5.57 Hz, 2 H) 2.77-2.85 (m, 2 H) 2.53-2.61 (m, 1 H) 2.21 (s, 3 H) 2.06 (td, J = 11.79, 1.91 Hz, 2 H) 1.93-2.00 (m, 2 H) 1.57-1.77 (m, 8 H) 1.44-1.54 (m, 2 H). | E |
| 276 | 471 | 13.10 (br. s., 1 H) 8.04-8.09 (m, 2 H) 8.00 (t, J = 5.42 Hz, 1 H) 7.91 (s, 1 H) 7.08-7.14 (m, 2 H) 5.75 (d, J = 8.85 Hz, 1 H) 4.86-4.95 (m, 1 H) 4.07 (t, J = 5.87 Hz, 2 H) 3.43 (td, J = 5.87, 5.42 Hz, 2 H) 2.77-2.84 (m, 2 H) 2.39 (spt, J = 6.87 Hz, 1 H) 2.21 (s, 3 H) 2.06 (td, J = 11.60, 1.68 Hz, 2 H) 1.93-2.00 (m, 2 H) 1.63-1.72 (m, 2 H) 1.00 (d, J = 6.87 Hz, 6 H). | E |
| 277 | 469 | 13.10 (br. s., 1 H) 8.35 (t, J = 5.65 Hz, 1 H) 8.05-8.09 (m, 2 H) 7.91 (s, 1 H) 7.10-7.14 (m, 2 H) 5.75 (d, J = 8.85 Hz, 1 H) 4.87-4.95 (m, 1 H) 4.07 (t, J = 5.72 Hz, 2 H) 3.46 (td, J = 5.72, 5.65 Hz, 2 H) 2.77-2.84 (m, 2 H) 2.21 (s, 3 H) 2.07 (td, J = 11.60, 1.83 Hz, 2 H) 1.94-2.00 (m, 2H) 1.63-1.72 (m, 2 H) 1.57-1.62 (m, 1 H) 0.67-0.71 (m, 2 H) 0.62-0.67 (m, 2 H). | E |
| 278 | 457 | 13.10 (br. s., 1 H) 8.12 (t, J = 5.49 Hz, 1 H) 8.05-8.09 (m, 2 H) 7.91 (s, 1 H) 7.09-7.13 (m, 2 H) 5.74 (d, J = 9.00 Hz, 1 H) 4.88-4.97 (m, 1 H) 4.06 (t, J = 5.72 Hz, 2 H) 3.43 (td, J = 5.72, 5.49 Hz, 2 H) 2.88-2.96 (m, 2 H) 2.36 (q, J = 7.20 Hz, 2 H) | C |

TABLE 2-continued

| Ex. | MS (ESI)+ m/z [M + H]+ | 1H NMR (600 MHz, DMSO-d6) δ ppm (unless otherwise stated) | GP |
|---|---|---|---|
| | | 2.04 (td, J = 11.60, 1.83 Hz, 2 H) 1.96-2.02 (m, 2 H) 1.84 (s, 3 H) 1.60-1.70 (m, 2 H) 1.03 (t, J = 7.20 Hz, 3 H). | |
| 279 | 525 | 13.10 (br. s., 1 H) 8.13 (t, J = 5.65 Hz, 1 H) 8.04-8.08 (m, 2 H) 7.90 (s, 1 H) 7.44 (dd, J = 4.73, 1.68 Hz, 1 H) 7.08-7.13 (m, 2 H) 6.96-7.00 (m, 2 H) 5.80 (d, J = 9.00 Hz, 1 H) 4.93-5.01 (m, 1 H) 4.07 (t, J = 5.65 Hz, 2 H) 3.74 (s, 2 H) 3.44 (q, J = 5.65 Hz, 2 H) 2.90-2.96 (m, 2 H) 2.18 (td, J = 11.70, 1.91 Hz, 2 H) 1.95-2.02 (m, 2 H) 1.84 (s, 3 H) 1.69 (qd, J = 11.70, 3.81 Hz, 2 H). | C |
| 280 | 563 | 13.10 (br. s., 1 H) 8.04-8.08 (m, 2 H) 8.04 (t, J = 5.65 Hz, 1 H) 7.90 (s, 1 H) 7.22-7.25 (m, 2 H) 7.09-7.13 (m, 2 H) 6.88-6.91 (m, 2 H) 5.75 (d, J = 8.70 Hz, 1 H) 4.92-5.00 (m, 1 H) 4.08 (t, J = 5.80 Hz, 2 H) 3.74 (s, 3 H) 3.44 (s, 2 H) 3.45 (td, J = 5.80, 5.65 Hz, 2 H) 2.82-2.88 (m, 2 H) 2.11 (q, J = 7.63 Hz, 2 H) 2.08-2.14 (m, 2 H) 1.93-2.01 (m, 2 H) 1.61-1.70 (m, 2 H) 1.00 (t, J = 7.63 Hz, 3 H). | E |
| 281 | 603 | 13.10 (br. s., 1 H) 8.04-8.07 (m, 2 H) 8.03 (t, J = 5.57 Hz, 1 H) 7.90 (s, 1 H) 7.21-7.26 (m, 2 H) 7.08-7.12 (m, 2 H) 6.88-6.91 (m, 2 H) 5.74 (d, J = 8.85 Hz, 1 H) 4.92-5.00 (m, 1 H) 4.08 (t, J = 5.80 Hz, 2 H) 3.74 (s, 3 H) 3.44 (s, 2 H) 3.44 (td, J = 5.80, 5.57 Hz, 2 H) 2.82-2.89 (m, 2 H) 2.54-2.62 (m, 1 H) 2.08-2.15 (m, 2 H) 1.93-2.01 (m, 2 H) 1.69-1.77 (m, 2 H) 1.62-1.70 (m, 2 H) 1.58-1.67 (m, 4 H) 1.44-1.53 (m, 2 H). | E |
| 282 | 577 | 13.10 (br. s., 1 H) 8.04-8.08 (m, 2 H) 8.00 (t, J = 5.57 Hz, 1 H) 7.90 (s, 1 H) 7.21-7.25 (m, 2 H) 7.09-7.13 (m, 2 H) 6.88-6.91 (m, 2 H) 5.75 (d, J = 8.85 Hz, 1 H) 4.91-5.00 (m, 1 H) 4.07 (t, J = 5.80 Hz, 2 H) 3.74 (s, 3 H) 3.44 (s, 2 H) 3.44 (td, J = 5.80, 5.57 Hz, 2 H) 2.82-2.89 (m, 2 H) 2.40 (spt, J = 6.84 Hz, 1 H) 2.07-2.15 (m, 2 H) 1.93-2.01 (m, 2 H) 1.61-1.71 (m, 2 H) 1.01 (d, J = 6.84 Hz, 6 H). | E |
| 283 | 612 | 13.10 (br. s., 1 H) 9.04 (t, J = 5.65 Hz, 1 H) 8.72-8.75 (m, 2 H) 8.04-8.08 (m, 2 H) 7.90 (s, 1 H) 7.77-7.79 (m, 2 H) 7.21-7.25 (m, 2 H) 7.12-7.16 (m, 2 H) 6.87-6.91 (m, 2 H) 5.75 (d, J = 8.70 Hz, 1 H) 4.91-5.00 (m, 1 H) 4.23 (t, J = 5.80 Hz, 2 H) 3.74 (s, 3 H) 3.70 (td, J = 5.80, 5.65 Hz, 2 H) 3.44 (s, 2 H) 2.81-2.89 (m, 2 H) 2.07-2.14 (m, 2 H) 1.94-2.00 (m, 2 H) 1.66 (qd, J = 11.70, 3.36 Hz, 2 H). | E |
| 284 | 616 | 13.14 (br. s., 1 H) 9.27 (s, 1 H) 8.23 (s, 1 H) 8.07 (br. s., 1 H) 8.08 (d, J = 8.9 Hz, 2 H) 8.00 (s, 1 H) 7.83 (d, J = 8.5 Hz, 2 H) 7.52 (d, J = 8.5 Hz, 2 H) 7.12 (d, J = 8.9 Hz, 2 H) 5.49 (d, J = 8.2 Hz, 1 H) 4.94-5.05 (m, 1 H) 4.56 (s, 2 H) 3.59 (s, 2 H) 2.88 (d, J = 11.9 Hz, 2 H) 2.68 (d, J = 4.6 Hz, 3 H) 2.22 (t, J = 11.6 Hz, 2 H) 2.02 (d, J = 10.4 Hz, 2 H) 1.69 (qd, J = 11.4, 3.1 Hz, 2 H). | C |
| 285 | 586 | 13.10 (br. s., 1 H) 9.27 (s, 1 H) 8.23 (s, 1 H) 8.13 (t, J = 5.57 Hz, 1 H) 8.04-8.09 (m, 2 H) 7.91 (s, 1 H) 7.81-7.85 (m, 2 H) 7.50-7.54 (m, 2 H) 7.08-7.13 (m, 2 H) 5.77 (d, J = 9.00 Hz, 1 H) 4.94-5.02 (m, 1 H) 4.07 (t, J = 5.72 Hz, 2 H) 3.59 (s, 2 H) 3.44 (td, J = 5.72, 5.57 Hz, 2 H) 2.86-2.93 (m, 2 H) 2.16-2.23 (m, 2 H) 1.97-2.03 (m, 2 H) 1.85 (s, 3 H) 1.66-1.75 (m, 2 H). | C |
| 286 | 632 | 13.13 (br. s., 1 H) 9.27 (s, 1 H) 8.23 (s, 1 H) 8.13 (t, J = 5.49 Hz, 1 H) 8.04-8.09 (m, 2 H) 8.00 (s, 1 H) 7.81-7.85 (m, 2 H) 7.50-7.54 (m, 2 H) 7.08-7.13 (m, 2 H) 5.49 (d, J = 8.70 Hz, 1 H) 4.95-5.03 (m, 1 H) 4.07 (t, J = 5.72 Hz, 2 H) 3.60 (s, 2 H) 3.44 (dt, J = 5.72, 5.49 Hz, 2 H) 2.84-2.92 (m, 2 H) 2.17-2.25 (m, 2 H) 1.98-2.06 (m, 2 H) 1.85 (s, 3 H) 1.64-1.73 (m, 2 H). | C |
| 287 | 537 | 13.11 (br. s., 1 H) 8.06-8.07 (m, 1 H) 8.08 (d, J = 8.9 Hz, 2 H) 7.90 (s, 1 H) 7.12 (d, J = 8.9 Hz, 2 H) 5.76 (d, J = 8.9 Hz, 1 H) 4.87-5.00 (m, 1 H) 4.56 (s, 2 H) 3.62 (s, 3 H) 3.23 (s, 2 H) 2.83 (d, J = 11.3 Hz, 2 H) 2.68 (d, J = 4.6 Hz, 3 H) 2.17 (s, 3 H) 2.08 (s, 3 H) 2.07 (td, J = 11.3, 1.5 Hz, 2 H) 1.97 (d, J = 10.1 Hz, 2 H) 1.61 (qd, J = 11.5, 3.8 Hz, 2 H). | C |
| 288 | 581 | 13.14 (br. s., 1 H) 8.08 (d, J = 9.2 Hz, 2 H) 8.06-8.07 (m, 1 H) 8.00 (s, 1 H) 7.12 (d, J = 8.9 Hz, 2 H) 5.48 (d, J = 8.5 Hz, 1 H) 4.90-5.01 (m, 1 H) 4.56 (s, 2 H) 3.62 (s, 3 H) 3.23 (s, 2 H) 2.82 (d, J = 11.3 Hz, 2 H) 2.68 (d, J = 4.6 Hz, 3 H) 2.17 (s, 3 H) 2.08 (s, 3 H) 2.09 (td, J = 11.8, 2.1 Hz, 2 H) 1.98 (d, J = 10.7 Hz, 2 H) 1.60 (qd, J = 11.6, 2.7 Hz, 2 H). | C |
| 289 | 598 | 13.13 (s, 1 H) 10.37 (s, 1 H) 8.81 (d, J = 2.44 Hz, 1 H) 8.31 (dd, J = 4.65, 1.45 Hz, 1 H) 8.07-8.11 (m, 3 H) 7.91 (s, 1 H) 7.38 (dd, J = 8.32, 4.65 Hz, 1 H) 7.21-7.26 (m, 2 H) 7.16-7.20 (m, 2 H) 6.87-6.91 (m, 2 H) 5.77 (d, J = 9.16 Hz, 1 H) 4.91-5.00 (m, 1 H) 4.85 (s, 2 H) 3.74 (s, 3 H) 3.44 (br. s., 2 H) 2.81-2.90 (m, 2 H) 2.07-2.16 (m, 2 H) 1.94-2.01 (m, 2 H) 1.61-1.71 (m, 2 H). | D |
| 290 | 601 | 13.13 (s, 1 H) 10.19 (s, 1 H) 8.06-8.12 (m, 2 H) 7.91 (s, 1 H) 7.36 (d, J = 1.83 Hz, 1 H) 7.21-7.27 (m, 2 H) 7.15-7.20 (m, 2 H) 6.87-6.92 (m, 2 H) 6.21 (d, J = 1.83 Hz, 1 H) 5.77 (d, J = 8.55 Hz, 1 H) 4.91-5.00 (m, 1 H) 4.87 (s, 2 H) 3.74 (s, 3 H) 3.66 (s, 3 H) 3.44 (br. s., 2 H) 2.81-2.90 (m, 2 H) 2.06-2.18 (m, 2 H) 1.94-2.01 (m, 2 H) 1.60-1.72 (m, 2 H). | D |
| 291 | 492 | 13.13 (br. s., 1 H) 10.36 (s, 1 H) 8.81 (dd, J = 2.59, 0.66 Hz, 1 H) 8.30 (dd, J = 4.71, 1.50 Hz, 1 H) 8.08-8.11 (m, 2 H) 8.08 (ddd, J = 8.32, 2.59, 1.50 Hz, 1 H) 7.91 (s, 1 H) 7.38 (ddd, J = 8.32, 4.71, 0.66 Hz, 1 H) 7.16-7.21 (m, 2 H) 5.77 (d, 1 H) 4.87-4.95 (m, 1 H) 4.84 (s, 2 H) 2.76-2.85 (m, 2 H) 2.21 (s, 3 H) 2.07 (td, J = 11.60, 1.83 Hz, 2 H) 1.94-2.00 (m, 2 H) 1.63-1.72 (dtd, J = 11.83, 11.60, 3.89 Hz, 2 H). | D |
| 292 | 493 | 13.13 (s, 1 H) 10.96 (s, 1 H) 9.31 (s, 1 H) 8.45 (dd, J = 2.59, 1.53 Hz, 1 H) 8.41 (d, J = 2.59 Hz, 1 H) 8.06-8.10 (m, 2 H) 7.91 (s, 1 H) 7.13-7.17 (m, 2 H) 5.77 (d, J = 8.85 Hz, 1 H) 4.95 (s, 2 H) 4.86-4.95 (m, 1 H) 2.77-2.84 (m, 2 H) 2.21 (s, 3 H) 2.03-2.11 (m, 2 H) 1.94-2.00 (m, 2 H) 1.63-1.72 (dtd, J = 11.94, 11.65, 3.66 Hz, 2 H). | D |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
| 293 | 472 | 12.87 (br. s., 1 H) 7.95 (s, 1 H) 7.88 (d, J = 8.5 Hz, 2 H) 7.86 (q, J = 4.9 Hz, 1 H) 6.64 (d, J = 8.9 Hz, 2 H) 6.44 (t, J = 6.0 Hz, 1 H) 5.36 (d, J = 8.9 Hz, 1 H) 4.86-4.97 (m, 1 H) 3.70 (d, J = 6.1 Hz, 2 H) 2.78 (d, J = 11.3 Hz, 2 H) 2.62 (d, J = 4.6 Hz, 3 H) 2.21 (s, 3 H) 2.08 (t, J = 10.5 Hz, 2 H) 1.98 (d, J = 11.6 Hz, 2 H) 1.63 (qd, J = 11.4, 3.7 Hz, 2 H). | C |
| 294 | 428 | 12.84 (br. s., 1 H) 7.88 (d, J = 8.5 Hz, 2 H) 7.86-7.86 (m, 1 H) 7.85 (s, 1 H) 6.64 (d, J = 8.9 Hz, 2 H) 6.43 (t, J = 6.0 Hz, 1 H) 5.64 (d, J = 8.9 Hz, 1 H) 4.85-4.96 (m, 1 H) 3.70 (d, J = 5.8 Hz, 2 H) 2.80 (d, J = 11.6 Hz, 2 H) 2.62 (d, J = 4.6 Hz, 3 H) 2.21 (s, 3 H) 2.06 (td, J = 11.7, 1.8 Hz, 2 H) 1.96 (d, J = 9.8 Hz, 2 H) 1.65 (qd, J = 11.6, 3.7 Hz, 2 H). | C |
| 295 | 456 | 12.84 (br. s., 1 H) 7.87 (d, J = 8.9 Hz, 2 H) 7.85 (s, 1 H) 7.83-7.85 (m, 1 H) 6.64 (d, J = 8.9 Hz, 2 H) 6.42 (t, J = 6.0 Hz, 1 H) 5.59 (d, J = 9.2 Hz, 1 H) 4.83-4.95 (m, 1 H) 3.70 (d, J = 5.8 Hz, 2 H) 2.84 (d, J = 11.9 Hz, 2 H) 2.72 (spt, J = 6.6, 6.4 Hz, 1 H) 2.62 (d, J = 4.6 Hz, 3 H) 2.27 (td, J = 11.4, 1.8 Hz, 2 H) 1.99 (d, J = 10.7 Hz, 2 H) 1.59 (qd, J = 11.5, 3.7 Hz, 2 H) 1.00 (d, J = 6.7 Hz, 6 H). | C |
| 296 | 534 | 12.84 (br. s., 1 H) 7.87-7.88 (m, 1 H) 7.87 (d, J = 8.9 Hz, 2 H) 7.85 (s, 1 H) 7.23 (d, J = 8.5 Hz, 2 H) 6.89 (d, J = 8.9 Hz, 2 H) 6.64 (d, J = 8.5 Hz, 2 H) 6.44 (t, J = 5.8 Hz, 1 H) 5.64 (d, J = 8.9 Hz, 1 H) 4.89-5.02 (m, 1 H) 3.74 (s, 3 H) 3.70 (d, J = 6.1 Hz, 2 H) 3.44 (s, 2 H) 2.84 (d, J = 11.6 Hz, 2 H) 2.63 (d, J = 4.9 Hz, 3 H) 2.11 (t, J = 10.8 Hz, 2 H) 1.97 (d, J = 9.5 Hz, 2 H) 1.63 (qd, J = 11.6, 3.7 Hz, 2 H). | C |
| 297 | 442 | 12.84 (br. s., 1 H) 7.87 (d, J = 8.9 Hz, 2 H) 7.86 (s, 1 H) 7.85-7.85 (m, 1 H) 6.64 (d, J = 8.9 Hz, 2 H) 6.43 (t, J = 6.0 Hz, 1 H) 5.63 (d, J = 8.9 Hz, 1 H) 4.88-4.98 (m, 1 H) 3.70 (d, J = 5.8 Hz, 2 H) 2.91 (d, J = 11.6 Hz, 2 H) 2.62 (d, J = 4.9 Hz, 3 H) 2.36 (q, J = 7.3 Hz, 2 H) 2.04 (td, J = 11.7, 1.7 Hz, 2 H) 1.98 (d, J = 9.8 Hz, 2 H) 1.63 (qd, J = 11.6, 3.7 Hz, 2 H) 1.02 (t, J = 7.2 Hz, 3 H). | C |
| 298 | 492 | 13.12 (br. s., 1 H) 10.56 (s, 1 H) 8.35 (ddd, J = 4.88, 1.98, 0.92 Hz, 1 H) 8.06-8.10 (m, 2 H) 8.03-8.09 (m, 1 H) 7.91 (s, 1 H) 7.81 (ddd, J = 8.32, 7.40, 1.98 Hz, 1 H) 7.13-7.16 (m, 3 H) 5.76 (d, J = 8.85 Hz, 1 H) 4.90 (s, 1 H) 4.87-4.95 (m, 1 H) 2.77-2.84 (m, 2 H) 2.21 (s, 3 H) 2.07 (td, J = 11.64, 1.14 Hz, 2 H) 1.94-2.00 (m, 2 H) 1.63-1.72 (m, J = 11.75, 11.64, 11.64, 3.59 Hz, 2 H). | D |
| 299 | 482 | 13.13 (br. s., 1 H) 11.31 (br. s., 1 H) 8.83 (d, J = 1.83 Hz, 1 H) 8.05-8.10 (m, 2 H) 7.91 (s, 1 H) 7.11-7.16 (m, 2 H) 6.93 (br. s., 1 H) 5.77 (d, J = 8.85 Hz, 1 H) 4.87-4.95 (m, 1 H) 4.88 (s, 2 H) 2.77-2.85 (m, 2 H) 2.21 (s, 3 H) 2.03-2.11 (m, 2 H) 1.94-2.00 (m, 2 H) 1.68 (qd, J = 11.75, 3.66 Hz, 2 H). | D |
| 300 | 506 | 13.13 (br. s., 1 H) 8.78 (t, J = 6.26 Hz, 1 H) 8.46-8.49 (m, 2 H) 8.07-8.11 (m, 2 H) 7.92 (s, 1 H) 7.22-7.26 (m, 2 H) 7.13-7.17 (m, 2 H) 5.78 (d, J = 9.00 Hz, 1 H) 4.87-4.96 (m, 1 H) 4.70 (s, 2 H) 4.38 (d, J = 6.26 Hz, 2 H) 2.78-2.85 (m, 2 H) 2.21 (s, 3 H) 2.03-2.11 (m, 2 H) 1.94-2.01 (m, 2 H) 1.68 (qd, J = 11.65, 3.66 Hz, 2 H). | D |
| 301 | 486 | 12.84 (br. s., 1 H) 7.94 (s, 1 H) 7.87 (d, J = 8.5 Hz, 2 H) 7.83 (q, J = 4.3 Hz, 1 H) 6.67 (d, J = 8.5 Hz, 2 H) 6.15 (t, J = 5.6 Hz, 1 H) 5.34 (d, J = 8.9 Hz, 1 H) 4.85-4.99 (m, 1 H) 3.32 (q, J = 6.6 Hz, 2 H) 2.78 (d, J = 11.0 Hz, 2 H) 2.58 (d, J = 4.6 Hz, 3 H) 2.36 (t, J = 7.0 Hz, 2 H) 2.21 (s, 3 H) 2.08 (t, J = 10.8 Hz, 2 H) 1.98 (d, J = 9.5 Hz, 2 H) 1.63 (qd, J = 11.5, 3.7 Hz, 2 H). | C |
| 302 | 442 | 12.81 (br. s., 1 H) 7.87 (d, J = 8.9 Hz, 2 H) 7.85 (s, 1 H) 7.83 (q, J = 4.6 Hz, 1 H) 6.67 (d, J = 8.5 Hz, 2 H) 6.14 (t, J = 5.8 Hz, 1 H) 5.62 (d, J = 8.9 Hz, 1 H) 4.85-4.98 (m, 1 H) 3.32 (q, J = 6.6 Hz, 2 H) 2.80 (d, J = 11.3 Hz, 2 H) 2.58 (d, J = 4.6 Hz, 3 H) 2.36 (t, J = 7.0 Hz, 2 H) 2.21 (s, 3 H) 2.06 (td, J = 11.6, 1.5 Hz, 2 H) 1.96 (d, J = 11.3 Hz, 2 H) 1.65 (qd, J = 11.7, 3.5 Hz, 2 H). | C |
| 303 | 470 | 12.81 (br. s., 1 H) 7.86 (d, J = 8.9 Hz, 2 H) 7.85 (s, 1 H) 7.83 (q, J = 4.3 Hz, 1 H) 6.67 (d, J = 8.9 Hz, 2 H) 6.13 (t, J = 5.8 Hz, 1 H) 5.57 (d, J = 8.9 Hz, 1 H) 4.84-4.95 (m, 1 H) 3.32 (q, J = 7.0 Hz, 2 H) 2.84 (d, J = 11.9 Hz, 2 H) 2.72 (spt, J = 6.6, 1 H) 2.58 (d, J = 4.6 Hz, 3 H) 2.36 (t, J = 7.0 Hz, 2 H) 2.27 (td, J = 11.6, 2.1 Hz, 2 H) 2.00 (d, J = 10.7 Hz, 2 H) 1.59 (qd, J = 11.4, 3.7 Hz, 2 H) 1.01 (d, J = 6.7 Hz, 6 H). | C |
| 304 | 548 | 12.81 (br. s., 1 H) 7.86 (d, J = 8.5 Hz, 2 H) 7.84 (s, 1 H) 7.82-7.84 (m, 1 H) 7.24 (d, J = 8.9 Hz, 2 H) 6.89 (d, J = 8.5 Hz, 2 H) 6.67 (d, J = 8.9 Hz, 2 H) 6.15 (t, J = 5.8 Hz, 1 H) 5.62 (d, J = 9.2 Hz, 1 H) 4.90-5.01 (m, 1 H) 3.74 (s, 3 H) 3.44 (s, 2 H) 3.33 (q, J = 6.6 Hz, 2 H) 2.85 (d, J = 11.6 Hz, 2 H) 2.59 (d, J = 4.6 Hz, 3 H) 2.37 (t, J = 7.0 Hz, 2 H) 2.10 (t, J = 10.8 Hz, 2 H) 1.97 (d, J = 10.7 Hz, 2 H) 1.63 (qd, J = 11.6, 3.7 Hz, 2 H). | C |
| 305 | 456 | 12.81 (br. s., 1 H) 7.86 (d, J = 8.8 Hz, 2 H) 7.85 (s, 1 H) 7.83 (q, J = 4.0 Hz, 1 H) 6.67 (d, J = 8.9 Hz, 2 H) 6.13 (t, J = 5.5 Hz, 1 H) 5.61 (d, J = 8.9 Hz, 1 H) 4.88-4.99 (m, 1 H) 3.32 (q, J = 6.6 Hz, 2 H) 2.91 (d, J = 11.3 Hz, 2 H) 2.58 (d, J = 4.6 Hz, 3 H) 2.36 (t, J = 7.0 Hz, 2 H) 2.36 (q, J = 7.3 Hz, 2 H) 2.04 (t, J = 11.6 Hz, 2 H) 1.99 (d, J = 11.9 Hz, 2 H) 1.62 (qd, J = 11.3, 3.4 Hz, 2 H) 1.02 (t, J = 7.2 Hz, 3 H). | C |
| 306 | 612 | 13.13 (s, 1 H) 8.79 (t, J = 6.15 Hz, 1 H) 8.47-8.49 (m, 2 H) 8.06-8.10 (m, 2 H) 7.91 (s, 1 H) 7.21-7.26 (m, 4 H) 7.13-7.17 (m, 2 H) 6.87-6.91 (m, 2 H) 5.77 (d, J = 8.70 Hz, 1 H) 4.92-5.00 (m, 1 H) 4.71 (s, 2 H) 4.39 (d, J = 6.15 Hz, 2 H) 3.74 (s, 3 H) 3.45 (s, 2 H) 2.82-2.89 (m, 2 H) 2.08-2.15 (m, 2 H) 1.95-2.02 (m, 2 H) 1.62-1.71 (m, J = 11.90, 11.75, 11.75, 3.66 Hz, 2 H). | B |
| 307 | 599 | 13.12 (s, 1 H) 10.80 (s, 1 H) 8.69 (d, J = 4.88 Hz, 2 H) 8.04-8.08 (m, 2 H) 7.90 (s, 1 H) 7.22-7.25 (m, 2 H) 7.22 (t, J = 4.88 Hz, 1 H) 7.09-7.12 (m, 2 H) 6.87-6.90 (m, 2 H) 5.76 (d, J = 8.85 Hz, 1 H) 5.11 (s, 2 H) 4.91-5.00 (m, 1 H) 3.73 (s, 3 H) 3.44 (s, 2 H) 2.82-2.89 (m, 2 H) 2.07-2.15 (m, 2 H) 1.94-2.01 (m, 2 H) 1.61-1.70 (m, 2 H). | C |

TABLE 2-continued

| Ex. | MS (ESI)+ m/z [M + H]+ | 1H NMR (600 MHz, DMSO-d6) δ ppm (unless otherwise stated) | GP |
|---|---|---|---|
| 308 | 493 | 13.12 (br. s., 1 H) 10.80 (s, 1 H) 8.69 (d, J = 4.88 Hz, 2 H) 8.04-8.09 (m, 2 H) 7.91 (s, 1 H) 7.21 (t, J = 4.88 Hz, 1 H) 7.08-7.13 (m, 2 H) 5.76 (d, J = 8.70 Hz, 1 H) 5.10 (s, 2 H) 4.87-4.95 (m, 1 H) 2.77-2.85 (m, 2 H) 2.21 (s, 3 H) 2.02-2.12 (m, 2 H) 1.94-2.00 (m, 2 H) 1.67 (dtd, J = 11.83, 11.67, 3.74 Hz, 2 H). | C |
| 309 | 575 | 13.12 (s, 1 H) 10.81 (s, 1 H) 8.69 (d, J = 4.88 Hz, 2 H) 8.04-8.07 (m, 2 H) 7.90 (s, 1 H) 7.43 (dd, J = 4.81, 1.45 Hz, 1 H) 7.22 (t, J = 4.88 Hz, 1 H) 7.08-7.11 (m, 2 H) 6.95-6.99 (m, 2 H) 5.81 (d, J = 8.85 Hz, 1 H) 5.10 (s, 2 H) 4.92-5.01 (m, 1 H) 3.73 (s, 2 H) 2.89-2.96 (m, 2 H) 2.18 (td, J = 11.80, 2.14 Hz, 2 H) 1.95-2.02 (m, 2 H) 1.69 (m, J = 12.02, 11.80, 3.81 Hz, 2 H). | C |
| 310 | 493 | 13.12 (br. s., 1 H) 10.96 (br. s., 1 H) 9.31 (s, 1 H) 8.45 (dd, J = 2.50, 1.53 Hz, 1 H) 8.41 (d, J = 2.50 Hz, 1 H) 8.06-8.10 (m, 2 H) 7.91 (s, 1 H) 7.13-7.17 (m, 2 H) 5.76 (d, J = 8.70 Hz, 1 H) 4.95 (s, 2 H) 4.87-4.95 (m, 1 H) 2.77-2.84 (m, 2 H) 2.20 (s, 3 H) 2.06 (td, J = 11.63, 1.91 Hz, 2 H) 1.94-2.00 (m, 2 H) 1.67 (dtd J = 11.75, 11.63, 3.81 Hz, 2 H). | C |
| 311 | 537 | 13.14 (br. s., 1 H) 10.96 (br. s., 1 H) 9.31 (s, 1 H) 8.45 (dd, J = 2.59, 1.53 Hz, 1 H) 8.41 (d, J = 2.59 Hz, 1 H) 8.06-8.10 (m, 2 H) 8.01 (s, 1 H) 7.13-7.17 (m, 2 H) 5.47 (d, J = 9.00 Hz, 1 H) 4.95 (s, 2 H) 4.88-4.95 (m, 1 H) 2.75-2.82 (m, 2 H) 2.21 (s, 3 H) 2.09 (td, J = 11.50, 1.60 Hz, 2 H) 1.96-2.02 (m, 2 H) 1.65 (dtd, J = 11.79, 11.50, 3.66 Hz, 2 H). | C |
| 312 | 521 | 13.12 (br. s., 1 H) 10.95 (br. s., 1 H) 9.31 (s, 1 H) 8.44 (dd, J = 2.59, 1.53 Hz, 1 H) 8.40 (d, J = 2.59 Hz, 1 H) 8.06-8.10 (m, 2 H) 7.91 (s, 1 H) 7.13-7.17 (m, 2 H) 5.69 (d, J = 8.09 Hz, 1 H) 4.95 (s, 2 H) 4.85-4.94 (m, 1 H) 2.81-2.87 (m, 2 H) 2.71 (spt, J = 6.60 Hz, 1 H) 2.27 (td, J = 11.50, 1.83 Hz, 2 H) 1.97-2.03 (m, 2 H) 1.61 (qd, J = 11.50, 3.81 Hz, 2 H) 1.00 (d, J = 6.60 Hz, 6 H). | C |
| 313 | 575 | 13.12 (br. s., 1 H) 10.98 (br. s., 1 H) 9.32 (s, 1 H) 8.45 (dd, J = 2.60, 1.53 Hz, 1 H) 8.41 (d, J = 2.60 Hz, 1 H) 8.05-8.09 (m, 2 H) 7.90 (s, 1 H) 7.48 (dd, J = 4.90, 2.94 Hz, 1 H) 7.30-7.32 (m, 1 H) 7.12-7.16 (m, 2 H) 7.07 (dd, J = 4.90, 1.22 Hz, 1 H) 5.77 (d, 1 H) 4.95 (s, 2 H) 4.90-5.00 (m, 1 H) 3.52 (s, 2 H) 2.84-2.91 (m, 2 H) 2.09-2.16 (m, 2 H) 1.94-2.01 (m, 2 H) 1.67 (dtd, J = 11.86, 11.65, 3.89 Hz, 2 H). | C |
| 314 | 611 | 13.12 (br. s., 1 H) 10.97 (br. s., 1 H) 9.32 (s, 1 H) 8.45 (dd, J = 2.59, 1.53 Hz, 1 H) 8.41 (d, J = 2.59 Hz, 1 H) 8.06-8.10 (m, 2 H) 7.91 (s, 1 H) 7.16-7.18 (m, 1 H) 7.13-7.17 (m, 2 H) 6.99-7.02 (m, 2 H) 6.69 (d, J = 8.09 Hz, 1 H) 5.74 (d, J = 9.00 Hz, 1 H) 4.96 (s, 2 H) 4.91-4.99 (m, 1 H) 4.49 (t, J = 8.70 Hz, 2 H) 3.41 (s, 2 H) 3.15 (t, J = 8.70 Hz, 2 H) 2.82-2.89 (m, 2 H) 2.07-2.14 (m, 2 H) 1.94-2.01 (m, 2 H) 1.65 (dtd, J = 11.79, 11.65, 3.51 Hz, 2 H). | C |
| 315 | 496 | 13.10 (br. s., 1 H) 11.15 (br. s., 1 H) 8.07 (d, J = 8.85 Hz, 2 H) 7.91 (s, 1 H) 7.13 (d, J = 9.16 Hz, 2 H) 6.63 (s, 1 H) 5.76 (d, J = 8.85 Hz, 1 H) 4.87-4.96 (m, 1 H) 4.85 (s, 2 H) 2.76-2.84 (m, 2 H) 2.38 (s, 3 H) 2.21 (s, 3 H) 2.07 (td, J = 11.67, 1.98 Hz, 2 H) 1.92-2.00 (m, 2 H) 1.67 (qd, J = 11.70, 3.66 Hz, 2 H). | C |
| 316 | 505 | 12.89 (br. s., 1 H) 10.27 (s, 1 H) 8.76 (d, J = 2.44 Hz, 1 H) 8.26 (dd, J = 4.73, 1.37 Hz, 1 H) 8.04 (dt, J = 8.70, 1.98 Hz, 1 H) 7.96 (d, J = 9.16 Hz, 2 H) 7.86 (s, 1 H) 7.34 (dd, J = 8.39, 4.73 Hz, 1 H) 6.84 (d, J = 8.85 Hz, 2 H) 5.66 (d, J = 9.16 Hz, 1 H) 4.86-4.95 (m, J = 15.18, 15.18, 4.43, 4.27 Hz, 1 H) 4.30 (s, 2 H) 3.12 (s, 3 H) 2.76-2.84 (m, 2 H) 2.20 (s, 3 H) 2.01-2.10 (m, 2 H) 1.96 (dd, J = 11.75, 1.68 Hz, 2 H) 1.65 (dq, J = 11.75, 11.60, 3.81 Hz, 2 H). | C |
| 317 | 526 | 10.56 (br. s., 1 H) 8.74 (d, J = 2.14 Hz, 1 H) 8.37 (d, J = 2.14 Hz, 1 H) 8.28 (t, J = 2.14 Hz, 1 H) 8.10 (d, J = 9.16 Hz, 2 H) 7.91 (s, 1 H) 7.19 (d, J = 9.16 Hz, 2 H) 5.77 (d, J = 8.85 Hz, 1 H) 4.88-4.96 (m, 1 H) 4.86 (s, 2 H) 2.73-2.86 (m, 2 H) 2.21 (s, 3 H) 2.07 (td, J = 11.60, 2.14 Hz, 2 H) 1.97 (dd, J = 11.60, 1.83 Hz, 2 H) 1.68 (dq, J = 11.90, 11.60, 3.36 Hz, 2 H). | C |
| 318 | 588 | 13.10 (br. s., 1 H) 11.32 (br. s., 1 H) 8.83 (d, J = 1.83 Hz, 1 H) 8.05-8.09 (m, 2 H) 7.90 (s, 1 H) 7.21-7.25 (m, 2 H) 7.11-7.15 (m, 2 H) 6.93 (d, J = 1.83 Hz, 1 H) 6.87-6.91 (m, 2 H) 5.74 (d, J = 8.24 Hz, 1 H) 4.91-5.00 (m, 1 H) 4.88 (s, 2 H) 3.74 (s, 3 H) 3.44 (s, 2 H) 2.81-2.89 (m, 2 H) 2.08-2.15 (m, 2 H) 1.94-2.01 (m, 2 H) 1.60-1.70 (m, 2 H). | C |
| 319 | 526 | 13.15 (br. s., 1 H) 11.31 (br. s., 1 H) 8.82 (d, J = 1.83 Hz, 1 H) 8.06-8.10 (m, 2 H) 8.01 (s, 1 H) 7.12-7.16 (m, 2 H) 6.93 (d, J = 1.83 Hz, 1 H) 5.47 (d, J = 8.54 Hz, 1 H) 4.88-4.96 (m, 1 H) 4.88 (s, 2 H) 2.75-2.83 (m, 2 H) 2.21 (s, 3 H) 2.05-2.13 (m, 2 H) 1.95-2.02 (m, 2 H) 1.61-1.70 (m, 2 H). | C |
| 320 | 510 | 13.11 (br. s., 1 H) 11.30 (br. s., 1 H) 8.82 (d, J = 1.83 Hz, 1 H) 8.05-8.09 (m, 2 H) 7.91 (s, 1 H) 7.12-7.16 (m, 2 H) 6.93 (d, J = 1.83 Hz, 1 H) 5.70 (d, J = 8.85 Hz, 1 H) 4.86-4.93 (m, 1 H) 4.88 (s, 2 H) 2.81-2.88 (m, 2 H) 2.72 (spt, J = 6.56 Hz, 1 H) 2.28 (td, J = 11.48, 1.75 Hz, 2 H) 1.97-2.04 (m, 2 H) 1.61 (dtd, J = 11.67, 11.48, 3.59 Hz, 2 H) 1.00 (d, J = 6.56 Hz, 6 H). | C |
| 321 | 564 | 13.12 (br. s., 1 H) 11.32 (br. s., 1 H) 8.83 (d, J = 1.68 Hz, 1 H) 8.04-8.08 (m, 2 H) 7.91 (s, 1 H) 7.49 (dd, J = 4.92, 2.97 Hz, 1 H) 7.32 (ddt, J = 2.97, 1.22, 0.80 Hz, 1 H) 7.11-7.15 (m, 2 H) 7.07 (dd, J = 4.92, 1.22 Hz, 1 H) 6.93 (d, J = 1.68 Hz, 1 H) 5.77 (d, J = 9.16 Hz, 1 H) 4.91-4.99 (m, 1 H) 4.88 (s, 2 H) 3.53 (s, 2 H) 2.84-2.91 (m, 2 H) 2.13 (td, J = 11.64, 1.60 Hz, 2 H) 1.94-2.01 (m, 2 H) 1.67 (dtd, J = 11.83, 11.63, 3.59 Hz, 2 H). | C |
| 322 | 510 | 13.10 (br. s., 1 H) 11.31 (br. s., 1 H) 8.82 (d, J = 1.68 Hz, 1 H) 8.05-8.10 (m, 2 H) 7.90 (s, 1 H) 7.10-7.16 (m, 2 H) 6.93 (d, J = 1.68 Hz, 1 H) 5.72 (br. s., 1 H) 4.89-4.98 (m, 1 H) 4.87 (s, 2 H) 2.87-2.93 (m, 2 H) 2.24-2.30 (m, 2 H) | C |

TABLE 2-continued

| Ex. | MS (ESI)+ m/z [M + H]+ | $^1H$ NMR (600 MHz, DMSO-$d_6$) δ ppm (unless otherwise stated) | GP |
|---|---|---|---|
|  |  | 2.06 (td, J = 11.60, 1.75 Hz, 2 H) 1.96-2.01 (m, 2 H) 1.65 (dtd, J = 11.75, 11.60, 3.89 Hz, 2 H) 1.46 (s × t, J = 7.35 Hz, 2 H) 0.87 (t, J = 7.35 Hz, 3 H). |  |
| 323 | 599 | 13.12 (br. s., 1 H) 10.97 (br. s., 1 H) 9.32 (s, 1 H) 8.45 (dd, J = 2.55, 1.60 Hz, 1 H) 8.41 (d, J = 2.55 Hz, 1 H) 8.05-8.09 (m, 2 H) 7.91 (s, 1 H) 7.21-7.25 (m, 2 H) 7.13-7.17 (m, 2 H) 6.87-6.90 (m, 2 H) 5.76 (d, J = 8.54 Hz, 1 H) 4.96 (s, 2 H) 4.91-5.00 (m, 1 H) 3.74 (s, 3 H) 3.44 (s, 2 H) 2.82-2.88 (m, 2 H) 2.08-2.15 (m, 2 H) 1.95-2.00 (m, 2 H) 1.61-1.70 (m, 2 H). | C |
| 324 | 495 | 13.13 (br. s., 1 H) 10.18 (br. s., 1 H) 8.07-8.12 (m, 2 H) 7.92 (s, 1 H) 7.35 (d, J = 1.83 Hz, 1 H) 7.15-7.20 (m, 2 H) 6.20 (d, J = 1.83 Hz, 1 H) 5.77 (d, J = 9.00 Hz, 1 H) 4.87-4.96 (m, 1 H) 4.86 (s, 2 H) 3.66 (s, 3 H) 2.78-2.84 (m, 2 H) 2.21 (s, 3 H) 2.07 (td, J = 11.60, 1.60 Hz, 2 H) 1.94-2.00 (m, 2 H) 1.68 (qd, J = 11.60, 3.66 Hz, 2 H). | C |
| 325 | 588 | 13.50 (s, 1 H) 13.10 (br. s., 1 H) 8.04-8.09 (m, 2 H) 7.91 (s, 1 H) 7.93 (br. s., 1 H) 7.21-7.25 (m, 2 H) 7.11-7.17 (m, 2 H) 6.87-6.91 (m, 2 H) 5.76 (d, J = 8.85 Hz, 1 H) 4.91-5.00 (m, 1 H) 4.89 (br. s., 2 H) 3.74 (s, 3 H) 3.44 (s, 2 H) 2.82-2.88 (m, 2 H) 2.08-2.15 (m, 2 H) 1.94-2.01 (m, 2 H) 1.66 (qd, J = 11.80, 3.97 Hz, 2 H). | C |
| 326 | 482 | 13.56 (br. s., 1 H) 13.13 (br. s., 1 H) 11.47 (br. s., 1 H) 8.05-8.10 (m, 2 H) 7.91 (s, 1 H) 7.94 (br. s., 1 H) 7.11-7.17 (m, 2 H) 5.77 (d, J = 8.85 Hz, 1 H) 4.86-4.96 (m, 3 H) 2.78-2.84 (m, 2 H) 2.21 (s, 3 H) 2.03-2.11 (m, 2 H) 1.94-2.00 (m, 2 H) 1.68 (dtd, J = 11.79, 11.58, 3.51 Hz, 2 H). | C |
| 327 | 499 | 13.13 (br. s., 1 H) 12.61 (br. s., 1 H) 9.15 (s, 1 H) 8.05-8.10 (m, 2 H) 7.91 (s, 1 H) 7.12-7.16 (m, 2 H) 5.79 (d, J = 8.85 Hz, 1 H) 4.99 (s, 2 H) 4.88-4.96 (m, 1 H) 2.81-2.90 (m, 2 H) 2.25 (s, 3 H) 2.10-2.20 (m, 2 H) 1.95-2.03 (m, 2 H) 1.69 (m, J = 11.86, 11.69, 3.81 Hz, 2 H). | C |
| 328 | 496 | 13.12 (br. s., 1 H) 11.79 (br. s., 1 H) 8.07 (d, J = 8.9 Hz, 2 H) 7.91 (s, 1 H) 7.13 (d, J = 8.9 Hz, 2 H) 6.15 (s, 1 H) 5.77 (d, J = 8.5 Hz, 1 H) 4.87-4.96 (m, 1 H) 4.85 (s, 2 H) 2.81 (d, J = 11.3 Hz, 2 H) 2.21 (s, 3 H) 2.17 (s, 3 H) 2.07 (t, J = 11.9 Hz, 2 H) 1.97 (d, J = 10.1 Hz, 2 H) 1.67 (qd, J = 11.6, 3.7 Hz, 2 H). | C |
| 329 | 498 | 13.13 (br. s., 1 H) 12.38 (br. s., 1 H) 8.08 (d, J = 8.8 Hz, 2 H) 7.91 (s, 1 H) 7.50 (d, J = 3.4 Hz, 1 H) 7.25 (d, J = 3.7 Hz, 1 H) 7.14 (d, J = 8.9 Hz, 2 H) 5.76 (d, J = 8.9 Hz, 1 H) 4.95 (s, 2 H) 4.87-4.94 (m, 1 H) 2.81 (d, J = 11.3 Hz, 2 H) 2.21 (s, 3 H) 2.07 (td, J = 11.9, 1.8 Hz, 2 H) 1.97 (d, J = 10.1 Hz, 2 H) 1.67 (qd, J = 11.6, 3.8 Hz, 2 H). | C |
| 330 | 538 | 13.11 (br. s., 1 H) 11.21 (br. s., 1 H) 8.07 (d, J = 9.2 Hz, 2 H) 7.91 (s, 1 H) 7.12 (d, J = 8.9 Hz, 2 H) 6.59 (s, 1 H) 5.76 (d, J = 8.9 Hz, 1 H) 4.87-4.95 (m, 1 H) 4.86 (s, 2 H) 2.81 (d, J = 11.6 Hz, 2 H) 2.21 (s, 3 H) 2.07 (td, J = 11.4, 1.7 Hz, 2 H) 1.97 (d, J = 11.3 Hz, 2 H) 1.67 (qd, J = 11.6, 4.0 Hz, 2 H) 1.29 (s, 9 H). | C |
| 331 | 493 | 13.03 (br. s., 1 H) 10.57 (br. s., 1 H) 9.07 (s, 2 H) 8.93 (s, 1 H) 8.10 (d, J = 8.85 Hz, 2 H) 7.91 (s, 1 H) 7.20 (d, J = 8.85 Hz, 2 H) 5.77 (d, J = 8.55 Hz, 1 H) 4.89-4.96 (m, 1 H) 4.88 (s, 2 H) 2.75-2.86 (m, 2 H) 2.21 (s, 3 H) 2.07 (td, J = 11.67, 1.98 Hz, 2 H) 1.89-2.01 (m, 2 H) 1.68 (dq, J = 11.75, 11.52, 3.36 Hz, 2 H). | C |

Biological Examples

Method for Measurement of Cell Toxicity

The CellTiter-Blue® Cell Viability Assay provides a homogeneous, fluorometric method for estimating the number of viable cells present in multi-well plates. The assay uses the indicator dye resazurin to measure the metabolic capacity of cells. Viable cells retain the ability to reduce resazurin into resorufin, which is highly fluorescent. Non-viable cells rapidly lose metabolic capacity and do not reduce the indicator dye, and thus do not generate a fluorescent signal.

Stock solutions (10 or 100 mM in DMSO) of compounds were serially diluted 1:2 in 11 concentrations and 25 nL/well (100 mM stock) or 50 nL/well (10 mM stock) were acoustically dispensed in assay plates with an EDC acoustic dispenser. Final starting concentration in the assay was 20 μM (0.2% DMSO) or 100 μM (0.1% DMSO) for test compounds.

Peripheral blood mononuclear cells (PBMC) from CLL patients or healthy volunteers were seeded in assay plates (384-well black/clear, Greiner #781091) pre-dispensed with compounds, 25 μL/well, and cultured for 24, 48 and 72 h. The cell concentration was 50 000 cells/well for PBMC from CLL patients or healthy volunteers. After 24, 48 and 72 h culture, Celltiter Blue reagent was added (5 μL/well) and the plates were incubated for 2 h. The plates were read in an Envision fluorescence reader (PerkinElmer) with Ex544 nm/Em590 nm. Results were calculated as % cytotoxicity compared to background (cells treated with 0.2% DMSO).

Examples demonstrating effects on cell toxicity in PBMC from CLL patients and healthy volunteers are illustrated in Table 3. Thus, $IC_{50}$ values for cell toxicity in PBMC from CLL patients as well as healthy volunteers for some compounds of the invention are shown in Table 3.

TABLE 3

| Ex. | PBMC CLL patients $IC_{50}$ (μM) | PBMC healthy volunteers $IC_{50}$ (μM) |
|---|---|---|
| 2 | 1.30 | 13.8 |
| 3 | 1.20 | 9.90 |
| 11 | 0.44 | 14.8 |
| 15 | 0.79 | 13.9 |
| 19 | 3.23 | >20 |
| 27 | 1.42 | 14.1 |
| 34 | 3.11 | 17.7 |
| 43 | 1.74 | >20 |
| 56 | 0.37 | >20 |
| 64 | 0.89 | 13.9 |
| 71 | 1.90 | >20 |
| 75 | 1.12 | >20 |
| 82 | 0.48 | >20 |

TABLE 3-continued

| Ex. | PBMC CLL patients IC$_{50}$ (μM) | PBMC healthy volunteers IC$_{50}$ (μM) |
|---|---|---|
| 96 | 0.31 | 13.6 |
| 99 | 0.27 | >20 |
| 117 | 0.32 | >20 |
| 132 | 0.86 | >20 |
| 147 | 0.14 | >20 |
| 159 | 0.31 | >20 |
| 168 | 0.25 | >20 |
| 184 | 0.11 | >20 |
| 232 | 0.57 | >20 |
| 259 | 0.033 | 11.1 |
| 265 | 0.26 | >20 |
| 272 | 0.25 | >20 |
| 288 | 0.40 | >20 |
| 294 | 0.36 | >20 |
| 302 | 0.62 | >20 |

The invention claimed is:

1. A compound of formula (I'') or (I'')

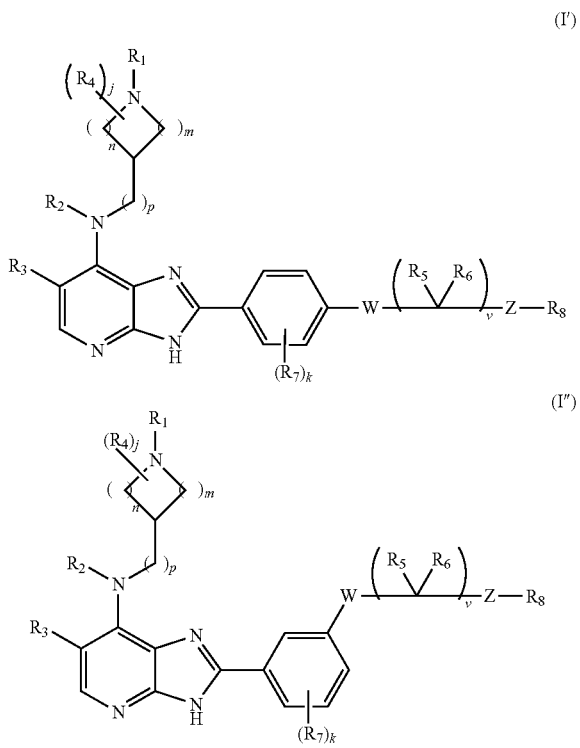

or a pharmaceutically acceptable salt thereof,
wherein
m is 1 or 2;
n is 2 or 3;
p is 0 or 1;
$R_1$ is C1-C6 alkyl, C1-C6 alkyl-Q-(CH$_2$)$_x$, or $R_{1a}$—X—;
Q is O or S;
x is an integer of from 1 to 3;
X is a direct bond or (CH$_2$)$_s$—Y—(CH$_2$)$_t$;
Y is a direct bond, O or S;
s is 1 or 2;
t is 0 or 1;
$R_{1a}$ is a cyclic moiety selected from 3- to 6-membered carbocyclyl and 5- to 6-membered heterocyclyl, said cyclic moiety optionally being substituted by one or more $R_{1b}$;

each $R_{1b}$ is independently selected from halogen, C1-C6 alkyl, $R_{1c}$O—, $R_{1d}$C(O)N(R$_{1e}$)—, cyano, $R_{1f}R_{1g}$N—, $R_{1h}$S(O)$_2$—, C3-C6 carbocyclyl, and 5- to 6-membered heterocyclyl; and two $R_{1b}$ attached to adjacent atoms of the cyclic moiety may form, together with the atoms to which they are attached, a 5- or 6-membered ring;
each $R_{1c}$, $R_{1d}$, $R_{1e}$, $R_{1f}$, $R_{1g}$, $R_{1h}$ and $R_{1i}$ is independently selected from H and C1-C6 alkyl;
$R_2$ is H or C1-C6 alkyl;
$R_3$ is halogen;
j is an integer of from 0 to 4;
$R_4$ is C1-C3 alkyl;
W is a direct bond, O, S, CR$_{w1}$R$_{w2}$, or NR$_{w3}$;
$R_{w1}$ and $R_{w2}$ are independently selected from H and C1-C3 alkyl;
$R_{w3}$ is H or C1-C3 alkyl;
v is 1 or 2;
each $R_5$ and $R_6$ is independently selected from H and C1-C3 alkyl;
k is an integer of from 0 to 2;
each $R_7$ is independently selected from halogen, C1-C3 alkyl, and $R_{7a}$O;
each $R_{7a}$ is independently from C1-C3 alkyl;
Z—$R_8$ is C(O)NR$_8$R$_9$ or NR$_{10}$C(O)R$_8$;
$R_8$ is selected from $R_{8a}$(CR$_{8b}$R$_{8c}$)$_q$—, $R_{8d}$O—, and C1-C6 alkyl, said alkyl optionally being substituted by a moiety selected from R$_{8e}$R$_{8f}$N— and R$_{8g}$O—;
q is an integer of from 0 to 2;
$R_{8a}$ is a cyclic moiety selected from C3-C7 carbocyclyl and 5- to 7-membered heterocyclyl, said cyclic moiety optionally being substituted by one or more moieties selected from halogen, C1-C6 alkyl, C3-C5 cycloalkyl, and R$_{8h}$O;
$R_{8b}$ and $R_{8c}$ are independently selected from H and C1-C3 alkyl; or
$R_{8d}$ is H, C1-C6 alkyl, or C3-C6 cycloalkyl;
$R_{8e}$ and $R_{8f}$ are independently selected from H and C1-C6 alkyl; or
$R_{8e}$ and $R_{8f}$, together with the nitrogen atom to which they are both attached, form a 5- or 6 membered heterocyclyl optionally containing a further heteroatom in the ring;
$R_{8g}$ is H or C1-C6 alkyl;
$R_{8h}$ is H or C1-C6 alkyl;
$R_9$ is H or C1-C6 alkyl;
$R_{10}$ is H or C1-C3 alkyl;
and any alkyl is saturated or unsaturated and is optionally substituted by one or more F.

2. The compound or pharmaceutically acceptable salt according to claim 1, wherein n is 2.

3. The compound or pharmaceutically acceptable salt according to claim 1, wherein p is 0.

4. The compound or pharmaceutically acceptable salt according to claim 1 wherein $R_1$ is $R_{1a}$—X—.

5. The compound or pharmaceutically acceptable salt according to claim 1 wherein X is (CH$_2$)$_s$—Y—(CH$_2$)$_t$.

6. The compound or pharmaceutically acceptable salt according to claim 1 wherein $R_{1a}$ is a cyclic moiety selected from C3-C6 cycloalkyl, phenyl and 5- to 6-membered heteroaryl, said cyclic moiety optionally being substituted by one or more $R_{1b}$.

7. The compound or pharmaceutically acceptable salt according to claim 1 wherein $R_{1a}$ is a cyclic moiety selected from phenyl and 5- or 6-membered heteroaryl, said cyclic moiety optionally being substituted by one or more $R_{1b}$.

8. The compound or pharmaceutically acceptable salt according to claim 1 wherein $R_{1a}$ is phenyl, optionally substituted by one or more $R_{1b}$.

9. The compound or pharmaceutically acceptable salt according to claim 1 wherein W is 0.

10. The compound or pharmaceutically acceptable salt of claim 1 wherein $R_8$ is C1-C6 alkyl, said alkyl optionally being substituted by a moiety selected from $NR_{8e}R_{8f}$ and $OR_{8g}$.

11. The compound or pharmaceutically acceptable salt of claim 1 wherein $R_8$ is $R_{8a}(CR_{8b}R_{8c})_q$.

12. The compound or pharmaceutically acceptable salt of claim 1 wherein $Z-R_8$ is $C(O)NR_8R_9$.

13. The compound or pharmaceutically acceptable salt of any claim 1 wherein $Z-R_8$ is $NR_{10}C(O)R_8$.

14. The compound according to claim 1, which is a compound of formula (I").

15. A compound according to claim 1, selected from
2-(4-{7-[(1-benzylpiperidin-4-yl)amino]-6-chloro-3H-imidazo[4,5-b]pyridin-2-yl}phenoxy)-N-[2-(dimethylamino)ethyl]acetamide,
2-[4-(7-{[(3S)-1-benzylpyrrolidin-3-yl]amino}-6-chloro-3H-imidazo[4,5-b]pyridin-2-yl)phenoxy]-N-[2-(dimethylamino)ethyl]acetamide,
2-[4-(6-chloro-7-{[1-(2-phenylethyl)piperidin-4-yl]amino}-3H-imidazo[4,5-b]pyridin-2-yl)phenoxy]-N-[2-(dimethylamino)ethyl]acetamide,
2-[4-(7-{[(3S)-1-benzylpyrrolidin-3-yl]amino}-6-chloro-3H-imidazo[4,5-b]pyridin-2-yl)phenoxy]-N-[2-(dimethylamino)-1,1-dimethylethyl]acetamide,
2-(4-{7-[(1-benzylpiperidin-4-yl)amino]-6-chloro-3H-imidazo[4,5-b]pyridin-2-yl}phenoxy)-N-[2-(dimethylamino)-1,1-dimethylethyl]acetamide,
2-[4-(6-chloro-7-{[1-(4-fluorobenzyl)piperidin-4-yl]amino}-3H-imidazo[4,5-b]pyridin-2-yl)phenoxy]-N-[2-(dimethylamino)-1,1-dimethylethyl]acetamide,
2-(4-{7-[(1-benzylpiperidin-3-yl)amino]-6-chloro-3H-imidazo[4,5-b]pyridin-2-yl}phenoxy)-N-[2-(dimethylamino)-1,1-dimethylethyl]acetamide,
2-{4-[6-chloro-7-({1-[(3-methyl-2-thienyl)methyl]piperidin-4-yl}amino)-3H-imidazo[4,5-b]pyridin-2-yl]phenoxy}-N-[2-(dimethylamino)-1,1-dimethylethyl]acetamide,
2-[4-(6-chloro-7-{[1-(3-methylbenzyl)piperidin-4-yl]amino}-3H-imidazo[4,5-b]pyridin-2-yl)phenoxy]-N-[2-(dimethylamino)ethyl]acetamide,
2-[4-(6-chloro-7-{[1-(4-methylbenzyl)piperidin-4-yl]amino}-3H-imidazo[4,5-b]pyridin-2-yl)phenoxy]-N-[2-(dimethylamino)ethyl]acetamide,
2-(4-{7-[(1-benzylpiperidin-4-yl)amino]-6-chloro-3H-imidazo[4,5-b]pyridin-2-yl}phenoxy)-N-m ethylacetamide,
2-[4-(7-{[(3S)-1-benzylpyrrolidin-3-yl]amino}-6-chloro-3H-imidazo[4,5-b]pyridin-2-yl)phenoxy]-N-methylacetamide,
2-[4-(7-{[1-(1,3-benzodioxol-5-ylmethyl)piperidin-4-yl]amino}-6-chloro-3H-imidazo[4,5-b]pyridin-2-yl)phenoxy]-N-[2-(dimethylamino)ethyl]acetamide,
2-[4-(6-chloro-7-{[1-(1,3-thiazol-2-ylmethyl)piperidin-4-yl]amino}-3H-imidazo[4,5-b]pyridin-2-yl)phenoxy]-N-[2-(dimethylamino)ethyl]acetamide,
2-[4-(6-chloro-7-{[1-(thiophen-3-ylmethyl)piperidin-4-yl]amino}-3H-imidazo[4,5-b]pyridin-2-yl)phenoxy]-N-[2-(dimethylamino)ethyl]acetamide,
2-[4-(7-{[(1-benzylpiperidin-4-yl)methyl]amino}-6-chloro-3H-imidazo[4,5-b]pyridin-2-yl)phenoxy]-N-[2-(dimethylamino)ethyl]acetamide,
2-(4-{7-[(1-benzylpiperidin-4-yl)(methyl)amino]-6-chloro-3H-imidazo[4,5-b]pyridin-2-yl}phenoxy)-N-[2-(diethylamino)ethyl]acetamide,
2-(4-{7-[(1-benzylpiperidin-4-yl)(methyl)amino]-6-chloro-3H-imidazo[4,5-b]pyridin-2-yl}phenoxy)-N-[2-(dimethylamino)-2-methylpropyl]acetamide,
2-(4-{7-[(1-benzylpiperidin-4-yl)(methyl)amino]-6-chloro-3H-imidazo[4,5-b]pyridin-2-yl}phenoxy)-N-methylacetamide,
2-(4-{7-[(1-benzylpiperidin-4-yl)(methyl)amino]-6-chloro-3H-imidazo[4,5-b]pyridin-2-yl}phenoxy)-N-[2-(dimethylamino)ethyl]acetamide,
2-(4-{7-[(1-benzylpiperidin-4-yl)(methyl)amino]-6-chloro-3H-imidazo[4,5-b]pyridin-2-yl}phenoxy)-N-[2-(dimethylamino)-1-methylethyl]acetamide,
2-[4-(6-chloro-7-{[1-(4-chlorobenzyl)piperidin-4-yl]amino}-3H-imidazo[4,5-b]pyridin-2-yl)phenoxy]-N-[2-(dimethylamino)ethyl]acetamide,
2-(4-{7-[(1-benzylpiperidin-4-yl)amino]-6-chloro-3H-imidazo[4,5-b]pyridin-2-yl}phenoxy)-N-[2-(dimethylamino)-2-methylpropyl]acetamide,
2-[4-(7-{[(3R)-1-benzylpyrrolidin-3-yl]amino}-6-chloro-3H-imidazo[4,5-b]pyridin-2-yl)phenoxy]-N-[2-(dimethylamino)-2-methylpropyl]acetamide,
2-[4-(7-{[(3S)-1-benzylpyrrolidin-3-yl]amino}-6-chloro-3H-imidazo[4,5-b]pyridin-2-yl)phenoxy]-N-[2-(dimethylamino)-2-methylpropyl]acetamide,
2-[4-(6-chloro-7-{[1-(4-fluorobenzyl)piperidin-4-yl]amino}-3H-imidazo[4,5-b]pyridin-2-yl)phenoxy]-N-[2-(dimethylamino)-2-methylpropyl]acetamide,
2-[4-(6-chloro-7-{[1-(4-methylbenzyl)piperidin-4-yl]amino}-3H-imidazo[4,5-b]pyridin-2-yl)phenoxy]-N-[2-(dimethylamino)-2-methylpropyl]acetamide,
2-[4-(6-chloro-7-{[1-(3-methylbenzyl)piperidin-4-yl]amino}-3H-imidazo[4,5-b]pyridin-2-yl)phenoxy]-N-[2-(dimethylamino)-2-methylpropyl]acetamide,
2-{4-[6-chloro-7-({1-[(5-methylfuran-2-yl)methyl]piperidin-4-yl}amino)-3H-imidazo[4,5-b]pyridin-2-yl]phenoxy}-N-[2-(dimethylamino)ethyl]acetamide,
2-[4-(7-{[(3R)-1-benzylpyrrolidin-3-yl]amino}-6-chloro-3H-imidazo[4,5-b]pyridin-2-yl)phenoxy]-N-[2-(dimethylamino)ethyl]acetamide,
2-[4-(7-{[(1-benzylpiperidin-4-yl)methyl]amino}-6-chloro-3H-imidazo[4,5-b]pyridin-2-yl)phenoxy]-N-[2-(dimethylamino)-2-methylpropyl]acetamide,
2-[4-(6-chloro-7-{[(3S)-1-(3,4-difluorobenzyl)pyrrolidin-3-yl]amino}-3H-imidazo[4,5-b]pyridin-2-yl)phenoxy]-N-[2-(dimethylamino)ethyl]acetamide,
2-[4-(6-chloro-7-{[(3S)-1-(4-fluorobenzyl)pyrrolidin-3-yl]amino}-3H-imidazo[4,5-b]pyridin-2-yl)phenoxy]-N-[2-(dimethylamino)ethyl]acetamide,
2-[4-(6-chloro-7-{[(3S)-1-(3,4-difluorobenzyl)pyrrolidin-3-yl]amino}-3H-imidazo[4,5-b]pyridin-2-yl)phenoxy]-N-methylacetamide,
2-[4-(6-chloro-7-{[(3S)-1-(4-fluorobenzyl)pyrrolidin-3-yl]amino}-3H-imidazo[4,5-b]pyridin-2-yl)phenoxy]-N-methylacetamide,
2-[4-(6-chloro-7-{[(3R)-1-(4-fluorobenzyl)pyrrolidin-3-yl]amino}-3H-imidazo[4,5-b]pyridin-2-yl)phenoxy]-N-[2-(dimethylamino)ethyl]acetamide,
2-[4-(6-chloro-7-{[(3R)-1-(4-fluorobenzyl)pyrrolidin-3-yl]amino}-3H-imidazo[4,5-b]pyridin-2-yl)phenoxy]-N-methylacetamide,
2-[4-(7-{[(3R)-1-benzylpyrrolidin-3-yl]amino}-6-chloro-3H-imidazo[4,5-b]pyridin-2-yl)phenoxy]-N-methylacetamide, 2-[4-(6-chloro-7-{[1-(thiophen-3-ylmethyl)piperidin-4-yl]amino}-3H-imidazo[4,5-b]pyridin-2-yl)phenoxy]-N-methylacetamide,
2-[4-(6-chloro-7-{[1-(3-methylbenzyl)piperidin-4-yl]amino}-3H-imidazo[4,5-b]pyridin-2-yl)phenoxy]-N-methylacetamide,
2-[4-(6-chloro-7-{[(3S)-1-(2-phenylethyl)pyrrolidin-3-yl]amino}-3H-imidazo[4,5-b]pyridin-2-yl)phenoxy]-N-methylacetamide,
2-{4-[6-chloro-7-({1-[(3-methyl-2-thienyl)methyl]piperidin-4-yl}amino)-3H-imidazo[4,5-b]pyridin-2-yl]phenoxy}-N-methylacetamide,
2-[4-(6-chloro-7-{[(3S)-1-(4-methoxybenzyl)pyrrolidin-3-yl]amino}-3H-imidazo[4,5-b]pyridin-2-yl)phenoxy]-N-methylacetamide,
2-[4-(6-chloro-7-{[1-(4-methoxybenzyl)piperidin-4-yl]amino}-3H-imidazo[4,5-b]pyridin-2-yl)phenoxy]-N-methylacetamide,
2-[4-(7-{[1-(1,3-benzodioxol-5-ylmethyl)piperidin-4-yl]amino}-6-chloro-3H-imidazo[4,5-b]pyridin-2-yl)phenoxy]-N-methylacetamide,
2-{4-[6-chloro-7-({1-[(5-methylfuran-2-yl)methyl]piperidin-4-yl}amino)-3H-imidazo[4,5-b]pyridin-2-yl]phenoxy}-N-methylacetamide,
2-[4-(6-chloro-7-{[(3S)-1-(thiophen-3-ylmethyl)pyrrolidin-3-yl]amino}-3H-imidazo[4,5-b]pyridin-2-yl)phenoxy]-N-methylacetamide,
2-[4-(6-chloro-7-{[1-(furan-3-ylmethyl)piperidin-4-yl]amino}-3H-imidazo[4,5-b]pyridin-2-yl)phenoxy]-N-methylacetamide,
2-[4-(7-{[(3S)-1-(1,3-benzodioxol-5-ylmethyl)pyrrolidin-3-yl]amino}-6-chloro-3H-imidazo[4,5-b]pyridin-2-yl)phenoxy]-N-methylacetamide,
2-[4-(6-chloro-7-{[(3S)-1-(1,3-thiazol-2-ylmethyl)pyrrolidin-3-yl]amino}-3H-imidazo[4,5-b]pyridin-2-yl)phenoxy]-N-methylacetamide,
2-{4-[6-chloro-7-({(3S)-1-[(3-methyl-2-thienyl)methyl]pyrrolidin-3-yl}amino)-3H-imidazo[4,5-b]pyridin-2-yl]phenoxy}-N-methylacetamide,
2-{4-[6-chloro-7-({(3S)-1-[4-(trifluoromethyl)benzyl]pyrrolidin-3-yl}amino)-3H-imidazo[4,5-b]pyridin-2-yl]phenoxy}-N-methylacetamide,
2-[4-(6-chloro-7-{[(3S)-1-(3-methylbenzyl)pyrrolidin-3-yl]amino}-3H-imidazo[4,5-b]pyridin-2-yl)phenoxy]-N-methylacetamide,
2-[4-(6-chloro-7-{[(3S)-1-(4-methylbenzyl)pyrrolidin-3-yl]amino}-3H-imidazo[4,5-b]pyridin-2-yl)phenoxy]-N-methylacetamide,
2-[4-(6-chloro-7-{[(3S)-1-(2-thienylmethyl)pyrrolidin-3-yl]amino}-3H-imidazo[4,5-b]pyridin-2-yl)phenoxy]-N-methylacetamide,
2-(4-{6-chloro-7-[(1-cyclohexylpiperidin-4-yl)amino]-3H-imidazo[4,5-b]pyridin-2-yl}phenoxy)-N-m ethylacetamide,
2-[4-(6-chloro-7-{[(3S)-1-(3-methoxybenzyl)pyrrolidin-3-yl]amino}-3H-imidazo[4,5-b]pyridin-2-yl)phenoxy]-N-methylacetamide,
2-[4-(6-chloro-7-{[(3S)-1-(2-methoxybenzyl)pyrrolidin-3-yl]amino}-3H-imidazo[4,5-b]pyridin-2-yl)phenoxy]-N-methylacetamide,
2-[4-(6-chloro-7-{[(3S)-1-(2-methylbenzyl)pyrrolidin-3-yl]amino}-3H-imidazo[4,5-b]pyridin-2-yl)phenoxy]-N-methylacetamide,
2-[4-(6-chloro-7-{[1-(2,4-dimethoxybenzyl)piperidin-4-yl]amino}-3H-imidazo[4,5-b]pyridin-2-yl)phenoxy]-N-methylacetamide,
2-[4-(6-chloro-7-{[1-(2-methoxybenzyl)piperidin-4-yl]amino}-3H-imidazo[4,5-b]pyridin-2-yl)phenoxy]-N-methylacetamide,
2-[4-(6-chloro-7-{[1-(3-methoxybenzyl)piperidin-4-yl]amino}-3H-imidazo[4,5-b]pyridin-2-yl)phenoxy]-N-methylacetamide,
2-(4-{7-[(1-benzylpiperidin-4-yl)amino]-6-chloro-3H-imidazo[4,5-b]pyridin-2-yl}phenoxy)-N,N-dimethyl-acetamide,
2-[4-(7-{[(3S)-1-benzylpyrrolidin-3-yl]amino}-6-chloro-3H-imidazo[4,5-b]pyridin-2-yl)phenoxy]-N,N-dimethylacetamide,
2-[4-(6-chloro-7-{[1-(2,3-dihydro-1,4-benzodioxin-6-ylmethyl)piperidin-4-yl]amino}-3H-imidazo[4,5-b]pyridin-2-yl)phenoxy]-N-methylacetamide,
2-[4-(6-chloro-7-{[1-(cyclohexylmethyl)piperidin-4-yl]amino}-3H-imidazo[4,5-b]pyridin-2-yl)phenoxy]-N-methylacetamide,
2-[4-(6-chloro-7-{[1-(2,2-dimethylpropyl)piperidin-4-yl]amino}-3H-imidazo[4,5-b]pyridin-2-yl)phenoxy]-N-methylacetamide,
2-[4-(6-chloro-7-{[1-(3-hydroxybenzyl)piperidin-4-yl]amino}-3H-imidazo[4,5-b]pyridin-2-yl)phenoxy]-N-methylacetamide,
2-{4-[6-chloro-7-({1-[4-(difluoromethoxy)benzyl]piperidin-4-yl}amino)-3H-imidazo[4,5-b]pyridin-2-yl]phenoxy}-N-methylacetamide,
2-[4-(6-chloro-7-{[1-(4-methoxy-3-methylbenzyl)piperidin-4-yl]amino}-3H-imidazo[4,5-b]pyridin-2-yl)phenoxy]-N-methylacetamide,
2-[4-(6-chloro-7-{[1-(pyridin-4-ylmethyl)piperidin-4-yl]amino}-3H-imidazo[4,5-b]pyridin-2-yl)phenoxy]-N-methylacetamide,
2-[4-(6-chloro-7-{[1-(pyridin-3-ylmethyl)piperidin-4-yl]amino}-3H-imidazo[4,5-b]pyridin-2-yl)phenoxy]-N-methylacetamide,
2-{4-[6-chloro-7-({1-[(1-methyl-1H-pyrrol-2-yl)methyl]piperidin-4-yl}amino)-3H-imidazo[4,5-b]pyridin-2-yl]phenoxy}-N-methylacetamide,
2-{4-[6-chloro-7-({1-[(6-methylpyridin-2-yl)methyl]piperidin-4-yl}amino)-3H-imidazo[4,5-b]pyridin-2-yl]phenoxy}-N-methylacetamide,
2-[4-(7-{[1-(4-acetamidobenzyl)piperidin-4-yl]amino}-6-chloro-3H-imidazo[4,5-b]pyridin-2-yl)phenoxy]-N-methylacetamide,
2-[4-(6-chloro-7-{[1-(1,3-thiazol-2-ylmethyl)piperidin-4-yl]amino}-3H-imidazo[4,5-b]pyridin-2-yl)phenoxy]-N-methylacetamide,
2-[4-(6-chloro-7-{[1-(4-ethoxybenzyl)piperidin-4-yl]amino}-3H-imidazo[4,5-b]pyridin-2-yl)phenoxy]-N-methylacetamide,
2-[4-(6-chloro-7-{[1-(4-isopropoxybenzyl)piperidin-4-yl]amino}-3H-imidazo[4,5-b]pyridin-2-yl)phenoxy]-N-methylacetamide,
2-[4-(7-{[(1-benzylpiperidin-4-yl)methyl]amino}-6-chloro-3H-imidazo[4,5-b]pyridin-2-yl)phenoxy]-N-methylacetamide,
2-[4-(6-chloro-7-{[1-(4-methoxy-3,5-dimethylbenzyl)piperidin-4-yl]amino}-3H-imidazo[4,5-b]pyridin-2-yl)phenoxy]-N-methylacetamide,
2-[4-(6-chloro-7-{[1-(4-chlorobenzyl)piperidin-4-yl]amino}-3H-imidazo[4,5-b]pyridin-2-yl)phenoxy]-N-methylacetamide,
2-[4-(6-chloro-7-{[1-(4-methylbenzyl)piperidin-4-yl]amino}-3H-imidazo[4,5-b]pyridin-2-yl)phenoxy]-N-methylacetamide, 2-[4-(6-chloro-7-{[1-(4-cyanobenzyl)piperidin-4-yl]amino}-3H-imidazo[4,5-b]pyridin-2-yl)phenoxy]-N-methylacetamide, 2-[4-(6-chloro-7-{[1-(3-cyanobenzyl)piperidin-4-yl]amino}-3H-imidazo[4,5-b]pyridin-2-yl)phenoxy]-N-methylacetamide, 2-[4-(6-chloro-7-{[1-(4-hydroxybenzyl)piperidin-4-yl]amino}-3H-imidazo[4,5-b]pyridin-2-yl)phenoxy]-N-methylacetamide, 2-[4-(6-chloro-7-{[1-(4-fluorobenzyl)piperidin-4-yl]amino}-3H-imidazo[4,5-b]pyridin-2-yl)phenoxy]-N-methylacetamide, 2-[4-(6-chloro-7-{[1-(3,4-difluorobenzyl)piperidin-4-yl]amino}-3H-imidazo[4,5-b]pyridin-2-yl)phenoxy]-N-methylacetamide, 2-{4-[6-chloro-7-({1-[4-(dimethylamino)benzyl]piperidin-4-yl}amino)-3H-imidazo[4,5-b]pyridin-2-yl]phenoxy}-N-methylacetamide, 2-{4-[6-chloro-7-({1-[4-(methylsulfonyl)benzyl]piperidin-4-yl}amino)-3H-imidazo[4,5-b]pyridin-2-yl]phenoxy}-N-methylacetamide, 2-[4-(6-chloro-7-{[1-(2,3-dihydro-1-benzofuran-5-ylmethyl)piperidin-4-yl]amino}-3H-imidazo[4,5-b]pyridin-2-yl)phenoxy]-N-methylacetamide, 2-(4-{6-chloro-7-[(1-methylpiperidin-4-yl)amino]-3H-imidazo[4,5-b]pyridin-2-yl}phenoxy)-N-m ethylacetamide, 2-[4-(6-chloro-7-{[1-(2-thienylmethyl)piperidin-4-yl]amino}-3H-imidazo[4,5-b]pyridin-2-yl)phenoxy]-N-methylacetamide, 2-[4-(6-chloro-7-{[1-(2-phenylethyl)piperidin-4-yl]amino}-3H-imidazo[4,5-b]pyridin-2-yl)phenoxy]-N-methylacetamide, 2-{4-[6-chloro-7-({1-[2-(4-methoxyphenyl)ethyl]piperidin-4-yl}amino)-3H-imidazo[4,5-b]pyridin-2-yl]phenoxy}-N-methylacetamide, 2-[4-(6-chloro-7-{[1-(2-phenoxyethyl)piperidin-4-yl]amino}-3H-imidazo[4,5-b]pyridin-2-yl)phenoxy]-N-methylacetamide, 2-[4-(6-chloro-7-{[1-(3,4-dimethoxybenzyl)piperidin-4-yl]amino}-3H-imidazo[4,5-b]pyridin-2-yl)phenoxy]-N-methylacetamide, 2-[4-(6-chloro-7-{[1-(4-hydroxy-3-methoxybenzyl)piperidin-4-yl]amino}-3H-imidazo[4,5-b]pyridin-2-yl)phenoxy]-N-methylacetamide, 2-{4-[6-chloro-7-({1-[4-(1H-1,2,4-triazol-1-yl)benzyl]piperidin-4-yl}amino)-3H-imidazo[4,5-b]pyridin-2-yl]phenoxy}-N-methylacetamide, 2-{4-[6-chloro-7-({1-[4-(methylthio)benzyl]piperidin-4-yl}amino)-3H-imidazo[4,5-b]pyridin-2-yl]phenoxy}-N-methylacetamide, 2-[4-(6-chloro-7-{[1-(4-methoxybenzyl)piperidin-4-yl]amino}-3H-imidazo[4,5-b]pyridin-2-yl)phenoxy]-N-(2-hydroxyethyl)acetamide, 2-[4-(6-chloro-7-{[1-(4-methoxybenzyl)piperidin-4-yl]amino}-3H-imidazo[4,5-b]pyridin-2-yl)phenoxy]-N-[2-(dimethylamino)ethyl]acetamide, 2-[4-(6-chloro-7-{[1-(4-methoxybenzyl)piperidin-4-yl]amino}-3H-imidazo[4,5-b]pyridin-2-yl)phenoxy]-N-[2-(dimethylamino)-2-methylpropyl]acetamide, 2-[4-(6-chloro-7-{[1-(4-methoxybenzyl)piperidin-4-yl]amino}-3H-imidazo[4,5-b]pyridin-2-yl)phenoxy]-N-isopropylacetamide, 2-[4-(6-chloro-7-{[1-(4-methoxybenzyl)piperidin-4-yl]amino}-3H-imidazo[4,5-b]pyridin-2-yl)phenoxy]-N-(2-isopropoxyethyl)acetamide, 3-[4-(6-chloro-7-{[1-(4-methoxybenzyl)piperidin-4-yl]amino}-3H-imidazo[4,5-b]pyridin-2-yl)phenyl]-N-methylpropanamide, 3-[4-(6-chloro-7-{[1-(4-methoxybenzyl)piperidin-4-yl]amino}-3H-imidazo[4,5-b]pyridin-2-yl)phenyl]-N-[2-(dimethylamino)ethyl]propanamide, 3-[4-(6-chloro-7-{[1-(4-methoxybenzyl)piperidin-4-yl]amino}-3H-imidazo[4,5-b]pyridin-2-yl)phenyl]-N-methoxypropanamide, 2-(4-{6-chloro-7-[(1-ethylpiperidin-4-yl)amino]-3H-imidazo[4,5-b]pyridin-2-yl}phenoxy)-N-m ethylacetamide, 2-[4-(6-chloro-7-{[1-(1-methylethyl)piperidin-4-yl]amino}-3H-imidazo[4,5-b]pyridin-2-yl)phenoxy]-N-methylacetamide, 2-[4-(6-bromo-7-{[1-(4-methoxybenzyl)piperidin-4-yl]amino}-3H-imidazo[4,5-b]pyridin-2-yl)phenoxy]-N-methylacetamide, 2-[4-(6-bromo-7-{[1-(2,3-dihydro-1-benzofuran-5-ylmethyl)piperidin-4-yl]amino}-3H-imidazo[4,5-b]pyridin-2-yl)phenoxy]-N-methylacetamide, 2-[4-(6-bromo-7-{[1-(thiophen-2-ylmethyl)piperidin-4-yl]amino}-3H-imidazo[4,5-b]pyridin-2-yl)phenoxy]-N-methylacetamide, 2-(4-{6-bromo-7-[(1-methylpiperidin-4-yl)amino]-3H-imidazo[4,5-b]pyridin-2-yl}phenoxy)-N-m ethylacetamide, 2-[4-(6-bromo-7-{[(3S)-1-(2-methoxybenzyl)pyrrolidin-3-yl]amino}-3H-imidazo[4,5-b]pyridin-2-yl)phenoxy]-N-methylacetamide, 2-[3-(6-chloro-7-{[1-(4-methoxybenzyl)piperidin-4-yl]amino}-3H-imidazo[4,5-b]pyridin-2-yl)phenoxy]-N-methylacetamide, 2-(3-{6-chloro-7-[(1-methylpiperidin-4-yl)amino]-3H-imidazo[4,5-b]pyridin-2-yl}phenoxy)-N-m ethylacetamide, 2-[3-(6-chloro-7-{[1-(2,3-dihydro-1-benzofuran-5-ylmethyl)piperidin-4-yl]amino}-3H-imidazo[4,5-b]pyridin-2-yl)phenoxy]-N-methylacetamide, 2-[3-(6-chloro-7-{[1-(thiophen-2-ylmethyl)piperidin-4-yl]amino}-3H-imidazo[4,5-b]pyridin-2-yl)phenoxy]-N-methylacetamide, 2-[3-(7-{[1-(1,3-benzodioxol-5-ylmethyl)piperidin-4-yl]amino}-6-chloro-3H-imidazo[4,5-b]pyridin-2-yl)phenoxy]-N-methylacetamide, 2-[3-(6-chloro-7-{[1-(2-phenoxyethyl)piperidin-4-yl]amino}-3H-imidazo[4,5-b]pyridin-2-yl)phenoxy]-N-methylacetamide, 2-[3-(6-chloro-7-{[(3S)-1-(2-methoxybenzyl)pyrrolidin-3-yl]amino}-3H-imidazo[4,5-b]pyridin-2-yl)phenoxy]-N-methylacetamide, 2-[3-(7-{[(3S)-1-benzylpyrrolidin-3-yl]amino}-6-chloro-3H-imidazo[4,5-b]pyridin-2-yl)phenoxy]-N-methylacetamide, 2-(4-{6-chloro-7-[(1,2,2,6,6-pentamethylpiperidin-4-yl)amino]-3H-imidazo[4,5-b]pyridin-2-yl}phenoxy)-N-methylacetamide, 2-{3-[6-chloro-7-({1-[4-(1H-1,2,4-triazol-1-yl)benzyl]piperidin-4-yl}amino)-3H-imidazo[4,5-b]pyridin-2-yl]phenoxy}-N-methylacetamide, 2-[4-(6-chloro-7-{[(3S)-1-methylpyrrolidin-3-yl]amino}-3H-imidazo[4,5-b]pyridin-2-yl)phenoxy]-N-methylacetamide, 2-[3-(6-chloro-7-{[1-(3-thienylmethyl)piperidin-4-yl]amino}-3H-imidazo[4,5-b]pyridin-2-yl)phenoxy]-N-methylacetamide, 2-[3-(6-chloro-7-{[1-(3-hydroxybenzyl)piperidin-4-yl]amino}-3H-imidazo[4,5-b]pyridin-2-yl)phenoxy]-N-methylacetamide,
2-[4-(6-chloro-7-{[(3S)-1-ethylpyrrolidin-3-yl]amino}-3H-imidazo[4,5-b]pyridin-2-yl)phenoxy]-N-methylacetamide,
2-[4-(6-chloro-7-{[(3S)-1-propylpyrrolidin-3-yl]amino}-3H-imidazo[4,5-b]pyridin-2-yl)phenoxy]-N-methylacetamide,
2-[4-(6-chloro-7-{[(3S)-1-(1-methylethyl)pyrrolidin-3-yl]amino}-3H-imidazo[4,5-b]pyridin-2-yl)phenoxy]-N-methylacetamide,
2-(4-{6-chloro-7-[(1-methylpiperidin-4-yl)amino]-3H-imidazo[4,5-b]pyridin-2-yl}phenoxy)-N-ethylacetamide,
2-(4-{6-chloro-7-[(1-methylpiperidin-4-yl)amino]-3H-imidazo[4,5-b]pyridin-2-yl}phenoxy)-N-isopropylacetamide,
2-(4-{6-chloro-7-[(1-methylpiperidin-4-yl)amino]-3H-imidazo[4,5-b]pyridin-2-yl}phenoxy)-N-cyclopentylacetamide,
2-(4-{6-bromo-7-[(1-ethylpiperidin-4-yl)amino]-3H-imidazo[4,5-b]pyridin-2-yl}phenoxy)-N-methylacetamide,
2-(4-{6-chloro-7-[(1-methylpiperidin-4-yl)amino]-3H-imidazo[4,5-b]pyridin-2-yl}phenoxy)-N-m ethoxyacetamide,
2-(4-{6-bromo-7-[(1-propylpiperidin-4-yl)amino]-3H-imidazo[4,5-b]pyridin-2-yl}phenoxy)-N-methylacetamide,
2-[4-(6-bromo-7-{[1-(1-methylethyl)piperidin-4-yl]amino}-3H-imidazo[4,5-b]pyridin-2-yl)phenoxy]-N-methylacetamide,
2-(4-{6-chloro-7-[(1-methylpiperidin-4-yl)amino]-3H-imidazo[4,5-b]pyridin-2-yl}phenoxy)-N-(2-isopropoxyethyl)acetamide,
2-(4-{6-chloro-7-[(1-methylpiperidin-4-yl)amino]-3H-imidazo[4,5-b]pyridin-2-yl}phenoxy)-N-[2-(dimethylamino)ethyl]acetamide,
2-[4-(6-bromo-7-{[(3S)-1-methylpyrrolidin-3-yl]amino}-3H-imidazo[4,5-b]pyridin-2-yl)phenoxy]-N-methylacetamide,
2-(4-{6-chloro-7-[(1-methylpiperidin-4-yl)amino]-3H-imidazo[4,5-b]pyridin-2-yl}phenoxy)-N-(2-cyclohexylethyl)acetamide,
2-(4-{6-chloro-7-[(1-methylpiperidin-4-yl)amino]-3H-imidazo[4,5-b]pyridin-2-yl}phenoxy)-N-(cyclohexylmethyl)acetamide,
2-(4-{6-chloro-7-[(1-methylpiperidin-4-yl)amino]-3H-imidazo[4,5-b]pyridin-2-yl}phenoxy)-N-[2-(tetrahydro-2H-pyran-4-yl)ethyl]acetamide,
2-(4-{6-chloro-7-[(1-methylpiperidin-4-yl)amino]-3H-imidazo[4,5-b]pyridin-2-yl}phenoxy)-N-(tetrahydro-2H-pyran-4-ylmethyl)acetamide,
2-(4-{6-chloro-7-[(1-methylpiperidin-4-yl)amino]-3H-imidazo[4,5-b]pyridin-2-yl}phenoxy)-N-[2-(1-methylpiperidin-4-yl)ethyl]acetamide,
2-(4-{6-chloro-7-[(1-methylpiperidin-4-yl)amino]-3H-imidazo[4,5-b]pyridin-2-yl}phenoxy)-N-[(1-methylpiperidin-4-yl)methyl]acetamide,
2-(4-{6-chloro-7-[(1-methylpiperidin-4-yl)amino]-3H-imidazo[4,5-b]pyridin-2-yl}phenoxy)-N-(piperidin-4-ylmethyl)acetamide,
2-(4-{6-chloro-7-[(1-methylpiperidin-4-yl)amino]-3H-imidazo[4,5-b]pyridin-2-yl}phenoxy)-N-(2-morpholin-4-ylethyl)acetamide,
2-(4-{6-chloro-7-[(1-methylpiperidin-4-yl)amino]-3H-imidazo[4,5-b]pyridin-2-yl}phenoxy)-N-(3-morpholin-4-ylpropyl)acetamide,
2-[4-(6-chloro-7-{[1-(2-methoxyethyl)piperidin-4-yl]amino}-3H-imidazo[4,5-b]pyridin-2-yl)phenoxy]-N-methylacetamide,
2-(4-{6-chloro-7-[(1-methylpiperidin-4-yl)amino]-3H-imidazo[4,5-b]pyridin-2-yl}phenoxy)-N-(2-piperidin-4-ylethyl)acetamide,
2-(4-{6-chloro-7-[(1-methylpiperidin-4-yl)amino]-3H-imidazo[4,5-b]pyridin-2-yl}-3-methylphenoxy)-N-methylacetamide,
2-[4-(6-chloro-7-{[1-(4-methoxybenzyl)piperidin-4-yl]amino}-3H-imidazo[4,5-b]pyridin-2-yl)-3-methylphenoxy]-N-methylacetamide,
2-(4-{6-bromo-7-[(1-ethylpiperidin-4-yl)amino]-3H-imidazo[4,5-b]pyridin-2-yl}-3-methylphenoxy)-N-methylacetamide,
2-(4-{6-bromo-7-[(1-methylpiperidin-4-yl)amino]-3H-imidazo[4,5-b]pyridin-2-yl}-3-methylphenoxy)-N-methylacetamide,
2-[4-(6-bromo-7-{[1-(4-methoxybenzyl)piperidin-4-yl]amino}-3H-imidazo[4,5-b]pyridin-2-yl)-3-methylphenoxy]-N-methylacetamide,
2-[4-(6-chloro-7-{[1-(4-methoxybenzyl)piperidin-4-yl]amino}-3H-imidazo[4,5-b]pyridin-2-yl)-2-methylphenoxy]-N-methylacetamide,
2-(4-{6-chloro-7-[(1-methylpiperidin-4-yl)amino]-3H-imidazo[4,5-b]pyridin-2-yl}-2-methylphenoxy)-N-methylacetamide,
2-(4-{6-bromo-7-[(1-methylpiperidin-4-yl)amino]-3H-imidazo[4,5-b]pyridin-2-yl}-2-methylphenoxy)-N-methylacetamide,
2-(4-{6-bromo-7-[(1-ethylpiperidin-4-yl)amino]-3H-imidazo[4,5-b]pyridin-2-yl}-2-methylphenoxy)-N-methylacetamide,
2-(4-{6-bromo-7-[(1-propylpiperidin-4-yl)amino]-3H-imidazo[4,5-b]pyridin-2-yl}-2-methylphenoxy)-N-methylacetamide,
2-[4-(6-chloro-7-{[(3S)-1-(1-methylethyl)pyrrolidin-3-yl]amino}-3H-imidazo[4,5-b]pyridin-2-yl)-2-methylphenoxy]-N-methylacetamide,
2-(4-{6-bromo-7-[(1-methylpiperidin-4-yl)amino]-3H-imidazo[4,5-b]pyridin-2-yl}-2-methoxyphenoxy)-N-methylacetamide,
2-(4-{6-chloro-7-[(1-methylpiperidin-4-yl)amino]-3H-imidazo[4,5-b]pyridin-2-yl}-2-methoxyphenoxy)-N-methylacetamide,
2-[4-(6-chloro-7-{[1-(4-methoxybenzyl)piperidin-4-yl]amino}-3H-imidazo[4,5-b]pyridin-2-yl)-2-methoxyphenoxy]-N-methylacetamide,
2-(4-{6-bromo-7-[(1-propylpiperidin-4-yl)amino]-3H-imidazo[4,5-b]pyridin-2-yl}-2-methoxyphenoxy)-N-methylacetamide,
2-[4-(6-chloro-7-{[(3S)-1-(1-methylethyl)pyrrolidin-3-yl]amino}-3H-imidazo[4,5-b]pyridin-2-yl)-2-methoxyphenoxy]-N-methylacetamide,
2-[4-(6-chloro-7-{[1-(2,3-dihydro-1-benzofuran-5-ylmethyl)piperidin-4-yl]amino}-3H-imidazo[4,5-b]pyridin-2-yl)-3-methylphenoxy]-N-methylacetamide,
2-(4-{6-chloro-7-[(1-ethylpiperidin-4-yl)amino]-3H-imidazo[4,5-b]pyridin-2-yl}-3-methylphenoxy)-N-methylacetamide,
2-[4-(6-chloro-7-{[1-(thiophen-3-ylmethyl)piperidin-4-yl]amino}-3H-imidazo[4,5-b]pyridin-2-yl)-3-methylphenoxy]-N-methylacetamide, 2-[4-(6-chloro-7-{[(3S)-1-(2-methoxybenzyl)pyrrolidin-3-yl]amino}-3H-imidazo[4,5-b]pyridin-2-yl)-2-methylphenoxy]-N-methylacetamide, 2-[4-(6-chloro-7-{[1-(thiophen-3-ylmethyl)piperidin-4-yl]amino}-3H-imidazo[4,5-b]pyridin-2-yl)-2-methylphenoxy]-N-methylacetamide, 2-(4-{6-chloro-7-[(1-ethylpiperidin-4-yl)amino]-3H-imidazo[4,5-b]pyridin-2-yl}-2-methylphenoxy)-N-methylacetamide, 2-[4-(6-chloro-7-{[1-(2-methoxyethyl)piperidin-4-yl]amino}-3H-imidazo[4,5-b]pyridin-2-yl)-2-m ethylphenoxy]-N-m ethylacetamide, 2-(4-{6-bromo-7-[(1-methylpiperidin-4-yl)amino]-3H-imidazo[4,5-b]pyridin-2-yl}phenoxy)-N,2-dimethylpropanamide, 2-(4-{6-chloro-7-[(1-methylpiperidin-4-yl)amino]-3H-imidazo[4,5-b]pyridin-2-yl}phenoxy)-N,2-dimethylpropanamide, 2-[4-(6-chloro-7-{[1-(4-methoxybenzyl)piperidin-4-yl]amino}-3H-imidazo[4,5-b]pyridin-2-yl)phenoxy]-N,2-dimethylpropanamide, 2-(4-{6-bromo-7-[(1-ethylpiperidin-4-yl)amino]-3H-imidazo[4,5-b]pyridin-2-yl}phenoxy)-N,2-dimethylpropanamide, 2-[4-(6-chloro-7-{[(3S)-1-(1-methylethyl)pyrrolidin-3-yl]amino}-3H-imidazo[4,5-b]pyridin-2-yl)phenoxy]-N,2-dimethylpropanamide, 2-(4-{6-bromo-7-[(1-methylpiperidin-4-yl)amino]-3H-imidazo[4,5-b]pyridin-2-yl}-2-fluorophenoxy)-N-methylacetamide, 2-(4-{6-chloro-7-[(1-methylpiperidin-4-yl)amino]-3H-imidazo[4,5-b]pyridin-2-yl}-2-fluorophenoxy)-N-methylacetamide, 2-[4-(6-chloro-7-{[1-(4-methoxybenzyl)piperidin-4-yl]amino}-3H-imidazo[4,5-b]pyridin-2-yl)-2-fluorophenoxy]-N-methylacetamide, 2-(4-{6-bromo-7-[(1-ethylpiperidin-4-yl)amino]-3H-imidazo[4,5-b]pyridin-2-yl}-2-fluorophenoxy)-N-methylacetamide, 2-[4-(6-chloro-7-{[(3S)-1-ethylpyrrolidin-3-yl]amino}-3H-imidazo[4,5-b]pyridin-2-yl)-2-fluorophenoxy]-N-methylacetamide, 3-(4-{6-bromo-7-[(1-methylpiperidin-4-yl)amino]-3H-imidazo[4,5-b]pyridin-2-yl}phenyl)-N-methylpropanamide, 3-(4-{6-chloro-7-[(1-methylpiperidin-4-yl)amino]-3H-imidazo[4,5-b]pyridin-2-yl}phenyl)-N-methylpropanamide, 3-[4-(6-bromo-7-{[1-(1-methylethyl)piperidin-4-yl]amino}-3H-imidazo[4,5-b]pyridin-2-yl)phenyl]-N-methylpropanamide, 3-(4-{6-bromo-7-[(1-ethylpiperidin-4-yl)amino]-3H-imidazo[4,5-b]pyridin-2-yl}phenyl)-N-methylpropanamide, 3-[4-(6-chloro-7-{[(3S)-1-ethylpyrrolidin-3-yl]amino}-3H-imidazo[4,5-b]pyridin-2-yl)phenyl]-N-methylpropanamide, 2-[4-(6-chloro-7-{[1-(4-methoxybenzyl)piperidin-4-yl]amino}-3H-imidazo[4,5-b]pyridin-2-yl)-2,6-dimethylphenoxy]-N-methylacetamide, 2-(4-{6-chloro-7-[(1-methylpiperidin-4-yl)amino]-3H-imidazo[4,5-b]pyridin-2-yl}-2,6-dimethylphenoxy)-N-methylacetamide, 2-(4-{6-bromo-7-[(1-methylpiperidin-4-yl)amino]-3H-imidazo[4,5-b]pyridin-2-yl}-2,6-dimethylphenoxy)-N-methylacetamide, 2-[4-(6-bromo-7-{[1-(1-methylethyl)piperidin-4-yl]amino}-3H-imidazo[4,5-b]pyridin-2-yl)-2,6-dimethylphenoxy]-N-methylacetamide, 2-[4-(6-chloro-7-{[(3S)-1-(1-methylethyl)pyrrolidin-3-yl]amino}-3H-imidazo[4,5-b]pyridin-2-yl)-2,6-dimethylphenoxy]-N-methylacetamide, 2-[4-(6-bromo-7-{[1-(thiophen-2-ylmethyl)piperidin-4-yl]amino}-3H-imidazo[4,5-b]pyridin-2-yl)-2,6-dimethylphenoxy]-N-methylacetamide, 2-[4-(6-chloro-7-{[(3S)-1-ethylpyrrolidin-3-yl]amino}-3H-imidazo[4,5-b]pyridin-2-yl)-2,6-dimethylphenoxy]-N-methylacetamide, 2-[4-(6-chloro-7-{[1-(4-methoxybenzyl)piperidin-4-yl]amino}-3H-imidazo[4,5-b]pyridin-2-yl)-2,5-dimethylphenoxy]-N-methylacetamide, 2-(4-{6-chloro-7-[(1-methylpiperidin-4-yl)amino]-3H-imidazo[4,5-b]pyridin-2-yl}-2,5-dimethylphenoxy)-N-methylacetamide, 2-(4-{6-bromo-7-[(1-methylpiperidin-4-yl)amino]-3H-imidazo[4,5-b]pyridin-2-yl}-2,5-dimethylphenoxy)-N-methylacetamide, 2-(4-{6-chloro-7-[(1-propylpiperidin-4-yl)amino]-3H-imidazo[4,5-b]pyridin-2-yl}-2,5-dimethylphenoxy)-N-methylacetamide, 2-(4-{6-chloro-7-[(1-ethylpiperidin-4-yl)amino]-3H-imidazo[4,5-b]pyridin-2-yl}-2,5-dimethylphenoxy)-N-methylacetamide, 2-(4-{6-chloro-7-[(1-propylpiperidin-4-yl)amino]-3H-imidazo[4,5-b]pyridin-2-yl}-2-methylphenoxy)-N-methylacetamide, 2-(4-{6-chloro-7-[(1-ethylpiperidin-4-yl)amino]-3H-imidazo[4,5-b]pyridin-2-yl}-2,6-dimethylphenoxy)-N-methylacetamide, 2-(4-{6-chloro-7-[(1-methylpiperidin-4-yl)amino]-3H-imidazo[4,5-b]pyridin-2-yl}phenoxy)-N-(4-methylcyclohexyl)acetamide, N-tert-butyl-2-(4-{6-chloro-7-[(1-methylpiperidin-4-yl)amino]-3H-imidazo[4,5-b]pyridin-2-yl}phenoxy)acetamide, 2-(4-{6-chloro-7-[(1-methylpiperidin-4-yl)amino]-3H-imidazo[4,5-b]pyridin-2-yl}phenoxy)-N-(1,1-dimethylpropyl)acetamide, 2-(4-{6-chloro-7-[(1-methylpiperidin-4-yl)amino]-3H-imidazo[4,5-b]pyridin-2-yl}phenoxy)-N-cyclohexylacetamide, 3-(4-{6-chloro-7-[(1-ethylpiperidin-4-yl)amino]-3H-imidazo[4,5-b]pyridin-2-yl}phenyl)-N-methylpropanamide, 3-[4-(6-chloro-7-{[1-(1-methylethyl)piperidin-4-yl]amino}-3H-imidazo[4,5-b]pyridin-2-yl)phenyl]-N-methylpropanamide, 2-(4-{6-chloro-7-[(1-ethylpiperidin-4-yl)amino]-3H-imidazo[4,5-b]pyridin-2-yl}-2-fluorophenoxy)-N-methylacetamide, 2-[4-(6-chloro-7-{[1-(1-methylethyl)piperidin-4-yl]amino}-3H-imidazo[4,5-b]pyridin-2-yl)-2-fluorophenoxy]-N-methylacetamide, 2-(4-{6-chloro-7-[(1-ethylpiperidin-4-yl)amino]-3H-imidazo[4,5-b]pyridin-2-yl}phenoxy)-N,2-dimethylpropanamide, 2-[4-(6-chloro-7-{[1-(1-methylethyl)piperidin-4-yl]amino}-3H-imidazo[4,5-b]pyridin-2-yl)phenoxy]-N,2-dimethylpropanamide, 2-(4-{6-chloro-7-[(1-ethylpiperidin-4-yl)amino]-3H-imidazo[4,5-b]pyridin-2-yl}-2-methoxyphenoxy)-N-methylacetamide, 2-[4-(6-chloro-7-{[1-(1-methylethyl)piperidin-4-yl]amino}-3H-imidazo[4,5-b]pyridin-2-yl)-2-methoxyphenoxy]-N-methylacetamide,
2-(4-{6-chloro-7-[(1-methylpiperidin-4-yl)amino]-3H-imidazo[4,5-b]pyridin-2-yl}phenoxy)-N-propylacetamide,
2-(4-{6-chloro-7-[(1-methylpiperidin-4-yl)amino]-3H-imidazo[4,5-b]pyridin-2-yl}phenoxy)-N-(2-methylpropyl)acetamide,
2-(4-{6-chloro-7-[(1-methylpiperidin-4-yl)amino]-3H-imidazo[4,5-b]pyridin-2-yl}phenoxy)-N-(tetrahydrofuran-2-ylmethyl)acetamide,
2-(4-{6-chloro-7-[(1-methylpiperidin-4-yl)amino]-3H-imidazo[4,5-b]pyridin-2-yl}phenoxy)-N-[1-(methoxymethyl)propyl]acetamide,
2-(4-{6-chloro-7-[(1-methylpiperidin-4-yl)amino]-3H-imidazo[4,5-b]pyridin-2-yl}phenoxy)-N-(2-m ethoxy-1-methylethyl)acetamide,
N-benzyl-2-(4-{6-chloro-7-[(1-methylpiperidin-4-yl)amino]-3H-imidazo[4,5-b]pyridin-2-yl}phenoxy)acetamide,
2-(4-{6-chloro-7-[(1-methylpiperidin-4-yl)amino]-3H-imidazo[4,5-b]pyridin-2-yl}phenoxy)-N-(1-phenylethyl)acetamide,
2-(4-{6-chloro-7-[(1-methylpiperidin-4-yl)amino]-3H-imidazo[4,5-b]pyridin-2-yl}phenoxy)-N-cycloheptylacetamide,
2-(4-{6-bromo-7-[(1-methylpiperidin-4-yl)amino]-3H-imidazo[4,5-b]pyridin-2-yl}-2-fluorophenoxy)-N-(1-methylethyl)acetamide,
2-(4-{6-chloro-7-[(1-methylpiperidin-4-yl)amino]-3H-imidazo[4,5-b]pyridin-2-yl}-2-fluorophenoxy)-N-(1-methylethyl)acetamide,
2-(4-{6-chloro-7-[(1-ethylpiperidin-4-yl)amino]-3H-imidazo[4,5-b]pyridin-2-yl}-2-fluorophenoxy)-N-(1-methylethyl)acetamide,
2-[4-(6-chloro-7-{[1-(1-methylethyl)piperidin-4-yl]amino}-3H-imidazo[4,5-b]pyridin-2-yl)-2-fluorophenoxy]-N-(1-methylethyl)acetamide,
2-(4-{6-chloro-7-[(1-methylpiperidin-4-yl)amino]-3H-imidazo[4,5-b]pyridin-2-yl}phenyl)-N-m ethylacetamide,
2-[4-(6-chloro-7-{[1-(4-methoxybenzyl)piperidin-4-yl]amino}-3H-imidazo[4,5-b]pyridin-2-yl)phenyl]-N-methylacetamide,
2-[4-(6-chloro-7-{[1-(4-methoxybenzyl)piperidin-4-yl]amino}-3H-imidazo[4,5-b]pyridin-2-yl)phenoxy]-N-cyclopentylacetamide,
2-[4-(6-chloro-7-{[1-(4-methoxybenzyl)piperidin-4-yl]amino}-3H-imidazo[4,5-b]pyridin-2-yl)phenoxy]-N-(cyclohexylmethyl)acetamide,
2-[4-(6-chloro-7-{[1-(4-methoxybenzyl)piperidin-4-yl]amino}-3H-imidazo[4,5-b]pyridin-2-yl)phenoxy]-N-cycloheptylacetamide,
2-[4-(6-chloro-7-{[1-(4-methoxybenzyl)piperidin-4-yl]amino}-3H-imidazo[4,5-b]pyridin-2-yl)phenoxy]-N-(2-cyclohexylethyl)acetamide,
2-[4-(6-chloro-7-{[1-(4-methoxybenzyl)piperidin-4-yl]amino}-3H-imidazo[4,5-b]pyridin-2-yl)phenoxy]-N-[2-(tetrahydro-2H-pyran-4-yl)ethyl]acetamide,
2-(4-{6-chloro-7-[(1-methylpiperidin-4-yl)amino]-3H-imidazo[4,5-b]pyridin-2-yl}phenoxy)-N-(4-m ethoxybenzyl)acetamide,
2-(4-{6-chloro-7-[(1-methylpiperidin-4-yl)amino]-3H-imidazo[4,5-b]pyridin-2-yl}phenoxy)-N-(furan-2-ylmethyl)acetamide,
2-(4-{6-chloro-7-[(1-methylpiperidin-4-yl)amino]-3H-imidazo[4,5-b]pyridin-2-yl}phenoxy)-N-(thiophen-2-ylmethyl)acetamide,
2-(4-{6-chloro-7-[(1-methylpiperidin-4-yl)amino]-3H-imidazo[4,5-b]pyridin-2-yl}phenoxy)-N-(2-methoxyethyl)acetamide,
2-(4-{6-chloro-7-[(1-methylpiperidin-4-yl)amino]-3H-imidazo[4,5-b]pyridin-2-yl}phenoxy)-N-pyridin-4-ylacetamide,
2-(4-{6-chloro-7-[(1-ethylpiperidin-4-yl)amino]-3H-imidazo[4,5-b]pyridin-2-yl}phenyl)-N-m ethylacetamide,
2-[4-(6-chloro-7-{[1-(1-methylethyl)piperidin-4-yl]amino}-3H-imidazo[4,5-b]pyridin-2-yl)phenyl]-N-methylacetamide,
2-(4-{6-chloro-7-[(1-propylpiperidin-4-yl)amino]-3H-imidazo[4,5-b]pyridin-2-yl}phenyl)-N-m ethylacetamide,
2-(4-{6-bromo-7-[(1-propylpiperidin-4-yl)amino]-3H-imidazo[4,5-b]pyridin-2-yl}phenyl)-N-m ethylacetamide,
2-[4-(6-bromo-7-{[1-(1-methylethyl)piperidin-4-yl]amino}-3H-imidazo[4,5-b]pyridin-2-yl)phenyl]-N-methylacetamide,
2-(4-{6-bromo-7-[(1-methylpiperidin-4-yl)amino]-3H-imidazo[4,5-b]pyridin-2-yl}phenyl)-N-methylacetamide,
2-[4-(6-chloro-7-{[1-(thiophen-2-ylmethyl)piperidin-4-yl]amino}-3H-imidazo[4,5-b]pyridin-2-yl)phenoxy]-N-cyclopentylacetamide,
2-[4-(6-chloro-7-{[1-(thiophen-2-ylmethyl)piperidin-4-yl]amino}-3H-imidazo[4,5-b]pyridin-2-yl)phenoxy]-N-cyclohexylacetamide,
2-(4-{6-bromo-7-[(1-methylpiperidin-4-yl)amino]-3H-imidazo[4,5-b]pyridin-2-yl}phenoxy)-N-(1-methylethyl)acetamide,
2-(4-{6-bromo-7-[(1-methylpiperidin-4-yl)amino]-3H-imidazo[4,5-b]pyridin-2-yl}phenoxy)-N-propylacetamide,
2-(4-{6-bromo-7-[(1-methylpiperidin-4-yl)amino]-3H-imidazo[4,5-b]pyridin-2-yl}phenoxy)-N-[1-(methoxymethyl)propyl]acetamide,
2-(4-{6-bromo-7-[(1-methylpiperidin-4-yl)amino]-3H-imidazo[4,5-b]pyridin-2-yl}phenoxy)-N-(2-methylpropyl)acetamide,
2-(4-{6-bromo-7-[(1-methylpiperidin-4-yl)amino]-3H-imidazo[4,5-b]pyridin-2-yl}phenoxy)-N-tert-butylacetamide,
2-(4-{6-bromo-7-[(1-methylpiperidin-4-yl)amino]-3H-imidazo[4,5-b]pyridin-2-yl}phenoxy)-N-(1,1-dimethylpropyl)acetamide,
2-(4-{6-bromo-7-[(1-methylpiperidin-4-yl)amino]-3H-imidazo[4,5-b]pyridin-2-yl}phenoxy)-N-cyclohexylacetamide,
2-(4-{6-bromo-7-[(1-methylpiperidin-4-yl)amino]-3H-imidazo[4,5-b]pyridin-2-yl}phenoxy)-N-cyclopentylacetamide,
2-(4-{6-bromo-7-[(1-methylpiperidin-4-yl)amino]-3H-imidazo[4,5-b]pyridin-2-yl}phenoxy)-N-ethylacetamide,
2-(4-{6-chloro-7-[(1-methylpiperidin-4-yl)amino]-3H-imidazo[4,5-b]pyridin-2-yl}phenoxy)-N-(tetrahydro-2H-thiopyran-4-yl)acetamide,
2-(4-{6-chloro-7-[(1-methylpiperidin-4-yl)amino]-3H-imidazo[4,5-b]pyridin-2-yl}phenoxy)-N-(tetrahydro-2H-pyran-4-yl)acetamide, 2-(4-{6-chloro-7-[(1-methylpiperidin-4-yl)amino]-3H-imidazo[4,5-b]pyridin-2-yl}phenoxy)-N-(2,2,2-trifluoroethyl)acetamide,
N-{2-[4-(6-chloro-7-{[1-(4-methoxybenzyl)piperidin-4-yl]amino}-3H-imidazo[4,5-b]pyridin-2-yl)phenoxy]ethyl}acetamide,
N-[2-(4-{6-chloro-7-[(1-methylpiperidin-4-yl)amino]-3H-imidazo[4,5-b]pyridin-2-yl}phenoxy)ethyl]acetamide,
N-[2-(4-{6-bromo-7-[(1-methylpiperidin-4-yl)amino]-3H-imidazo[4,5-b]pyridin-2-yl}phenoxy)ethyl]acetamide,
N-{2-[4-(6-chloro-7-{[1-(1-methylethyl)piperidin-4-yl]amino}-3H-imidazo[4,5-b]pyridin-2-yl)phenoxy]ethyl}acetamide,
N-[2-(4-{6-chloro-7-[(1-methylpiperidin-4-yl)amino]-3H-imidazo[4,5-b]pyridin-2-yl}phenoxy)ethyl]cyclohexanecarboxamide,
N-[2-(4-{6-chloro-7-[(1-methylpiperidin-4-yl)amino]-3H-imidazo[4,5-b]pyridin-2-yl}phenoxy)ethyl]-2,2-dimethylpropanamide,
2-(4-{6-bromo-7-[(1-methylpiperidin-4-yl)amino]-3H-imidazo[4,5-b]pyridin-2-yl}phenoxy)-N-pyridin-4-ylacetamide,
2-[4-(6-chloro-7-{[1-(1-methylethyl)piperidin-4-yl]amino}-3H-imidazo[4,5-b]pyridin-2-yl)phenoxy]-N-cyclohexylacetamide,
N-[2-(4-{6-chloro-7-[(1-methylpiperidin-4-yl)amino]-3H-imidazo[4,5-b]pyridin-2-yl}phenoxy)ethyl]pyridine-4-carboxamide,
N-[2-(4-{6-chloro-7-[(1-methylpiperidin-4-yl)amino]-3H-imidazo[4,5-b]pyridin-2-yl}phenoxy)ethyl]pyridine-3-carboxamide,
N-[2-(4-{6-chloro-7-[(1-methylpiperidin-4-yl)amino]-3H-imidazo[4,5-b]pyridin-2-yl}phenoxy)ethyl]-2-methoxyacetamide,
N-[2-(4-{6-chloro-7-[(1-methylpiperidin-4-yl)amino]-3H-imidazo[4,5-b]pyridin-2-yl}phenoxy)ethyl]cyclopentanecarboxamide,
N-[2-(4-{6-chloro-7-[(1-methylpiperidin-4-yl)amino]-3H-imidazo[4,5-b]pyridin-2-yl}phenoxy)ethyl]-2-methylpropanamide,
N-[2-(4-{6-chloro-7-[(1-methylpiperidin-4-yl)amino]-3H-imidazo[4,5-b]pyridin-2-yl}phenoxy)ethyl]cyclopropanecarboxamide,
N-[2-(4-{6-chloro-7-[(1-ethylpiperidin-4-yl)amino]-3H-imidazo[4,5-b]pyridin-2-yl}phenoxy)ethyl]acetamide,
N-{2-[4-(6-chloro-7-{[1-(thiophen-2-ylmethyl)piperidin-4-yl]amino}-3H-imidazo[4,5-b]pyridin-2-yl)phenoxy]ethyl}acetamide,
N-{2-[4-(6-chloro-7-{[1-(4-methoxybenzyl)piperidin-4-yl]amino}-3H-imidazo[4,5-b]pyridin-2-yl)phenoxy]ethyl}propanamide,
N-{2-[4-(6-chloro-7-{[1-(4-methoxybenzyl)piperidin-4-yl]amino}-3H-imidazo[4,5-b]pyridin-2-yl)phenoxy]ethyl}cyclopentanecarboxamide,
N-{2-[4-(6-chloro-7-{[1-(4-methoxybenzyl)piperidin-4-yl]amino}-3H-imidazo[4,5-b]pyridin-2-yl)phenoxy]ethyl}-2-methylpropanamide,
N-{2-[4-(6-chloro-7-{[1-(4-methoxybenzyl)piperidin-4-yl]amino}-3H-imidazo[4,5-b]pyridin-2-yl)phenoxy]ethyl}pyridine-4-carboxamide,
2-{4-[6-Bromo-7-({1-[4-(1H-1,2,4-triazol-1-yl)benzyl]piperidin-4-yl}amino)-3H-imidazo[4,5-b]pyridin-2-yl]phenoxy}-N-methylacetamide,
N-(2-{4-[6-chloro-7-({1-[4-(1H-1,2,4-triazol-1-yl)benzyl]piperidin-4-yl}amino)-3H-imidazo[4,5-b]pyridin-2-yl]phenoxy}ethyl)acetamide,
N-(2-{4-[6-bromo-7-({1-[4-(1H-1,2,4-triazol-1-yl)benzyl]piperidin-4-yl}amino)-3H-imidazo[4,5-b]pyridin-2-yl]phenoxy}ethyl)acetamide,
2-{4-[6-chloro-7-({1-[(1,3,5-trimethyl-1H-pyrazol-4-yl)methyl]piperidin-4-yl}amino)-3H-imidazo[4,5-b]pyridin-2-yl]phenoxy}-N-methylacetamide,
2-{4-[6-bromo-7-({1-[(1,3,5-trimethyl-1H-pyrazol-4-yl)methyl]piperidin-4-yl}amino)-3H-imidazo[4,5-b]pyridin-2-yl]phenoxy}-N-methylacetamide,
2-[4-(6-chloro-7-{[1-(4-methoxybenzyl)piperidin-4-yl]amino}-3H-imidazo[4,5-b]pyridin-2-yl)phenoxy]-N-pyridin-3-ylacetamide,
2-[4-(6-chloro-7-{[1-(4-methoxybenzyl)piperidin-4-yl]amino}-3H-imidazo[4,5-b]pyridin-2-yl)phenoxy]-N-(1-methyl-1H-pyrazol-5-yl)acetamide,
2-(4-{6-chloro-7-[(1-methylpiperidin-4-yl)amino]-3H-imidazo[4,5-b]pyridin-2-yl}phenoxy)-N-pyridin-3-ylacetamide,
2-(4-{6-chloro-7-[(1-methylpiperidin-4-yl)amino]-3H-imidazo[4,5-b]pyridin-2-yl}phenoxy)-N-pyrazin-2-ylacetamide,
$N^2$-(4-{6-bromo-7-[(1-methylpiperidin-4-yl)amino]-3H-imidazo[4,5-b]pyridin-2-yl}phenyl)-N-methylglycinamide,
$N^2$-(4-{6-chloro-7-[(1-methylpiperidin-4-yl)amino]-3H-imidazo[4,5-b]pyridin-2-yl}phenyl)-N-methylglycinamide,
$N^2$-[4-(6-chloro-7-{[1-(1-methylethyl)piperidin-4-yl]amino}-3H-imidazo[4,5-b]pyridin-2-yl)phenyl]-N-methylglycinamide,
$N^2$-[4-(6-chloro-7-{[1-(4-methoxybenzyl)piperidin-4-yl]amino}-3H-imidazo[4,5-b]pyridin-2-yl)phenyl]-N-methylglycinamide,
$N^2$-(4-{6-chloro-7-[(1-ethylpiperidin-4-yl)amino]-3H-imidazo[4,5-b]pyridin-2-yl}phenyl)-N-methylglycinamide,
2-(4-{6-chloro-7-[(1-methylpiperidin-4-yl)amino]-3H-imidazo[4,5-b]pyridin-2-yl}phenoxy)-N-pyridin-2-ylacetamide,
2-(4-{6-chloro-7-[(1-methylpiperidin-4-yl)amino]-3H-imidazo[4,5-b]pyridin-2-yl}phenoxy)-N-isoxazol-3-ylacetamide,
2-(4-{6-chloro-7-[(1-methylpiperidin-4-yl)amino]-3H-imidazo[4,5-b]pyridin-2-yl}phenoxy)-N-(pyridin-4-ylmethyl)acetamide,
$N^3$-(4-{6-bromo-7-[(1-methylpiperidin-4-yl)amino]-3H-imidazo[4,5-b]pyridin-2-yl}phenyl)-N-methyl-b-alaninamide,
$N^3$-(4-{6-chloro-7-[(1-methylpiperidin-4-yl)amino]-3H-imidazo[4,5-b]pyridin-2-yl}phenyl)-N-methyl-b-alaninamide,
$N^3$-[4-(6-chloro-7-{[1-(1-methylethyl)piperidin-4-yl]amino}-3H-imidazo[4,5-b]pyridin-2-yl)phenyl]-N-methyl-b-alaninamide,
$N^3$-[4-(6-chloro-7-{[1-(4-methoxybenzyl)piperidin-4-yl]amino}-3H-imidazo[4,5-b]pyridin-2-yl)phenyl]-N-methyl-b-alaninamide,
$N^3$-(4-{6-chloro-7-[(1-ethylpiperidin-4-yl)amino]-3H-imidazo[4,5-b]pyridin-2-yl}phenyl)-N-methyl-b-alaninamide,
2-[4-(6-chloro-7-{[1-(4-methoxybenzyl)piperidin-4-yl]amino}-3H-imidazo[4,5-b]pyridin-2-yl)phenoxy]-N-(pyridin-4-ylmethyl)acetamide, 2-[4-(6-chloro-7-{[1-(4-methoxybenzyl)piperidin-4-yl]amino}-3H-imidazo[4,5-b]pyridin-2-yl)phenoxy]-N-pyrimidin-2-ylacetamide, 2-(4-{6-chloro-7-[(1-methylpiperidin-4-yl)amino]-3H-imidazo[4,5-b]pyridin-2-yl}phenoxy)-N-pyrimidin-2-ylacetamide, 2-[4-(6-chloro-7-{[1-(thiophen-2-ylmethyl)piperidin-4-yl]amino}-3H-imidazo[4,5-b]pyridin-2-yl)phenoxy]-N-pyrimidin-2-ylacetamide, 2-(4-{6-chloro-7-[(1-methylpiperidin-4-yl)amino]-3H-imidazo[4,5-b]pyridin-2-yl}phenoxy)-N-pyrazin-2-ylacetamide, 2-(4-{6-bromo-7-[(1-methylpiperidin-4-yl)amino]-3H-imidazo[4,5-b]pyridin-2-yl}phenoxy)-N-pyrazin-2-ylacetamide, 2-[4-(6-chloro-7-{[1-(1-methylethyl)piperidin-4-yl]amino}-3H-imidazo[4,5-b]pyridin-2-yl)phenoxy]-N-pyrazin-2-ylacetamide, 2-[4-(6-chloro-7-{[1-(thiophen-3-ylmethyl)piperidin-4-yl]amino}-3H-imidazo[4,5-b]pyridin-2-yl)phenoxy]-N-pyrazin-2-ylacetamide, 2-[4-(6-chloro-7-{[1-(2,3-dihydro-1-benzofuran-5-ylmethyl)piperidin-4-yl]amino}-3H-imidazo[4,5-b]pyridin-2-yl)phenoxy]-N-pyrazin-2-ylacetamide, 2-(4-{5-chloro-4-[(1-methylpiperidin-4-yl)amino]-1H-pyrrolo[2,3-b]pyridin-2-yl}phenoxy)-N-(5-methylisoxazol-3-yl)acetamide, $N^2$-(4-{6-chloro-7-[(1-methylpiperidin-4-yl)amino]-3H-imidazo[4,5-b]pyridin-2-yl}phenyl)-N2-methyl-N-pyridin-3-ylglycinamide, 2-(4-{6-chloro-7-[(1-methylpiperidin-4-yl)amino]-3H-imidazo[4,5-b]pyridin-2-yl}phenoxy)-N-(5-chloropyridin-3-yl)acetamide, 2-[4-(6-chloro-7-{[1-(4-methoxybenzyl)piperidin-4-yl]amino}-3H-imidazo[4,5-b]pyridin-2-yl)phenoxy]-N-isoxazol-3-ylacetamide, 2-(4-{6-bromo-7-[(1-methylpiperidin-4-yl)amino]-3H-imidazo[4,5-b]pyridin-2-yl}phenoxy)-N-isoxazol-3-ylacetamide, 2-[4-(6-chloro-7-{[1-(1-methylethyl)piperidin-4-yl]amino}-3H-imidazo[4,5-b]pyridin-2-yl)phenoxy]-N-isoxazol-3-ylacetamide, 2-[4-(6-chloro-7-{[1-(thiophen-3-ylmethyl)piperidin-4-yl]amino}-3H-imidazo[4,5-b]pyridin-2-yl)phenoxy]-N-isoxazol-3-ylacetamide, 2-(4-{6-chloro-7-[(1-propylpiperidin-4-yl)amino]-3H-imidazo[4,5-b]pyridin-2-yl}phenoxy)-N-isoxazol-3-ylacetamide, 2-[4-(6-chloro-7-{[1-(4-methoxybenzyl)piperidin-4-yl]amino}-3H-imidazo[4,5-b]pyridin-2-yl)phenoxy]-N-pyrazin-2-ylacetamide, 2-(4-{6-chloro-7-[(1-methylpiperidin-4-yl)amino]-3H-imidazo[4,5-b]pyridin-2-yl}phenoxy)-N-(1-methyl-1H-pyrazol-5-yl)acetamide, 2-[4-(6-chloro-7-{[1-(4-methoxybenzyl)piperidin-4-yl]amino}-3H-imidazo[4,5-b]pyridin-2-yl)phenoxy]-N-1H-1,2,4-triazol-3-ylacetamide, 2-(4-{6-chloro-7-[(1-methylpiperidin-4-yl)amino]-3H-imidazo[4,5-b]pyridin-2-yl}phenoxy)-N-1H-1,2,4-triazol-3-ylacetamide, 2-(4-{6-chloro-7-[(1-methylpiperidin-4-yl)amino]-3H-imidazo[4,5-b]pyridin-2-yl}phenoxy)-N-1,3,4-thiadiazol-2-ylacetamide, 2-(4-{6-chloro-7-[(1-methylpiperidin-4-yl)amino]-3H-imidazo[4,5-b]pyridin-2-yl}phenoxy)-N-(3-methylisoxazol-5-yl)acetamide, 2-(4-{6-chloro-7-[(1-methylpiperidin-4-yl)amino]-3H-imidazo[4,5-b]pyridin-2-yl}phenoxy)-N-1,3-thiazol-2-ylacetamide, N-(5-tert-butylisoxazol-3-yl)-2-(4-{6-chloro-7-[(1-methylpiperidin-4-yl)amino]-3H-imidazo[4,5-b]pyridin-2-yl}phenoxy)acetamide, and 2-(4-{6-chloro-7-[(1-methylpiperidin-4-yl)amino]-3H-imidazo[4,5-b]pyridin-2-yl}phenoxy)-N-pyrimidin-5-ylacetamide, or a pharmaceutically acceptable salt thereof.

16. A pharmaceutical composition comprising a compound or pharmaceutically acceptable salt according to claim 1, and optionally a pharmaceutically acceptable excipient.

17. A method of treatment of a malignant hyperproliferative disorder, an obesity-associated metabolic complication, an autoimmune disorder or an inflammatory disorder, by administering a therapeutically effective amount of a compound of claim 1, to a mammal in need thereof.

* * * * *